(12) United States Patent
Zhao et al.

(10) Patent No.: US 8,883,801 B2
(45) Date of Patent: Nov. 11, 2014

(54) SUBSTITUTED PYRAZOLO[1,5-A]PYRIMIDINES AS MTOR INHIBITORS

(75) Inventors: Lianyun Zhao, Blue Bell, PA (US); Duan Liu, Arlington, MA (US); Shuyi Tang, Belmont, MA (US); Amit K. Mandal, Shrewsbury, MA (US); Umar Faruk Mansoor, Framingham, MA (US); Lalanthi Dilrukshi Vitharana, Somerville, MA (US); Panduranga Adulla P. Reddy, Walpole, MA (US); M. Arshad Siddiqui, Newton, MA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 13/818,177

(22) PCT Filed: Aug. 22, 2011

(86) PCT No.: PCT/US2011/048541
§ 371 (c)(1),
(2), (4) Date: Feb. 21, 2013

(87) PCT Pub. No.: WO2012/027236
PCT Pub. Date: Mar. 1, 2012

(65) Prior Publication Data
US 2013/0150362 A1 Jun. 13, 2013

Related U.S. Application Data

(60) Provisional application No. 61/375,944, filed on Aug. 23, 2010.

(51) Int. Cl.
| | | |
|---|---|---|
| A61K 31/519 | (2006.01) | |
| C07D 239/70 | (2006.01) | |
| A61K 31/5377 | (2006.01) | |
| C07D 487/04 | (2006.01) | |
| A61K 45/06 | (2006.01) | |

(52) U.S. Cl.
CPC .......... *C07D 487/04* (2013.01); *A61K 31/5377* (2013.01); *A61K 31/519* (2013.01); *A61K 45/06* (2013.01)
USPC ........ 514/259.3; 544/117; 544/282; 546/152; 546/275.7; 548/131; 548/143; 548/202; 548/250; 548/266.4; 548/335.1; 548/373.1

(58) Field of Classification Search
CPC ............................ A61K 31/519; C07D 239/70
USPC ................ 514/259.3; 544/117, 282; 546/152, 546/275.7; 548/131, 143, 202, 250, 266.4, 548/335.1, 373.1
See application file for complete search history.

(56) References Cited

U.S. PATENT DOCUMENTS

| | | | |
|---|---|---|---|
| 7,084,271 B2 | 8/2006 | Guzi et al. | |
| 7,468,372 B2 | 12/2008 | Guzi et al. | |
| 7,605,155 B2 * | 10/2009 | Guzi et al. | .................... 514/218 |
| 8,591,943 B2 | 11/2013 | Deng et al. | |
| 8,609,675 B2 | 12/2013 | Cheng et al. | |
| 2006/0079536 A1 | 4/2006 | Yasuma et al. | |
| 2007/0072881 A1 | 3/2007 | Guzi et al. | |

FOREIGN PATENT DOCUMENTS

| | | | |
|---|---|---|---|
| WO | 2004022062 A1 | 3/2004 | |
| WO | WO 2010/118207 | * 10/2010 | |
| WO | 2011002887 A1 | 1/2011 | |
| WO | 2011090935 A1 | 7/2011 | |
| WO | 2012027239 A1 | 3/2012 | |

OTHER PUBLICATIONS

Jordan, V. C. Nature Reviews: Drug Discovery, 2, 2003, 205.*
Hackam, et al. JAMA, 296(14), 2006, 1731-1732.*
U.S. Appl. No. 13/818,153, filed Feb. 21, 2013 titled: "Fused Tricyclic Inhibitors of Mammalian Target of Rapamycin".
Notice of Allowance mailed on Nov. 20, 2013 for U.S. Appl. No. 13/818,153.

* cited by examiner

*Primary Examiner* — Douglas M Willis
(74) *Attorney, Agent, or Firm* — Richard S. Parr; Laura M. Ginkel

(57) ABSTRACT

The present invention relates to certain pyrazolo[1,5-a]pyrimidine compounds of Formula (I)

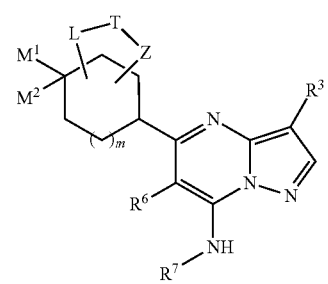

as inhibitors of mammalian Target Of Rapamycin (mTOR) kinase, which is also known as FRAP, RAFT, RAPT or SEP. The compounds may be used in the treatment of cancer and other disorders where mTOR is deregulated. The present invention further provides pharmaceutical compositions comprising the pyrazolo[1,5-a]pyrimidine compounds.

13 Claims, No Drawings

SUBSTITUTED PYRAZOLO[1,5-A]PYRIMIDINES AS MTOR INHIBITORS

FIELD OF THE INVENTION

This invention is directed to certain pyrazolo[1,5-a]pyrimidine compounds of Formula (I) as inhibitors of mammalian Target Of Rapamycin (mTOR) kinase, which is also known as FRAP, RAFT, RAPT or SEP. The compounds may be useful in the treatment of cancer and other disorders where mTOR is deregulated.

BACKGROUND OF THE INVENTION

The mammalian target of rapamycin (mTOR) is a central regulator of cell growth and proliferation and plays a gatekeeper role in the control of cell cycle progression. The mTOR signaling pathway, which integrates both extracellular and intracellular signals, is activated in certain cellular processes such as tumor formation, angiogenesis, insulin resistance, adipogenesis, and T-lymphocyte activation. In addition, the mTOR signaling pathway is deregulated in diseases such as cancer and type 2 diabetes. See Laplante et al., J. Cell Science 122, pp 3589-3593 (2009).

mTOR mediates mitogenic signals from PI3K/AKT through to the downstream targets S6K1 (ribosomal S6 kinase 1), 4E-BP1 (eukaryotic translation initiation factor 4E-binding protein) and AKT. Recently, it has been shown that mTOR exists in two complexes. Raptor-mTOR complex (mTORC1) is a rapamycin-sensitive complex that phosphorylates S6K1 and 4E-BP1. Rictor-mTOR complex (mTORC2) is a rapamycin-insensitive complex that phosphorylates AKT at Ser473. Although the precise mechanism by which rapamycin inhibits mTOR function is not well understood, rapamycin partially inhibits mTOR function through mTORC1. Since mTORC2 is involved in the regulation of cell survival, metabolism, proliferation, and cytoskeletal organization in a rapamycin-independent manner, complete inhibition of mTOR function through inhibition of both mTORC1 and mTORC2 may lead to a broader spectrum antitumor activity in the treatment of cancer or better efficacy. In addition, inhibition of both mTORC1 and mTORC2 may lead to better efficacy in treating other diseases than through inhibition of mTORC1 alone.

There exists a need in the art for small-molecule compounds having desirable physicochemical properties that are useful for treating cancer and other disorders associated with deregulated mTOR activity. Specifically, there exists a need for small molecule inhibitors of mTOR kinase that block signaling through mTORC1 and mTORC2 for treating cancer and other disorders.

SUMMARY OF THE INVENTION

The present invention relates to certain pyrazolo[1,5-a]pyrimidine compounds of Formula (I) as inhibitors of mammalian Target Of Rapamycin (mTOR) kinase, which is also known as FRAP, RAFT, RAPT or SEP. The compounds may be used in the treatment of cancer and other disorders where mTOR is deregulated. The present invention further provides pharmaceutical compositions comprising the pyrazolo[1,5-a]pyrimidine compounds.

The present invention thus relates to compounds of Formula I and pharmaceutically acceptable salts thereof, as detailed herein:

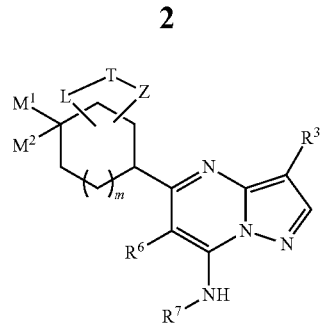

DETAILED DESCRIPTION OF THE INVENTION

The present invention provides Pyrazolopyrimidine Compounds, pharmaceutical compositions comprising a Pyrazolopyrimidine Compound, and methods of using the Pyrazolopyrimidine Compounds for treating cancer in a patient. In addition, the present invention provides methods of using the Pyrazolopyrimidine Compounds for treating a disease or disorder associated with deregulated mTOR activity in a patient.

Compounds

The present invention provides compounds of Formula I

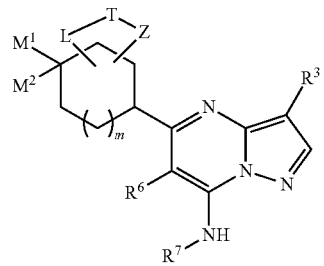

wherein $M^1$ and $M^2$ are independently selected from the group consisting of CN, —$(CR^aR^b)_nOR^1$, —$(CR^aR^b)_nNR^1R^2$, —$(CR^aR^b)_nR^1$, —$(CR^aR^b)_nSR^1$, —$(CR^aR^b)_nS(O)_2R^1$, —$(CR^aR^b)_nS(O)R^1$, $(CR^aR^b)_nS(O)_2NR^1R^2$, —$(CR^aR^b)_n NR^1S(O)_2R^4$, —$(CR^aR^b)_nC(O)NR^1S(O)_2R^2$, —$(CR^aR^b)_nC(O)R^1$, —$(CR^aR^b)_nC(O)OR^1$, —$(CR^aR^b)_nC(O)NR^1R^2$, —$(CR^aR^b)_nC(=NR^4)NR^1R^2$, —$(CR^aR^b)_nNR^1C(O)R^4$, —$(CR^aR^b)_nNR^1C(O)OR^4$, —$(CR^aR^b)_nNR^4C(O)NR^1R^2$, —$(CR^aR^b)_nOR^1$ and —$(CR^aR^b)_nO(CR^cR^d)_qOR^4$;

L and Z are not present, or

L and Z are bonded to any two carbons of the ring which $M^1$ and $M^2$ are not attached and are independently selected from the group consisting of $CH_2$, $C(H)(R^{10})$, $C(R^{10})(R^{11})$, $N(R^{10})$, C(O), O, S, S(O) and $S(O)_2$, T is not present such that L is bonded directly to Z, or T is selected from the group consisting of $CH_2$, $C(H)(R^{10})$, $C(R^{10})(R^{11})$, $N(R^{10})$, C(O), O, S, S(O) and $S(O)_2$ and $C_1$-$C_4$ alkylene, wherein said alkylene of T is unsubstituted or substituted with 1 to two substituents selected from the group consisting of $C_1$-$C_3$ alkyl, halo, hydroxyl, $C_1$-$C_3$ alkoxy, amino, $C_1$-$C_3$ alkylamino and $C_1$-$C_3$ dialkylamino;

$R^a$, $R^b$, $R^c$ and $R^d$ are independently selected from H, halogen and $C_1$-$C_6$ alkyl;

$R^1$, $R^2$ and $R^4$ are independently selected from H, OH, halogen, $NH_2$, —$(CR^aR^b)_nO(CR^cR^d)_qR^8$, $C_1$-$C_6$alkyl $C_3$-$C_8$cycloalkyl, $C_3$-$C_8$cycloalkyl$C_1$-$C_6$alkyl, $C_6$-$C_{10}$aryl$C_1$-$C_6$alkyl, $C_6$-$C_{10}$aryl, 5- to 10-membered heteroaryl$C_1$-$C_6$alkyl, 5- to 10-membered heteroaryl, 5- to 10-membered heterocyclyl$C_1$-$C_6$alkyl, 5- to 10-membered heterocyclenyl$C_1$-$C_6$alkyl, 5- to 10-membered heterocyclyl and 5- to 10-membered heterocyclenyl, wherein the alkyl, cycloalkyl, cycloalkylalkyl, arylalkyl, aryl, heteroarylalkyl, heteroaryl, heterocyclylalkyl, heterocyclenylalkyl, heterocyclyl or heterocyclenyl is unsubstituted or substituted with one to three moieties which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —$OR^9$, —$C(O)R^9$, —$NR^8R^9$, —$C(O)O$—$C_1$-$C_6$alkyl, —$C(O)NR^8R^9$, —$NR^8C(O)R^9$, —$S(O_2)NR^8R^9$, —$NR^8S(O_2)R^9$, —$SR^9$, —$S(O_2)R^9$, $C_6$-$C_{10}$aryl, 5- to 10-membered heteroaryl, 5- to 10-membered heterocyclenyl and 5- to 10-membered heterocyclyl;

Or $R^1$ and $R^2$ form a 3- to 8-membered cycloalkyl, 5- to 6-membered heterocyclyl or 5- to 6-membered heterocyclenyl;

$R^3$ is selected from the group consisting of H, halogen, $C_1$-$C_6$ alkyl, $C_2$-$C_6$ alkenyl, $C_2$-$C_6$ alkynyl, halo $C_1$-$C_6$alkyl, —$CF_3$, —$C(O)R^9$, $C_6$-$C_{10}$aryl, $C_3$-$C_8$cycloalkyl, 5- to 10-membered heteroaryl, 5- to 10-membered heterocyclyl, 5- to 10-membered heterocyclenyl, $C_6$-$C_{10}$aryl$C_1$-$C_6$alkyl, $C_3$-$C_8$cycloalkyl$C_1$-$C_6$alkyl, 5- to 10-membered heteroaryl$C_1$-$C_6$alkyl, 5- to 10-membered heterocyclyl$C_1$-$C_6$alkyl and 5- to 10-membered heterocyclenyl$C_1$-$C_6$alkyl, wherein each of said aryl, cycloalkyl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to three moieties which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —$(CR^aR^b)_nOR^9$, —$(CR^aR^b)_nC(O)R^9$, —$(CR^aR^b)_nNR^8R^9$, —$(CR^aR^b)_nNR^8$, —$NR^8R^9$, —$(CR^aR^b)_nC(O)O$—$C_1$-$C_6$alkyl, —O-halo$C_1$-$C_6$alkyl, —$(CR^aR^b)_nC(O)NR^8R^9$, —$(CR^aR^b)_n C(O)NR^8S(O)_2R^9$, —$(CR^aR^b)_nNR^8C(O)R^9$, —$(CR^aR^b)_nNR^8C(O)OR^9$, —$(CR^aR^b)_nNR^8C(O)NR^8R^9$, —$(CR^aR^b)_nS(O_2)NR^8R^9$, —$(CR^aR^b)_nS(O_2)NR^8C(O)R^9$, —$(CR^aR^b)_n NR^8S(O_2)R^9$, —$(CR^aR^b)_nSR^9$, —$(CR^aR^b)_nS(O_2)R^9$, $C_6$-$C_{10}$aryl, 5- to 10-membered heteroaryl, 5- to 10-membered heterocyclenyl, 5- to 10-membered heterocyclyl, $C_6$-$C_{10}$arylalkyl, 5- to 10-membered heteroarylalkyl, 5- to 10-membered heterocyclenylalkyl and 5- to 10-membered heterocyclylalkyl wherein each of said alkyl, cycloalkyl, aryl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to five moieties, which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —O-halo$C_1$-$C_6$alkyl, —$OR^9$, —$C(O)R^9$, —$NR^8R^9$, —$C(O)O$—$C_1$-$C_6$alkyl, —$C(O)NR^8R^9$, —$NR^8C(O)R^9$, —$S(O_2)NR^8R^9$, —$NR^8S(O_2)R^9$, —$SR^9$, and —$S(O_2)R^9$;

$R^6$ is selected from the group consisting of H, —$CHR^8R^9$, —$OR^8$, —$NR^8R^9$, —$SR^8$, —$S(O)R^8$, —$S(O_2)R^8$, —$C(O)C_1$-$C_6$alkyl, —$C(O)NR^8R^9$, —$C(O)OR^8$, —$S(O_2)NR^8R^9$, —$NR^8C(O)R^9$, —$NR^8S(O_2)R^9$, $C_1$-$C_6$alkyl, halo-$C_1$-$C_6$alkyl, $C_1$-$C_6$alkoxy, halogen, hydroxyl, amino, —CN, 5- to 10-membered heteroaryl, 5- to 10 membered heterocyclyl, $C_3$-$C_8$cycloalkyl and $C_6$-$C_{10}$aryl, wherein each of said heteroaryl, heterocyclyl, cycloalkyl and aryl can be unsubstituted or substituted with one to three moieties selected from the group consisting of $C_1$-$C_3$alkyl, $C_1$-$C_3$alkoxy, $C_1$-$C_3$alkylamino, $C_1$-$C_3$dialkylamino, amino, halo;

$R^7$ is selected from the group consisting of H, OH, $OR^8$, $C_1$-$C_6$alkyl, $C_6$-$C_{10}$aryl, $C_6$-$C_{10}$aryl$C_1$-$C_6$alkyl, 5- to 10-membered heteroaryl, 5- to 10-membered heteroaryl$C_1$-$C_6$alkyl, $C_3$-$C_8$cycloalkyl, $C_3$-$C_8$cycloalkyl$C_1$-$C_6$alkyl, 5- to 10-membered heterocyclyl, 5- to 10-membered heterocyclenyl, 5- to 10-membered heterocyclyl$C_1$-$C_6$alkyl, 5- to 10-membered heterocyclenyl$C_1$-$C_6$alkyl, $C_2$-$C_6$alkenyl, $C_2$-$C_6$alkynyl, $C_6$-$C_{10}$aryl-$S(O)C_1$-$C_6$alkyl, —$S(O_2)C_1$-$C_6$alkyl, —$C(O)C_1$-$C_6$alkyl, —$C(O)NR^8R^9$, —$C(O)OR^s$ and —$S(O_2)NR^8R^9$, wherein each of said alkyl, aryl, arylalkyl, heteroaryl, heteroarylalkyl, cycloalkyl, cycloalkylalkyl, heterocyclyl, heterocyclylalkyl, heterocyclenyl, heterocyclenylalkyl, alkenyl and alkynyl can be unsubstituted or substituted with one to three moieties, which can be the same or different, each moiety being selected from the group consisting of halogen, $C_1$-$C_6$alkyl, $C_3$-$C_8$cycloalkyl, —$CF_3$, —CN, —$(CR^aR^b)_nC(O)OH$, —$OCF_3$, —$OR^9$, —$C(O)R^9$, —$NR^8R^9$, —$C(O)O$—$C_1$-$C_6$alkyl, —$C(O)NR^8R^9$, —$SR^9$, and —$S(O_2)R^9$;

$R^8$ and $R^9$ are independently selected from the group consisting of H, OH, $C_1$-$C_6$alkyl, $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl, and said alkyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, $C_1$-$C_6$alkyl, $C_3$-$C_8$cycloalkyl, —$CF_3$, —CN, —$(CR^aR^b)_nC(O)OH$, —$OCF_3$, —$OR^a$, —C(O), amino, —$C(O)O$—$C_1$-$C_6$alkyl, —$C(O)NR^aR^b$, —$SR^a$, and —$S(O_2)R^a$; or $R^8$ and $R^9$ together with the nitrogen atom to which they are attached form a 3- to 6-membered heterocyclyl ring;

$R^{10}$ and $R^{11}$ are independently selected from the group consisting of H, $C_1$-$C_3$alkyl, halo, hydroxyl, $C_1$-$C_3$alkoxy, amino, $C_1$-$C_3$alkylamino and $C_1$-$C_3$dialkylamino;

n is independently 0, 1, 2, 3 or 4;

m is independently 0, 1, 2, 3 or 4;

q is independently 0, 1, 2, 3 or 4;

Or a pharmaceutically acceptable salt thereof.

In one embodiment, $M^1$ and $M^2$ are independently selected from the group consisting of CN, —$(CR^aR^b)_nOR^1$, —$(CR^aR^b)_nNR^1R^2$, —$(CR^aR^b)_nR^1$, —$(CR^aR^b)_nSR^1$, —$(CR^aR^b)_nS(O)_2R^1$, —$(CR^aR^b)_nS(O)R^1$, —$(CR^aR^b)_nS(O)_2NR^1R^2$, —$(CR^aR^b)_nNR^1S(O)_2R^4$, —$(CR^aR^b)_nC(O)NR^1S(O)_2R^2$, —$(CR^aR^b)_nC(O)R^1$, —$(CR^aR^b)_nC(O)OR^1$, —$(CR^aR^b)_nC(O)NR^1R^2$, —$(CR^aR^b)_nC(=NR^4)NR^1R^2$, —$(CR^aR^b)_nNR^1C(O)R^4$, —$(CR^aR^b)_nNR^1C(O)OR^4$, —$(CR^aR^b)_nNR^4C(O)NR^1R^2$, —$(CR^aR^b)_nOR^1$ and —$(CR^aR^b)_nO(CR^cR^d)_qOR^4$;

L, T and Z are not present, or

L and Z are bonded to any two carbons of the ring which are not attached to $M^1$ and $M^2$ and are both $CH_2$, and T is not present;

$R^a$, $R^b$, $R^c$ and $R^d$ are independently selected from H and $C_1$-$C_6$ alkyl;

$R^1$, $R^2$ and $R^4$ are independently selected from H, OH, halogen, —$(CR^aR^b)_nO(CR^cR^d)_qR^8$, $C_1$-$C_6$alkyl, $C_3$-$C_8$cycloalkyl, $C_3$-$C_8$cycloalkyl$C_1$-$C_6$alkyl, $C_6$-$C_{10}$aryl$C_1$-$C_6$alkyl, $C_6$-$C_{10}$aryl, 5- to 10-membered heteroaryl$C_1$-$C_6$alkyl, 5- to 10-membered heteroaryl, 5- to 10-membered heterocyclyl$C_1$-$C_6$alkyl, 5- to 10-membered heterocyclyl, 5- to 10-membered heterocyclenyl$C_1$-$C_6$alkyl and 5- to 10-membered heterocyclenyl, wherein the alkyl, cycloalkyl, cycloalkylalkyl, arylalkyl, aryl, heteroarylalkyl, heteroaryl, heterocyclylalkyl, heterocyclyl, heterocyclenylalkyl or heterocyclenyl is unsubstituted or substituted with one to three moieties which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —$OR^a$, —$C(O)R^a$, —$NR^aR^b$, —C(O)O-alkyl, —$C(O)NR^aR^b$, —$NR^aC(O)R^b$, —$S(O_2)NR^aR^b$, —$NR^aS(O_2)R^b$, —$SR^a$, —$S(O_2)R^a$, $C_6$-$C_{10}$aryl, 5- to 10-membered heteroaryl, 5- to 10-membered heterocyclenyl and 5- to 10-membered heterocyclyl;

$R^3$ is selected from the group consisting of $C_6$-$C_{10}$aryl, 5- to 10-membered heteroaryl, wherein each of said aryl or heteroaryl is unsubstituted or substituted with one to three moieties which can be the same or different, each moiety being selected from the group consisting of halogen, $C_1$-$C_6$alkyl, $C_6$-$C_{10}$aryl, 5- to 10-membered heteroaryl, —$CF_3$, —CN, —C(O)OH, —$(CR^aR^b)_nC(O)OH$, —$OCF_3$, —O-halo$C_1$-$C_6$alkyl, —$OR^8$, —$C(O)R^8$, —$NR^8R^9$, —C(O)O—$C_1$-$C_6$alkyl, —$C(O)NR^8R^9$, —$NR^8C(O)R^9$, —$S(O_2)NR^8R^9$, —$NR^8S(O_2)R^9$, —$SR^8$, and —$S(O_2)R^8$, wherein each of said heteroaryl or aryl is unsubstituted or substituted with one to three moieties, which can be the same or different, each moiety being selected from the group consisting of halogen, $C_1$-$C_6$alkyl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$;

$R^6$ is selected from the group consisting of H, —$CHR^aR^b$, —$OR^a$, —$NR^aR^b$, —$SR^a$, —$S(O)R^a$, —$S(O_2)R^a$, —$C(O)C_1$-$C_6$alkyl, —$C(O)NR^aR^b$, —$C(O)OR^a$, —$S(O_2)NR^aR^b$, —$NR^aC(O)R^b$, —$NR^aS(O_2)R^b$, $C_1$-$C_6$alkyl, $C_1$-$C_6$alkoxy, halogen, hydroxyl, amino and —CN;

$R^7$ is selected from the group consisting of H, OH, $OR^a$, $C_1$-$C_6$alkyl, $C_2$-$C_6$alkenyl, $C_2$-$C_6$alkynyl, —$S(O_2)C_1$-$C_6$alkyl, —$C(O)C_1$-$C_6$alkyl, —$C(O)NR^aR^b$, —$C(O)OR^a$ and —$S(O_2)NR^aR^b$, wherein each of said alkyl, alkenyl, alkynyl can be unsubstituted or substituted with one to three moieties, which can be the same or different, each moiety being selected from the group consisting of halogen, —$CF_3$, —CN, —$(CR^aR^b)_nC(O)OH$, —$OCF_3$, —OH, amino, —$C(O)R^a$, —$NR^aR^b$, —C(O)O—$C_1$-$C_6$alkyl, —$C(O)NR^aR^b$, —$SR^a$, and —$S(O_2)R^a$;

$R^8$ and $R^9$ are independently selected from the group consisting of H, OH, $C_1$-$C_6$alkyl, $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl, and said alkyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, $C_1$-$C_6$alkyl, $C_3$-$C_8$cycloalkyl, —$CF_3$, —CN, —$(CR^aR^b)_nC(O)OH$, —$OCF_3$, —$OR^a$, —C(O), amino, —C(O)O—$C_1$-$C_6$alkyl, —$C(O)NR^aR^b$, —$SR^a$, and —$S(O_2)R^a$;

n is independently 0, 1 or 2;

m is 1;

q is independently 0, 1, or 2;

Or a pharmaceutically acceptable salt thereof.

In another embodiment, the compounds of the invention are under the following Formula:

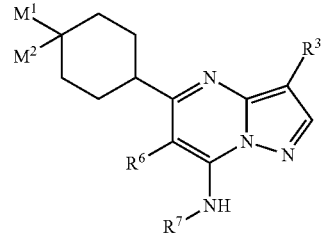

$M^1$ and $M^2$ are independently selected from the group consisting of CN, —$(CR^aR^b)_nOR^1$, —$(CR^aR^b)_nNR^1R^2$, —$(CR^aR^b)_nR^1$, —$(CR^aR^b)_nSR^1$, —$(CR^aR^b)_nS(O)_2R^1$, —$(CR^aR^b)_nS(O)R^1$, —$(CR^aR^b)_nS(O)_2NR^1R^2$, —$(CR^aR^b)_nNR^1S(O)_2R^4$, —$(CR^aR^b)_nC(O)NR^1S(O)_2R^2$, —$(CR^aR^b)_nC(O)R^1$, —$(CR^aR^b)_nC(O)OR^1$, —$(CR^aR^b)_nC(O)NR^1R^2$, —$(CR^aR^b)_nC(=NR^4)NR^1R^2$, —$(CR^aR^b)_nNR^1C(O)R^4$, —$(CR^aR^b)_nNR^1C(O)OR^4$, —$(CR^aR^b)_nNR^4C(O)NR^1R^2$, —$(CR^aR^b)_nOR^1$ and —$(CR^aR^b)_nO(CR^cR^d)_qOR^4$;

$R^a$, $R^b$, $R^c$ and $R^d$ are independently selected from H and $C_1$-$C_3$ alkyl;

$R^1$, $R^2$ and $R^4$ are independently selected from H, OH, $NH_2$, —$(CR^aR^b)_nO(CR^cR^d)_qR^8$, $C_1$-$C_3$alkyl, 5- to 10-membered heteroaryl$C_1$-$C_6$alkyl, 5- to 10-membered heteroaryl, 5- to 10-membered heterocyclyl$C_1$-$C_6$alkyl, 5- to 10-membered heterocyclyl, 5- to 10-membered heterocyclenyl$C_1$-$C_6$alkyl and 5- to 10-membered heterocyclenyl, wherein the alkyl, heteroarylalkyl, heteroaryl, heterocyclylalkyl, heterocyclyl, heterocyclenylalkyl or heterocyclenyl is unsubstituted or substituted with one to three moieties which can be the same or different, each moiety being selected from the group consisting of halogen, $C_1$-$C_6$alkyl, —$CF_3$, —CN, —C(O)OH, —$(CR^aR^b)_nC(O)OH$, —$OCF_3$, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$ and —$S(O_2)R^a$;

wherein all other substituents are as defined above.

In another embodiment, $M^1$ is —$(CR^aR^b)_nO(CR^cR^d)_qOC_1$-$C_3$alkyl, —$(CR^aR^b)_nO(CR^cR^d)_qOH$, COOH, or —$(CR^aR^b)_nC(O)OC_1$-$C_3$alkyl;

$M^2$ is selected from the group consisting of CN, —$(CR^aR^b)_nOR^1$, —$(CR^aR^b)_nNR^1R^2$, —$(CR^aR^b)_nR^1$, —$(CR^aR^b)_nSR^1$, —$(CR^aR^b)_nS(O)_2R^1$, —$(CR^aR^b)_nS(O)R^1$, —$(CR^aR^b)_nS(O)_2NR^1R^2$, —$(CR^aR^b)_nNR^1S(O)_2R^4$, —$(CR^aR^b)_nC(O)NR^1S(O)_2R^2$, —$(CR^aR^b)_nC(O)R^1$, —$(CR^aR^b)_nC(O)OR^1$, —$(CR^aR^b)_nC(O)NR^1R^2$, —$(CR^aR^b)_nC(=NR^4)NR^1R^2$, —$(CR^aR^b)_nNR^1C(O)R^4$, —$(CR^aR^b)_nNR^1C(O)OR^4$, —$(CR^aR^b)_nNR^4C(O)NR^1R^2$, —$(CR^aR^b)_nOR^1$ and —$(CR^aR^b)_nO(CR^cR^d)_qOR^4$;

Wherein all other substituents are as defined above.

In a further embodiment, $M^1$ and $M^2$ are independently selected from the group consisting of halo, —$OCH_2CH_2OCH_3$, —$OCH_2CH_2OH$, —$OCH_3$, —$SCH_3$, —OH, —C(O)OH, —$C(O)NHOCH_3$, —C(O)NHOH, —$C(O)NHCH_2CH_2OH$, —$CONH_2$ and —$CH_3$ and all other substituents are as defined above.

In yet a further embodiment, $M^1$ and $M^2$ are independently selected from the group consisting of halo, CN, $NH_2$, —$OCH_3$, —$CH_2OCH_3$, —$SCH_3$, —OH, —$CH_2OH$, —$CH_2CH_2OH$, —C(O)OH, —$C(O)CH_2OH$, —$OCH_2CH_2OCH_3$, —$OCH_2CH_2OH$, —$C(O)N(CH_3)_2$, —$CONH_2$, C(=NH)$NH_2$, C(O)NH—$NH_2$, —$CONHCH_3$, —$C(O)NHOCH_3$, —$C(O)N(CH_3)OCH_3$, —C(O)NHOH, —$C(O)NHCH_2CH_2OH$, —$CH_3$, —$SO_2CH_3$, —$CH_2SO_2CH_3$, —$CH_2NHSO_2CH_3$, —$C(O)NHS(O)_2CH_3$, —OCH₂CH₂-morpholinyl, triazolyl, tetrazolyl, oxadiazolyl, wherein said triazolyl, tetrazolyl or oxadiazolyl are optionally substituted with methyl or halo; and all other substituents are as defined above.

In one embodiment, M¹ is —OCH₂CH₂OCH₃, and M² is selected from the group consisting of halo, CN, —OCH₃, —SCH₃, —OH, —CH₂OH, —C(O)OH, —C(O)CH₂OH, —C(O)N(CH₃)₂, —CONH₂, C(=NH)NH₂, C(O)NH—NH₂, —CONHCH₃, —C(O)NHOCH₃, —C(O)NHS(O)₂CH₃, —C(O)N(CH₃)OCH₃, —C(O)NHOH, —C(O)NHCH₂CH₂OH, —CH₃, triazolyl, tetrazolyl, oxadiazolyl, wherein said triazolyl, tetrazolyl or oxadiazolyl are optionally substituted with methyl or halo; and all other substituents are as defined above.

In another embodiment,

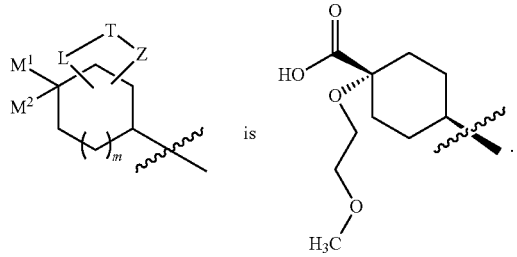

In a further embodiment,

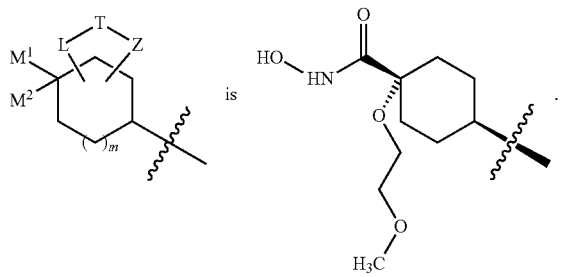

In yet a further embodiment,

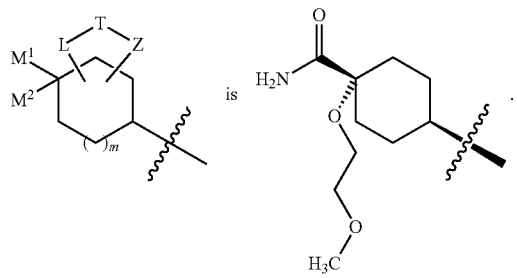

In another embodiment,

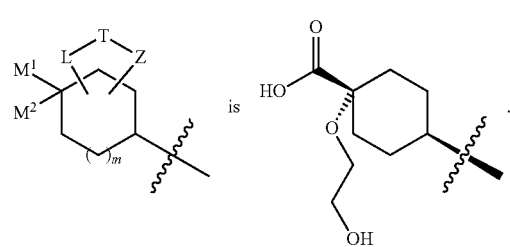

In a further embodiment,

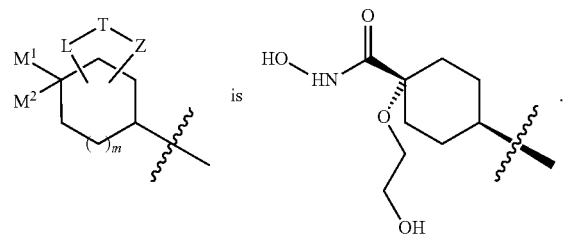

In yet a further embodiment,

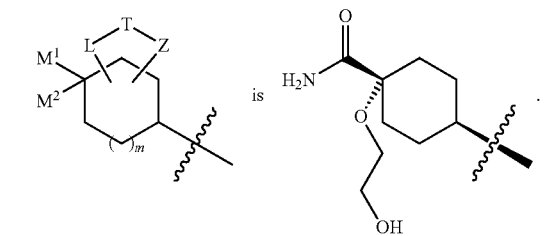

In one embodiment, M¹ is —OCH₂CH₂OCH₃, and M² is selected from the group consisting of —C(O)OH, —CONH₂ and —C(O)NHOH; and all other substituents are as defined above.

In one embodiment, M¹ is —OCH₂CH₂OCH₃, —OCH₂CH₂OH, —OH, —CH₂OH or —CH₂CH₂OH, and M² is selected from the group consisting of halo, CN, —OCH₃, —CH₂OCH₃, —SCH₃, —OCH₂CH₂OCH₃, —OH, —CH₂OH, —CH₂CH₂OH, —C(O)OH, —C(O)CH₂OH, —C(O)N(CH₃)₂, —CONH₂, C(=NH)NH₂, C(O)NH—NH₂, —CONHCH₃, —C(O)NHOCH₃, —C(O)N(CH₃)OCH₃, —C(O)NHOH, —C(O)NHCH₂CH₂OH, —CH₃, —CH₂SO₂CH₃, CH₂NHSO₂CH₃, —C(O)NHS(O)₂CH₃, triazolyl, tetrazolyl, oxadiazolyl, wherein said triazolyl, tetrazolyl or oxadiazolyl are optionally substituted with methyl or halo; and all other substituents are as defined above.

In one embodiment, M¹ is —OH, —CH₂OH or —CH₂CH₂OH, and M² is selected from the group consisting of halo, CN, —OCH₃, —CH₂OCH₃, —SCH₃, —OCH₂CH₂OCH₃, —OH, —CH₂OH, —CH₂CH₂OH, —C(O)OH, —C(O)CH₂OH, —C(O)N(CH₃)₂, —CONH₂, —CONHCH₃, —C(O)NHOCH₃, —C(O)N(CH₃)OCH₃, —C(O)NHOH, —C(O)NHCH₂CH₂OH, —CH₃, —CH₂SO₂CH₃, CH₂NHSO₂CH₃, triazolyl, and oxadiazolyl, wherein said triazolyl, or oxadiazolyl are optionally substituted with methyl or halo; and all other substituents are as defined above.

In another embodiment, M¹ is —OH, —CH₂OH or —CH₂CH₂OH, and M² is selected from the group consisting of CN, —OCH₃, —CH₂OCH₃, —SCH₃, —OCH₂CH₂OCH₃, —OH, —CH₂OH, —CH₂CH₂OH, —C(O)OH, —C(O)CH₂OH, —CH₃, —CH₂SO₂CH₃, CH₂NHSO₂CH₃; and all other substituents are as defined above.

In one embodiment, M¹ is —C(O)OH, and M² is selected from the group consisting of halo, CN, NH₂, —OCH₃, —CH₂OCH₃, —SCH₃, —OCH₂CH₂OCH₃, —OH, —CH₂OH, —CH₂CH₂OH, —C(O)OH, —C(O)CH₂OH, —C(O)N(CH₃)₂, —CONH₂, —CONHCH₃, —C(O)NHOCH₃, —C(O)N(CH₃)OCH₃, —C(O)NHOH, —C(O)NHCH₂CH₂OH, —CH₃, —SO₂CH₃, —CH₂SO₂CH₃, CH₂NHSO₂CH₃, —OCH₂CH₂-morpholinyl, triazolyl and oxadiazolyl, wherein said triazolyl or oxadiazolyl are optionally substituted with methyl or halo; and all other substituents are as defined above.

In another embodiment, $M^1$ is —C(O)OH, and $M^2$ is selected from the group consisting of halo, CN, $NH_2$, —$OCH_3$, —$SCH_3$, —$CH_3$, —$SO_2CH_3$, —$OCH_2CH_2$-morpholinyl; and all other substituents are as defined above.

In a further embodiment, $R^3$ is a 5- to 6-membered heteroaryl or phenyl unsubstituted or substituted with one to three moieties, which can be the same or different, each moiety being selected from the group consisting of halogen, $C_1$-$C_6$alkyl, phenyl, 5- to 6-membered heteroaryl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$, wherein the alkyl, phenyl or heteroaryl is optionally substituted with one to three moieties, which can be the same or different, each moiety being selected from the group consisting of halogen, $C_1$-$C_6$alkyl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$; and all other substituents are as defined above.

In one embodiment, $R^3$ is pyrazolyl, isoquinolinyl, pyrimidinyl, phenyl or pyridyl, unsubstituted or substituted with one to three moieties as defined above.

In one embodiment, $R^3$ is unsubstituted or substituted pyrazolyl or pyridyl as defined above.

In another embodiment, $R^3$ is

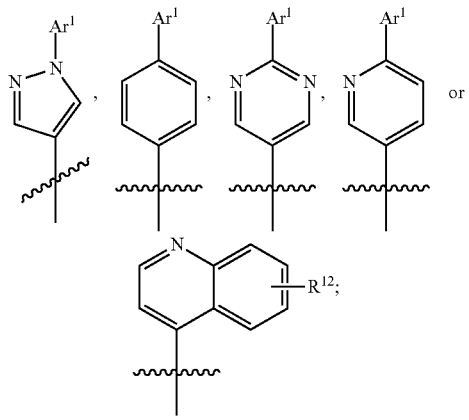

$Ar^1$ is $C_6$-$C_{10}$aryl or a 5- to 10-membered heteroaryl optionally substituted with one to three of $R^{12}$, which can be the same or different, each $R^{12}$ being selected from the group consisting of halogen, $C_1$-$C_6$alkyl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$. In one embodiment, $Ar^1$ is phenyl or a 5- to 6-membered heteroaryl optionally substituted.

In a another embodiment, $R^3$ is

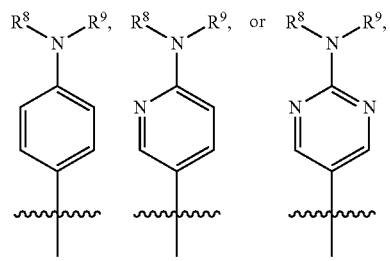

wherein $R^8$ and $R^9$ are as defined above. In one embodiment, $R^8$ is H and $R^9$ is cyclopropyl.

In a further embodiment, $Ar^1$ is phenyl, pyrazolyl, pyrimidinyl, pyridyl, imidazolyl, pyrazinyl or thiazolyl optionally substituted with one to three of $R^{12}$. In a another embodiment, $Ar^1$ is phenyl, pyridyl or imidazolyl optionally substituted with one to three of $R^{12}$.

In another embodiment, $R^3$ is

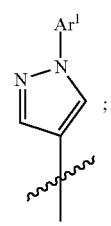

$Ar^1$ is phenyl, pyridyl, pyrazinyl or imidazolyl optionally substituted with one to three of $R^{12}$ as defined above.

In another embodiment, $R^3$ is

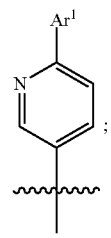

$Ar^1$ is phenyl, pyridyl, pyrazinyl or imidazolyl optionally substituted with one to three of $R^{12}$ as defined above.

In another embodiment, $R^3$ is selected from the group consisting of

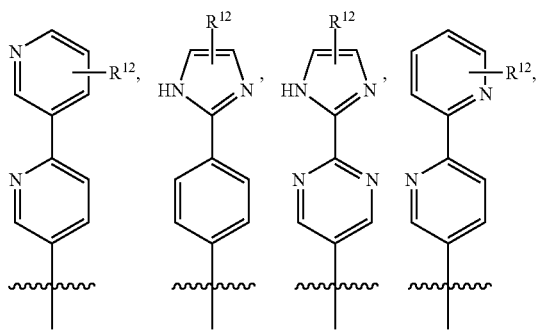

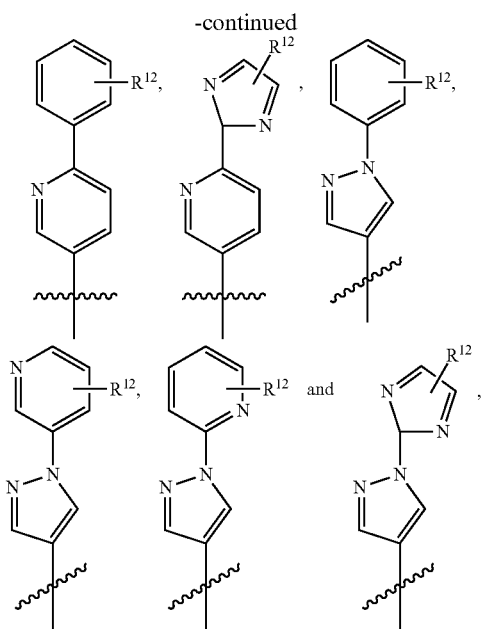

and $R^{12}$ is defined above.

In one embodiment, in the foregoing embodiments, $R^{12}$ is selected from the group consisting of halogen, $C_1$-$C_6$alkyl, —$CF_3$, and —$OCF_3$. In another embodiment, $R^{12}$ is selected from the group consisting of F and methyl.

In one embodiment,
$R^6$ is selected from the group consisting of halo, —C(O)$C_1$-$C_6$alkyl, —S(O)$_2$$C_1$-$C_6$alkyl and CN;
$R^7$ is H; and all other substituents are as defined above.

Specific embodiments depicting non-limiting Examples of the above Formulas are provided in the Experimental Section hereinbelow.

Specific examples of the compounds of the instant invention include:

(1R,4R)-4-(7-amino-6-bromo-3-(6-phenylpyridin-3-yl)pyrazolo[1,5-a]pyrimidin-5-yl)-1-methylcyclohexanecarboxylic acid;

(1S,4S)-4-(7-amino-6-bromo-3-(6-phenylpyridin-3-yl)pyrazolo[1,5-a]pyrimidin-5-yl)-1-methylcyclohexanecarboxylic acid;

(1S,4S)-4-(7-amino-6-bromo-3-(6-phenylpyridin-3-yl)pyrazolo[1,5-a]pyrimidin-5-yl)-1-fluorocyclohexanecarboxylic acid;

(1R,4R)-4-(7-amino-6-bromo-3-(6-phenylpyridin-3-yl)pyrazolo[1,5-a]pyrimidin-5-yl)-1-fluorocyclohexanecarboxylic acid;

4-(7-amino-6-bromo-3-(6-phenylpyridin-3-yl)pyrazolo[1,5-a]pyrimidin-5-yl)-1-(methoxymethyl)cyclohexanecarboxylic acid;

4-(7-amino-6-bromo-3-(1-phenyl-1H-pyrazol-4-yl)pyrazolo[1,5-a]pyrimidin-5-yl)-1-(methoxymethyl)cyclohexanecarboxylic acid;

(1R,4R)-4-(7-amino-6-bromo-3-(6-fluoroquinolin-3-yl)pyrazolo[1,5-a]pyrimidin-5-yl)-1-(methoxymethyl)cyclohexanecarboxylic acid;

(1S,4S)-4-(7-amino-6-bromo-3-(6-fluoroquinolin-3-yl)pyrazolo[1,5-a]pyrimidin-5-yl)-1-(methoxymethyl)cyclohexanecarboxylic acid;

(1S,4S)-4-(7-amino-6-bromo-3-(1-phenyl-1H-pyrazol-4-yl)pyrazolo[1,5-a]pyrimidin-5-yl)-1-(methylthio)cyclohexanecarboxylic acid;

(1R,4R)-4-(7-amino-6-bromo-3-(1-phenyl-1H-pyrazol-4-yl)pyrazolo[1,5-a]pyrimidin-5-yl)-1-(methylthio)cyclohexanecarboxylic acid;

(1R,4R)-4-(7-amino-6-bromo-3-(6-phenylpyridin-3-yl)pyrazolo[1,5-a]pyrimidin-5-yl)-1-((2-methoxyethoxy)methyl)cyclohexanecarboxylic acid;

(1S,4S)-4-(7-amino-6-bromo-3-(6-phenylpyridin-3-yl)pyrazolo[1,5-a]pyrimidin-5-yl)-1-((2-methoxyethoxy)methyl)cyclohexanecarboxylic acid;

(1R,4R)-4-(7-amino-6-bromo-3-(1-phenyl-1H-pyrazol-4-yl)pyrazolo[1,5-a]pyrimidin-5-yl)-1-((2-methoxyethoxy)methyl)cyclohexanecarboxylic acid;

(1S,4S)-4-(7-amino-6-bromo-3-(1-phenyl-1H-pyrazol-4-yl)pyrazolo[1,5-a]pyrimidin-5-yl)-1-((2-methoxyethoxy)methyl)cyclohexanecarboxylic acid;

(1R,4R)-4-(6-acetyl-7-amino-3-(6-phenylpyridin-3-yl)pyrazolo[1,5-a]pyrimidin-5-yl)-1-methylcyclohexanecarboxylic acid;

(1S,4S)-4-(6-acetyl-7-amino-3-(6-phenylpyridin-3-yl)pyrazolo[1,5-a]pyrimidin-5-yl)-1-fluorocyclohexanecarboxylic acid;

(1R,4R)-4-(6-acetyl-7-amino-3-(6-phenylpyridin-3-yl)pyrazolo[1,5-a]pyrimidin-5-yl)-1-fluorocyclohexanecarboxylic acid;

(1R,4R)-4-(6-acetyl-7-amino-3-(6-phenylpyridin-3-yl)pyrazolo[1,5-a]pyrimidin-5-yl)-1-(methoxymethyl)cyclohexanecarboxylic acid;

(1S,4S)-4-(6-acetyl-7-amino-3-(6-phenylpyridin-3-yl)pyrazolo[1,5-a]pyrimidin-5-yl)-1-(methoxymethyl)cyclohexanecarboxylic acid;

(1R,4R)-4-(6-acetyl-7-amino-3-(1-phenyl-1H-pyrazol-4-yl)pyrazolo[1,5-a]pyrimidin-5-yl)-1-(methoxymethyl)cyclohexanecarboxylic acid;

(1S,4S)-4-(6-acetyl-7-amino-3-(1-phenyl-1H-pyrazol-4-yl)pyrazolo[1,5-a]pyrimidin-5-yl)-1-(methoxymethyl)cyclohexanecarboxylic acid;

(1R,4R)-4-(6-acetyl-7-amino-3-(6-fluoroquinolin-3-yl)pyrazolo[1,5-a]pyrimidin-5-yl)-1-(methoxymethyl)cyclohexanecarboxylic acid;

(1S,4S)-4-(6-acetyl-7-amino-3-(6-fluoroquinolin-3-yl)pyrazolo[1,5-a]pyrimidin-5-yl)-1-(methoxymethyl)cyclohexanecarboxylic acid;

4-(6-acetyl-7-amino-3-(6-phenylpyridin-3-yl)pyrazolo[1,5-a]pyrimidin-5-yl)-1-((2-methoxyethoxy)methyl)cyclohexanecarboxylic acid;

(1R,4R)-4-(7-amino-6-cyano-3-(6-phenylpyridin-3-yl)pyrazolo[1,5-a]pyrimidin-5-yl)-1-methylcyclohexanecarboxylic acid;

(1S,4S)-4-(7-amino-6-cyano-3-(6-phenylpyridin-3-yl)pyrazolo[1,5-a]pyrimidin-5-yl)-1-methylcyclohexanecarboxylic acid;

4-(7-amino-6-bromo-3-(1-phenyl-1H-pyrazol-4-yl)pyrazolo[1,5-a]pyrimidin-5-yl)-1-(methylsulfonyl)cyclohexanecarboxylic acid;

(1S,4S)-4-(7-amino-6-bromo-3-(6-phenylpyridin-3-yl)pyrazolo[1,5-a]pyrimidin-5-yl)-1-methoxycyclohexanecarboxylic acid;

(1R,4R)-4-(7-amino-6-bromo-3-(6-phenylpyridin-3-yl)pyrazolo[1,5-a]pyrimidin-5-yl)-1-methoxycyclohexanecarboxylic acid;

(1R,4R)-4-(7-amino-6-bromo-3-(1-phenyl-1H-pyrazol-4-yl)pyrazolo[1,5-a]pyrimidin-5-yl)-1-methoxycyclohexanecarboxylic acid;

(1S,4S)-4-(7-amino-6-bromo-3-(1-phenyl-1H-pyrazol-4-yl)pyrazolo[1,5-a]pyrimidin-5-yl)-1-methoxycyclohexanecarboxylic acid;

(1S,4S)-4-(7-amino-6-bromo-3-(6-fluoroquinolin-3-yl)
   pyrazolo[1,5-a]pyrimidin-5-yl)-1-methoxycyclohexan-
   ecarboxylic acid;
(1R,4R)-4-(7-amino-6-bromo-3-(6-fluoroquinolin-3-yl)
   pyrazolo[1,5-a]pyrimidin-5-yl)-1-methoxycyclohexan-
   ecarboxylic acid;
(1S,4S)-4-(6-acetyl-7-amino-3-(6-phenylpyridin-3-yl)pyra-
   zolo[1,5-a]pyrimidin-5-yl)-1-methoxycyclohexanecar-
   boxylic acid;
(1R,4R)-4-(6-acetyl-7-amino-3-(6-phenylpyridin-3-yl)pyra-
   zolo[1,5-a]pyrimidin-5-yl)-1-methoxycyclohexanecar-
   boxylic acid;
(1R,4R)-4-(6-acetyl-7-amino-3-(1-phenyl-1H-pyrazol-4-
   yl)pyrazolo[1,5-a]pyrimidin-5-yl)-1-methoxycyclohexan-
   ecarboxylic acid;
(1S,4S)-4-(6-acetyl-7-amino-3-(1-phenyl-1H-pyrazol-4-yl)
   pyrazolo[1,5-a]pyrimidin-5-yl)-1-methoxycyclohexan-
   ecarboxylic acid;
(1S,4S)-4-(6-acetyl-7-amino-3-(6-fluoroquinolin-3-yl)pyra-
   zolo[1,5-a]pyrimidin-5-yl)-1-methoxycyclohexanecar-
   boxylic acid;
(1R,4R)-4-(6-acetyl-7-amino-3-(6-fluoroquinolin-3-yl)
   pyrazolo[1,5-a]pyrimidin-5-yl)-1-methoxycyclohexan-
   ecarboxylic acid;
(1R,4R)-4-(7-amino-6-(methylsulfonyl)-3-(1-phenyl-1H-
   pyrazol-4-yl)pyrazolo[1,5-a]pyrimidin-5-yl)-1-(2-meth-
   oxyethoxy)cyclohexanecarboxylic acid;
(1S,4S)-4-(7-amino-6-(methylsulfonyl)-3-(1-phenyl-1H-
   pyrazol-4-yl)pyrazolo[1,5-a]pyrimidin-5-yl)-1-(2-meth-
   oxyethoxy)cyclohexanecarboxylic acid;
(1R,4R)-4-(7-amino-3-(6-(1-methyl-1H-pyrazol-3-yl)pyri-
   din-3-yl)-6-(methylsulfonyl)pyrazolo[1,5-a]pyrimidin-5-
   yl)-1-(2-methoxyethoxy)cyclohexanecarboxylic acid;
(1R,4R)-4-(7-amino-3-(1-(4-fluorophenyl)-1H-pyrazol-4-
   yl)-6-(methylsulfonyl)pyrazolo[1,5-a]pyrimidin-5-yl)-1-
   (2-methoxyethoxy)cyclohexanecarboxylic acid;
(1R,4R)-4-(7-amino-6-(methylsulfonyl)-3-(6-phenylpyri-
   din-3-yl)pyrazolo[1,5-a]pyrimidin-5-yl)-1-(2-methoxy-
   ethoxy)cyclohexanecarboxylic acid;
5-(7-amino-5-((1R,4R)-4-carboxy-4-(2-methoxyethoxy)cy-
   clohexyl)-6-(methylsulfonyl)pyrazolo[1,5-a]pyrimidin-3-
   yl)-2-(1-methyl-1H-pyrazol-3-yl)pyridine 1-oxide;
(1R,4R)-4-(7-amino-6-(methylsulfonyl)-3-(2-phenylpyrimi-
   din-5-yl)pyrazolo[1,5-a]pyrimidin-5-yl)-1-(2-methoxy-
   ethoxy)cyclohexanecarboxylic acid;
(1R,4R)-4-(7-amino-6-(methylsulfonyl)-3-(6-(thiazol-2-yl)
   pyridin-3-yl)pyrazolo[1,5-a]pyrimidin-5-yl)-1-(2-meth-
   oxyethoxy)cyclohexanecarboxylic acid;
(1R,4R)-4-(7-amino-3-(6-(3-fluoro-4-hydroxyphenyl)pyri-
   din-3-yl)-6-(methylsulfonyl)pyrazolo[1,5-a]pyrimidin-5-
   yl)-1-(2-methoxyethoxy)cyclohexanecarboxylic acid;
(1R,4R)-4-(7-amino-3-(2-(1-methyl-1H-pyrazol-3-yl)pyri-
   midin-5-yl)-6-(methylsulfonyl)pyrazolo[1,5-a]pyrimidin-
   5-yl)-1-(2-methoxyethoxy)cyclohexanecarboxylic acid;
(1R,4R)-4-(3-(2,2'-bipyridin-5-yl)-7-amino-6-(methylsulfo-
   nyl)pyrazolo[1,5-a]pyrimidin-5-yl)-1-(2-methoxyethoxy)
   cyclohexanecarboxylic acid;
(1R,4R)-4-(7-amino-6-(methylsulfonyl)-3-(2-(5-methylthi-
   azol-2-yl)pyrimidin-5-yl)pyrazolo[1,5-a]pyrimidin-5-yl)-
   1-(2-methoxyethoxy)cyclohexanecarboxylic acid;
(1R,4R)-4-(7-amino-3-(6-fluoroquinolin-3-yl)-6-(methyl-
   sulfonyl)pyrazolo[1,5-a]pyrimidin-5-yl)-1-(2-methoxy-
   ethoxy)cyclohexanecarboxylic acid;
(1R,4R)-4-(7-amino-6-(methylsulfonyl)-3-(1-(4-(methyl-
   sulfonyl)phenyl)-1H-pyrazol-4-yl)pyrazolo[1,5-a]pyrimi-
   din-5-yl)-1-(2-methoxyethoxy)cyclohexanecarboxylic
   acid;
(1S,4S)-4-(6-acetyl-7-amino-3-(1-phenyl-1H-pyrazol-4-yl)
   pyrazolo[1,5-a]pyrimidin-5-yl)-1-(2-methoxyethoxy)cy-
   clohexanecarboxylic acid;
(1R,4R)-4-(6-acetyl-7-amino-3-(1-phenyl-1H-pyrazol-4-yl)
   pyrazolo[1,5-a]pyrimidin-5-yl)-1-(2-methoxyethoxy)cy-
   clohexanecarboxylic acid;
(1S,4S)-4-(6-acetyl-7-amino-3-(6-phenylpyridin-3-yl)pyra-
   zolo[1,5-a]pyrimidin-5-yl)-1-(2-methoxyethoxy)cyclo-
   hexanecarboxylic acid;
(1R,4R)-4-(6-acetyl-7-amino-3-(6-phenylpyridin-3-yl)pyra-
   zolo[1,5-a]pyrimidin-5-yl)-1-(2-methoxyethoxy)cyclo-
   hexanecarboxylic acid;
(1R,4R)-4-(6-acetyl-7-amino-3-(6-phenylpyridin-3-yl)pyra-
   zolo[1,5-a]pyrimidin-5-yl)-1-(2-morpholinoethoxy)cy-
   clohexanecarboxylic acid;
(1S,4S)-4-(6-acetyl-7-amino-3-(6-(thiazol-2-yl)pyridin-3-
   yl)pyrazolo[1,5-a]pyrimidin-5-yl)-1-(2-methoxyethoxy)
   cyclohexanecarboxylic acid;
(1R,4R)-4-(6-acetyl-7-amino-3-(6-(thiazol-2-yl)pyridin-3-
   yl)pyrazolo[1,5-a]pyrimidin-5-yl)-1-(2-methoxyethoxy)
   cyclohexanecarboxylic acid;
(1S,4S)-4-(6-acetyl-7-amino-3-(6-(thiazol-4-yl)pyridin-3-
   yl)pyrazolo[1,5-a]pyrimidin-5-yl)-1-(2-methoxyethoxy)
   cyclohexanecarboxylic acid;
(1R,4R)-4-(6-acetyl-7-amino-3-(6-(thiazol-4-yl)pyridin-3-
   yl)pyrazolo[1,5-a]pyrimidin-5-yl)-1-(2-methoxyethoxy)
   cyclohexanecarboxylic acid;
(1R,4R)-4-(7-amino-6-(methylthio)-3-(6-phenylpyridin-3-
   yl)pyrazolo[1,5-a]pyrimidin-5-yl)-1-(2-methoxyethoxy)
   cyclohexanecarboxylic acid;
(1R,4R)-4-(7-amino-6-bromo-3-(6-phenylpyridin-3-yl)
   pyrazolo[1,5-a]pyrimidin-5-yl)-1-(2-methoxyethoxy)cy-
   clohexanecarboxylic acid;
(1R,4R)-4-(7-amino-6-bromo-3-(6-phenylpyridin-3-yl)
   pyrazolo[1,5-a]pyrimidin-5-yl)-1-(2-morpholinoethoxy)
   cyclohexanecarboxylic acid;
(1S,4S)-4-(7-amino-6-bromo-3-(6-phenylpyridin-3-yl)pyra-
   zolo[1,5-a]pyrimidin-5-yl)-1-(2-morpholinoethoxy)cy-
   clohexanecarboxylic acid;
(1R,4R)-4-(7-amino-6-bromo-3-(1-phenyl-1H-pyrazol-4-
   yl)pyrazolo[1,5-a]pyrimidin-5-yl)-1-(2-morpholinoet-
   hoxy)cyclohexanecarboxylic acid;
(1R,4R)-4-(7-amino-6-bromo-3-(6-(3-fluoro-4-methox-
   yphenyl)pyridin-3-yl)pyrazolo[1,5-a]pyrimidin-5-yl)-1-
   (2-methoxyethoxy)cyclohexanecarboxylic acid;
(1R,4R)-4-(7-amino-6-cyano-3-(1-phenyl-1H-pyrazol-4-yl)
   pyrazolo[1,5-a]pyrimidin-5-yl)-1-(2-methoxyethoxy)cy-
   clohexanecarboxylic acid;
(1R,4R)-4-(6-acetyl-7-amino-3-(1-phenyl-1H-pyrazol-4-yl)
   pyrazolo[1,5-a]pyrimidin-5-yl)-1-(2-methoxyethoxy)-N-
   (methylsulfonyl)cyclohexanecarboxamide;
4-(7-amino-6-(methylsulfonyl)-3-(1-phenyl-1H-pyrazol-4-
   yl)pyrazolo[1,5-a]pyrimidin-5-yl)-1-(2-methoxyethoxy)-
   N-(methylsulfonyl)cyclohexanecarboxamide;
8-(7-amino-6-bromo-3-(6-phenylpyridin-3-yl)pyrazolo[1,5-
   a]pyrimidin-5-yl)-1,3-diazaspiro[4.5]decane-2,4-dione;
1-amino-4-(7-amino-6-bromo-3-(6-phenylpyridin-3-yl)
   pyrazolo[1,5-a]pyrimidin-5-yl)cyclohexanecarboxylic
   acid;
4-(7-amino-6-bromo-3-(6-phenylpyridin-3-yl)pyrazolo[1,5-
   a]pyrimidin-5-yl)-1-hydroxycyclohexanecarbonitrile;
4-(7-amino-6-bromo-3-(6-phenylpyridin-3-yl)pyrazolo[1,5-
   a]pyrimidin-5-yl)-1-methoxycyclohexanecarbonitrile;
2-((1R,4R)-4-(7-amino-6-bromo-3-(6-phenylpyridin-3-yl)
   pyrazolo[1,5-a]pyrimidin-5-yl)-1-hydroxycyclohexyl)
   acetic acid;

2-((1S,4S)-4-(7-amino-6-bromo-3-(6-phenylpyridin-3-yl)
pyrazolo[1,5-a]pyrimidin-5-yl)-1-hydroxycyclohexyl)
acetic acid;
2-((1S,4S)-4-(7-amino-6-bromo-3-(1-phenyl-1H-pyrazol-4-
yl)pyrazolo[1,5-a]pyrimidin-5-yl)-1-hydroxycyclohexyl)
acetic acid;
2-((1R,4R)-4-(7-amino-6-bromo-3-(1-phenyl-1H-pyrazol-
4-yl)pyrazolo[1,5-a]pyrimidin-5-yl)-1-hydroxycyclo-
hexyl)acetic acid;
2-((1S,4S)-4-(7-amino-6-bromo-3-(6-phenylpyridin-3-yl)
pyrazolo[1,5-a]pyrimidin-5-yl)-1-methoxycyclohexyl)
acetic acid;
2-((1R,4R)-4-(7-amino-6-bromo-3-(6-phenylpyridin-3-yl)
pyrazolo[1,5-a]pyrimidin-5-yl)-1-methoxycyclohexyl)
acetic acid;
(4-(7-amino-6-bromo-3-(6-phenylpyridin-3-yl)pyrazolo[1,
5-a]pyrimidin-5-yl)-1-methoxycyclohexyl)methanol;
(4-(7-amino-6-bromo-3-(1-phenyl-1H-pyrazol-4-yl)pyra-
zolo[1,5-a]pyrimidin-5-yl)-1-(2-methoxyethoxy)cyclo-
hexyl)methanol;
(4-(7-amino-6-bromo-3-(1-phenyl-1H-pyrazol-4-yl)pyra-
zolo[1,5-a]pyrimidin-5-yl)-1-(methoxymethyl)cyclo-
hexyl)methanol;
((1S,4S)-4-(7-amino-6-bromo-3-(6-phenylpyridin-3-yl)
pyrazolo[1,5-a]pyrimidin-5-yl)-1-((2-methoxyethoxy)
methyl)cyclohexyl)methanol;
((1R,4R)-4-(7-amino-6-bromo-3-(6-phenylpyridin-3-yl)
pyrazolo[1,5-a]pyrimidin-5-yl)-1-((2-methoxyethoxy)
methyl)cyclohexyl)methanol;
1-(7-amino-5-((1R,4R)-4-(hydroxymethyl)-4-methoxycy-
clohexyl)-3-(6-phenylpyridin-3-yl)pyrazolo[1,5-a]pyri-
midin-6-yl)ethanone;
1-(7-amino-5-((1S,4S)-4-(hydroxymethyl)-4-methoxycy-
clohexyl)-3-(6-phenylpyridin-3-yl)pyrazolo[1,5-a]pyri-
midin-6-yl)ethanone;
1-(7-amino-5-(4-(hydroxymethyl)-4-(2-methoxyethoxy)cy-
clohexyl)-3-(6-phenylpyridin-3-yl)pyrazolo[1,5-a]pyri-
midin-6-yl)ethanone;
1-(7-amino-5-(4-(hydroxymethyl)-4-(2-methoxyethoxy)cy-
clohexyl)-3-(1-phenyl-1H-pyrazol-4-yl)pyrazolo[1,5-a]
pyrimidin-6-yl)ethanone;
1-(7-amino-5-(4-(hydroxymethyl)-4-(methoxymethyl)cy-
clohexyl)-3-(6-phenylpyridin-3-yl)pyrazolo[1,5-a]pyri-
midin-6-yl)ethanone;
1-(7-amino-5-(4-(hydroxymethyl)-4-methoxycyclohexyl)-
3-(6'-methoxy-2,3'-bipyridin-5-yl)pyrazolo[1,5-a]pyrimi-
din-6-yl)ethanone;
1-(7-amino-5-(4,4-bis(hydroxymethyl)cyclohexyl)-3-(6-
phenylpyridin-3-yl)pyrazolo[1,5-a]pyrimidin-6-yl)etha-
none;
(1R,4R)-4-(7-amino-6-(methylsulfonyl)-3-(1-phenyl-1H-
pyrazol-4-yl)pyrazolo[1,5-a]pyrimidin-5-yl)-N-hydroxy-
1-(2-methoxyethoxy)cyclohexanecarboxamide;
(1R,4R)-4-(7-amino-6-(methylsulfonyl)-3-(1-phenyl-1H-
pyrazol-4-yl)pyrazolo[1,5-a]pyrimidin-5-yl)-N-methoxy-
1-(2-methoxyethoxy)cyclohexanecarboxamide;
(1R,4R)-4-(7-amino-6-(methylsulfonyl)-3-(1-phenyl-1H-
pyrazol-4-yl)pyrazolo[1,5-a]pyrimidin-5-yl)-1-(2-meth-
oxyethoxy)-N-methylcyclohexanecarboxamide;
(1R,4R)-4-(7-amino-6-(methylsulfonyl)-3-(1-phenyl-1H-
pyrazol-4-yl)pyrazolo[1,5-a]pyrimidin-5-yl)-1-(2-meth-
oxyethoxy)-N,N-dimethylcyclohexanecarboxamide;
(1R,4R)-4-(7-amino-6-(methylsulfonyl)-3-(1-phenyl-1H-
pyrazol-4-yl)pyrazolo[1,5-a]pyrimidin-5-yl)-N-(2-hy-
droxyethyl)-1-(2-methoxyethoxy)cyclohexanecarboxam-
ide;
(1R,4R)-4-(7-amino-6-(methylsulfonyl)-3-(1-phenyl-1H-
pyrazol-4-yl)pyrazolo[1,5-a]pyrimidin-5-yl)-1-(2-meth-
oxyethoxy)-N-(2-methoxyethyl)cyclohexanecarboxam-
ide;
1-((1R,4R)-4-(7-amino-6-(methylsulfonyl)-3-(1-phenyl-
1H-pyrazol-4-yl)pyrazolo[1,5-a]pyrimidin-5-yl)-1-(2-
methoxyethoxy)cyclohexanecarbonyl)-1H-pyrazol-3
(2H)-one;
1-((1R,4R)-4-(7-amino-6-(methylsulfonyl)-3-(1-phenyl-
1H-pyrazol-4-yl)pyrazolo[1,5-a]pyrimidin-5-yl)-1-(2-
methoxyethoxy)cyclohexanecarbonyl)pyrazolidin-3-one;
(1R,4R)-4-(7-amino-6-(methylsulfonyl)-3-(1-phenyl-1H-
pyrazol-4-yl)pyrazolo[1,5-a]pyrimidin-5-yl)-1-(2-meth-
oxyethoxy)-N-morpholinocyclohexanecarboxamide;
(1R,4R)-4-(7-amino-6-(methylsulfonyl)-3-(1-phenyl-1H-
pyrazol-4-yl)pyrazolo[1,5-a]pyrimidin-5-yl)-N-methoxy-
1-(2-methoxyethoxy)-N-methylcyclohexanecarboxam-
ide;
(1R,4R)-4-(7-amino-6-(methylsulfonyl)-3-(1-phenyl-1H-
pyrazol-4-yl)pyrazolo[1,5-a]pyrimidin-5-yl)-N-ethoxy-1-
(2-methoxyethoxy)cyclohexanecarboxamide;
(1R,4R)-4-(7-amino-6-(methylsulfonyl)-3-(1-phenyl-1H-
pyrazol-4-yl)pyrazolo[1,5-a]pyrimidin-5-yl)-N-(cyclo-
propylmethoxy)-1-(2-methoxyethoxy)cyclohexanecar-
boxamide;
(1R,R-4-(7-amino-6-(methylsulfonyl)-3-(1-phenyl-1H-
pyrazol-4-yl)pyrazolo[1,5-a]pyrimidin-5-yl)-N-(2-hy-
droxyethoxy)-1-(2-methoxyethoxy)cyclohexanecarboxa-
mide;
(1R,4R)-4-(7-amino-6-(methylsulfonyl)-3-(1-phenyl-1H-
pyrazol-4-yl)pyrazolo[1,5-a]pyrimidin-5-yl)-N,1-bis(2-
methoxyethoxy)cyclohexanecarboxamide;
(1R,4R)-4-(6-acetyl-7-amino-3-(6-phenylpyridin-3-yl)pyra-
zolo[1,5-a]pyrimidin-5-yl)-N-hydroxy-1-(2-methoxy-
ethoxy)cyclohexanecarboxamide;
(1R,4R)-4-(6-acetyl-7-amino-3-(6-phenylpyridin-3-yl)pyra-
zolo[1,5-a]pyrimidin-5-yl)-N-methoxy-1-(2-methoxy-
ethoxy)cyclohexanecarboxamide;
(1R,4R)-4-(7-amino-6-(methylsulfonyl)-3-(6-phenylpyri-
din-3-yl)pyrazolo[1,5-a]pyrimidin-5-yl)-N-hydroxy-1-(2-
methoxyethoxy)cyclohexanecarboxamide;
(1R,4R)-4-(7-amino-6-(methylsulfonyl)-3-(6-phenylpyri-
din-3-yl)pyrazolo[1,5-a]pyrimidin-5-yl)-N-methoxy-1-
(2-methoxyethoxy)cyclohexanecarboxamide;
(1R,4R)-4-(7-amino-6-(methylsulfonyl)-3-(6-phenylpyri-
din-3-yl)pyrazolo[1,5-a]pyrimidin-5-yl)-N-(cyclopropyl-
methoxy)-1-(2-methoxyethoxy)cyclohexanecarboxam-
ide;
(1R,4R)-4-(7-amino-6-(methylsulfonyl)-3-(1-phenyl-1H-
pyrazol-4-yl)pyrazolo[1,5-a]pyrimidin-5-yl)-1-(2-meth-
oxyethoxy)cyclohexanecarbohydrazide;
5-((1R,4R)-4-(7-amino-6-(methylsulfonyl)-3-(1-phenyl-
1H-pyrazol-4-yl)pyrazolo[1,5-a]pyrimidin-5-yl)-1-(2-
methoxyethoxy)cyclohexyl)-1,3,4-oxadiazol-2-amine;
5-((1R,4R)-4-(2-methoxyethoxy)-4-(5-methyl-1,3,4-oxa-
diazol-2-yl)cyclohexyl)-6-(methylsulfonyl)-3-(1-phenyl-
1H-pyrazol-4-yl)pyrazolo[1,5-a]pyrimidin-7-amine;
(1R,4R)-4-(7-amino-6-(methylsulfonyl)-3-(1-phenyl-1H-
pyrazol-4-yl)pyrazolo[1,5-a]pyrimidin-5-yl)-1-(2-meth-
oxyethoxy)cyclohexanecarboxamide;
(1R,4R)-4-(7-amino-6-(methylsulfonyl)-3-(6-phenylpyri-
din-3-yl)pyrazolo[1,5-a]pyrimidin-5-yl)-1-(2-methoxy-
ethoxy)cyclohexanecarboxamide;
(1R,4R)-4-(3-(6-(1H-imidazol-2-yl)pyridin-3-yl)-6-acetyl-
7-aminopyrazolo[1,5-a]pyrimidin-5-yl)-1-(2-methoxy-
ethoxy)cyclohexanecarboxamide;

(1S,4S)-4-(3-(6-(1H-imidazol-2-yl)pyridin-3-yl)-6-acetyl-7-aminopyrazolo[1,5-a]pyrimidin-5-yl)-1-(2-methoxyethoxy)cyclohexanecarboxamide;

(1S,4S)-4-(3-(6-(1H-imidazol-2-yl)pyridin-3-yl)-6-acetyl-7-aminopyrazolo[1,5-a]pyrimidin-5-yl)-N-hydroxy-1-(2-methoxyethoxy)cyclohexanecarboxamide;

(1R,4R)-4-(3-(6-(1H-imidazol-2-yl)pyridin-3-yl)-6-acetyl-7-aminopyrazolo[1,5-a]pyrimidin-5-yl)-N-hydroxy-1-(2-methoxyethoxy)cyclohexanecarboxamide;

(1R,4R)-4-(3-(6-(1H-imidazol-2-yl)pyridin-3-yl)-7-amino-6-(methylsulfonyl)pyrazolo[1,5-a]pyrimidin-5-yl)-N-hydroxy-1-(2-methoxyethoxy)cyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarbonitrile;

5-((1R,4R)-4-(2-methoxyethoxy)-4-(1H-tetrazol-5-yl)cyclohexyl)-6-(methylsulfonyl)-3-(1-phenyl-1H-pyrazol-4-yl)pyrazolo[1,5-a]pyrimidin-7-amine;

5-((1R,4R)-4-(2-methoxyethoxy)-4-(1H-tetrazol-5-yl)cyclohexyl)-6-(methylsulfonyl)-3-(6-phenylpyridin-3-yl)pyrazolo[1,5-a]pyrimidin-7-amine;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboximidamide;

3-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-1,2,4-oxadiazol-5(4H)-one;

((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)(4H-1,2,4-triazol-3-yl)methanone;

((1S,4S)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)(4H-1,2,4-triazol-3-yl)methanone;

((1S,4S)-4-(7-amino-6-(methylsulfonyl)-3-(6-phenylpyridin-3-yl)pyrazolo[1,5-a]pyrimidin-5-yl)-1-(2-methoxyethoxy)cyclohexyl)(4H-1,2,4-triazol-3-yl)methanone;

((1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexyl)(4H-1,2,4-triazol-3-yl)methanone;

((1R,4R)-4-(7-amino-3-(6-phenylpyridin-3-yl)pyrazolo[1,5-a]pyrimidin-5-yl)-1-(2-methoxyethoxy)cyclohexyl)(4H-1,2,4-triazol-3-yl)methanone;

5-((1R,4R)-4-(2-methoxyethoxy)-4-(4H-1,2,4-triazol-3-yl)cyclohexyl)-6-(methylsulfonyl)-3-(1-phenyl-1H-pyrazol-4-yl)pyrazolo[1,5-a]pyrimidin-7-amine;

5-((1R,4R)-4-(2-methoxyethoxy)-4-(4H-1,2,4-triazol-3-yl)cyclohexyl)-6-(methylsulfonyl)-3-(6-phenylpyridin-3-yl)pyrazolo[1,5-a]pyrimidin-7-amine;

1-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-2-hydroxyethanone;

1-((1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexyl)-2-hydroxyethanone;

4-(7-amino-6-bromo-3-(6-phenylpyridin-3-yl)pyrazolo[1,5-a]pyrimidin-5-yl)-1-hydroxycyclohexanecarboxylic acid;

4-(6-acetyl-7-amino-3-(1-phenyl-1H-pyrazol-4-yl)pyrazolo[1,5-a]pyrimidin-5-yl)-1-(hydroxymethyl)cyclohexanecarboxylic acid;

4-(6-acetyl-7-amino-3-(6-phenylpyridin-3-yl)pyrazolo[1,5-a]pyrimidin-5-yl)-1-(hydroxymethyl)cyclohexanecarboxylic acid;

4-(7-amino-6-bromo-3-(6-phenylpyridin-3-yl)pyrazolo[1,5-a]pyrimidin-5-yl)-1-(hydroxymethyl)cyclohexanol;

4-(7-amino-6-bromo-3-(1-phenyl-1H-pyrazol-4-yl)pyrazolo[1,5-a]pyrimidin-5-yl)-1-(hydroxymethyl)cyclohexanol;

4-(7-amino-6-bromo-3-(6-fluoroquinolin-3-yl)pyrazolo[1,5-a]pyrimidin-5-yl)-1-(hydroxymethyl)cyclohexanol;

(1S,4S)-4-(7-amino-6-bromo-3-(6-phenylpyridin-3-yl)pyrazolo[1,5-a]pyrimidin-5-yl)-1-(2-hydroxyethyl)cyclohexanol;

1-(7-amino-5-(4-hydroxy-4-(hydroxymethyl)cyclohexyl)-3-(6-phenylpyridin-3-yl)pyrazolo[1,5-a]pyrimidin-6-yl)ethanone;

1-(7-amino-5-((1R,4R)-4-hydroxy-4-(hydroxymethyl)cyclohexyl)-3-(6-phenylpyridin-3-yl)pyrazolo[1,5-a]pyrimidin-6-yl)ethanone;

1-(7-amino-5-((1S,4S)-4-hydroxy-4-(hydroxymethyl)cyclohexyl)-3-(6-phenylpyridin-3-yl)pyrazolo[1,5-a]pyrimidin-6-yl)ethanone;

1-(7-amino-5-(4-hydroxy-4-(hydroxymethyl)cyclohexyl)-3-(1-phenyl-1H-pyrazol-4-yl)pyrazolo[1,5-a]pyrimidin-6-yl)ethanone;

1-(7-amino-3-(6-fluoroquinolin-3-yl)-5-(4-hydroxy-4-(hydroxymethyl)cyclohexyl)pyrazolo[1,5-a]pyrimidin-6-yl)ethanone;

1-(3-(2,3'-bipyridin-5-yl)-7-amino-5-(4-hydroxy-4-(hydroxymethyl)cyclohexyl)pyrazolo[1,5-a]pyrimidin-6-yl)ethanone;

1-(7-amino-5-(4-hydroxy-4-(hydroxymethyl)cyclohexyl)-3-(6-(thiazol-4-yl)pyridin-3-yl)pyrazolo[1,5-a]pyrimidin-6-yl)ethanone;

1-(7-amino-5-(4-hydroxy-4-(hydroxymethyl)cyclohexyl)-3-(6-(1-methyl-1H-pyrazol-4-yl)pyridin-3-yl)pyrazolo[1,5-a]pyrimidin-6-yl)ethanone;

1-(7-amino-5-(4-hydroxy-4-(hydroxymethyl)cyclohexyl)-3-(6'-methoxy-2,3'-bipyridin-5-yl)pyrazolo[1,5-a]pyrimidin-6-yl)ethanone;

1-(7-amino-3-(6'-hydroxy-2,3'-bipyridin-5-yl)-5-(4-hydroxy-4-(hydroxymethyl)cyclohexyl)pyrazolo[1,5-a]pyrimidin-6-yl)ethanone;

1-(7-amino-5-((1R,4R)-4-hydroxy-4-(hydroxymethyl)cyclohexyl)-3-(1'-methyl-1'H-1,4'-bipyrazol-4-yl)pyrazolo[1,5-a]pyrimidin-6-yl)ethanone;

1-(7-amino-5-((1S,4S)-4-hydroxy-4-(hydroxymethyl)cyclohexyl)-3-(1'-methyl-1'H-1,4'-bipyrazol-4-yl)pyrazolo[1,5-a]pyrimidin-6-yl)ethanone;

methyl 3-(5-(6-acetyl-7-amino-5-(4-hydroxy-4-(hydroxymethyl)cyclohexyl)pyrazolo[1,5-a]pyrimidin-3-yl)pyridin-2-yl)benzoate;

3-(5-(6-acetyl-7-amino-5-(4-hydroxy-4-(hydroxymethyl)cyclohexyl)pyrazolo[1,5-a]pyrimidin-3-yl)pyridin-2-yl)benzoic acid;

1-(7-amino-5-(4-hydroxy-4-(hydroxymethyl)cyclohexyl)-3-(1-(thiazol-4-yl)-1H-pyrazol-4-yl)pyrazolo[1,5-a]pyrimidin-6-yl)ethanone;

methyl 5-(5-(6-acetyl-7-amino-5-((1R,4R)-4-hydroxy-4-(hydroxymethyl)cyclohexyl)pyrazolo[1,5-a]pyrimidin-3-yl)pyridin-2-yl)-2-methoxybenzoate;

methyl 5-(5-(6-acetyl-7-amino-5-((1S,4S)-4-hydroxy-4-(hydroxymethyl)cyclohexyl)pyrazolo[1,5-a]pyrimidin-3-yl)pyridin-2-yl)-2-methoxybenzoate;

5-(5-(6-acetyl-7-amino-5-(4-hydroxy-4-(hydroxymethyl)cyclohexyl)pyrazolo[1,5-a]pyrimidin-3-yl)pyridin-2-yl)-2-methoxybenzoic acid;

1-(7-amino-5-(4-hydroxy-4-(hydroxymethyl)cyclohexyl)-3-(6-(thiazol-2-yl)pyridin-3-yl)pyrazolo[1,5-a]pyrimidin-6-yl)ethanone;

1-(7-amino-5-(4-hydroxy-4-(hydroxymethyl)cyclohexyl)-3-(6-(thiazol-5-yl)pyridin-3-yl)pyrazolo[1,5-a]pyrimidin-6-yl)ethanone;

1-(7-amino-5-(4-hydroxy-4-(hydroxymethyl)cyclohexyl)-3-(2-phenylpyrimidin-5-yl)pyrazolo[1,5-a]pyrimidin-6-yl) ethanone;

1-(7-amino-5-((1S,4S)-4-hydroxy-4-(2-hydroxyethyl)cyclohexyl)-3-(6-phenylpyridin-3-yl)pyrazolo[1,5-a]pyrimidin-6-yl)ethanone;

N-((4-(6-acetyl-7-amino-3-(6-phenylpyridin-3-yl)pyrazolo[1,5-a]pyrimidin-5-yl)-1-hydroxycyclohexyl)methyl) methanesulfonamide;

1-(7-amino-5-((1R,4R)-4-hydroxy-4-(methylsulfonylmethyl)cyclohexyl)-3-(6-phenylpyridin-3-yl)pyrazolo[1,5-a]pyrimidin-6-yl)ethanone;

1-(7-amino-5-((1S,4S)-4-hydroxy-4-(methylsulfonylmethyl)cyclohexyl)-3-(6-phenylpyridin-3-yl)pyrazolo[1,5-a]pyrimidin-6-yl)ethanone;

(1R,4R)-4-(7-amino-6-bromo-3-(6-phenylpyridin-3-yl) pyrazolo[1,5-a]pyrimidin-5-yl)-1-(methoxymethyl)cyclohexanol;

(1S,4S)-4-(7-amino-6-bromo-3-(6-phenylpyridin-3-yl)pyrazolo[1,5-a]pyrimidin-5-yl)-1-(methoxymethyl)cyclohexanol;

4-(7-amino-6-bromo-3-(6-fluoroquinolin-3-yl)pyrazolo[1,5-a]pyrimidin-5-yl)-1-(methoxymethyl)cyclohexanol; and 4-(7-amino-6-(methylsulfonyl)-3-(1-phenyl-1H-pyrazol-4-yl)pyrazolo[1,5-a]pyrimidin-5-yl)-1-(hydroxymethyl)cyclohexanol;

Or a stereoisomer thereof;

Or a pharmaceutically acceptable salt thereof;

Or a pharmaceutically acceptable salt of the stereoisomer thereof.

Chemical Definitions

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on.

When used in the phrases "alkylaryl", "alkylcycloalkyl" and "alkylheterocyclyl" the term "alkyl" refers to the alkyl portion of the moiety and does not describe the number of atoms in the heterocyclyl portion of the moiety. In an embodiment, if the number of carbon atoms is not specified, the "alkyl" of "alkylaryl", "alkylcycloalkyl" and "alkylheterocyclyl" refers to $C_1$-$C_{12}$ alkyl and in a further embodiment, refers to $C_1$-$C_6$ alkyl.

The term "cycloalkyl" means a monocyclic saturated or unsaturated aliphatic hydrocarbon group having the specified number of carbon atoms. The cycloalkyl is optionally bridged (i.e., forming a bicyclic moiety), for example with a methylene, ethylene or propylene bridge. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, cyclopentenyl, cyclobutenyl and so on.

In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, CH($CH_3$) $CH_2CH(CH_3)$Ph, and so on.

"Aryl" is intended to mean any stable monocyclic, bicyclic or tricyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In one embodiment, "aryl" is an aromatic ring of 6 to 14 carbons atoms, and includes a carbocyclic aromatic group fused with a 5- or 6-membered cycloalkyl group such as indan. Examples of carbocyclic aromatic groups include, but are not limited to, phenyl, naphthyl, e.g. 1-naphthyl and 2-naphthyl; anthracenyl, e.g. 1-anthracenyl, 2-anthracenyl; phenanthrenyl; fluorenonyl, e.g. 9-fluorenonyl, indanyl and the like.

The term heteroaryl, as used herein, represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

Heteroaryl groups within the scope of this definition include but are not limited to acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. Additional examples of heteroaryl include, but are not limited to pyridyl, e.g., 2-pyridyl (also referred to as α-pyridyl), 3-pyridyl (also referred to as β-pyridyl) and 4-pyridyl (also referred to as γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g. 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g. 2-benzofuranyl and 3-benzofuranyl; dibenzofuranyl, e.g. 2,3-dihydrobenzofuranyl; dibenzothiophenyl; benzothienyl, e.g. 2-benzothienyl and 3-benzothienyl; indolyl, e.g. 2-indolyl and 3-indolyl; benzothiazolyl, e.g., 2-benzothiazolyl; benzooxazolyl, e.g., 2-benzooxazolyl; benzimidazolyl, e.g. 2-benzoimidazolyl; isoindolyl, e.g. 1-isoindolyl and 3-isoindolyl; benzotriazolyl; purinyl; thianaphthenyl, pyrazinyl and the like.

"Heterocyclyl" means a non-aromatic saturated monocyclic, bicyclic, tricyclic or spirocyclic ring system comprising up to 7 atoms in each ring. Preferably, the heterocyclyl contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. Preferred heterocyclyls contain about 5 to about 6 ring atoms. The heterocycle may be fused with an aromatic aryl group such as phenyl or heterocyclenyl. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such a moiety is pyrrolidone:

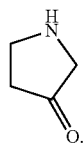

In describing the heteroatoms contained in a specified heterocyclyl group, the expression, "having one to x heteroatoms selected from the group of N, O, P and S" (wherein x is an a specified integer), for example, means that each heteroatom in the specified heterocyclyl is independently selected from the specified selection of heteroatoms. Attachment of a heterocyclyl substituent can occur via a carbon atom or via a heteroatom.

"Heterocyclenyl" means a non-aromatic monocyclic, bicyclic, tricyclic or spirocyclic ring system comprising up to 7 atoms in each ring. Preferably, the heterocyclenyl contains 3 to 14, or 5 to 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen, phosphor or sulfur atom respectively is present as a ring atom. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such a moiety is pyrrolidinone:

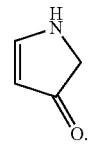

In describing the heteroatoms contained in a specified heterocyclenyl group, the expression, "having one to x heteroatoms selected from the group of N, O, P and S" (wherein x is an a specified integer), for example, means that each heteroatom in the specified heterocyclenyl is independently selected from the specified selection of heteroatoms.

It should also be noted that tautomeric forms such as, for example, the moieties:

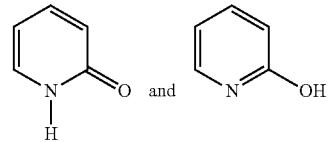 [SMILES: O=c1cccc[nH]1 ; Oc1ccccn1]

are considered equivalent in certain embodiments of this invention.

An "alkylaryl group" is an alkyl group substituted with an aryl group, for example, a phenyl group. Suitable aryl groups are described herein and suitable alkyl groups are described herein. The bond to the parent moiety is through the aryl group.

An "alkylheteroaryl group" is an alkyl group substituted with a heteroaryl group. Suitable heteroaryl groups are described herein and suitable alkyl groups are described herein. The bond to the parent moiety is through the heteroaryl group.

An "alkylheterocyclyl group" is an alkyl group substituted with a heterocyclyl group. Suitable heterocyclyl groups are described herein and suitable alkyl groups are described herein. The bond to the parent moiety is through the heterocyclyl group.

An "alkylheterocyclenyl group" is an alkyl group substituted with a heterocyclenyl group. Suitable heterocyclenyl groups are described herein and suitable alkyl groups are described herein. The bond to the parent moiety is through the heterocyclenyl group.

An "alkylcycloalkyl group" is an alkyl group substituted with a cycloalkyl group. Suitable cycloalkyl groups are described herein and suitable alkyl groups are described herein. The bond to the parent moiety is through the cycloalkyl group.

An "arylalkyl group" is an aryl group substituted with an alkyl group, for example, a phenyl group. Suitable aryl groups are described herein and suitable alkyl groups are described herein. The bond to the parent moiety is through the alkyl group.

A "heteroarylalkyl group" is a heteroaryl group substituted with an alkyl group. Suitable heteroaryl groups are described herein and suitable alkyl groups are described herein. The bond to the parent moiety is through the alkyl group.

A "heterocyclylalkyl group" is a heterocyclyl group substituted with an alkyl group. Suitable heterocyclyl groups are described herein and suitable alkyl groups are described herein. The bond to the parent moiety is through the alkyl group.

A "heterocyclenylalkyl group" is a heterocyclenyl group substituted with an alkyl group. Suitable heterocyclenyl groups are described herein and suitable alkyl groups are described herein. The bond to the parent moiety is through the alkyl group.

A "cycloalkylalkyl group" is a cycloalkyl group substituted with an alkyl group. Suitable cycloalkyl groups are described herein and suitable alkyl groups are described herein. The bond to the parent moiety is through the alkyl group.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

An "alkylamino group" as used herein, is an alkyl group that is attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

When a moiety is referred to as "unsubstituted" or not referred to as "substituted" or "optionally substituted", it means that the moiety does not have any substituents. When a moiety is referred to as substituted, it denotes that any portion of the moiety that is known to one skilled in the art as being available for substitution can be substituted. The phrase "optionally substituted with one or more substituents" means, in one embodiment, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl, alkenyl or alkynyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), aryl (which can be substituted), cycloalkyl (which can be substituted) alkylaryl (which can be substituted), alkylheterocyclyl (which can be substituted), alkylcycloalkyl (which can be substituted), and aryloxy.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. For instance those compounds labeled with positron-emitting isotopes like $^{11}$C or $^{18}$F can be useful for application in Positron Emission Tomography (PET) and those labeled with gamma ray emitting isotopes like $^{123}$I can be useful for application in Single Photon Emission Computed Tomography (SPECT). Additionally, isotopic substitution of a compound at a site where epimerization occurs may slow or reduce the epimerization process and thereby retain the more active or efficacious form of the compound for a longer period of time.

It is also possible that the compounds of Formula (I) may exist in different tautomeric forms, and all such forms are embraced within the scope of the invention. Also, for example, all keto-enol and imine-enamine forms of the compounds are included in the invention.

Stereochemistry

When structures of the same constitution differ in respect to the spatial arrangement of certain atoms or groups, they are stereoisomers, and the considerations that are significant in analyzing their interrelationships are topological. If the relationship between two stereoisomers is that of an object and its nonsuperimposable mirror image, the two structures are enantiomeric, and each structure is said to be chiral. Stereoisomers also include diastereomers, cis-trans isomers and conformational isomers. Diastereoisomers can be chiral or achiral, and are not mirror images of one another. Cis-trans isomers differ only in the positions of atoms relative to a specified planes in cases where these atoms are, or are considered as if they were, parts of a rigid structure. Conformational isomers are isomers that can be interconverted by rotations about formally single bonds. Examples of such conformational isomers include cyclohexane conformations with chair and boat conformers, carbohydrates, linear alkane conformations with staggered, eclipsed and gauche confomers, etc. See J. Org. Chem. 35, 2849 (1970).

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, enantiomers are identical except that they are non-superimposable mirror images of one another. A mixture of such enantiomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the compounds of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

As used herein, "a," an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

This invention is also intended to encompass pro-drugs of the pyrazolopyrimidine compounds disclosed herein. A pro-drug of any of the compounds can be made using well-known pharmacological techniques.

Pharmaceutically Acceptable Salts

The pyrazolopyrimidine compounds described herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts organic and inorganic acids, for example, acid addition salts which may, for example, be hydrochloric acid, sulphuric acid, methanesulphonic acid, fumaric acid, maleic acid, succinic acid, acetic acid, benzoic acid, oxalic acid, citric acid, tartaric acid, carbonic acid, phosphoric acid, trifluoroacetic acid, formic acid and the like. Pharmaceutically acceptable salts can also be prepared from by treatment with inorganic bases, for example, sodium, potassium, ammonium, calcium, or ferric hydroxides, and such organic bases as isopropylamine, trimethylamine, 2-ethylamino ethanol, histidine, procaine, and the like. Pharmaceutically acceptable salts can also be formed from elemental anions such as chlorine, bromine and iodine.

The active compounds disclosed can, as noted above, also be prepared in the form of their hydrates. The term "hydrate"

includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

As used herein, "a," an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Methods of Treatment

The Pyrazolopyrimidine Compounds may be useful in human and veterinary medicine in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974, which is hereby incorporated by reference.

While not being bound by any specific theory it is believed that the Pyrazolopyrimidine Compounds may be useful in the treatment of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease because of their mTOR inhibitory activity.

The general value of the compounds of the invention in inhibiting mTOR can be determined, for example, using the assay described in Example 69. In addition, the general value in inhibiting mTORC1 or mTORC2 function can be evaluated using the assays described in Example 70.

More specifically, the Pyrazolopyrimidine Compounds can be useful in the treatment of a variety of cancers, including (but not limited to) the following:
tumor of the bladder, breast (including BRCA-mutated breast cancer), colorectal, colon, kidney, liver, lung, small cell lung cancer, non-small cell lung cancer, head and neck, esophagus, bladder, gall bladder, ovary, pancreas, stomach, cervix, thyroid, prostate, and skin, including squamous cell carcinoma;
leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma and Burkett's lymphoma; chronic lymphocytic leukemia ("CLL"),
acute and chronic myelogenous leukemia, myelodysplastic syndrome and promyelocytic leukemia;
fibrosarcoma, rhabdomyosarcoma;
head and neck, mantle cell lymphoma, myeloma;
astrocytoma, neuroblastoma, glioma, glioblastoma, malignant glial tumors, astrocytoma, hepatocellular carcinoma, gastrointestinal stromal tumors ("GIST") and schwannomas; melanoma, multiple myeloma, seminoma, teratocarcinoma, osteosarcoma, xenoderma pigmentosum, keratoctanthoma, thyroid follicular cancer, endometrial cancer, gastrointestinal tract cancer and Kaposi's sarcoma.

While not being bound by any specific theory, due to the key role of kinases in the regulation of cellular proliferation in general, inhibitors of kinases could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The Pyrazolopyrimidine Compounds may induce or inhibit apoptosis. The apoptotic response is aberrant in a variety of human diseases. The Pyrazolopyrimidine Compounds, as modulators of apoptosis, can be useful in the treatment of cancer (including but not limited to those types mentioned hereinabove), viral infections (including, but not limited to, herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

While not being bound by any specific theory, the Pyrazolopyrimidine Compounds, as inhibitors of kinases, can modulate the level of cellular RNA and DNA synthesis. These compounds would therefore be useful in the treatment of viral infections (including but not limited to HIV, human papilloma virus, herpesvirus, poxvirus, Epstein-Barr virus, Sindbis virus and adenovirus).

In particular embodiments of the invention, Pyrazolopyrimidine Compounds, as inhibitors of mTOR kinase could act in diseases or disorders other than cancer that are associated with dysregulated mTOR activity such as viral infections (including, but not limited to, herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The Pyrazolopyrimidine Compounds may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The Pyrazolopyrimidine Compounds may also be useful in inhibiting tumor angiogenesis and metastasis.

Another aspect of this invention is a method of treating a patient (e.g., human) having a disease or condition associated with mTOR kinases by administering a therapeutically effective amount of a Pyrazolopyrimidine Compound, or a pharmaceutically acceptable salt of said compound to the patient.

The present invention provides a method of treating cancer comprising the step of administering to a subject a therapeutically effective amount of the Pyrazolopyrimidine Compounds. The present invention also provides the Use of the Pyrazolopyrimidine Compounds for the preparation of a medicament for the treatment of cancer. The invention also provides the Pyrazolopyrimidine Compounds for use in the treatment of cancer.

In the therapies described above, an example dosage for administration to a patient is about 0.001 to 1000 mg/kg of body weight/day of the Pyrazolopyrimidine Compound. Another example dosage is about 0.01 to 25 mg/kg of body weight/day of the Pyrazolopyrimidine Compound, or a pharmaceutically acceptable salt of said compound.

The dosage regimen utilizing the compounds of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

DEFINITIONS

As used herein, the term "therapeutically effective amount" means that amount of active compound or pharmaceutical agent that elicits the biological or medicinal response in a tissue, system, animal or human that is being sought by a researcher, veterinarian, medical doctor or other clinician. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

Further, a therapeutically effective amount, can be an amount that selectively induces terminal differentiation, cell growth arrest and/or apoptosis of neoplastic cells, or an amount that induces terminal differentiation of tumor cells.

The method of the present invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

Combination Therapy

The compounds of the present invention can be administered alone or in combination with other therapies suitable for the disease or disorder being treated. Where separate dosage formulations are used, the compound and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the compound and the other therapeutic agent are realized by the patient at substantially the same time. In an embodiment, such beneficial effect is achieved when the target blood level concentrations of each active drug are maintained at substantially the same time.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Therefore, the present invention encompasses pharmaceutical compositions comprising a therapeutically effective amount of the compound of the invention and a pharmaceutically acceptable carrier and optionally other threrapeutic ingredients, such as an anti-cancer agent. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The instant compounds are particularly useful when co-administered with radiation therapy.

In one embodiment, the compound of the invention is (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboxylic acid.

In one embodiment, the compound of the invention is (1S,4S)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboxylic acid.

In one embodiment, the compound of the invention is (1R,4R)-4-(7-amino-3-(6-(1-methyl-1H-pyrazol-3-yl)pyridin-3-yl)-6-(methylsulfonyl)pyrazolo[1,5-a]pyrimidin-5-yl)-1-(2-methoxyethoxy)cyclohexanecarboxylic acid.

In one embodiment, the compound of the invention is (1R,4R)-4-(7-amino-3-(1-(4-fluorophenyl)-1H-pyrazol-4-yl)-6-(methylsulfonyl)pyrazolo[1,5-a]pyrimidin-5-yl)-1-(2-methoxyethoxy)cyclohexanecarboxylic acid.

In one embodiment, the compound of the invention is (1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexanecarboxylic acid.

In one embodiment, the compound of the invention is (1R,4R)-4-(7-amino-6-(methylsulfonyl)-3-(6-(thiazol-2-yl)pyridin-3-yl)pyrazolo[1,5-a]pyrimidin-5-yl)-1-(2-methoxyethoxy)cyclohexanecarboxylic acid.

In one embodiment, the compound of the invention is (1R,4R)-4-(7-amino-3-(6-(3-fluoro-4-hydroxyphenyl)pyridin-3-yl)-6-(methylsulfonyl)pyrazolo[1,5-a]pyrimidin-5-yl)-1-(2-methoxyethoxy)cyclohexanecarboxylic acid.

In another embodiment, the compound of the invention is (1R,4R)-4-(7-amino-6-(methylsulfonyl)-3-(2-(5-methylthiazol-2-yl)pyrimidin-5-yl)pyrazolo[1,5-a]pyrimidin-5-yl)-1-(2-methoxyethoxy)cyclohexanecarboxylic acid.

In another embodiment, the compound of the invention is (1R,4R)-4-(7-amino-3-(6-fluoroquinolin-3-yl)-6-(methylsulfonyl)pyrazolo[1,5-a]pyrimidin-5-yl)-1-(2-methoxyethoxy)cyclohexanecarboxylic acid.

In another embodiment, the compound of the invention is (1R,4R)-4-(7-amino-6-(methylsulfonyl)-3-(1-phenyl-1H-pyrazol-4-yl)pyrazolo[1,5-a]pyrimidin-5-yl)-N-hydroxy-1-(2-methoxyethoxy)cyclohexanecarboxamide.

In a further embodiment, the compound of the invention is (1R,4R)-4-(3-(6-(1H-imidazol-2-yl)pyridin-3-yl)-6-acetyl-7-aminopyrazolo[1,5-a]pyrimidin-5-yl)-1-(2-methoxyethoxy)cyclohexanecarboxamide.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, diethylstibestral, tamoxifen, raloxifene, idoxifene, LY353381, LY117081, toremifene, fluoxymestero, 1fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Other hormonal agents include: aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

"Androgen receptor modulators" refers to compounds which interfere or inhibit the binding of androgens to the receptor, regardless of mechanism. Examples of androgen receptor modulators include finasteride and other 5-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678, WO 03/39460 and WO2003/079973, WO2003/099211, WO2004/039774, WO2003/105855, WO2003/106417. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs shown as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PI3K kinase family (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

Examples of mTOR inhibitors include ridaforolimus, temsirolimus, everolimus, a rapamycin-analog. Ridaforolimus, also known as AP 23573, MK-8669 and deforolimus, is a unique, non-prodrug analog of rapmycin that has antiproliferative activity in a broad range of human tumor cell lines in vitro and in murine tumor xenograft models utilizing human tumor cell lines. Ridaforolimus has been administered to patients with advanced cancer and is currently in clinical development for various advanced malignancies, including studies in patients with advanced soft tissue or bone sarcomas. Thus far, these trials have demonstrated that ridaforolimus is generally well-tolerated with a predictable and manageable adverse even profile, and possess anti-tumor activity in a broad range of cancers. A description and preparation of ridaforolimus is described in U.S. Pat. No. 7,091,213 to Ariad Gene Therapeutics, Inc.

Temsirolimus, also known as Torisel®, is currently marketed for the treatment of renal cell carcinoma. A description and preparation of temsirolimus is described in U.S. Pat. No. 5,362,718 to American Home Products Corporation. Everolimus, also known as Certican® or RAD001, marketed by Novartis, has greater stability and enhanced solubility in organic solvents, as well as more favorable pharmokinetics with fewer side effects than rapamycin (sirolimus). Everolimus has been used in conjunction with microemulsion cyclosporin (Neoral®, Novartis) to increase the efficacy of the immunosuppressive regime.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862,5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors α and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), Duc-4, NF-1, NF-2, RB, WT1, BRCA1, BRCA2, a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, bacillus Calmette-Guerin, octreotide, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to anastrozole, letrozole and exemestane.

A compound of the instant invention may also be useful for treating or preventing cancer in combination with siRNA therapeutics.

A compound of the instant invention may also be useful for treating or preventing cancer in combination withcompounds which induce terminal differentiation of the neoplastic cells. Suitable differentiation agents include the compounds disclosed in any one or more of the following references.

a) Polar compounds (Marks et al (1987); Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature (Lond.)* 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Hematol.* 39: 943-954; Ebert, P. S., Wars, I., and Buell, D. N. (1976) *Cancer Res.* 36: 1809-1813; Hayashi, M., Okabe, J., and Hozumi, M. (1979) *Gann* 70: 235-238).

A compound of the instant invention may also be useful for treating or preventing cancer in combination with γ-secretase inhibitors.

Also included in the scope of the claims is a method of treating cancer that comprises administering a therapeutically effective amount of a compound of Formula I in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The compounds of the instant invention are useful in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane 1123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®); and zoledronate (Zometa®).

Non-limiting examples of other suitable anti-cancer agents for combination with the instant compounds are selected from the group consisting of a Cytostatic agent, Cisplatin, Deforolimus (described in PCT publication No. 2003/064383), Doxorubicin, liposomal doxorubicin (e.g., Caelyx®, Myocet®, Doxil®), Taxotere, Taxol, Etoposide, Irinotecan, Camptostar, Topotecan, Paclitaxel, Docetaxel, Epothilones, Tamoxifen, 5-Fluorouracil, Methoxtrexate, Temozolomide, cyclophosphamide, SCH 66336, R115777®, L778,123®, BMS 214662®, Iressa®, Tarceva®, Antibodies to EGFR, antibodies to IGFR (including, for example, those published in US 2005/0136063 published Jun. 23, 2005), ESK inhibitors, KSP inhibitors (such as, for example, those published in WO 2006/098962 and WO 2006/098961; ispinesib, SB-743921 from Cytokinetics), Centrosome associated protein E ("CENP-E") inhibitors (e.g., GSK-923295), Gleevec®, Intron, Ara-C, Adriamycin, Cytoxan, Gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6 Mercaptopurine, 6 Thioguanine, Fludarabine phosphate, Oxaliplatin, Leucovirin, ELOXATIN™, Vinblastine, Vincristine, Vindesine, Bleomycin, Dactinomycin, Daunorubicin, Doxorubicin, Epirubicin, Idarubicin, Mithramycin, Deoxycoformycin, Mitomycin C, L Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, bortezomib ("Velcade"), Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225®, Satriplatin, mylotarg, Avastin, Rituxan, Panitubimab, Sutent, Sorafinib, Sprycel (dastinib), Nilotinib, Tykerb (Lapatinib) and Campath.

In one embodiment, the invention provides a method of treating cancer, the method comprising administering an amount of a Pyrazolopyrimidine Compound or a pharmaceutically acceptable salt thereof, and an amount of one additional anticancer agent selected from the group consisting of Adriamycin, Altretamine, Amidox, Aminoglutethimide, Amsacrine, Anastrazole, Antibodies to EGFR, 3-AP, Aphidicolon, Ara-C, Arsenic trioxide, L Asparaginase, Bevacizumab, Bleomycin, BMS 214662, Bortezomib, Busulfan, Campath, Camptostar, Capecitabine, Carboplatin, Carmustine, Centrosome associated protein E ("CENP-E") inhibitors, Cetuximab, Cladribine, Chlorambucil, Chlormethine, Chlorotrianisene, Cisplatin, Clofarabine, cyclophosphamide, Cytarabine, a Cytostatic agent, Cytoxan, Dacarbazine, Dactinomycin, Daunorubicin, Dasatinib, Deforolimus, Deoxycoformycin, Didox, Diethylstilbestrol, Docetaxel, Doxorubicin, Dromostanolone, Droloxafine, Epirubicin, Epothilones, ERK inhibitors, Erlotinib, Etoposide, 17α-Ethinylestradiol, Estramustine, Exemestane, Floxuridine, Fludarabine, Fludarabine phosphate, 5-Fluorouracil, Fluoxymesterone, Flutamide, Fulvestrant, Gefitinib, Gemcitabine, Gemtuzumab ozogamcicin, Goserelin, GSK-923295, Hexamethylmelamine, Hydroxyprogesterone, Hydroxyurea, Ibritumomab Tiuxetan, Idarubicin, Ifosfamide, Imatinib mesylate, Intron, Irinotecan, ispinesib, KSP inhibitors, L778,123, Lapatinib, Leucovirin, Leuprolide, Lerozole, Letrazole, Levamisole, Liposomal Doxorubicin, Liposomal, Lomustine, Lonafarnib, Medroxyprogesteroneacetate, Megestrolacetate, Melphalan, 6 Mercaptopurine, Methoxtrexate, Methylprednisolone, Methyltestosterone, Mithramycin, Mitomycin C, Mitotane, Mitoxantrone, Navelbene, Nilotinib, Oxaliplatin, Paclitaxel, Panitubimab, Pentostatin, Pipobroman, Porfimer, Prednisolone, Prednisone propionate, Procarbazine, Reloxafine, Rituximab, Satriplatin, SB-743921, Sml1, Sorafinib, Streptozocin, Sunitinib, Tamoxifen, Taxotere, Taxol, Temozolomide, Teniposide, Testolactone, Testosterone, Tezacitabine, 6 Thioguanine, Thiotepa, Tipifarnib, Topotecan, Toremifene, Tositumomab, Trastuzumab, Triamcinolone, Triapine, Triethylenemelamine, Triethylenethiophosphoramine, Trimidox, Uracil mustard, Vinblastine, Vincristine, Vindesine, and Vinorelbine.

In one embodiment, the invention provides a method of treating cancer, the method comprising administering an amount of a Pyrazolopyrimidine Compound or a pharmaceutically acceptable salt thereof, and an amount of one or more of a MAP Kinase pathway inhibitor such as bRaf, MEK, or ERK inhibitors to a patient in need thereof.

In another embodiment, the invention provides a method of treating cancer, the method comprising administering an amount of a Pyrazolopyrimidine Compound or a pharmaceutically acceptable salt thereof, and an amount of one or more of ERK inhibitors (for example, compounds described in WO2008/156739, WO2007/070398, WO 2008/156739 and US publication 2007/0232610) to a patient in need thereof.

In one embodiment, the invention provides a method of treating cancer, the method comprising administering an amount of a Pyrazolopyrimidine Compound or a pharmaceutically acceptable salt thereof, and an amount of one or more of an anti-IGF-1R antibody. Specific anti-IGF-1R antibodies include, but are not limited to, dalotuzumab, figitumumab, cixutumumab, SHC 717454, Roche R1507, EM164 or Amgen AMG479.

The instant invention also includes a pharmaceutical composition useful for treating or preventing cancer that comprises a therapeutically effective amount of a compound of Formula I and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The use of all of these approaches in combination with the instant compounds described herein are within the scope of the present invention.

Compositions and Administration

This invention is also directed to pharmaceutical compositions which comprise at least one Pyrazolopyrimidine Compound, or a pharmaceutically acceptable salt of said compound and at least one pharmaceutically acceptable carrier.

When administered to a patient, the Pyrazolopyrimidine Compounds can be administered as a component of a composition that comprises a pharmaceutically acceptable carrier or vehicle. The present invention provides pharmaceutical compositions comprising an effective amount of at least one Pyrazolopyrimidine Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Pyrazolopyrimidine Compounds of the present invention may also be delivered transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize therapeutic effects, i.e., anticancer activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Pyrazolopyrimidine Compound is administered orally.

In another embodiment, the Pyrazolopyrimidine Compound is administered intravenously.

In another embodiment, the Pyrazolopyrimidine Compound is administered topically.

In still another embodiment, the Pyrazolopyrimidine Compounds is administered sublingually.

In one embodiment, a pharmaceutical preparation comprising at least one Pyrazolopyrimidine Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Pyrazolopyrimidine Compound(s) by weight or volume.

In various embodiments, the present compositions can contain, in one embodiment, from about 1% to about 70% or from about 5% to about 60% of the Pyrazolopyrimidine Compound(s) by weight or volume.

The quantity of Pyrazolopyrimidine Compound in a unit dose of preparation may be varied or adjusted from about 0.1 mg to about 5000 mg. In various embodiments, the quantity is from about 10 mg to about 5000 mg, about 10 mg to about 1000 mg, 1 mg to about 500 mg, 1 mg to about 100 mg, and 1 mg to about 50 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

For administration to human patients, the amount and frequency of administration of the Pyrazolopyrimidine Compounds will be regulated according to the judgment of the attending clinician considering such factors as age, condition and size of the patient as well as severity of the symptoms being treated. Generally, a total daily dosage of the Pyrazolopyrimidine Compounds range from about 0.1 to about 5000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 5000 mg/day, administered in a single dose or in 2-4 divided doses. In another embodiment, the dosage is from about 100 to about 5000 mg/day, administered in a single dose or in 2-4 divided doses. In still another embodiment, the dosage is from about 500 to about 5000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Pyrazolopyrimidine Compound or a pharmaceutically acceptable salt thereof; (ii) one or more additional therapeutic agents that are not a Pyrazolopyrimidine Compound; and (iii) a pharmaceutically acceptable carrier, wherein the amounts in the composition are together effective to treat disease or disorder associated with dysregulated mTOR activity, such as a cancer.

In Vitro and In Vivo Methods:

The present invention also provides methods of using the pyrazolopyrimidine compounds of the present invention for inducing terminal differentiation, cell growth arrest and/or apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the pyrazolopyrimidine compounds described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the pyrazolopyrimidine compounds described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the pyrazolopyrimidine compounds described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the pyrazolopyrimidine compounds described herein.

In another embodiment, the invention relates to an in vitro method of inducing terminal differentiation of tumor cells in a tumor comprising contacting the cells with an effective amount of any one or more of the pyrazolopyrimidine compounds described herein.

Although the methods of the present invention can be practiced in vitro, it is contemplated that the preferred embodiment for the methods of selectively inducing terminal differentiation, cell growth arrest and/or apoptosis of neoplastic cells, and of inhibiting mTor will comprise contacting the cells in vivo, i.e., by administering the compounds to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the pyrazolopyrimidine compounds described herein.

In a particular embodiment, the present invention relates to a method of selectively inducing terminal differentiation of neoplastic cells and thereby inhibiting proliferation of such cells in a subject. The method comprises administering to the subject an effective amount of one or more of the pyrazolopyrimidine compounds described herein.

In another embodiment, the invention relates to a method of selectively inducing cell growth arrest of neoplastic cells and thereby inhibiting proliferation of such cells in a subject. The method comprises administering to the subject an effective amount of one or more of the pyrazolopyrimidine compounds described herein.

In another embodiment, the invention relates to a method of selectively inducing apoptosis of neoplastic cells and thereby inhibiting proliferation of such cells in a subject. The method comprises administering to the subject an effective amount of one or more of the pyrazolopyrimidine compounds described herein.

In another embodiment, the invention relates to a method of treating a patient having a tumor characterized by proliferation of neoplastic cells. The method comprises administering to the patient one or more of the pyrazolopyrimidine compounds described herein. The amount of compound is effective to selectively induce terminal differentiation, induce cell growth arrest and/or induce apoptosis of such neoplastic cells and thereby inhibit their proliferation.

Kits

Another aspect of this invention is a kit comprising a therapeutically effective amount of at least one Pyrazolopyrimidine Compound, or a pharmaceutically acceptable salt of said compound, and a pharmaceutically acceptable carrier, vehicle or diluent.

Yet another aspect of this invention is a kit comprising an amount of at least one Pyrazolopyrimidine Compound, or a pharmaceutically acceptable salt of said compound and an amount of at least one additional anti-cancer agent listed above, wherein the amounts of the two or more active ingredients result in a desired therapeutic effect. In one embodiment, the at least one Pyrazolopyrimidine Compound and the at least one additional anti-cancer agent are provided in the same container. In one embodiment, the at least one Pyrazolopyrimidine Compound and the at least one additional anti-cancer agent are provided in separate containers.

The invention is illustrated in the examples in the Experimental Details Section that follows. This section is set forth to aid in an understanding of the invention but is not intended to, and should not be construed to limit in any way the invention as set forth in the claims which follow thereafter.

Experimental Details Section

Solvents, reagents, and intermediates that are commercially available were used as received. Reagents and intermediates that are not commercially available were prepared in the manner as described below. $^1$H NMR spectra were obtained on a Varian spectrometer (400 MHz and 500 MHz) are reported as ppm down field from Me$_4$Si with number of protons, multiplicities, and coupling constants, in Hertz indicated parenthetically. Where LC/MS data are presented, analyses was performed using an Agilent 1100 Series LC w/ MicroMass Quattro MS Varian Pursuit XRs C18, 5 micron, 150 mm×4.6 mm ID gradient flow (0.1% TFA or 0.2% FA): 0 min—5% ACN, 7.5 min—100% ACN, 8.5 min—100 ACN, 8.51 min—5% ACN, 10 min—stop 3 ml/min. The retention time and observed parent ion are given. Where the description indicates the reaction mixture was purified by HPLC, the description refers to using a preparative Agilent 1100 Series LC/MSD SL system: Column Reverse Phase-Varian Pursuit XRs 10 C-18 250×21.2 mm; elution with gradient Acetonitrile/water with 0.1% TFA or 0.2% formic acid. The desired product was detected and collected by a mass-triggered automatic sample collector. Flash column chromatography was performed using pre-packed normal phase silica from Biotage, Inc.

The following solvents, reagents and reaction conditions may be referred to by their abbreviations:

Aq: aqueous
g or gm: grams
psi: pounds per square inch
pH: concentration of hydronium ions in a solution
° C.: degrees Celsius
h: hours
THF: Tetrahydrofuran
Et$_2$O: diethyl ether
SEM: 2-(trimethylsilyl)ethoxymethyl
LC-MS: Liquid chromatography mass spectrometry
DCM: dichloromethane
N: Normal
ml: milliliter
NBS: N-Bromosuccinimide
NCS: N-Chlorosuccinimide
NIS: N-iodosuccinimide
r.t.: room temperature
MeOH: methanol
DIEA: diisopropylethylamine
EtOAc: ethyl acetate
EtOH: ethanol
DMF: dimethylformamide
wt %: weight percent
m/z: mass per charge
LiOH: lithium hydroxide
DMSO: dimethylsulfoxide
HPLC: high performance liquid chromatography
IPA: isopropanol
Ret: retention
Rt: retention time
RP: reverse phase
ACN: acetonitrile
CH$_3$CN: acetonitrile
MeCN: acetonitrile
MeI: iodomethane
r.t.: room temperature
pTSA: para-toluene sulfonic acid
CDI: N,N'-carbonyldiimidazole
mg: milligram
PMA: phosphomolybdic acid
LiHMDS: Lithium bis(trimethylsilyl)amide
HMDS: hexamethyldisilazane
Pd/C: palladium on carbon
H2: hydrogen gas
PdCl$_2$(dppf): [1,1'-bis(diphenylphosphino)ferrocene]dichloropalladium(II)
μmol: micromole
TFA: trifluoroacetic acid
NMP: N-methyl-2-pyrrolidone
min: minute
DME: dimethylethane
AcOH: acetic acid
BBN: 9-borabicyclo[3.3.1]nonane
BOC: tertiary-butyloxycarbonyl
M: Molar
mmol: millimolar
DIEA: diisopropylethylamine
Bu3SnCN: tributyltin cyanide
Pd[P(t-Bu)$_3$]$_2$: bis(tributyl)Phosphine) palladium
Pd(PPh$_3$)$_4$: tetrakis(triphenylphosphine) palladium
EDCI: 1-ethyl-3-(3-dimethylaminopropyl)-carbodiimide
UV: ultraviolet
LDA: lithium diisopropylamide
Tf: trifluoromethanesulfonyl

Example 1

Preparation of (1R,4R)-4-(7-amino-6-bromo-3-(6-phenylpyridin-3-yl)pyrazolo[1,5-a]pyrimidin-5-yl)-1-methylcyclohexanecarboxylic acid (Compound 1) and (1S,4S)-4-(7-amino-6-bromo-3-(6-phenylpyridin-3-yl)pyrazolo[1,5-a]pyrimidin-5-yl)-1-methylcyclohexanecarboxylic acid (Compound 2)

Step 1: Preparation of ethyl 1,4-dioxaspiro[4.5]decane-8-carboxylate

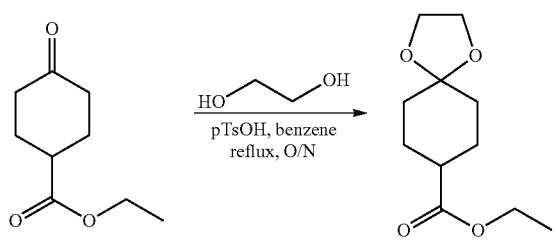

The ketone (25 g, 146.9 mmol) was mixed together with p-TsOH (2.85 g, 15 mmol) and ethylene glycol (25 mL) in benzene (300 mL). The mixture was refluxed with D-M trap and stirred overnight. After the concentration to remove the solvent, the residue was taken up with EtOAc (250 mL) and washed with NaHCO$_3$ (aq.) and brine. The organic was dried over Na$_2$SO$_4$ and concentrated. The crude product was purified with column (silica gel, 0~50% EtOAc/Hexane) to give the product (27.0 g).

Step 2: Preparation of ethyl 8-methyl-1,4-dioxaspiro[4.5]decane-8-carboxylate

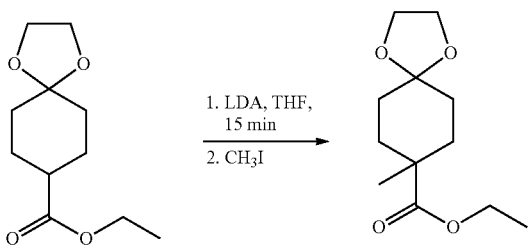 [SMILES: CCOC(=O)C1CCC2(CC1)OCCO2 ; CCOC(=O)C1(C)CCC2(CC1)OCCO2]

The ester (2.14 g, 10 mmol) was dissolved in dry THF (20 mL) and cooled to −78° C. LDA (1.8 M, 6.6 mL, 12 mmol) was added dropwise and the mixture was stirred at −78° C. for 15 min. Then CH$_3$I (1.87 mL, 30 mmol) was added at this temperature and the resulting mixture was allowed to warm to room temperature and stirred overnight. NH$_4$Cl (aq.) was added to quench the reaction and extracted with EtOAc. The organics was dried over Na$_2$SO$_4$, concentrated and purified with column (0~50% EtOAc/Hexane) to give the product (2.09 g). HPLC-MS $t_R$=1.68 min (UV$_{254\,nm}$); mass calculated for formula C$_{12}$H$_{20}$O$_4$ 228.1, observed LCMS m/z 229.2 (M+H).

Step 3: Preparation of ethyl 1-methyl-4-oxocyclohexanecarboxylate

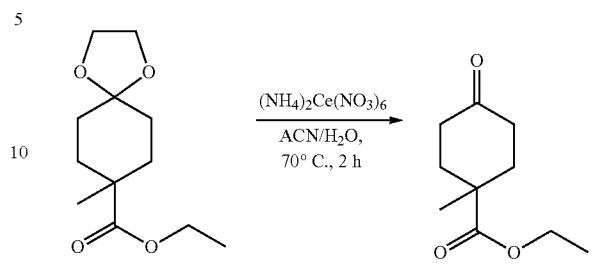

The ketal compound (2.09 g, 9.17 mmol) was dissolved in CAN (100 mL) and water (50 mL). (NH$_4$)$_2$Ce(NO$_3$)$_6$ (503 mg, 0.92 mmol) in water (50 mL) was added and the mixture was heated up to 70° C. and stirred for 1 hour. After cooling down to room temperature, water (100 mL) was added and extracted with Et$_2$O (100 mL×3) and the organics was dried over Na$_2$SO$_4$. After concentration, the crude was purified with column (0~30% EtOAc/Hexane) to give the product (1.72 g).

Step 4: Preparation of ethyl 1-methyl-4-(trifluoromethylsulfonyloxy)cyclohex-3-enecarboxylate

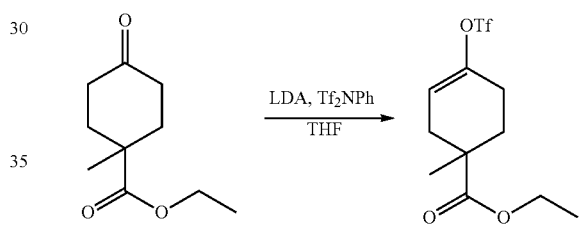

LDA (17.28 mmol) in THF (20 mL) was cooled to −78° C. and the ketone (2.65 g, 14.39 mmol) in THF (10 mL) was added dropwise and stirred for 30 min. Then N-phenylbis(trifluoromethanesulfonimide) (5.66 g, 15.8 mmol) in THF (10 mL) was added. The resulting mixture was allowed to warm up to room temperature and stirred overnight. The NH$_4$Cl(aq.) was added to quench the reaction and extracted with EtOAc. The organics was dried over Na$_2$SO$_4$, concentrated and purified with column (0~30%) to give the product (3.36 g).

Step 5: Preparation of ethyl 1-methyl-4-(4,4,5,5-tetramethyl-1,3,2-dioxaborolan-2-yl)cyclohex-3-enecarboxylate

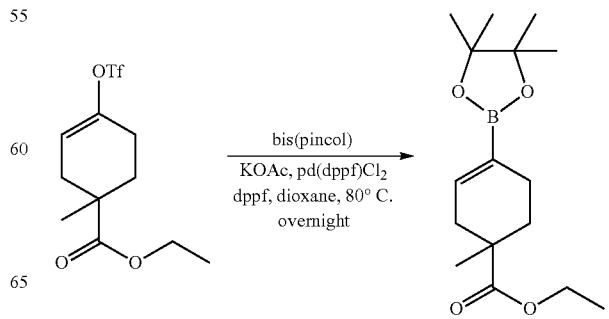

Under Ar, TfO-compound (3.36 g, 10.63 mmol) was mixed with Pd(dppf)Cl$_2$ (815 mg, 1.0 mmol, DPPF (554 mg, 1.0 mmol), KOAc (3.2 g, 33 mmol), bis(pinacolato)diboron (3.24 g, 12.76 mmol) and dioxane (20 mL). The resulting mixture was heated at 80° C. and stirred overnight. After cooled to room temperature, the mixture was diluted with EtOAc (60 mL) and filtered through celite. After concentration, the crude was purified with column (silica gel, 0~30% EtOAc/Hexane) to give the product (2.03 g). HPLC-MS $t_R$=2.35 min (UV$_{254\ nm}$); mass calculated for formula C$_{16}$H$_{27}$BO$_4$ 294.2, observed LCMS m/z 295.3 (M+H).

Step 6: Preparation of ethyl 4-(7-(bis((2-(trimethylsilyl)ethoxy)methyl)amino)pyrazolo[1,5-a]pyrimidin-5-yl)-1-methylcyclohex-3-enecarboxylate

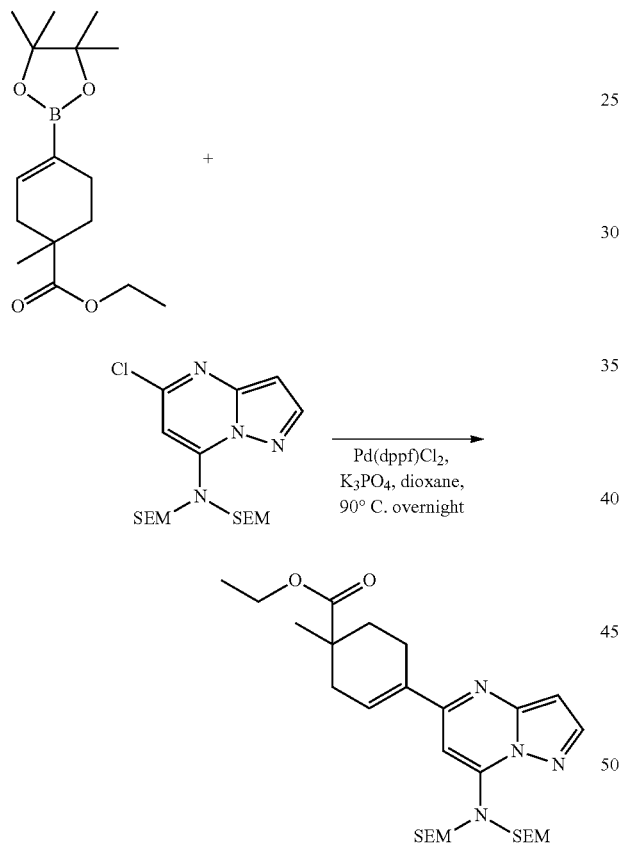

Under Ar, the chloro-compound (2.14 g, 5.0 mmol) was mixed with Pd(dppf)Cl$_2$ (400 mg, 0.5 mmol, K$_3$PO$_4$ (2.12 g, 10.0 mmol), bornated (1.7 g, 5.78 mmol) and dioxane (20 mL with 2 ml water). The resulting mixture was heated at 90° C. and stirred overnight. After cooling to room temperature, the mixture was diluted with EtOAc (60 mL) and filtered through celite. After concentration, the crude was purified with column (silica gel, 0~30% EtOAc/Hexane) to give the product (2.44 g). HPLC-MS $t_R$=2.67 min (UV$_{254\ nm}$); mass calculated for formula C$_{28}$H$_{48}$N$_4$O$_4$Si$_2$ 560.3, observed LCMS m/z 561.3 (M+H).

Step 7: Preparation of ethyl 4-(7-(bis((2-(trimethylsilyl)ethoxy)methyl)amino)-3-iodopyrazolo[1,5-a]pyrimidin-5-yl)-1-methylcyclohex-3-enecarboxylate

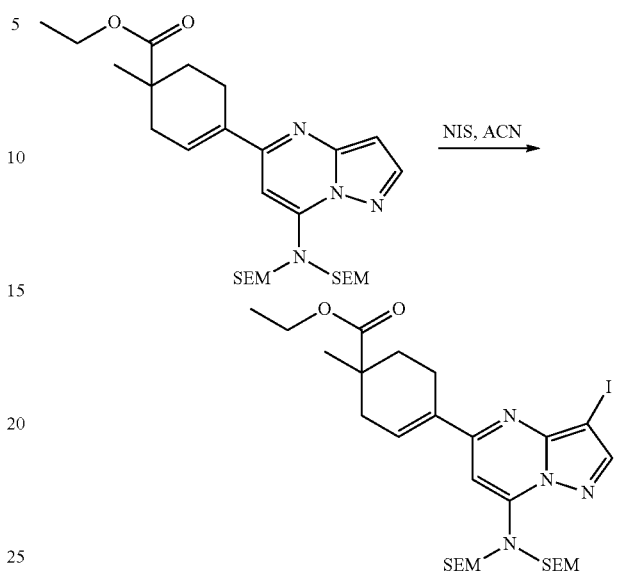

Compound (2.44 g, 4.33 mmol) was dissolved in ACN (20 mL). NIS (975 mg, 4.33 mmol) was added. The mixture was stirred at room temperature for 1 hour and concentrated. The residue was purified with column (silica gel, 0-30% EtOAc/Hexane) to give the iodo-product (2.71 mg). HPLC-MS $t_R$=3.03 min (UV$_{254\ nm}$); mass calculated for formula C$_{28}$H$_{47}$IN$_4$O$_4$Si$_2$ 686.2, observed LCMS m/z 687.1 (M+H).

Step 8: Preparation of ethyl 4-(7-(bis((2-(trimethylsilyl)ethoxy)methyl)amino)-3-(6-phenylpyridin-3-yl)pyrazolo[1,5-a]pyrimidin-5-yl)-1-methylcyclohex-3-enecarboxylate

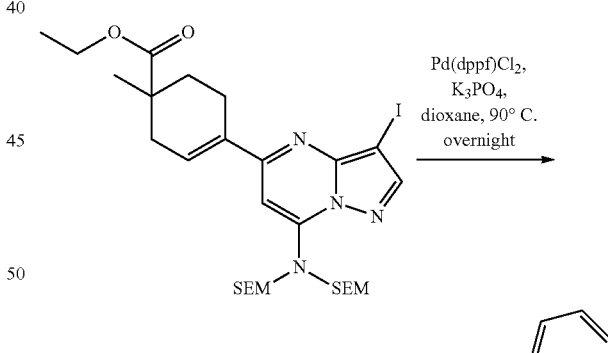

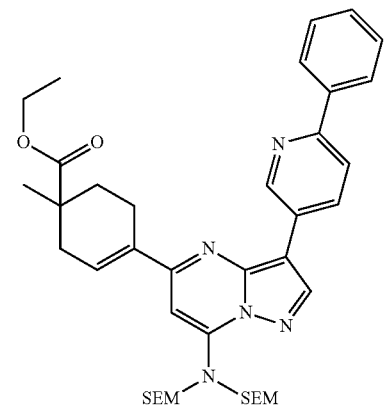

Under Ar, the iodo-compound (687 mg, 1.0 mmol) was mixed with Pd(dppf)Cl$_2$ (80 mg, 0.1 mmol, K$_3$PO$_4$ (636 g, 3.0 mmol), bornated (309 mg, 1.1 mmol) and dioxane (10 mL with 1 ml water). The resulting mixture was heated at 90° C. and stirred overnight. After cooled to room temperature, the mixture was diluted with EtOAc (30 mL) and filtered through celite. After concentration, the crude was purified with column (silica gel, 0~30% EtOAc/Hexane) to give the product (630 mg). HPLC-MS t$_R$=2.89 min (UV$_{254\,nm}$); mass calculated for formula C$_{39}$H$_{55}$N$_5$O$_4$Si$_2$ 713.4, observed LCMS m/z 714.4 (M+H).

Step 9: Preparation of ethyl 4-(7-(bis((2-(trimethylsilyl)ethoxy)methyl)amino)-3-(6-phenylpyridin-3-yl)pyrazolo[1,5-a]pyrimidin-5-yl)-1-methylcyclohexanecarboxylate

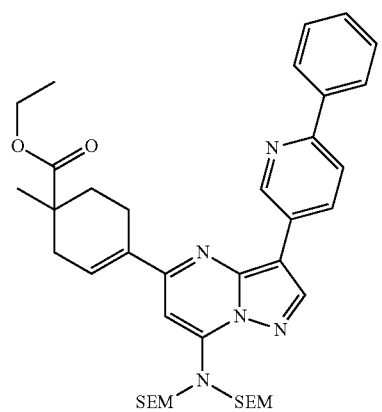

Under H$_2$ balloon, the compound (400 mg, 0.56 mmol) and 10% Pd/C (100 mg) in EtOAc (50 mL) was mixed and heated up to 45° C. The mixture was stirred overnight. After cooled to room temperature, the mixture was filtered through celite and concentrated. The crude was purified with column (silica gel, 0~50% EtOAc/Hexane) to give the product (373 mg). HPLC-MS t$_R$=2.76 min (UV$_{254\,nm}$); mass calculated for formula C$_{39}$H$_{57}$N$_5$O$_4$Si 715.4, observed LCMS m/z 716.3 (M+H).

Step 10: Preparation of ethyl 4-(7-(bis((2-(trimethylsilyl)ethoxy)methyl)amino)-6-bromo-3-(6-phenylpyridin-3-yl)pyrazolo[1,5-a]pyrimidin-5-yl)-1-methylcyclohexanecarboxylate

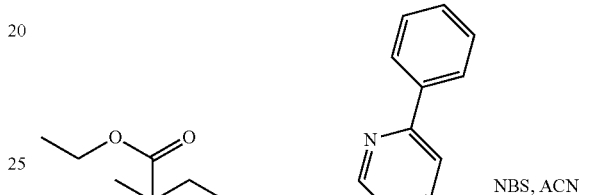

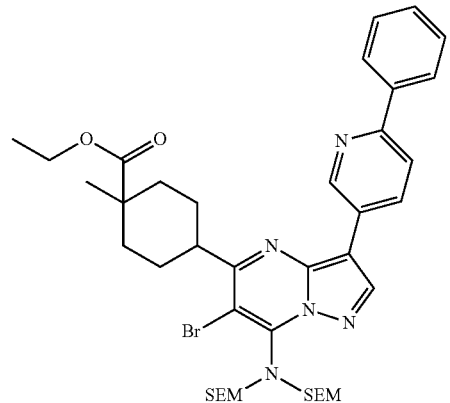

The compound (310 mg, 0.39 mmol) was dissolved in ACN (10 mL) and treated with NBS (70 mg, 0.39 mmol). The mixture was stirred at room temperature for 1 hour and concentrated. The crude was purified by HPLC to give the product (345 mG). HPLC-MS t$_R$=3.67 min (UV$_{254\,nm}$); mass calculated for formula C$_{39}$H$_{56}$BrN$_5$O$_4$Si$_2$ 793.3, observed LCMS m/z 794.2 (M+H).

Step 11: Preparation of (1S,4S)-ethyl 4-(7-amino-6-bromo-3-(6-phenylpyridin-3-yl)pyrazolo[1,5-a]pyrimidin-5-yl)-1-methylcyclohexanecarboxylate and (1R,4R)-ethyl 4-(7-amino-6-bromo-3-(6-phenylpyridin-3-yl)pyrazolo[1,5-a]pyrimidin-5-yl)-1-methylcyclohexanecarboxylate

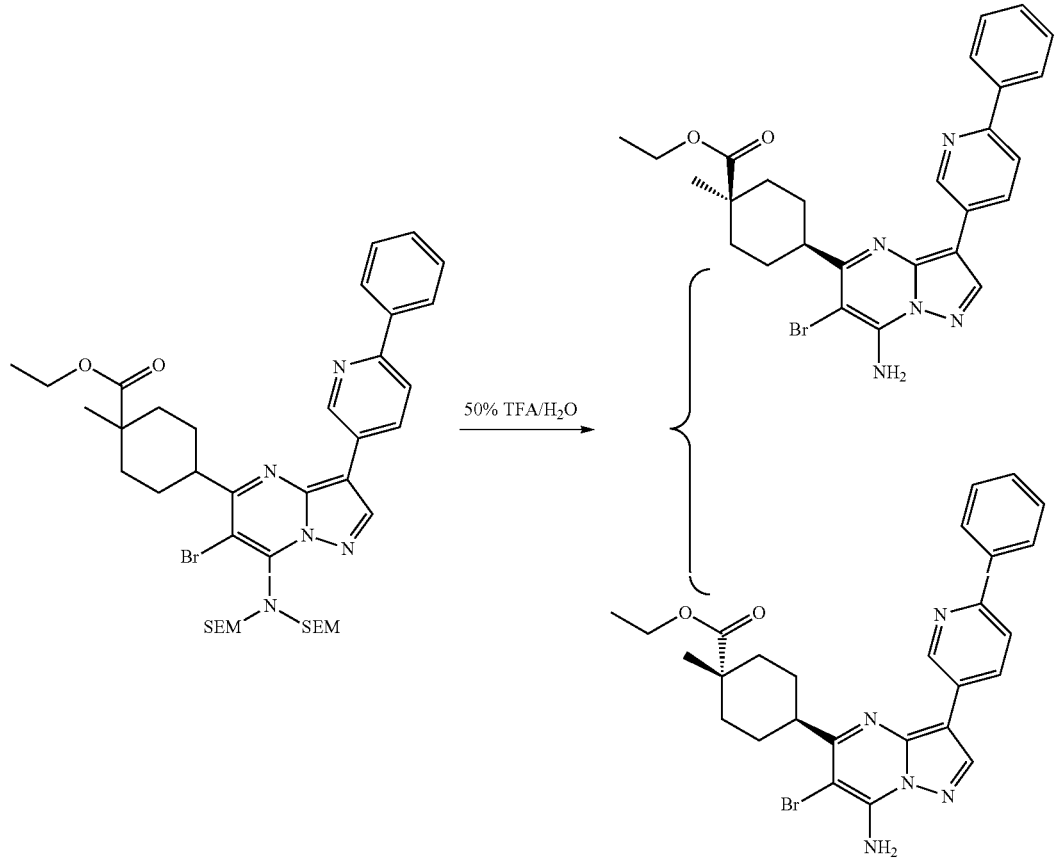 [SMILES: CCOC(=O)C1(C)CCC(c2nc3c(-c4ccc(-c5ccccc5)nc4)cnn3c(N(COCC[Si](C)(C)C)COCC[Si](C)(C)C)c2Br)CC1 ; CCOC(=O)[C@]1(C)CC[C@@H](c2nc3c(-c4ccc(-c5ccccc5)nc4)cnn3c(N)c2Br)CC1 ; CCOC(=O)[C@]1(C)CC[C@H](c2nc3c(-c4ccc(-c5ccccc5)nc4)cnn3c(N)c2Br)CC1]

The starting material (50 mg, 0.063 mmol) was dissolved in 50% TFA/water and stirred at room temperature for 1 hour. After concentration, the crude was purified with HPLC to give the two isomers.

Isomer 1: HPLC-MS $t_R$=1.97 min (UV$_{254\ nm}$); mass calculated for formula $C_{27}H_{28}BrN_5O_2$ 533.1, observed LCMS m/z 534.1 (M+H).

Isomer 2: HPLC-MS $t_R$=2.09 min (UV$_{254\ nm}$); mass calculated for formula $C_{27}H_{28}BrN_5O_2$ 533.1, observed LCMS m/z 534.2 (M+H).

Step 12: Preparation of (1s,4s)-4-(7-amino-6-bromo-3-(6-phenylpyridin-3-yl)pyrazolo[1,5-a]pyrimidin-5-yl)-1-methylcyclohexanecarboxylic acid (Compound 2) and (1R,4R)-4-(7-amino-6-bromo-3-(6-phenylpyridin-3-yl)pyrazolo[1,5-a]pyrimidin-5-yl)-1-methylcyclohexanecarboxylic acid (Compound 1)

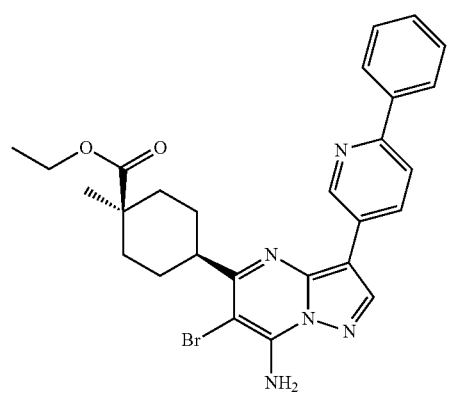

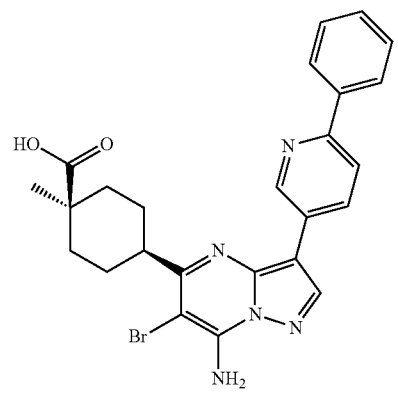 [SMILES: Nc1c(Br)c([C@H]2CC[C@@](F)(C(=O)O)CC2)nc2c(-c3ccc(-c4ccccc4)nc3)cnn12]

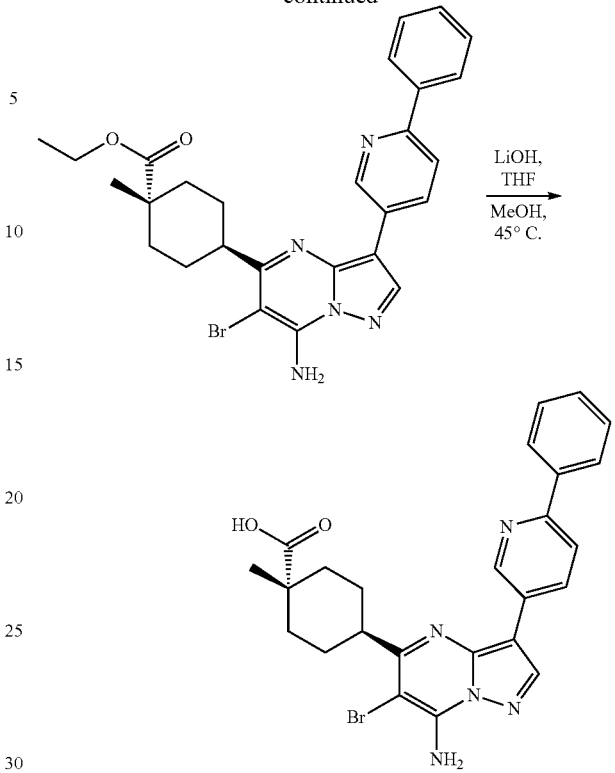

The ester (two isomers from above) was dissolved in THF/MeOH (4 mL/1 mL) and LiOH (1N,1 mL) was added. The mixture was heated up to 60° C. and stirred overnight. After concentration, the crude was purified with Prep-LC to give the product.

Compound 2: HPLC-MS $t_R$=1.69 min (UV$_{254\ nm}$); mass calculated for formula $C_{25}H_{24}BrN_5O_2$ 505.1, observed LCMS m/z 506.0 (M+H).

Compound 1: HPLC-MS $t_R$=1.65 min (UV$_{254\ nm}$); mass calculated for formula $C_{25}H_{24}BrN_5O_2$ 505.1, observed LCMS m/z 506.2 (M+H).

Example 2

By essentially the same procedure in Preparative Example 1, compounds in Column 2 of Table 1 can be prepared.

TABLE 1

| Example | Chemical name | Column 2 | Exact mass | MS m/z (M + H) | HPLC MS $t_R$ |
|---|---|---|---|---|---|
| 3 | (1S,4S)-4-(7-amino-6-bromo-3-(6-phenylpyridin-3-yl)pyrazolo[1,5-a]pyrimidin-5-yl)-1-fluorocyclohexanecarboxylic acid | | 509.1 | 510.0 | 1.68 |

TABLE 1-continued

| Example | Chemical name | Column 2 | Exact mass | MS m/z (M + H) | HPLC MS $t_R$ |
|---|---|---|---|---|---|
| 4 | (1R,4R)-4-(7-amino-6-bromo-3-(6-phenylpyridin-3-yl)pyrazolo[1,5-a]pyrimidin-5-yl)-1-fluorocyclohexane-carboxylic acid | | 509.1 | 510.0 | 1.71 |
| 5 | 4-(7-amino-6-bromo-3-(6-phenylpyridin-3-yl)pyrazolo[1,5-a]pyrimidin-5-yl)-1-(methoxymethyl)-cyclohexane-carboxylic acid | | 535.1 | 536.2 | 1.47 |
| 6 | 4-(7-amino-6-bromo-3-(1-phenyl-1H-pyrazol-4-yl)pyrazolo[1,5-a]pyrimidin-5-yl)-1-(methoxymethyl)-cyclohexane-carboxylic acid | | 524.1 | 525.2 | 1.84 |
| 7 | (1R,4R)-4-(7-amino-6-bromo-3-(6-fluoroquinolin-3-yl)pyrazolo[1,5-a]pyrimidin-5-yl)-1-(methoxymethyl)-cyclohexane-carboxylic acid | | 527.1 | 528.1 | 1.53 |

TABLE 1-continued

| Example | Chemical name | Column 2 | Exact mass | MS m/z (M + H) | HPLC MS t_R |
|---|---|---|---|---|---|
| 8 | (1S,4S)-4-(7-amino-6-bromo-3-(6-fluoroquinolin-3-yl)pyrazolo[1,5-a]pyrimidin-5-yl)-1-(methoxymethyl)-cyclohexane-carboxylic acid | | 527.1 | 528.1 | 1.60 |
| 9 | (1S,4S)-4-(7-amino-6-bromo-3-(1-phenyl-1H-pyrazol-4-yl)pyrazolo[1,5-a]pyrimidin-5-yl)-1-(methylthio)-cyclohexane-carboxylic acid | | 526.1 | 527.2 | 1.93 |
| 10 | (1R,4R)-4-(7-amino-6-bromo-3-(1-phenyl-1H-pyrazol-4-yl)pyrazolo[1,5-a]pyrimidin-5-yl)-1-(methylthio)-cyclohexane-carboxylic acid | | 526.1 | 527.2 | 2.04 |
| 11 | (1R,4R)-4-(7-amino-6-bromo-3-(6-phenylpyridin-3-yl)pyrazolo[1,5-a]pyrimidin-5-yl)-1-((2-methoxyethoxy)methyl)cyclohexane-carboxylic acid | | 579.1 | 580.1 | 1.45 |

TABLE 1-continued

| Example | Chemical name | Column 2 | Exact mass | MS m/z (M + H) | HPLC MS $t_R$ |
|---|---|---|---|---|---|
| 12 | (1S,4S)-4-(7-amino-6-bromo-3-(6-phenylpyridin-3-yl)pyrazolo[1,5-a]pyrimidin-5-yl)-1-((2-methoxyethoxy)methyl)cyclohexane-carboxylic acid | | 579.1 | 580.1 | 1.48 |
| 13 | (1R,4R)-4-(7-amino-6-bromo-3-(1-phenyl-1H-pyrazol-4-yl)pyrazolo[1,5-a]pyrimidin-5-yl)-1-((2-methoxyethoxy)methyl)cyclohexane-carboxylic acid | | 568.1 | 569.2 | 1.93 |
| 14 | (1S,4S)-4-(7-amino-6-bromo-3-(1-phenyl-1H-pyrazol-4-yl)pyrazolo[1,5-a]pyrimidin-5-yl)-1-((2-methoxyethoxy)methyl)cyclohexane-carboxylic acid | | 568.1 | 569.2 | 1.96 |

Example 3

Preparation of (1R,4R)-4-(6-acetyl-7-amino-3-(6-phenylpyridin-3-yl)pyrazolo[1,5-a]pyrimidin-5-yl)-1-methylcyclohexanecarboxylic acid (Compound 15)

Step 1: Preparation of ethyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-1-methylcyclohexanecarboxylate

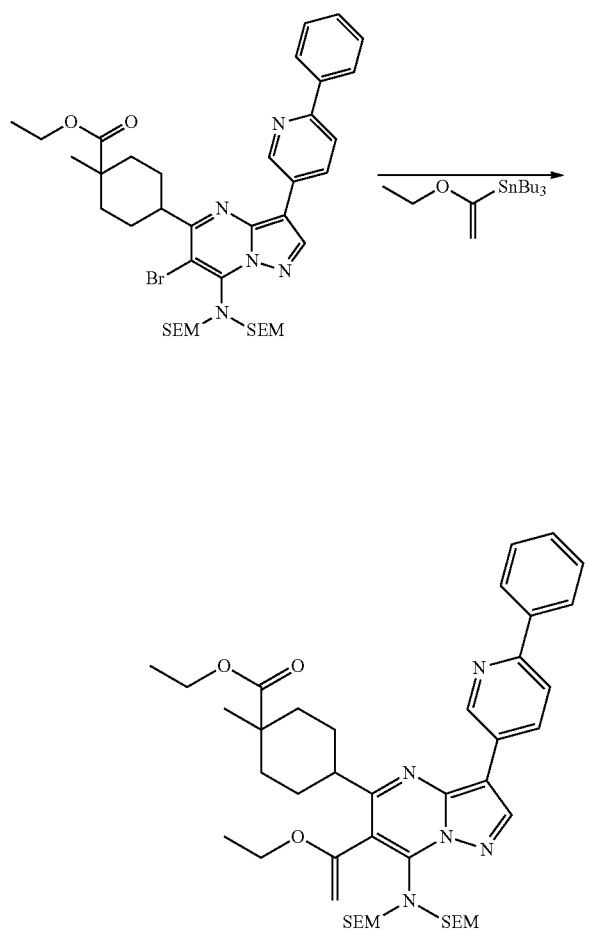

Under Ar, the bromo-compound (86 mg, 0.109 mmol) was mixed with Pd(PPh$_3$)$_4$ (23 mg, 0.02 mmol, (1-ethoxyvinyl)tributylstannane (118 mg, 0.33 mmol) and dioxane (5 mL). The resulting mixture was heated at 100° C. and stirred overnight. After cooled to room temperature, the mixture was filtered through 10% KF on silica gel and washed with EtOAc. After concentration, the crude was used in the next step directly without further purification. HPLC-MS t$_R$=2.92 min (UV$_{254\,nm}$); mass calculated for formula C$_{43}$H$_{63}$N$_5$O$_5$Si$_2$ 785.4, observed LCMS m/z 786.4 (M+H).

Step 2: Preparation of (1R,4R)-ethyl 4-(6-acetyl-7-amino-3-(6-phenylpyridin-3-yl)pyrazolo[1,5-a]pyrimidin-5-yl)-1-methylcyclohexanecarboxylate and (1S,4S)-ethyl 4-(6-acetyl-7-amino-3-(6-phenylpyridin-3-yl)pyrazolo[1,5-a]pyrimidin-5-yl)-1-methylcyclohexanecarboxylate

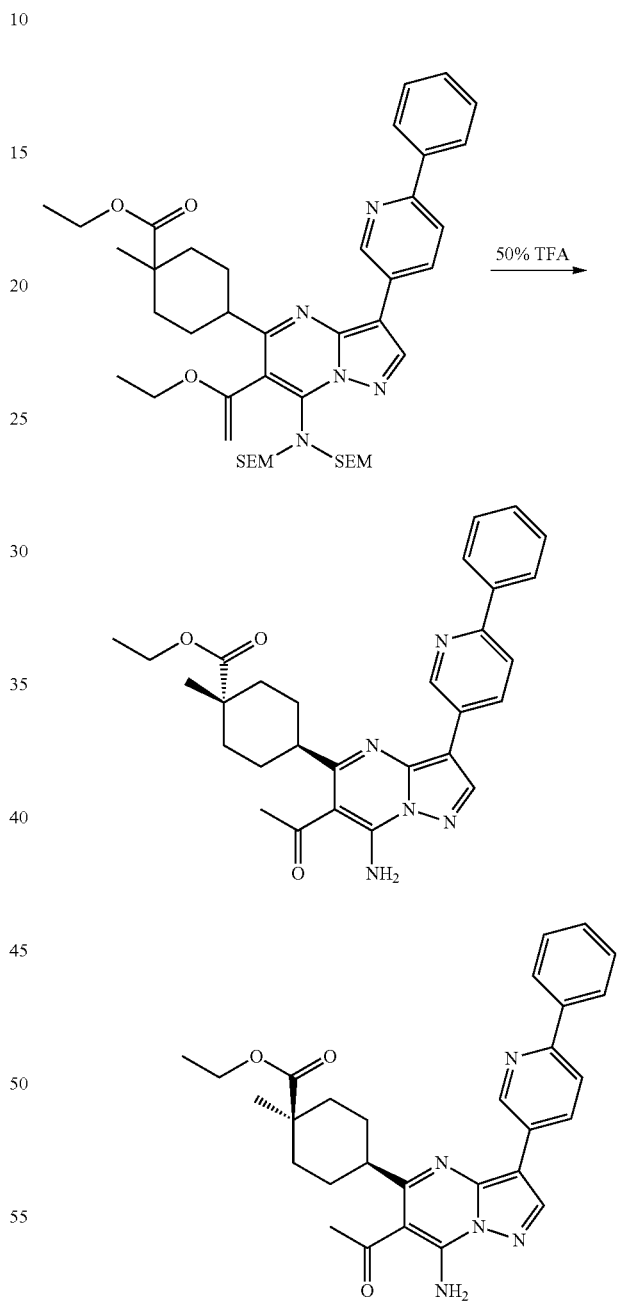

The vinyl ether compound was de-protected with the same condition described in example 1 Step 11 and gave two isomers after HPLC purification.

Isomer 1: HPLC-MS t$_R$=1.93 min (UV$_{254\,nm}$); mass calculated for formula C$_{29}$H$_{31}$N$_5$O$_3$ 497.2, observed LCMS m/z 498.2 (M+H).

Isomer 2: HPLC-MS $t_R$=1.99 min (UV$_{254\ nm}$); mass calculated for formula $C_{29}H_{31}N_5O_3$ 497.2, observed LCMS m/z 498.2 (M+H).

Step 3: Preparation of (1R,4R)-4-(6-acetyl-7-amino-3-(6-phenylpyridin-3-yl)pyrazolo[1,5-a]pyrimidin-5-yl)-1-methylcyclohexanecarboxylic acid (Compound 15)

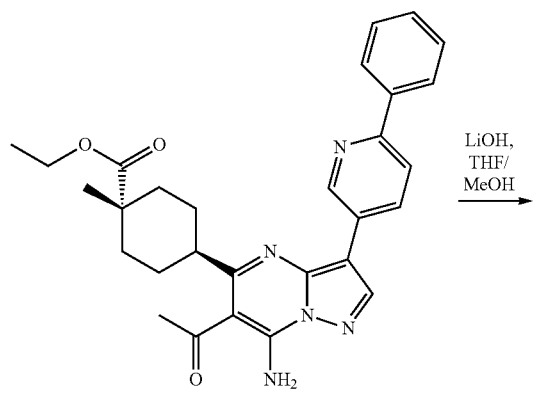

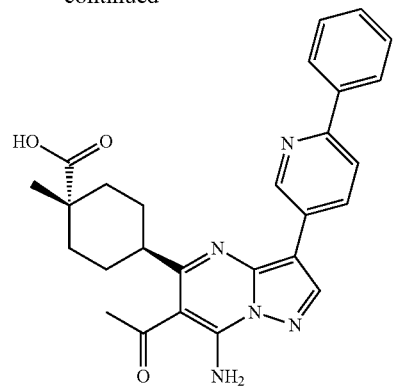

Isomer 2 was hydrolysized with the same condition described in example 1 Step 12. HPLC-MS $t_R$=1.49 min (UV$_{254\ nm}$); mass calculated for formula $C_{27}H_{27}N_5O_3$ 469.2, observed LCMS m/z 470.2 (M+H).

Example 4

By essentially the same procedure in Preparative Example 3, compounds in Table 2 can be prepared from respective bromo-compounds.

TABLE 2

| Example | Chemical name | Column 2 | Exact mass | MS m/z (M + H) | HPLC MS $t_R$ |
|---|---|---|---|---|---|
| 16 | (1S,4S)-(6-acetyl-7-amino-3-(6-phenylpyridin-3-yl)pyrazolo[1,5-a]pyrimidin-5-yl)-1-fluorocyclohexane-carboxylic acid | | 473.2 | 474.3 | 1.49 |
| 17 | (1R,4R)-4-(6-acetyl-7-amino-3-(6-phenylpyridin-3-yl)pyrazolo[1,5-a]pyrimidin-5-yl)-1-fluorocyclohexane-carboxylic acid | | 473.2 | 474.3 | 1.53 |

TABLE 2-continued

| Example | Chemical name | Column 2 | Exact mass | MS m/z (M + H) | HPLC MS $t_R$ |
|---|---|---|---|---|---|
| 18 | (1R,4R)-4-(6-acetyl-7-amino-3-(6-phenylpyridin-3-yl)pyrazolo[1,5-a]pyrimidin-5-yl)-1-(methoxymethyl)-cyclohexane-carboxylic acid | | 499.2 | 500.3 | 1.30 |
| 19 | (1S,4S)-4-(6-acetyl-7-amino-3-(6-phenylpyridin-3-yl)pyrazolo[1,5-a]pyrimidin-5-yl)-1-(methoxymethyl)-cyclohexane-carboxylic acid | | 499.2 | 500.3 | 1.49 |
| 20 | (1R,4R)-4-(6-acetyl-7-amino-3-(1-phenyl-1H-pyrazol-4-yl)pyrazolo[1,5-a]pyrimidin-5-yl)-1-(methoxymethyl)-cyclohexane-carboxylic acid | | 488.2 | 489.2 | 1.49 |
| 21 | (1S,4S)-4-(6-acetyl-7-amino-3-(1-phenyl-1H-pyrazol-4-yl)pyrazolo[1,5-a]pyrimidin-5-yl)-1-(methoxymethyl)-cyclohexane-carboxylic acid | | 488.2 | 489.2 | 1.83 |

TABLE 2-continued

| Example | Chemical name | Column 2 | Exact mass | MS m/z (M + H) | HPLC MS $t_R$ |
|---------|---------------|----------|------------|----------------|---------------|
| 22 | (1R,4R)-4-(6-acetyl-7-amino-3-(6-fluoroquinolin-3-yl)pyrazolo[1,5-a]pyrimidin-5-yl)-1-(methoxymethyl)-cyclohexane-carboxylic acid | | 491.2 | 492.1 | 1.66 |
| 23 | (1S,4S)-4-(6-acetyl-7-amino-3-(6-fluoroquinolin-3-yl)pyrazolo[1,5-a]pyrimidin-5-yl)-1-(methoxymethyl)-cyclohexane-carboxylic acid | | 491.2 | 492.1 | 1.74 |
| 24 | 4-(6-acetyl-7-amino-3-(6-phenylpyridin-3-yl)pyrazolo[1,5-a]pyrimidin-5-yl)-1-((2-methoxyethoxy)methyl)cyclohexane-carboxylic acid | | 543.2 | 544.3 | 1.47 |

Example 5

Preparation of (1R,4R)-4-(7-amino-6-cyano-3-(6-phenylpyridin-3-yl)pyrazolo[1,5-a]pyrimidin-5-yl)-1-methylcyclohexanecarboxylic acid (Compound 25) and (1S,4S)-4-(7-amino-6-cyano-3-(6-phenylpyridin-3-yl)pyrazolo[1,5-a]pyrimidin-5-yl)-1-methylcyclohexanecarboxylic acid (Compound 26)

Step 1: Preparation of ethyl 4-(7-(bis((2-(trimethylsilyl)ethoxy)methyl)amino)-6-cyano-3-(6-phenylpyridin-3-yl)pyrazolo[1,5-a]pyrimidin-5-yl)-1-methylcyclohexanecarboxylate

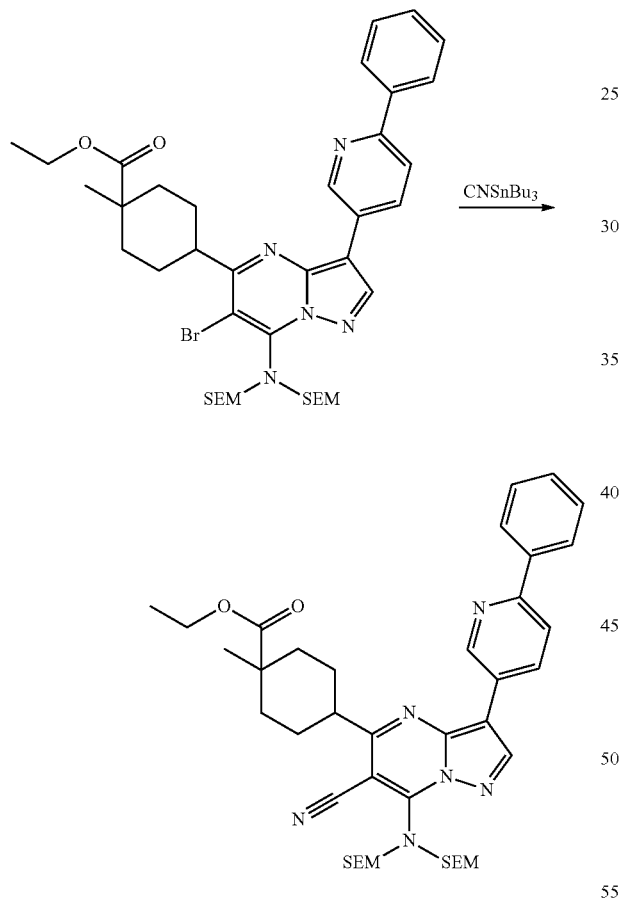

Under Ar, the bromo-compound (80 mg, 0.10 mmol) was mixed with Pd(PPh$_3$)$_4$ (12 mg, 0.01 mmol), (t-Bu$_3$P)$_3$Pd(0) (7 mg, 0.01 mmol), and cyanotributylstannane (96 mg, 0.3 mmol) and dioxane (5 mL). The resulting mixture was heated at 160° C. and stirred overnight. Cooled to room temperature and concentrated, the crude was used in the next step directly without further purification. HPLC-MS $t_R$=3.00 min (UV$_{254\ nm}$); mass calculated for formula C$_{40}$H$_{56}$N$_6$O$_4$Si$_2$ 740.4, observed LCMS m/z 741.3 (M+H).

Step 2: Preparation of (1R,4R)-ethyl 4-(7-amino-6-cyano-3-(6-phenylpyridin-3-yl)pyrazolo[1,5-a]pyrimidin-5-yl)-1-methylcyclohexanecarboxylate and (1S,4S)-ethyl 4-(7-amino-6-cyano-3-(6-phenylpyridin-3-yl)pyrazolo[1,5-a]pyrimidin-5-yl)-1-methylcyclohexanecarboxylate

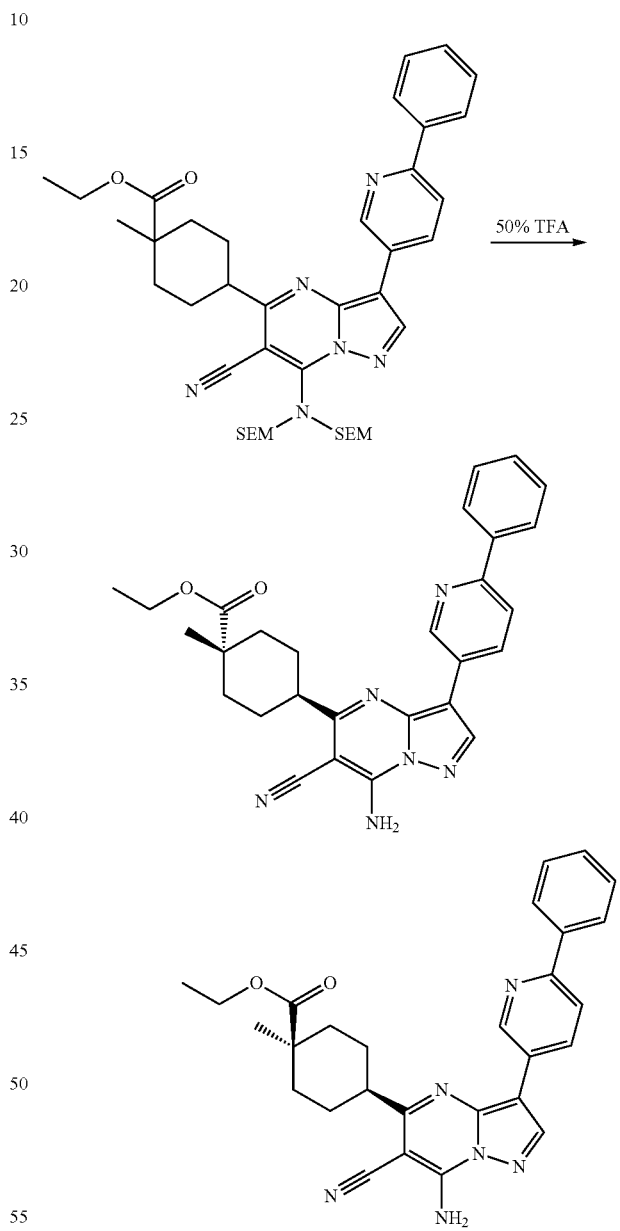

The cyano compound was de-protected with the same condition described in example 1 Step 11 and gave two isomers after HPLC purification.

Isomer 1: HPLC-MS $t_R$=1.96 min (UV$_{254\ nm}$); mass calculated for formula C$_{28}$H$_{28}$N$_6$O$_2$ 480.2, observed LCMS m/z 481.3 (M+H).

Isomer 2: HPLC-MS $t_R$=2.04 min (UV$_{254\ nm}$); mass calculated for formula C$_{28}$H$_{28}$N$_6$I$_2$ 480.2, observed LCMS m/z 481.3 (M+H).

Step 3: Preparation of (1R,4R)-ethyl 4-(7-amino-6-cyano-3-(6-phenylpyridin-3-yl)pyrazolo[1,5-a]pyrimidin-5-yl)-1-methylcyclohexanecarboxylate and (1S,4S)-ethyl 4-(7-amino-6-cyano-3-(6-phenylpyridin-3-yl)pyrazolo[1,5-a]pyrimidin-5-yl)-1-methylcyclohexanecarboxylate

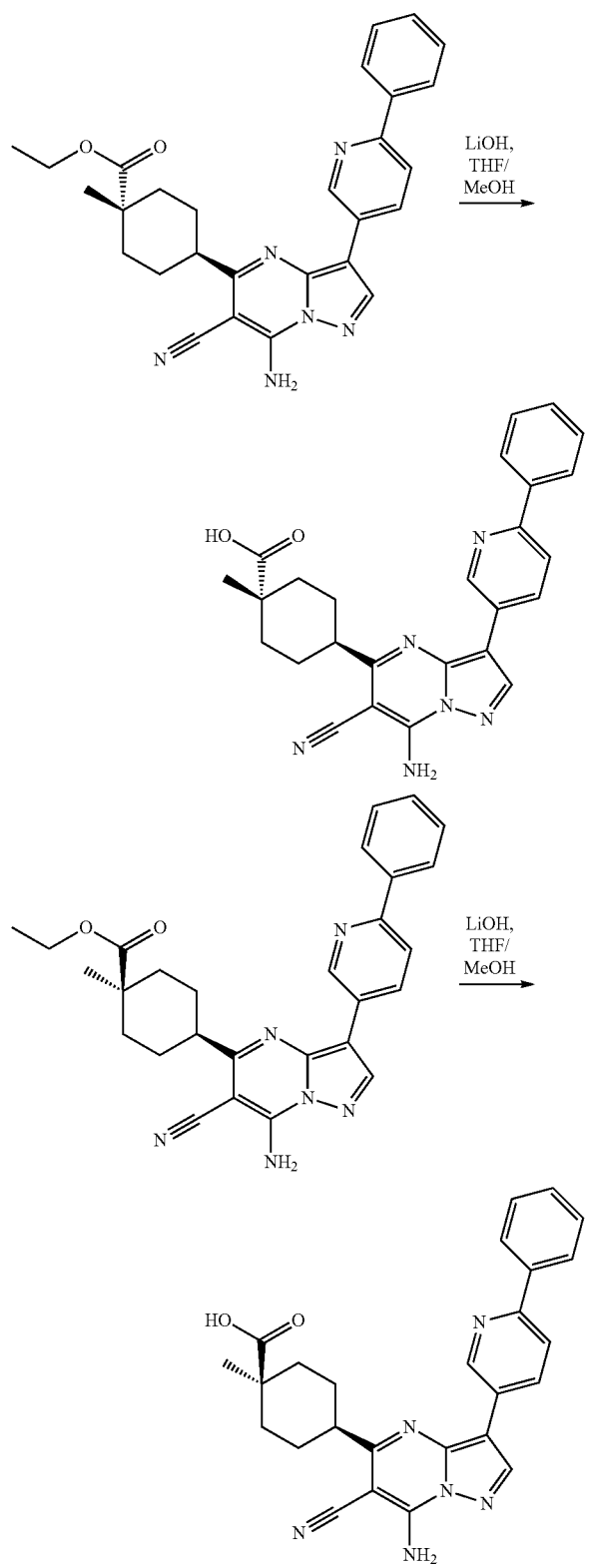

Isomer 1 and isomer 2 from step 2 were hydrolysized with the same condition described in example 1 Step 12.

Compound 25: HPLC-MS $t_R$=1.50 min (UV$_{254\ nm}$); mass calculated for formula $C_{26}H_{24}N_6O_2$ 452.2, observed LCMS m/z 453.3 (M+H).

Compound 26. HPLC-MS $t_R$=1.54 min (UV$_{254\ nm}$); mass calculated for formula $C_{26}H_{24}N_6O_2$ 452.2, observed LCMS m/z 453.3 (M+H).

Example 6

Preparation of 4-(7-amino-6-bromo-3-(1-phenyl-1H-pyrazol-4-yl)pyrazolo[1,5-a]pyrimidin-5-yl)-1-(methylsulfonyl)cyclohexanecarboxylic acid (Compound 27)

Step 1: Preparation of ethyl 4-(7-(bis((2-(trimethylsilyl)ethoxy)methyl)amino)-6-bromo-3-(1-phenyl-1H-pyrazol-4-yl)pyrazolo[1,5-a]pyrimidin-5-yl)-1-(methylsulfonyl)cyclohexanecarboxylate

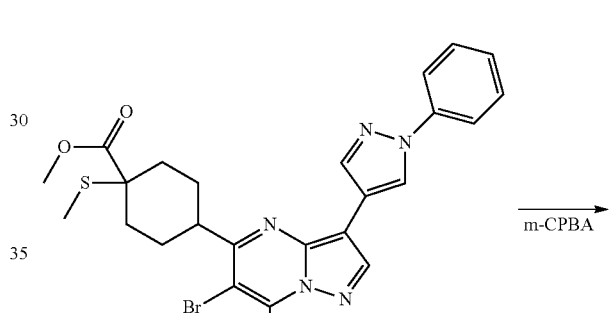

The methylsulfide compound was prepared as described in example 1 from the ester.

The methylsulfide compound (100 mg, 0.121 mmol) was dissolved in DCM (10 mL) and m-CPBA (54 mg, 77%, 0.242 mmol) was added. The mixture was stirred at room temperature for 2 hours and diluted with DCM (20 mL). The organics was washed with NaHCO$_3$ (aq.), brine and dried over Na$_2$SO$_4$. After concentration, the crude was used in the next step without further purification. HPLC-MS $t_R$=2.91 min (UV$_{254\ nm}$); mass calculated for formula $C_{37}H_{55}BrN_6O_6SSi_2$ 846.3, observed LCMS m/z 447.2 (M+H).

Step 2: Preparation of ethyl 4-(7-amino-6-bromo-3-(1-phenyl-1H-pyrazol-4-yl)pyrazolo[1,5-a]pyrimidin-5-yl)-1-(methylsulfonyl)cyclohexanecarboxylate

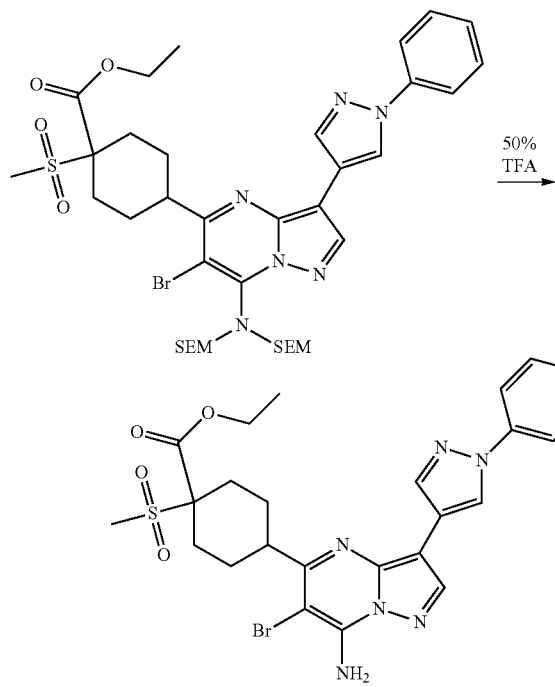

The methylsulfone compound was de-protected with the same condition described in example 1 Step 11 and gave the product after HPLC purification. HPLC-MS $t_R$=2.00 min (UV$_{254\ nm}$); mass calculated for formula $C_{25}H_{27}BrN_6O_4S$ 586.1, observed LCMS m/z 587.2 (M+H).

Step 3: Preparation of 4-(7-amino-6-bromo-3-(1-phenyl-1H-pyrazol-4-yl)pyrazolo[1,5-a]pyrimidin-5-yl)-1-(methylsulfonyl)cyclohexanecarboxylic acid (Compound 27)

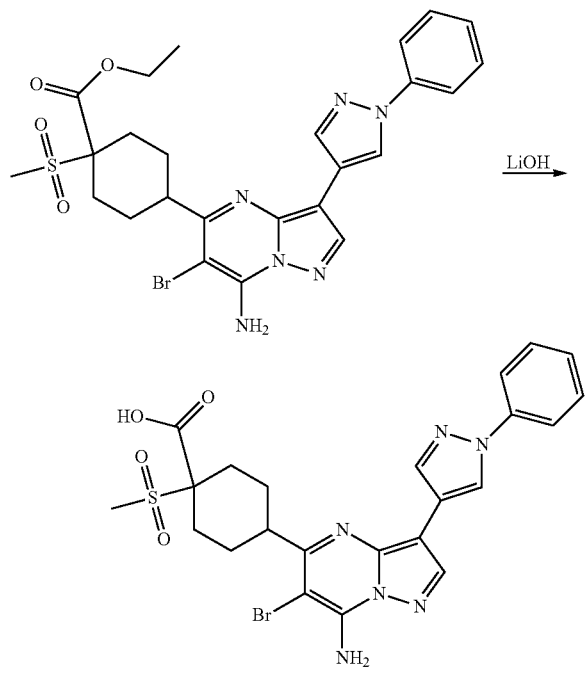

The ester was hydrolysized with the same condition described in example 1 Step 12. HPLC-MS $t_R$=1.71 min (UV$_{254\ nm}$); mass calculated for formula $C_{23}H_{23}BrN_6O_4S$ 558.1, observed LCMS m/z 559.0 (M+H).

Example 7

Preparation of (1S,4S)-4-(7-amino-6-bromo-3-(6-phenylpyridin-3-yl)pyrazolo[1,5-a]pyrimidin-5-yl)-1-methoxycyclohexanecarboxylic acid (Compound 28)

Step 1: Preparation of ethyl 4-cyano-4-hydroxycyclohexanecarboxylate

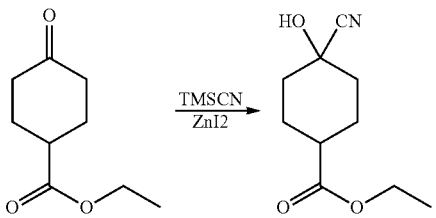

The starting material (25 g, 146.88 mmol) and TMSCN (29.14 g, 293.76 mmol) were dissolved in DCM (400 mL). ZnI$_2$ (4.686 g, 14.7 mmol) was added to the reaction and the resulting mixture was stirred at room temperature for 3 hours. Then HCl (1N,147 mL) was added and stirred for another 30 min. The mixture was extracted with EtOAc (200 ml×3) and the combined organics was dried over Na$_2$SO$_4$. The crude was purified with column after concentration (silica gel, 0-40%) to give the product (28.9 g). HPLC-MS $t_R$=1.25 min (UV$_{254\ nm}$); mass calculated for formula $C_{10}H_{15}NO_3$ 197.1, observed LCMS m/z 198.2 (M+H).

Step 2: Preparation of ethyl 4-cyano-4-methoxycyclohexanecarboxylate

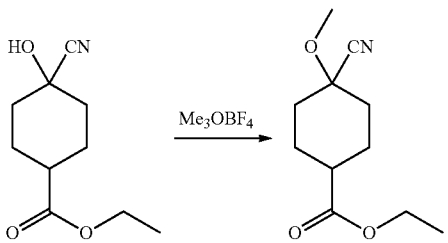

The hydroxyl compound (28.9 g, 146.7 mmol), trimethyloxonium tetrafluoroborate (26.62 g, 180 mmol) and 1,8-bis(dimethylamino)naphthalene (38.58 g, 180 mmol) were mixed in dry DCM (500 mL). The resulting mixture was stirred at room temperature overnight and then filtered through celite. The organics was washed with water, brine and dried over Na$_2$SO$_4$. After concentration, the crude was purified with column (silica gel, 0~30%) to give the product (19 g) and recovered the starting material (8.1 g). HPLC-MS $t_R$=1.64 min (UV$_{254\ nm}$); mass calculated for formula $C_{11}H_{17}NO_3$ 211.1, observed LCMS m/z 212.1 (M+H).

Step 3: Preparation of 4-(2-cyanoacetyl)-1-methoxycyclohexanecarbonitrile

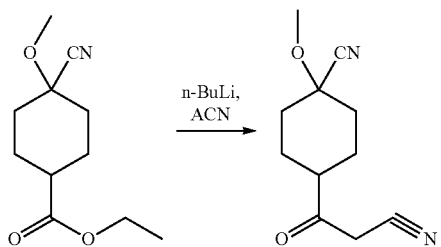

The ACN (9.4 mL, 180 mmol) in dry THF (300 mL) was cooled to −78° C. and n-BuLi (2.5 M in hexane, 72 mL, 180 mmol) was added carefully. The resulting mixture was stirred at −78° C. for 1 hour and the ester (19.0 g, 90 mmol) in THF (50 mL) was added slowly. The reaction was stirred at −78° C. for another 30 min after the addition then was allowed to warm to room temperature and stirred for another 30 min at room temperature. NH$_4$Cl (aq.) was added to quench the reaction and HCl (1N, 90 mL) was added. The mixture was extracted with EtOAc (300 mL×3) and the organics was washed with brine and dried over Na$_2$SO$_4$. After concentration, the crude was used in the next step directly without further purification.

Step 4: Preparation of 4-(7-aminopyrazolo[1,5-a]pyrimidin-5-yl)-1-methoxycyclohexanecarbonitrile

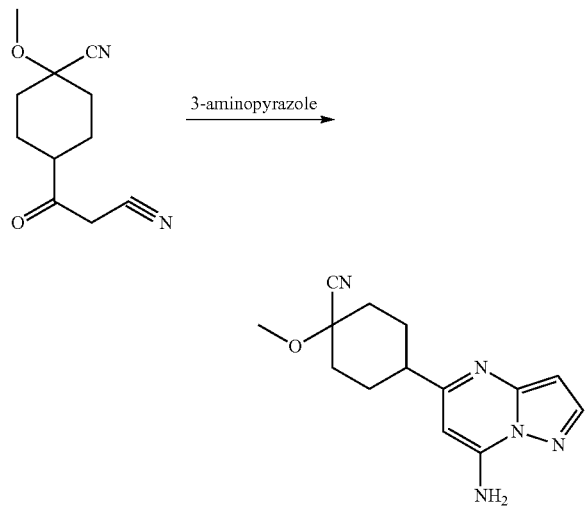

The cyanoketone from above was dissolved in HOAc (50 mL) and 3-aminopyrazole (7.5 g, 90 mmol) was added. The mixture was heated to reflux and stirred overnight. After concentration to remove the solvent, NaHCO$_3$ (aq.) was added carefully. The solid was collected and washed with water and dried under air. The crude product (24.3 g) was used in the next step directly without further purification. HPLC-MS t$_R$=0.81 min (UV$_{254\ nm}$); mass calculated for formula C$_{14}$H$_{17}$N$_5$O 271.1, observed LCMS m/z 272.2 (M+H).

Step 5: Preparation of (1R,4R)-4-(7-(bis((2-(trimethylsilyl)ethoxy)methyl)amino)pyrazolo[1,5-a]pyrimidin-5-yl)-1-methoxycyclohexanecarbonitrile and (1S,4S)-4-(7-(bis((2-(trimethylsilyl)ethoxy)methyl)amino)pyrazolo[1,5-a]pyrimidin-5-yl)-1-methoxycyclohexanecarbonitrile

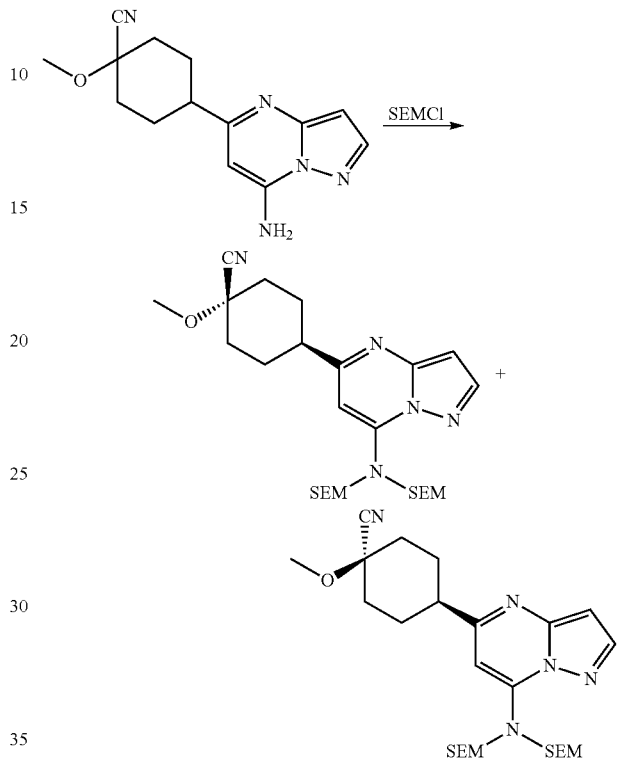

The crude compound from step 4 (~90 mmol) and DIEA (47 mL, 270 mmol) mixed in DCM (300 mL). To the mixture, SEMCl (45 g, 270 mmol) in DCM (100 mL) was added dropwise. After addition, the mixture was heated up to 50° C. and stirred for 6 h. After cooled to room temperature, NaHCO$_3$ (aq.) was added. The aqueous was extracted with EtOAc (100 mL×3). The combined organics was dried, concentrated and purified with column (silica gel, 0-30%) to give two isomers. Isomer 1, (13 g): HPLC-MS t$_R$=3.55 min (UV$_{254\ nm}$); mass calculated for formula C$_{26}$H$_{45}$N$_5$O$_3$Si$_2$ 531.3, observed LCMS m/z 532.3 (M+H). Isomer 2 (13 g): HPLC-MS t$_R$=3.60 min (UV$_{254\ nm}$); mass calculated for formula C$_{26}$H$_{45}$N$_5$O$_3$Si$_2$ 531.3, observed LCMS m/z 532.3 (M+H).

Step 6: Preparation of (1S,4S)-4-(7-(bis((2-(trimethylsilyl)ethoxy)methyl)amino)pyrazolo[1,5-a]pyrimidin-5-yl)-1-methoxycyclohexanecarboxylic acid

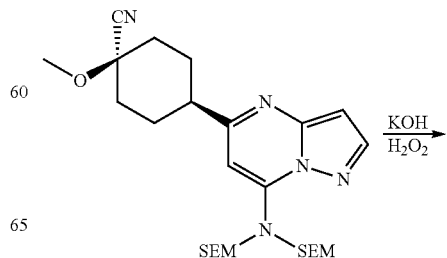

-continued

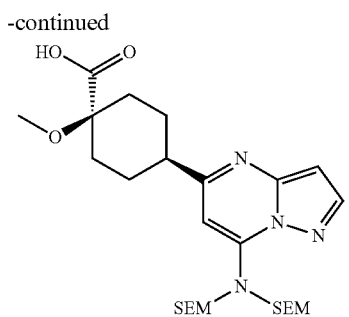

The cyano compound isomer 1 (13 g, 24.4 mmol) was dissolved in EtOH (50 mL) and KOH (20%, 30 mL) was added followed by $H_2O_2$ (30%, 3.0 mL). The resulting mixture was heated up to 100° C. and stirred overnight. After cooled to room temperature, the solvent was removed under reduced pressure. The aqueous pH value was adjusted to ~6 with 6N HCl and extracted with EtOAc (300 mL×3). The combined organics was dried over $Na_2SO_4$ and concentrated to give the crude product (9.7 g) and be used in the next step without further purification. HPLC-MS $t_R$=2.17 min ($UV_{254\ nm}$); mass calculated for formula $C_{26}H_{46}N_4O_5Si_2$ 550.3, observed LCMS m/z 551.3 (M+H).

Step 7: Preparation of (1S,4S)-methyl 4-(7-(bis((2-(trimethylsilyl)ethoxy)methyl)amino)pyrazolo[1,5-a]pyrimidin-5-yl)-1-methoxycyclohexanecarboxylate

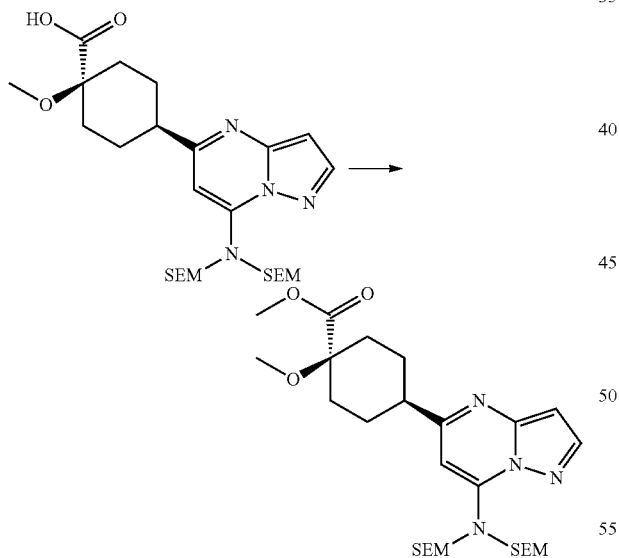

The carboxylic acid compound (9.7 g, 17.6 mmol) was dissolved in DCM (150 mL) and $TMSCHN_2$ (2.0 M in hexane, 24.4 mL) was added. The mixture was stirred at room temperature overnight and concentrated. The crude was purified with column (silica gel, 0-30% EtOAc/Hexane) to give the product (9.9 g, mixture of methyl ester and TMS-methyl ester). HPLC-MS $t_R$=2.38 min ($UV_{254\ nm}$); mass calculated for formula $C_{27}H_{48}N_4O_5Si_2$ 564.3, observed LCMS m/z 565.3 (M+H).

Step 8: Preparation of (1S,4S)-methyl 4-(7-(bis((2-(trimethylsilyl)ethoxy)methyl)amino)-3-iodopyrazolo[1,5-a]pyrimidin-5-yl)-1-methoxycyclohexanecarboxylate

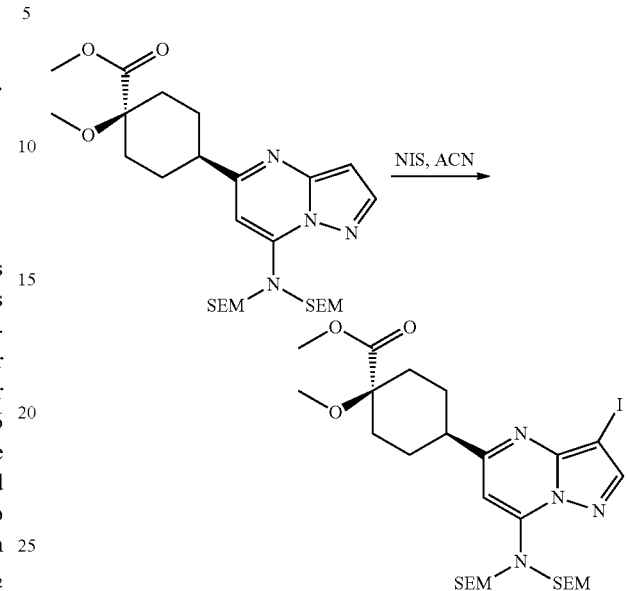

The iodo compound was prepared with the same condition described in example 1 Step 7. HPLC-MS $t_R$=2.81 min ($UV_{254\ nm}$); mass calculated for formula $C_{27}H_{47}IN_4O_5Si_2$ 690.2, observed LCMS m/z 691.2 (M+H).

Step 9: Preparation of (1S,4S)-methyl 4-(7-(bis((2-(trimethylsilyl)ethoxy)methyl)amino)-3-(6-phenylpyridin-3-yl)pyrazolo[1,5-a]pyrimidin-5-yl)-1-methoxycyclohexanecarboxylate

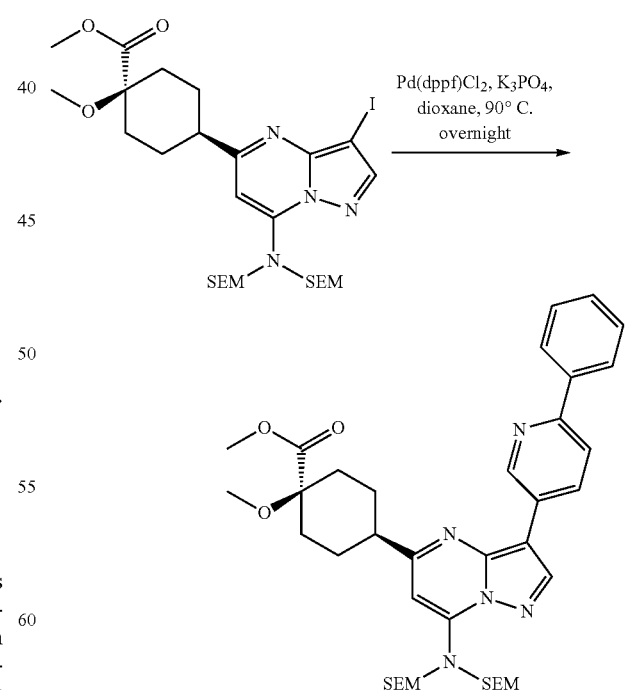

The 3-phenylpyridyl compound was prepared with the same condition described in example 1 Step 8. HPLC-MS $t_R$=2.77 min ($UV_{254\ nm}$); mass calculated for formula $C_{38}H_{55}N_5O_5Si_2$ 717.4, observed LCMS m/z 718.3 (M+H).

Step 10: Preparation of (1S,4S)-methyl 4-(7-(bis((2-(trimethylsilyl)ethoxy)methyl)amino)-6-bromo-3-(6-phenylpyridin-3-yl)pyrazolo[1,5-a]pyrimidin-5-yl)-1-methoxycyclohexanecarboxylate

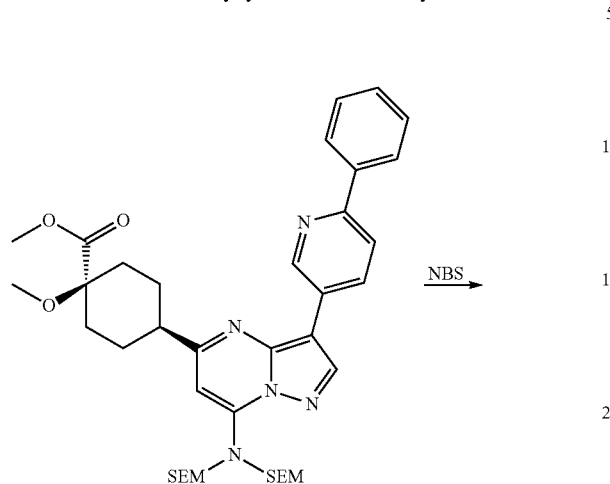

The bromo compound was prepared with the same condition described in example 1 step 10. HPLC-MS $t_R$=2.76 min (UV$_{254\ nm}$); mass calculated for formula $C_{38}H_{54}BrN_5O_5Si_2$ 795.3, observed LCMS m/z 796.2 (M+H).

Step 11: Preparation of (1S,4S)-methyl 4-(7-amino-6-bromo-3-(6-phenylpyridin-3-yl)pyrazolo[1,5-a]pyrimidin-5-yl)-1-methoxycyclohexanecarboxylate

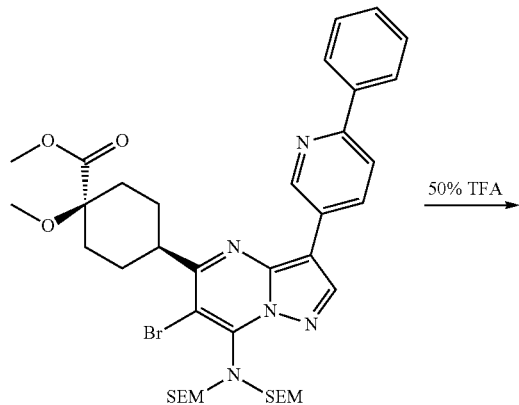

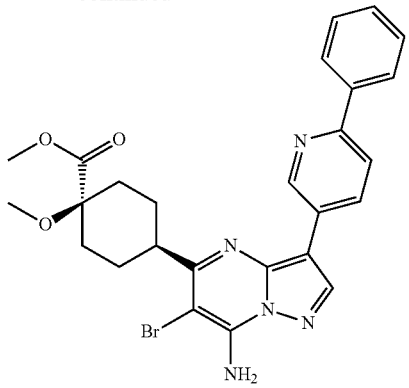

The bromo-compound was de-protected with the same condition described in example 1 Step 11. HPLC-MS $t_R$=2.17 min (UV$_{254\ nm}$); mass calculated for formula $C_{26}H_{26}BrN_5O_3$ 535.1, observed LCMS m/z 536.2 (M+H).

Step 12: Preparation of (1S,4S)-4-(7-amino-6-bromo-3-(6-phenylpyridin-3-yl)pyrazolo[1,5-a]pyrimidin-5-yl)-1-methoxycyclohexanecarboxylic acid (Compound 28)

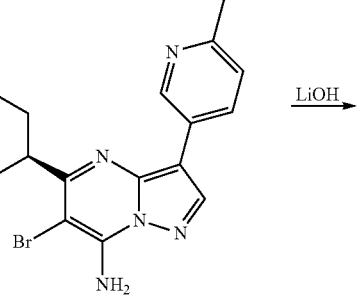

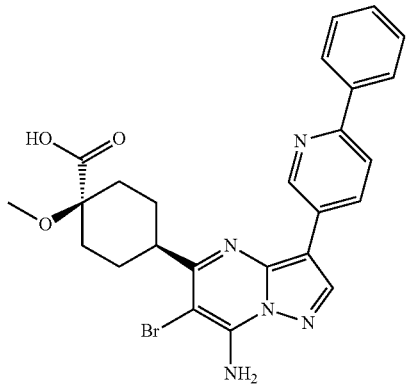 [SMILES: CO[C@]1(C(=O)O)CC[C@@H](c2nc3c(-c4ccc(-c5ccccc5)nc4)cnn3c(N)c2Br)CC1]

The ester were hydrolysized with the same condition described in example 3 Step 12. HPLC-MS $t_R$=1.42 min (UV$_{254\ nm}$); mass calculated for formula $C_{25}H_{24}BrN_5O_3$ 521.1, observed LCMS m/z 522.1 (M+H).

Example 8

By essentially the same procedure in Preparative Example 7, compounds in Table 3 can be prepared.

TABLE 3

| Example | Chemical name | Column 2 | Exact mass | MS m/z (M + H) | HPLC MS $t_R$ |
|---|---|---|---|---|---|
| 29 | (1R,4R)-4-(7-amino-6-bromo-3-(6-phenylpyridin-3-yl)pyrazolo[1,5-a]pyrimidin-5-yl)-1-methoxycyclohexanecarboxylic acid | | 521.1 | 522.2 | 1.51 |
| 30 | (1R,4R)-4-(7-amino-6-bromo-3-(1-phenyl-1H-pyrazol-4-yl)pyrazolo[1,5-a]pyrimidin-5-yl)-1-methoxycyclohexanecarboxylic acid | | 510.1 | 511.0 | 4.76 (10 min) |
| 31 | (1S,4S)-4-(7-amino-6-bromo-3-(1-phenyl-1H-pyrazol-4-yl)pyrazolo[1,5-a]pyrimidin-5-yl)-1-methoxycyclohexanecarboxylic acid | | 510.1 | 511.0 | 4.75 (10 min) |
| 32 | (1S,4S)-4-(7-amino-6-bromo-3-(6-fluoroquinolin-3-yl)pyrazolo[1,5-a]pyrimidin-5-yl)-1-methoxycyclohexanecarboxylic acid | | 513.1 | 514.2 | 1.59 |

TABLE 3-continued

| Example | Chemical name | Column 2 | Exact mass | MS m/z (M + H) | HPLC MS $t_R$ |
|---|---|---|---|---|---|
| 33 | (1R,4R)-4-(7-amino-6-bromo-3-(6-fluoroquinolin-3-yl)pyrazolo[1,5-a]pyrimidin-5-yl)-1-methoxycyclohexanecarboxylic acid | | 513.1 | 514.1 | 1.62 |

Example 9

Preparation of (1S,4S)-4-(6-acetyl-7-amino-3-(6-phenylpyridin-3-yl)pyrazolo[1,5-a]pyrimidin-5-yl)-1-methoxycyclohexanecarboxylic acid (Compound 34)

Step 1: Preparation of ethyl (1S,4S)-methyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-1-methoxycyclohexanecarboxylate

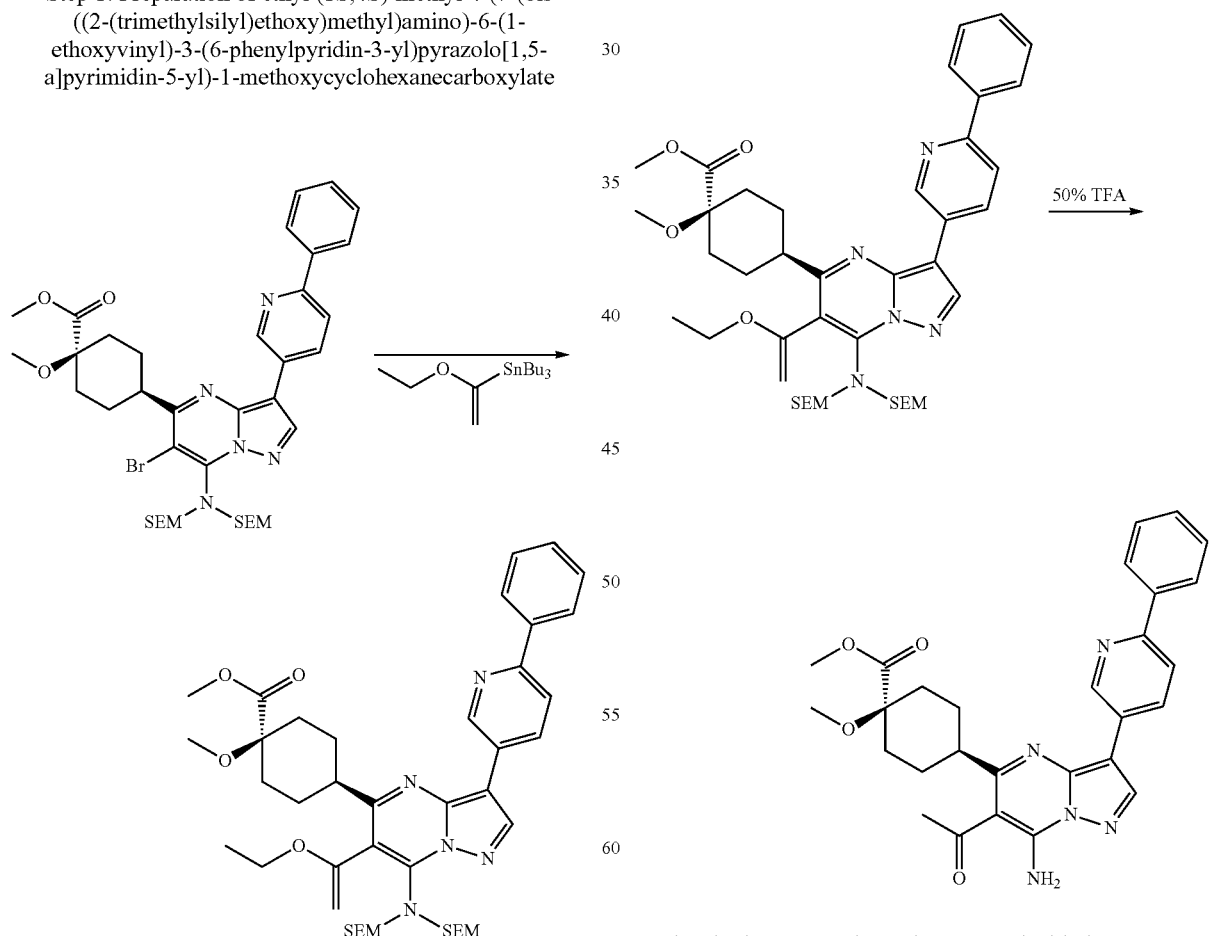

The Stille coupling reaction was performed with the same conditions described in example 3 Step 1. HPLC-MS $t_R$=3.11 min (UV$_{254\ nm}$); mass calculated for formula $C_{42}H_{61}N_5O_6Si_2$ 787.4, observed LCMS m/z 788.3 (M+H).

Step 2: Preparation of (1S,4S)-methyl 4-(6-acetyl-7-amino-3-(6-phenylpyridin-3-yl)pyrazolo[1,5-a]pyrimidin-5-yl)-1-methoxycyclohexanecarboxylate The vinyl-compound was de-protected with the same condition described in example 1 Step 11. HPLC-MS $t_R$=1.91 min (UV$_{254\ nm}$); mass calculated for formula $C_{28}H_{29}N_5O_4$ 499.2, observed LCMS m/z 500.2 (M+H).

Step 3: Preparation of (1S,4S)-4-(6-acetyl-7-amino-3-(6-phenylpyridin-3-yl)pyrazolo[1,5-a]pyrimidin-5-yl)-1-methoxycyclohexanecarboxylic acid (Compound 34)

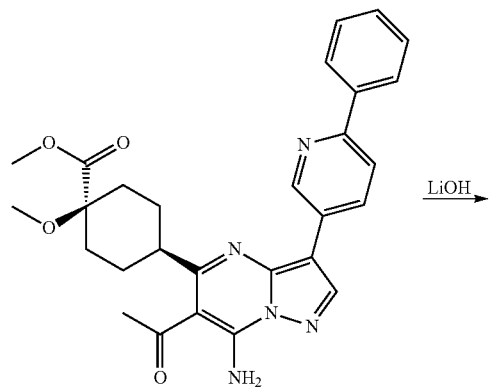

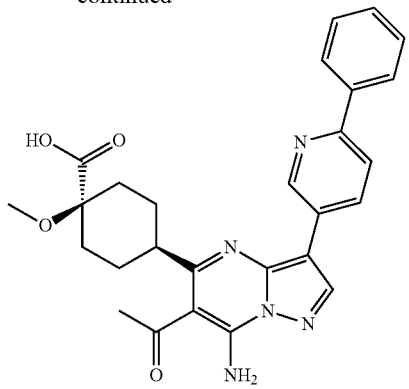

The carboxylic acid was prepared with the same hydrolysis condition described in example 1 Step 12. HPLC-MS $t_R$=1.40 min (UV$_{254\ nm}$); mass calculated for formula $C_{27}H_{27}N_5O_4$ 485.2, observed LCMS m/z 486.2 (M+H).

Example 10

By essentially the same procedure in Preparative Example 9, compounds in Column 2 of Table 4 can be prepared.

TABLE 4

| Example | Chemical name | Column 2 | Exact mass | MS m/z (M + H) | HPLC MS $t_R$ |
|---|---|---|---|---|---|
| 35 | (1R,4R)-4-(6-acetyl-7-amino-3-(6-phenylpyridin-3-yl)pyrazolo[1,5-a]pyrimidin-5-yl)-1-methoxycyclohexanecarboxylic acid | | 485.2 | 486.2 | 1.45 |
| 36 | (1R,4R)-4-(6-acetyl-7-amino-3-(1-phenyl-1H-pyrazol-4-yl)pyrazolo[1,5-a]pyrimidin-5-yl)-1-methoxycyclohexanecarboxylic acid | | 474.2 | 475.1 | 1.63 |

TABLE 4-continued

| Example | Chemical name | Column 2 | Exact mass | MS m/z (M + H) | HPLC MS $t_R$ |
|---|---|---|---|---|---|
| 37 | (1S,4S)-4-(6-acetyl-7-amino-3-(1-phenyl-1H-pyrazol-4-yl)pyrazolo[1,5-a]pyrimidin-5-yl)-1-methoxycyclohexane-carboxylic acid | | 474.2 | 475.1 | 1.62 |
| 38 | (1S,4S)-4-(6-acetyl-7-amino-3-(6-fluoroquinolin-3-yl)pyrazolo[1,5-a]pyrimidin-5-yl)-1-methoxycyclohexane-carboxylic acid | | 477.2 | 478.2 | 1.58 |
| 39 | (1R,4R)-4-(6-acetyl-7-amino-3-(6-fluoroquinolin-3-yl)pyrazolo[1,5-a]pyrimidin-5-yl)-1-methoxycyclohexane-carboxylic acid | | 477.2 | 478.2 | 1.59 |

Example 11

Preparation of (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboxylic acid (Compound 40)

Step 1: Preparation of ethyl 4-methylenecyclohexanecarboxylate

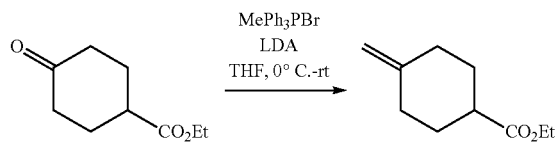

To a suspension of MePh₃PBr (37.1 g, 104 mmol) in THF (500 mL) at 0° C. was added slowly LDA (1.2 eq) over 1 h. The resulting orange solution was stirred for 30 min before ethyl 4-oxocyclohexanecarboxylate (16.1 g, 94.4 mmol) was added dropwise. The resulting suspension was warmed to rt and stirred overnight. A saturated NH₄Cl (aq) was added and THF was removed. The aqueous residue was extracted with EtOAc (100 ml×3). The combined organic layers were washed with brine, dried over Na₂SO₄ and concentrated. The residue was purified by passing through a short silica gel plug (hexanes/EtOAc 7:1). After being concentrated, ethyl 4-methylenecyclohexanecarboxylate was obtained as a pale yellow oil (12.1 g).

Step 2: Preparation of 3-(4-methylenecyclohexyl)-3-oxopropanenitrile

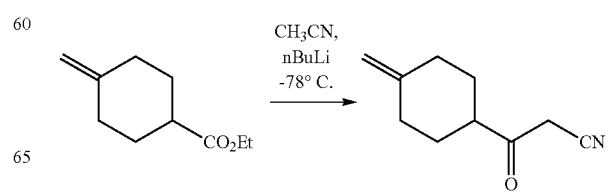

CH₃CN (2.55 mL, 48.8 mmol. 2.2 eq) was added dropwise to a solution of nBuLi (48.8 mmol) in 180 mL of THF at −78° C. After stirring for 1 h at −78° C., a solution of ethyl 4-methylenecyclohexanecarboxylate (3.73 g, 22.2 mmol) in 20 mL of THF was added dropwise and the resulting reaction mixture (turned into nearly clear solution after addition) was stirred at −78° C. for 1 h, then slowly warmed to 0° C. before being quenched with sat. NH₄Cl. THF was removed and the residue was diluted with EtOAc. The organic layer was separated and washed with brine, dried over Na₂SO₄, and concentrated. The crude product was purified by a SiO₂ column (0-30% EtOAc/Hexanes, R_f=0.2 in 20% EtOAc) to afford 3-(4-methylenecyclohexyl)-3-oxopropanenitrile as a colorless oil (3.25 g).

Step 3: Preparation of 5-(4-methylenecyclohexyl)-N,N-bis((2-(trimethylsilyl)ethoxy)methyl)pyrazolo[1,5-a]pyrimidin-7-amine

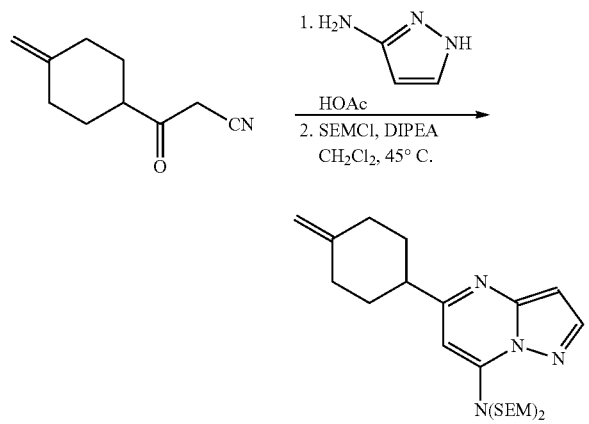

A mixture of 3-aminopyrazole (1.82 g, 21.9 mmol) and 3-(4-methylenecyclohexyl)-3-oxopropanenitrile (3.25 g, 19.9 mmol) in HOAc (10 mL) was heated at 100° C. in a sealed tube overnight (18 h). LCMS showed very good conversion to the desired product (229) and no SM (164) left. TLC also showed no SM left. After cooling to rt, all the volatiles were removed under reduced pressure to afford a light brown oil, which was used without further purification.

To a slurry of above crude material in CH₂Cl₂ (100 mL) was added SEMCl (14.0 mL, 79.6 mmol), followed by DIPEA (27.7 mL, 159 mmol). The resulting reaction mixture was stirred at 45° C. for 1 h. LCMS showed nearly complete conversion. After cooling to rt, all the volatiles were removed under reduced pressure. The residue was diluted with EtOAc, washed with H₂O and brine, and concentrated. The crude product was purified by a SiO₂ column (0-15% EtOAc/Hexane, R_f=0.65 in 20% EtOAc) to afford 5-(4-methylenecyclohexyl)-N,N-bis((2-(trimethylsilyl)ethoxy)methyl)pyrazolo[1,5-a]pyrimidin-7-amine as a pale yellow oil (10.3 g). HPLC-MS T_R=3.12 min (UV 254 nm, 5 min method); mass calculated for formula C₂₅H₄₄N₄O₂Si₂ 488.3, observed LCMS m/z 489.3 (M+H).

Step 4: Preparation of 4-(7-(bis((2-(trimethylsilyl)ethoxy)methyl)amino)pyrazolo[1,5-a]pyrimidin-5-yl)cyclohexanone

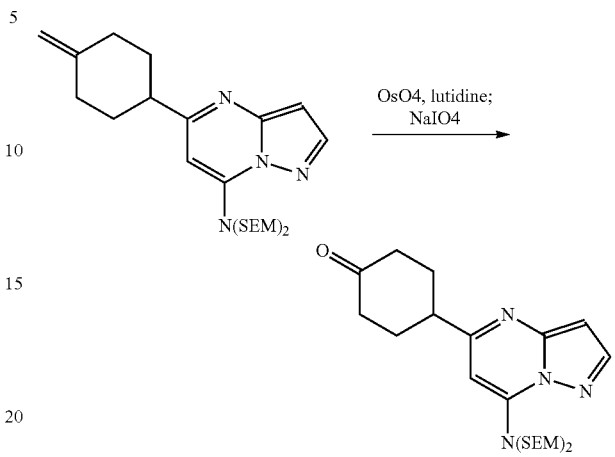

To 5-(4-methylenecyclohexyl)-N,N-bis((2-(trimethylsilyl)ethoxy)methyl)pyrazolo[1,5-a]pyrimidin-7-amine (4.60 g, 9.41 mmol) in dioxane (50 mL) was added OsO₄ (2.5 w % in tBuOH, 5 mol %), 2,6-Lutidine (4.37 mL, 37.6 mmol) and H₂O (10 mL). The resulting mixture was stirred at rt for 20 min, then NaIO₄ (8.05 g, 37.6 mmol) was added and the reaction mixture was stirred at rt overnight. LCMS showed very good conversion to the desired product (491). Na₂S₂O₃ (sat.) was added and the mixture was stirred for 10 min. Dioxane was removed and the residue was extracted with EtOAc, washed with H₂O and brine, dried over Na₂SO₄, and concentrated. The crude product was purified by a SiO₂ column (0-40% EtOAc/Hexanes, R_f=0.15 in 20% EtOAc) to afford 4-(7-(bis((2-(trimethylsilyl)ethoxy)methyl)amino)pyrazolo[1,5-a]pyrimidin-5-yl)cyclohexanone as a colorless oil (3.37 g). HPLC-MS T_R=2.84 min (UV 254 nm, 5 min method); mass calculated for formula C₂₄H₄₂N₄O₃Si₂ 490.3, observed LCMS m/z 491.2 (M+H).

Step 5: Preparation of 2-methoxyethyl 4-(7-(bis((2-(trimethylsilyl)ethoxy)methyl)amino)pyrazolo[1,5-a]pyrimidin-5-yl)-1-(2-methoxyethoxy)cyclohexanecarboxylate

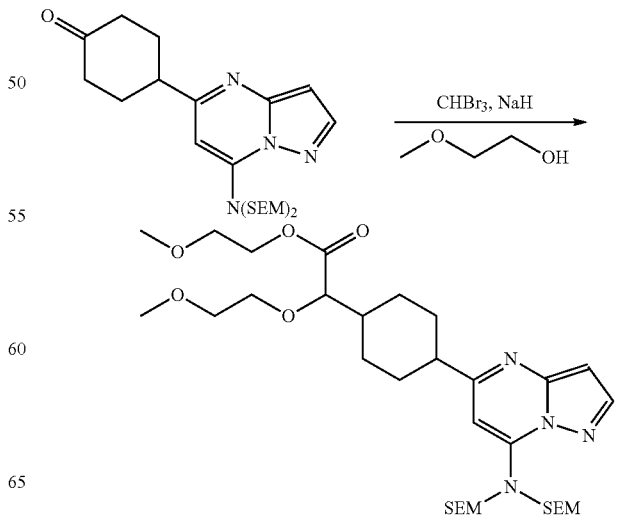

To a mixture of 4-(7-((bis((2-(trimethylsilyl)ethoxy)methyl)amino)pyrazolo[1,5-a]pyrimidin-5-yl)cyclohexanone (10.0 g, 20.4 mmol) and tribromomethane (7.8 mL, 204 mmol, 10 eq) in 80 mL of 2-methoxyethanol at −20° C. was added a preformed solution of sodium 2-methoxyethoxide (added NaH (9 eq) in portions carefully to 120 mL of cooled and stirred 2-methoxyethanol) in 2-methoxyethanol dropwise during 1.5 h. The resulting reaction mixture was stirred vigorously while slowly warming to rt and kept for 1 h. The reaction mixture was diluted with 800 mL of EtOAc, washed with water and brine, dried over $Na_2SO_4$, and concentrated. Purified by a $SiO_2$ column (0-50% EtOAc/Hexanes, $R_f$=0.4 in 50% EtOAc) to afford 2-methoxyethyl 4-(7-(bis((2-(trimethylsilyl)ethoxy)methyl)amino)pyrazolo[1,5-a]pyrimidin-5-yl)-1-(2-methoxyethoxy)cyclohexanecarboxylate as a light brown oil (3.48 g). HPLC-MS $T_R$=2.98 min (UV 254 nm, 5 min method); mass calculated for formula $C_{31}H_{56}N_4O_7Si_2$ 652.4, observed LCMS m/z 653.2 (M+H).

Step 6: Preparation of 2-methoxyethyl 4-(7-(bis((2-(trimethylsilyl)ethoxy)methyl)amino)-3-iodopyrazolo[1,5-a]pyrimidin-5-yl)-1-(2-methoxyethoxy)cyclohexanecarboxylate

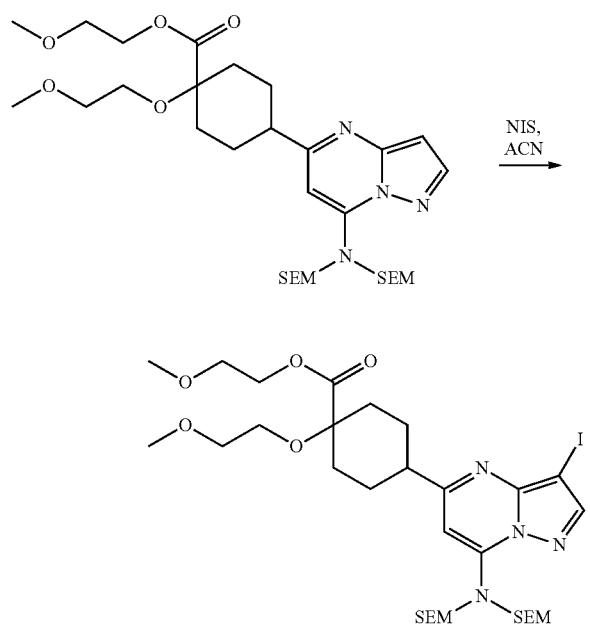 [SMILES: COCCOC(=O)C1(OCCOC)CCC(c2cc(N(COCC[Si](C)(C)C)COCC[Si](C)(C)C)n3nccc3n2)CC1 ; COCCOC(=O)C1(OCCOC)CCC(c2cc(N(COCC[Si](C)(C)C)COCC[Si](C)(C)C)n3ncc(I)c3n2)CC1]

To a solution of 4-(7-(bis((2-(trimethylsilyl)ethoxy)methyl)amino)pyrazolo[1,5-a]pyrimidin-5-yl)-1-(2-methoxyethoxy)cyclohexanecarboxylate (3.21 g, 4.92 mmol) in $CH_3CN$ (50 mL) was added NIS (1.1 eq). The resulting solution was stirred at rt for 1 h. TLC showed complete consumption of SM. The reaction mixture was evaporated and directly purified by a $SiO_2$ column (0-40% EtOAc/Hexanes, $R_f$=0.65 in 50% EtOAc) to afford 2-methoxyethyl 4-(7-(bis((2-(trimethylsilyl)ethoxy)methyl)amino)-3-iodopyrazolo[1,5-a]pyrimidin-5-yl)-1-(2-methoxyethoxy)cyclohexanecarboxylate as a pale yellow oil (3.83 g).

Step 7: Preparation of 2-methoxyethyl 4-(7-(bis((2-(trimethylsilyl)ethoxy)methyl)amino)-3-(1-phenyl-1H-pyrazol-4-yl)pyrazolo[1,5-a]pyrimidin-5-yl)-1-(2-methoxyethoxy)cyclohexanecarboxylate

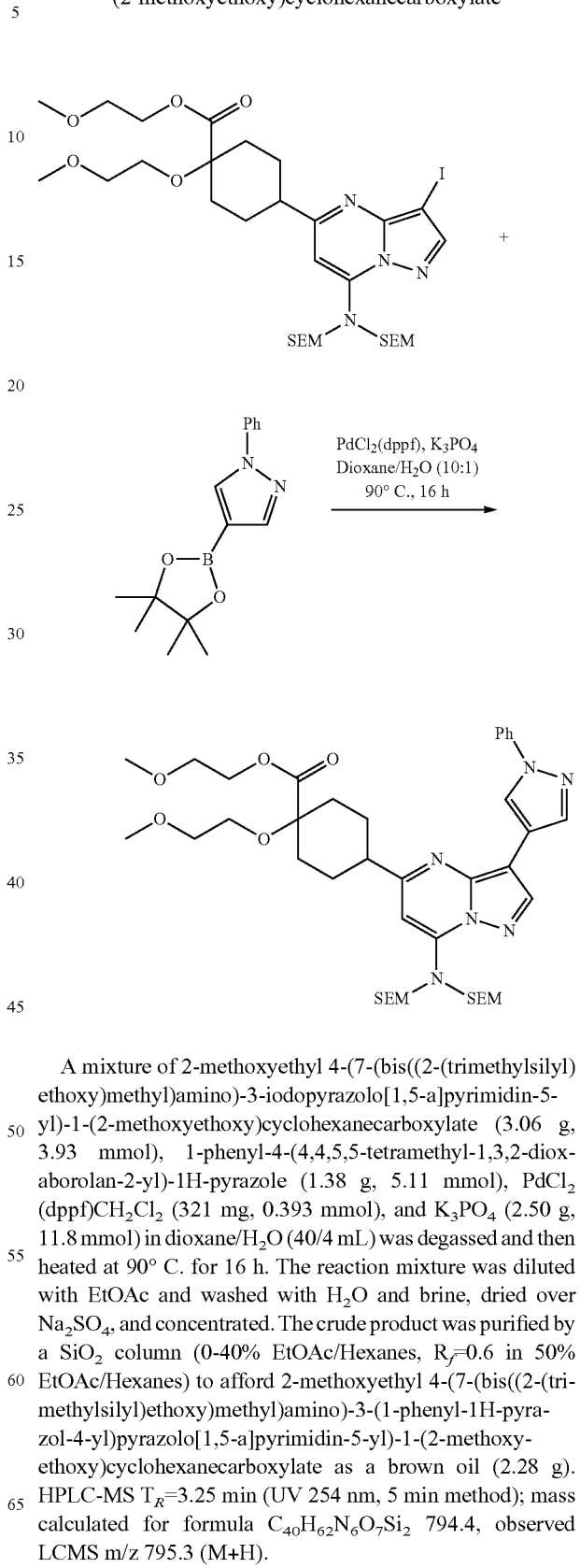

A mixture of 2-methoxyethyl 4-(7-(bis((2-(trimethylsilyl)ethoxy)methyl)amino)-3-iodopyrazolo[1,5-a]pyrimidin-5-yl)-1-(2-methoxyethoxy)cyclohexanecarboxylate (3.06 g, 3.93 mmol), 1-phenyl-4-(4,4,5,5-tetramethyl-1,3,2-dioxaborolan-2-yl)-1H-pyrazole (1.38 g, 5.11 mmol), $PdCl_2$(dppf)$CH_2Cl_2$ (321 mg, 0.393 mmol), and $K_3PO_4$ (2.50 g, 11.8 mmol) in dioxane/$H_2O$ (40/4 mL) was degassed and then heated at 90° C. for 16 h. The reaction mixture was diluted with EtOAc and washed with $H_2O$ and brine, dried over $Na_2SO_4$, and concentrated. The crude product was purified by a $SiO_2$ column (0-40% EtOAc/Hexanes, $R_f$=0.6 in 50% EtOAc/Hexanes) to afford 2-methoxyethyl 4-(7-(bis((2-(trimethylsilyl)ethoxy)methyl)amino)-3-(1-phenyl-1H-pyrazol-4-yl)pyrazolo[1,5-a]pyrimidin-5-yl)-1-(2-methoxyethoxy)cyclohexanecarboxylate as a brown oil (2.28 g). HPLC-MS $T_R$=3.25 min (UV 254 nm, 5 min method); mass calculated for formula $C_{40}H_{62}N_6O_7Si_2$ 794.4, observed LCMS m/z 795.3 (M+H).

Step 8: Preparation of 2-methoxyethyl 4-(7-(bis((2-(trimethylsilyl)ethoxy)methyl)amino)-6-bromo-3-(1-phenyl-1H-pyrazol-4-yl)pyrazolo[1,5-a]pyrimidin-5-yl)-1-(2-methoxyethoxy)cyclohexanecarboxylate

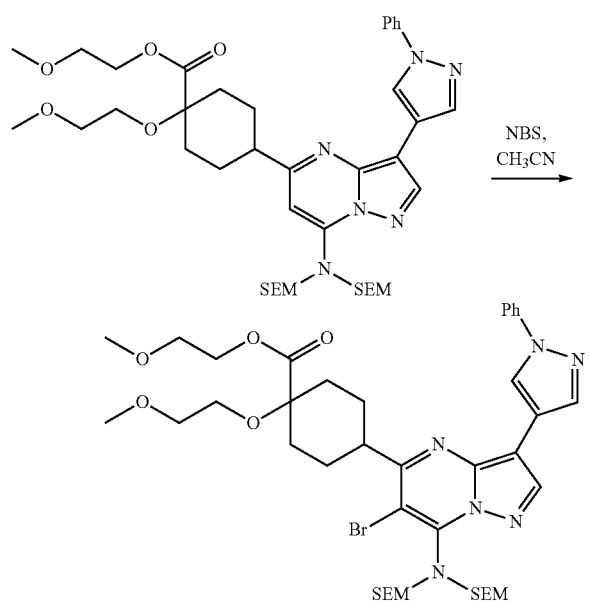

To a solution of 2-methoxyethyl 4-(7-(bis((2-(trimethylsilyl)ethoxy)methyl)amino)-3-(1-phenyl-1H-pyrazol-4-yl)pyrazolo[1,5-a]pyrimidin-5-yl)-1-(2-methoxyethoxy)cyclohexanecarboxylate (2.28 g, 2.87 mmol) in CH$_3$CN (50 mL) was added NBS (511 mg, 2.87 mmol) and stirred at rt for 30 min. Both TLC and LCMS showed complete conversion. All the volatiles were removed under reduced pressure and the residue was purified by a SiO$_2$ column (0-30%, EtOAc/Hexanes, R$_f$=0.65 in 50% EtOAc) to afford 2-methoxyethyl 4-(7-(bis((2-(trimethylsilyl)ethoxy)methyl)amino)-6-bromo-3-(1-phenyl-1H-pyrazol-4-yl)pyrazolo[1,5-a]pyrimidin-5-yl)-1-(2-methoxyethoxy)cyclohexanecarboxylate as a yellow oil (2.50 g). HPLC-MS T$_R$=1.99 min (UV 254 nm, 3 min method); mass calculated for formula C$_{40}$H$_{61}$BrN$_6$O$_7$Si$_2$ 872.3, observed LCMS m/z 873.3 (M+H).

Step 9: Preparation of 2-methoxyethyl 4-(7-(bis((2-(trimethylsilyl)ethoxy)methyl)amino)-6-(methylthio)-3-(1-phenyl-1H-pyrazol-4-yl)pyrazolo[1,5-a]pyrimidin-5-yl)-1-(2-methoxyethoxy)cyclohexanecarboxylate

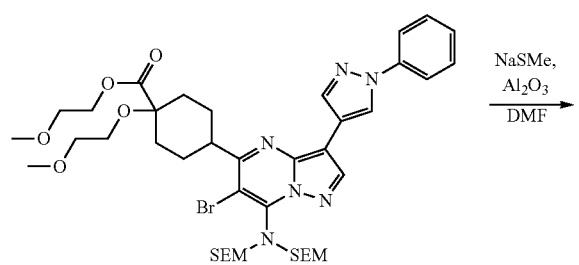

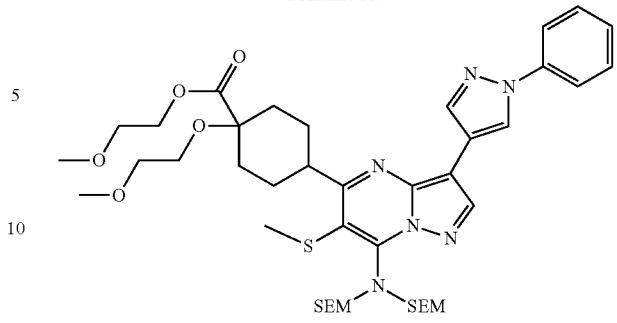

The bromo compound (437 mg, 0.5 mmol), NaSMe (175 mg, 2.5 mmol) and Al$_2$O$_3$ (activated, basic) (1.02 g, 10 mmol) were mixed in DMF (5 mL). The mixture was heated up from 100 to 130° C. and stirred at 130° C. for 2 h. Then the reaction was cooled to room temperature, diluted with EtOAc and filtered through celite. The crude was used in the next step directly without purification. HPLC-MS t$_R$=3.38 min (UV$_{254\ nm}$); mass calculated for formula C$_{41}$H$_{64}$N$_6$O$_7$SSi$_2$ 840.4, observed LCMS m/z 841.2 (M+H).

Step 10: Preparation of 2-methoxyethyl 4-(7-amino-6-(methylthio)-3-(1-phenyl-1H-pyrazol-4-yl)pyrazolo[1,5-a]pyrimidin-5-yl)-1-(2-methoxyethoxy)cyclohexanecarboxylate

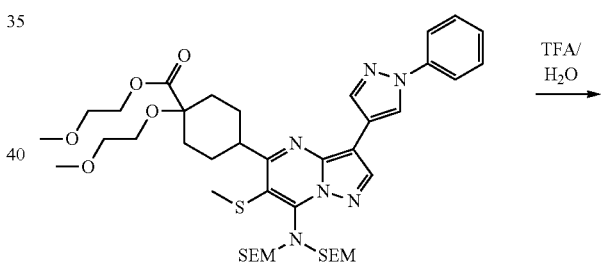

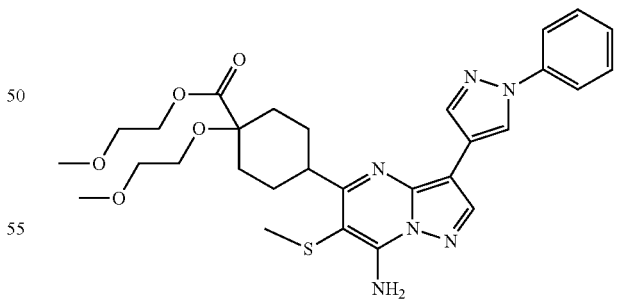

The crude of step 9 was treated with 50% TFA/H$_2$O (5 mL) and stirred at room temperature for 2 h. The mixture was concentrated and treated with NaHCO$_3$ (aq). The solid was collected by filtration with water and dried under air. The crude was used in the next step directly. HPLC-MS t$_R$=2.37 min (UV$_{254\ nm}$); mass calculated for formula C$_{29}$H$_{36}$N$_6$O$_5$S 580.2, observed LCMS m/z 581.2 (M+H).

Step 11: Preparation of (1R,4R)-4-(7-amino-6-(methylthio)-3-(1-phenyl-1H-pyrazol-4-yl)pyrazolo[1,5-a]pyrimidin-5-yl)-1-(2-methoxyethoxy)cyclohexanecarboxylic acid and (1S,4R)-4-(7-amino-6-(methylthio)-3-(1-phenyl-1H-pyrazol-4-yl)pyrazolo[1,5-a]pyrimidin-5-yl)-1-(2-methoxyethoxy)cyclohexanecarboxylic acid

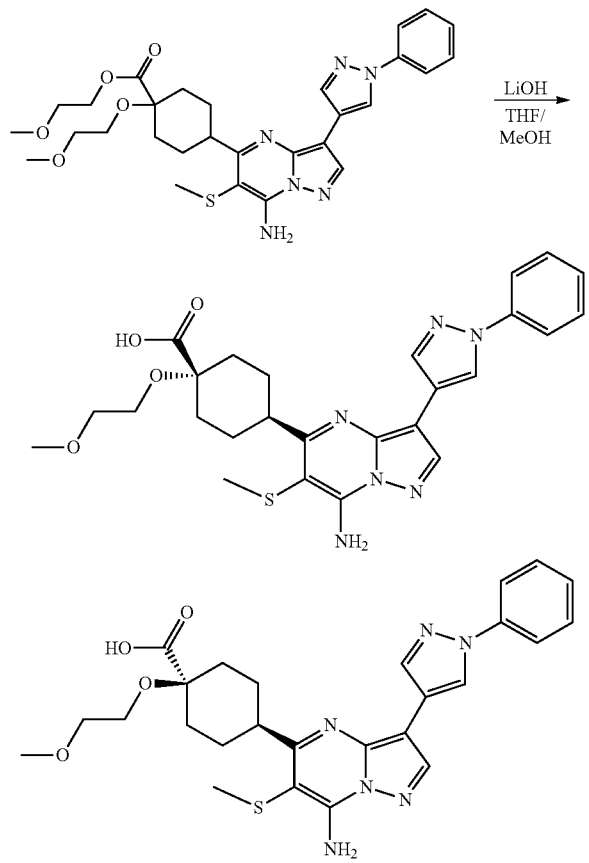

The crude from step 10 was dissolved in a mixture of THF/MeOH (6 mL/3 mL) and LiOH (1N, 3 mL) was added. The mixture was stirred at 50° C. overnight. The solvent was removed and water (5 mL) was added. The pH was adjusted to 6 with HCl (1N). The solid was collected and purified with Prep-LC and the product isomer 1 (23 mg) and isomer 2 (137 mg) was obtained. Isomer 1: HPLC-MS $t_R$=2.00 min (UV$_{254\ nm}$); mass calculated for formula $C_{26}H_{30}N_6O_4S$ 522.2, observed LCMS m/z 523.2 (M+H). Isomer 2: HPLC-MS $t_R$=2.09 min (UV$_{254\ nm}$); mass calculated for formula $C_{26}H_{30}N_6O_4S$ 522.2, observed LCMS m/z 523.2 (M+H).

Step 12: Preparation of (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboxylic acid

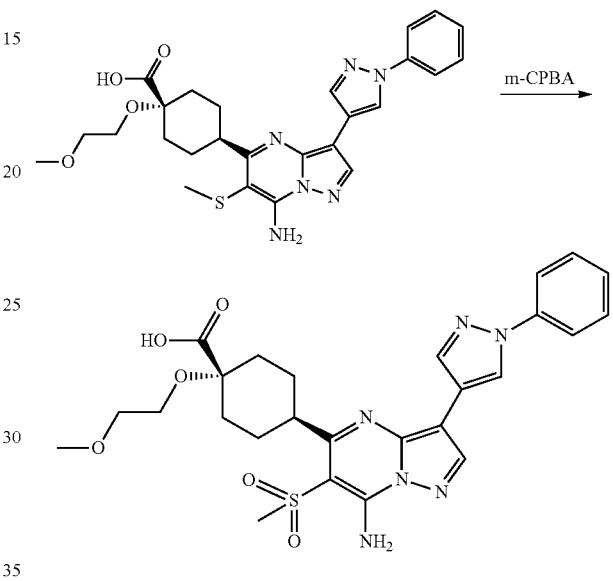

The methylsulfide (isomer 2 from step 11) (137 mg, 0.26 mmol) was dissolved in acetone/H$_2$O (10 mL/2 mL) and m-CPBA (110 mg, 70-75%) was added. The mixture was stirred at room temperature overnight. After concentration, the crude was purified with HPLC and the pure final compound was obtained. HPLC-MS $t_R$=1.79 min (UV$_{254\ nm}$); mass calculated for formula $C_{26}H_{30}N_6O_6S$ 554.2, observed LCMS m/z 555.1 (M+H).

Example 12

By essentially the same procedure in Preparative Example 11, compounds in Column 2 of Table 5 can be prepared.

TABLE 5

| Example | Chemical name | Column 2 | Exact mass | MS m/z (M + H) | HPLC MS $t_R$ |
|---------|---------------|----------|------------|----------------|---------------|
| 41 | (1S,4S)-4-(7-amino-6-(methylsulfonyl)-3-(1-phenyl-1H-pyrazol-4-yl)pyrazolo[1,5-a]pyrimidin-5-yl)-1-(2-methoxyethoxy)-cyclohexanecarboxylic acid | | 554.2 | 555.1 | 1.77 |

TABLE 5-continued

| Example | Chemical name | Exact mass | MS m/z (M + H) | HPLC MS $t_R$ |
|---|---|---|---|---|
| 42 | (1R,4R)-4-(7-amino-3-(6-(1-methyl-1H-pyrazol-3-yl)pyridin-3-yl)-6-(methylsulfonyl)-pyrazolo[1,5-a]-pyrimidin-5-yl)-1-(2-methoxyethoxy)-cyclohexanecarboxylic acid | 569.2 | 570.0 | 1.02 |
| 43 | (1R,4R)-4-(7-amino-3-(1-(4-fluorophenyl)-1H-pyrazol-4-yl)-6-(methylsulfonyl)-pyrazolo[1,5-a]-pyrimidin-5-yl)-1-(2-methoxyethoxy)-cyclohexanecarboxylic acid | 572.2 | 573.0 | 4.82 (10 min) |
| 44 | (1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexanecarboxylic acid | 565.2 | 566.1 | 1.15 |
| 45 | 5-(7-amino-5-((1R,4R)-4-carboxy-4-(2-methoxyethoxy)cyclohexyl)-6-(methylsulfonyl)-pyrazolo[1,5-a]pyrimidin-3-yl)-2-(1-methyl-1H-pyrazol-3-yl)pyridine 1-oxide | 585.2 | 586.2 | 0.88 |

TABLE 5-continued

| Example | Chemical name | Column 2 | Exact mass | MS m/z (M + H) | HPLC MS $t_R$ |
|---------|---------------|----------|------------|----------------|---------------|
| 46 | (1R,4R)-4-(7-amino-6-(methylsulfonyl)-3-(2-phenylpyrimidin-5-yl)pyrazolo[1,5-a]pyrimidin-5-yl)-1-(2-methoxyethoxy)cyclohexanecarboxylic acid | | 566.2 | 567.2 | 1.01 |
| 47 | (1R,4R)-4-(7-amino-6-(methylsulfonyl)-3-(6-(thiazol-2-yl)pyridin-3-yl)pyrazolo[1,5-a]pyrimidin-5-yl)-1-(2-methoxyethoxy)cyclohexanecarboxylic acid | | 572.2 | 573.2 | 1.03 |
| 48 | (1R,4R)-4-(7-amino-3-(6-(3-fluoro-4-hydroxyphenyl)pyridin-3-yl)-6-(methylsulfonyl)-pyrazolo[1,5-a]-pyrimidin-5-yl)-1-(2-methoxyethoxy)-cyclohexanecarboxylic acid | | 599.2 | 600.1 | 0.97 |
| 49 | (1R,4R)-4-(7-amino-3-(2-(1-methyl-1H-pyrazol-3-yl)pyrimidin-5-yl)-6-(methylsulfonyl)-pyrazolo[1,5-a]-pyrimidin-5-yl)-1-(2-methoxyethoxy)-cyclohexanecarboxylic acid | | 570.2 | 571.1 | 0.93 |

TABLE 5-continued

| Example | Chemical name | Column 2 | Exact mass | MS m/z (M + H) | HPLC MS $t_R$ |
|---------|---------------|----------|------------|----------------|---------------|
| 50 | (1R,4R)-4-(3-(2,2'-bipyridin-5-yl)-7-amino-6-(methylsulfonyl)-pyrazolo[1,5-a]-pyrimidin-5-yl)-1-(2-methoxyethoxy)-cyclohexanecarboxylic acid | | 566.2 | 567.3 | 0.86 |
| 51 | (1R,4R)-4-(7-amino-6-(methylsulfonyl)-3-(2-(5-methylthiazol-2-yl)pyrimidin-5-yl)pyrazolo[1,5-a]pyrimidin-5-yl)-1-(2-methoxyethoxy)cyclohexanecarboxylic acid | | 587.2 | 588.3 | 1.08 |
| 52 | (1R,4R)-4-(7-amino-3-(6-fluoroquinolin-3-yl)-6-(methylsulfonyl)-pyrazolo[1,5-a]-pyrimidin-5-yl)-1-(2-methoxyethoxy)-cyclohexanecarboxylic acid | | 557.2 | 558.3 | 1.74 |

Example 13

Preparation of (1R,4R)-4-(7-amino-6-(methylsulfonyl)-3-(1-(4-(methylsulfonyl)phenyl)-1H-pyrazol-4-yl)pyrazolo[1,5-a]pyrimidin-5-yl)-1-(2-methoxyethoxy)cyclohexanecarboxylic acid (Compound 53)

Step 1: Preparation of (1R,4R)-2-methoxyethyl 4-(7-(bis((2-(trimethylsilyl)ethoxy)methyl)amino)-3-(1-(4-fluorophenyl)-1H-pyrazol-4-yl)pyrazolo[1,5-a]pyrimidin-5-yl)-1-(2-methoxyethoxy)cyclohexanecarboxylate

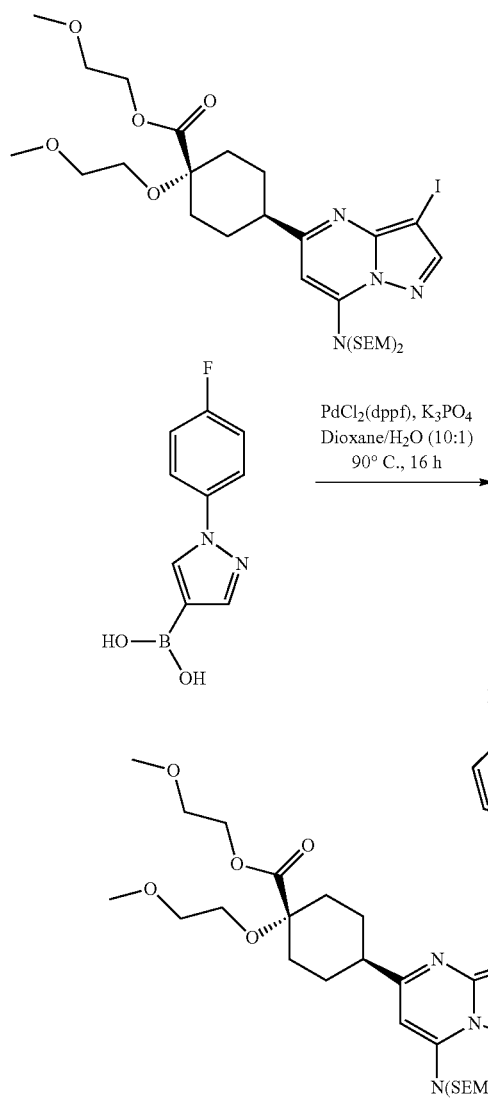

A mixture of (1R,4R)-2-methoxyethyl 4-(7-(bis((2-(trimethylsilyl)ethoxy)methyl)amino)-3-iodopyrazolo[1,5-a]pyrimidin-5-yl)-1-(2-methoxyethoxy)cyclohexanecarboxylate (800 mg, 1.03 mmol), 1-(4-fluorophenyl)-1H-pyrazol-4-ylboronic acid (276 mg, 1.34 mmol), $PdCl_2(dppf)CH_2Cl_2$ (84.1 mg, 0.103 mmol), and $K_3PO_4$ (656 mg, 3.09 mmol) in dioxane/$H_2O$ (10/1 mL) was degassed and then heated at 90° C. for 16 h. The reaction mixture was diluted with EtOAc and washed with $H_2O$ and brine, dried over $Na_2SO_4$, and concentrated. The crude product was purified by a $SiO_2$ column (0-30% EtOAc/Hexanes, $R_f$=0.65 in 50% EtOAc/Hexanes) to afford (1R,4R)-2-methoxyethyl 4-(7-(bis((2-(trimethylsilyl)ethoxy)methyl)amino)-3-(1-(4-fluorophenyl)-1H-pyrazol-4-yl)pyrazolo[1,5-a]pyrimidin-5-yl)-1-(2-methoxyethoxy)cyclohexanecarboxylate as a pale yellow oil (607 mg). HPLC-MS $T_R$=3.22 min (UV 254 nm, 10 min method); mass calculated for formula $C_{40}H_{61}FN_6O_7Si_2$ 812.4, observed LCMS m/z 813.3 (M+H).

Step 2: Preparation of (1R,4R)-2-methoxyethyl 4-(7-(bis((2-(trimethylsilyl)ethoxy)methyl)amino)-6-bromo-3-(1-(4-fluorophenyl)-1H-pyrazol-4-yl)pyrazolo[1,5-a]pyrimidin-5-yl)-1-(2-methoxyethoxy)cyclohexanecarboxylate

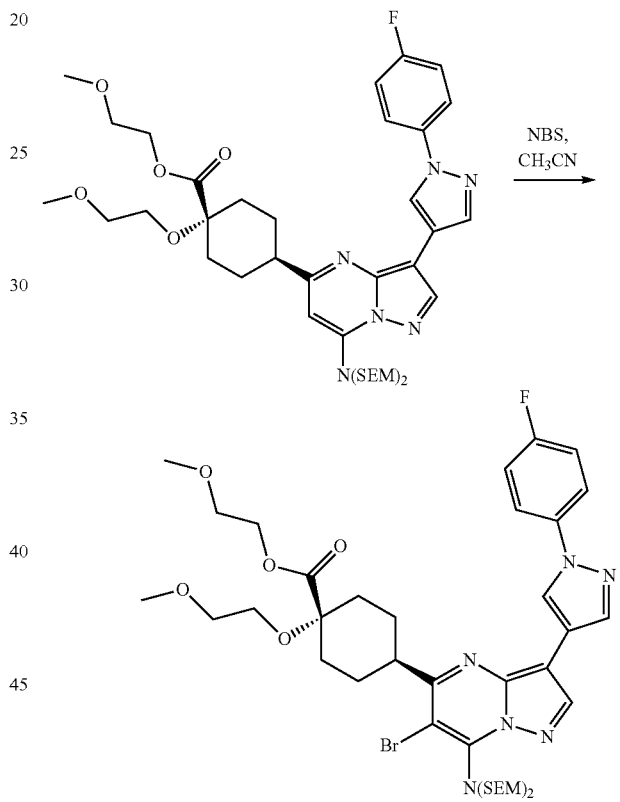

To a solution of (1R,4R)-2-methoxyethyl 4-(7-(bis((2-(trimethylsilyl)ethoxy)methyl)amino)-3-(1-(4-fluorophenyl)-1H-pyrazol-4-yl)pyrazolo[1,5-a]pyrimidin-5-yl)-1-(2-methoxyethoxy)cyclohexanecarboxylate (607 mg, 0.746 mmol) in $CH_3CN$ (8 mL) was added NBS (133 mg, 0.746 mmol) and stirred at rt for 30 min. TLC showed complete conversion. All the volatiles were removed under reduced pressure and the residue was purified by a $SiO_2$ column (0-40% EtOAc/Hexanes, $R_f$=0.75 in 50% EtOAc) to afford (1R,4R)-2-methoxyethyl 4-(7-(bis((2-(trimethylsilyl)ethoxy)methyl)amino)-6-bromo-3-(1-(4-fluorophenyl)-1H-pyrazol-4-yl)pyrazolo[1,5-a]pyrimidin-5-yl)-1-(2-methoxyethoxy)cyclohexanecarboxylate as a yellow oil (423 mg). HPLC-MS $T_R$=3.39 min (UV 254 nm, 5 min method); mass calculated for formula $C_{40}H_{60}BrFN_6O_7Si_2$ 890.3, observed LCMS m/z 891.1 (M+H).

Step 3: Preparation of (1R,4R)-4-(7-amino-6-bromo-3-(1-(4-fluorophenyl)-1H-pyrazol-4-yl)pyrazolo[1,5-a]pyrimidin-5-yl)-1-(2-methoxyethoxy)cyclohexanecarboxylic acid

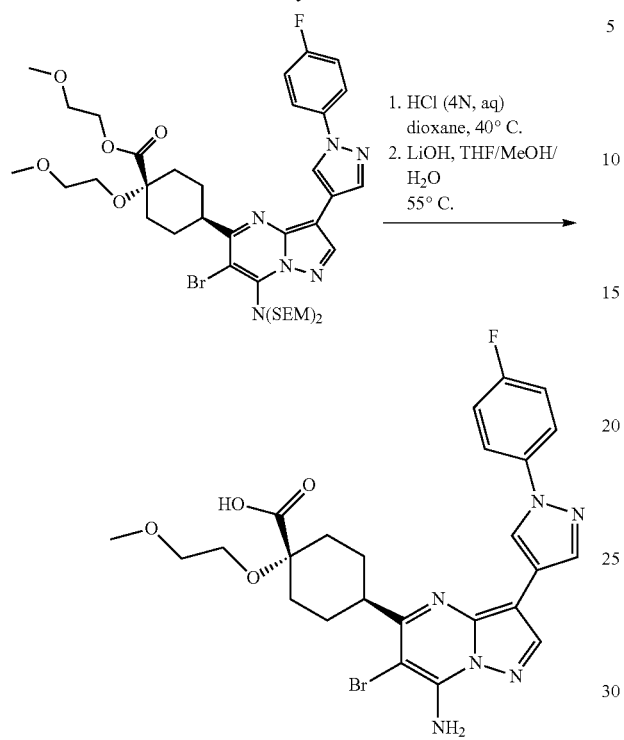

To a solution of (1R,4R)-4-(7-amino-6-bromo-3-(1-(4-fluorophenyl)-1H-pyrazol-4-yl)pyrazolo[1,5-a]pyrimidin-5-yl)-1-(2-methoxyethoxy)cyclohexanecarboxylic acid (423 mg, 0.474 mmol) in dioxane (4 mL) was added 4 mL of HCl (4 N, aq) and stirred at 40° C. for 1 h. The reaction mixture was evaporated to dryness and then treated with LiOH (10 eq) in THF/MeOH/H$_2$O (8/4/4 mL) at 55° C. overnight. The reaction mixture was evaporated to almost dryness and acidified with HCl (1.0N, aq) to pH about 6. The resulting slurry was filtered and washed with small amount of H$_2$O. After drying under high vacuum, (1R,4R)-4-(7-amino-6-bromo-3-(1-(4-fluorophenyl)-1H-pyrazol-4-yl)pyrazolo[1,5-a]pyrimidin-5-yl)-1-(2-methoxyethoxy)cyclohexanecarboxylic acid was obtained as an off-white solid (248 mg), which was used without further purification. HPLC-MS T$_R$=1.28 min (UV 254 nm, 3 min method); mass calculated for formula C$_{25}$H$_{26}$BrFN$_6$O$_4$ 572.1, observed LCMS m/z 573.1 (M+H).

Step 4: Preparation of (1R,4R)-4-(7-amino-6-(methylthio)-3-(1-(4-(methylthio)phenyl)-1H-pyrazol-4-yl)pyrazolo[1,5-a]pyrimidin-5-yl)-1-(2-methoxyethoxy)cyclohexanecarboxylic acid

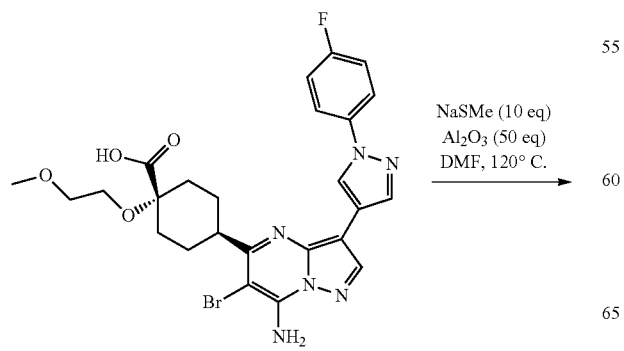

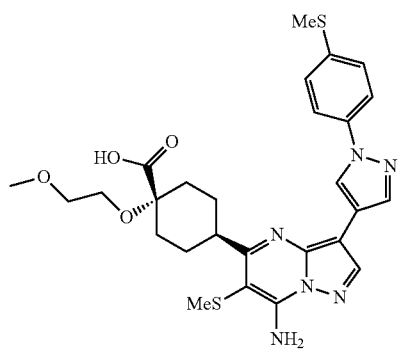

A mixture of (1R,4R)-4-(7-amino-6-bromo-3-(1-(4-fluorophenyl)-1H-pyrazol-4-yl)pyrazolo[1,5-a]pyrimidin-5-yl)-1-(2-methoxyethoxy)cyclohexanecarboxylic acid (248 mg, 0.432 mmol), NaSMe (303 mg, 4.32 mmol), Al$_2$O$_3$ (2.20 g, 21.6 mmol) in DMF (5 mL) was heated at 120° C. for 40 min. After cooling to rt, the reaction mixture was filtered and washed with DMF. The filtrate was evaporated and the residue was acidified with 1N HCl (aq) and evaporated again. The solid residue was dissolved in DMSO, filtered and purified by HPLC to afford (1R,4R)-4-(7-amino-6-(methylthio)-3-(1-(4-(methylthio)phenyl)-1H-pyrazol-4-yl)pyrazolo[1,5-a]pyrimidin-5-yl)-1-(2-methoxyethoxy)cyclohexanecarboxylic acid as a pale yellow solid (78 mg). HPLC-MS T$_R$=1.35 min (UV 254 nm, 3 min method); mass calculated for formula C$_{27}$H$_{32}$N$_6$O$_4$S$_2$ 568.2, observed LCMS m/z 569.0 (M+H).

Step 5: Preparation of (1R,4R)-4-(7-amino-6-(methylsulfonyl)-3-(1-(4-(methylsulfonyl)phenyl)-1H-pyrazol-4-yl)pyrazolo[1,5-a]pyrimidin-5-yl)-1-(2-methoxyethoxy)cyclohexanecarboxylic acid (Compound 53)

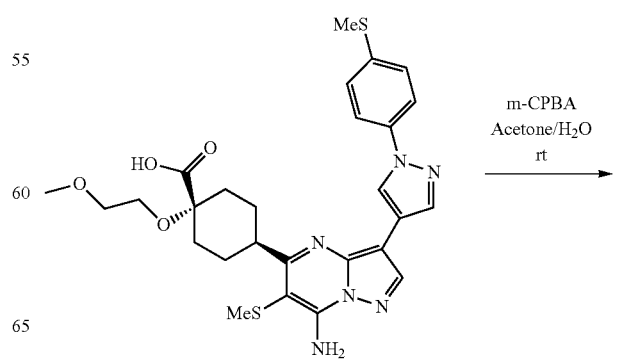

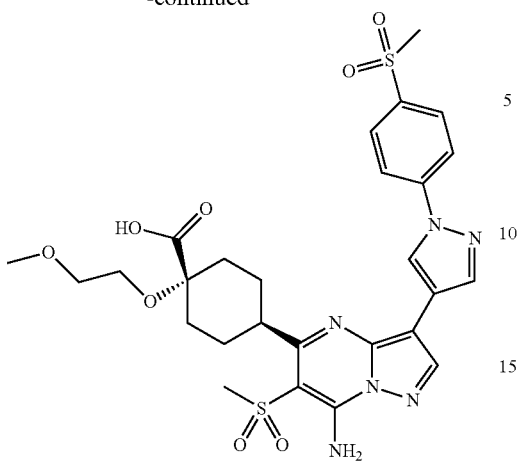

To a solution of (1R,4R)-4-(7-amino-6-(methylthio)-3-(1-(4-(methylthio)phenyl)-1H-pyrazol-4-yl)pyrazolo[1,5-a]pyrimidin-5-yl)-1-(2-methoxyethoxy)cyclohexanecarboxylic acid (78.0 mg, 0.137 mmol) in a mixed solvent of acetone/H₂O (12/3 mL) was added m-CPBA (10 eq) at rt. The resulting solution was stirred at rt overnight. The reaction mixture was evaporated to dryness and purified by a reverse phase HPLC to afford (1R,4R)-4-(7-amino-6-(methylsulfonyl)-3-(1-(4-(methylsulfonyl)phenyl)-1H-pyrazol-4-yl)pyrazolo[1,5-a]pyrimidin-5-yl)-1-(2-methoxyethoxy)cyclohexanecarboxylic acid (Compound 53) as a white solid (60.2 mg). HPLC-MS $T_R$=4.24 min (UV 254 nm, 10 min method); mass calculated for formula $C_{27}H_{32}N_6O_8S_2$ 632.2, observed LCMS m/z 633 (M+H).

Example 14

Preparation of (1S,4S)-4-(6-acetyl-7-amino-3-(1-phenyl-1H-pyrazol-4-yl)pyrazolo[1,5-a]pyrimidin-5-yl)-1-(2-methoxyethoxy)cyclohexanecarboxylic acid (Compound 54) and (1R,4R)-4-(6-acetyl-7-amino-3-(1-phenyl-1H-pyrazol-4-yl)pyrazolo[1,5-a]pyrimidin-5-yl)-1-(2-methoxyethoxy)cyclohexanecarboxylic acid (Compound 55)

Step 1: Preparation of 2-methoxyethyl 4-(7-(bis((2-(trimethylsilyl)ethoxy)methyl)amino)-6-(1-ethoxyvinyl)-3-(1-phenyl-1H-pyrazol-4-yl)pyrazolo[1,5-a]pyrimidin-5-yl)-1-(2-methoxyethoxy)cyclohexanecarboxylate

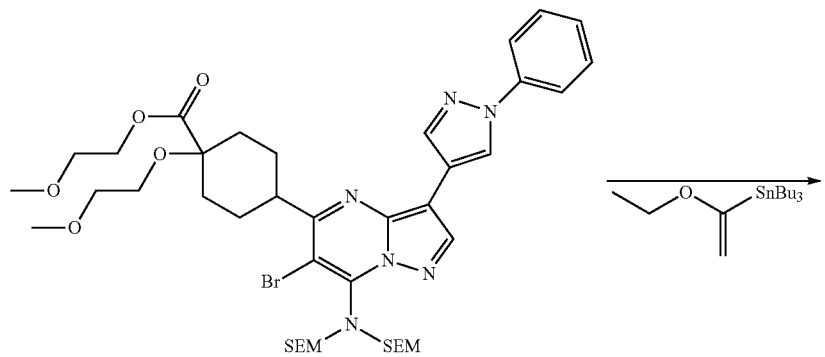

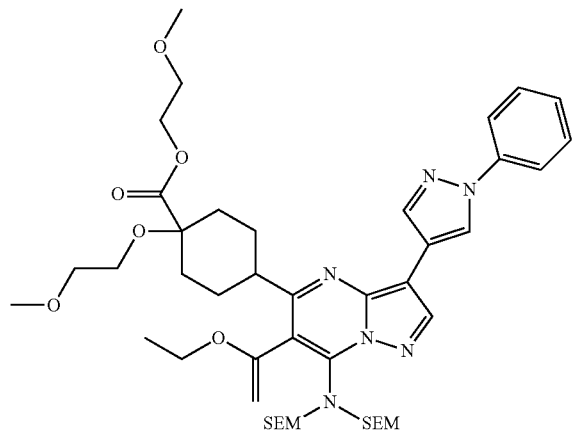

The Stille coupling reaction was performed with the same conditions described in example 3 Step 1. HPLC-MS $t_R$=3.29 min (UV$_{254\ nm}$); mass calculated for formula C$_{44}$H$_{68}$N$_6$O$_8$Si$_2$ 864.5, observed LCMS m/z 865.4 (M+H).

Step 2: Preparation of 2-methoxyethyl 4-(6-acetyl-7-amino-3-(1-phenyl-1H-pyrazol-4-yl)pyrazolo[1,5-a]pyrimidin-5-yl)-1-(2-methoxyethoxy)cyclohexanecarboxylate Step 3: Preparation of (1S,4S)-4-(6-acetyl-7-amino-3-(1-phenyl-1H-pyrazol-4-yl)pyrazolo[1,5-a]pyrimidin-5-yl)-1-(2-methoxyethoxy)cyclohexanecarboxylic acid (Compound 54) and (1R,4R)-4-(6-acetyl-7-amino-3-(1-phenyl-1H-pyrazol-4-yl)pyrazolo[1,5-a]pyrimidin-5-yl)-1-(2-methoxyethoxy)cyclohexanecarboxylic acid (Compound 55)

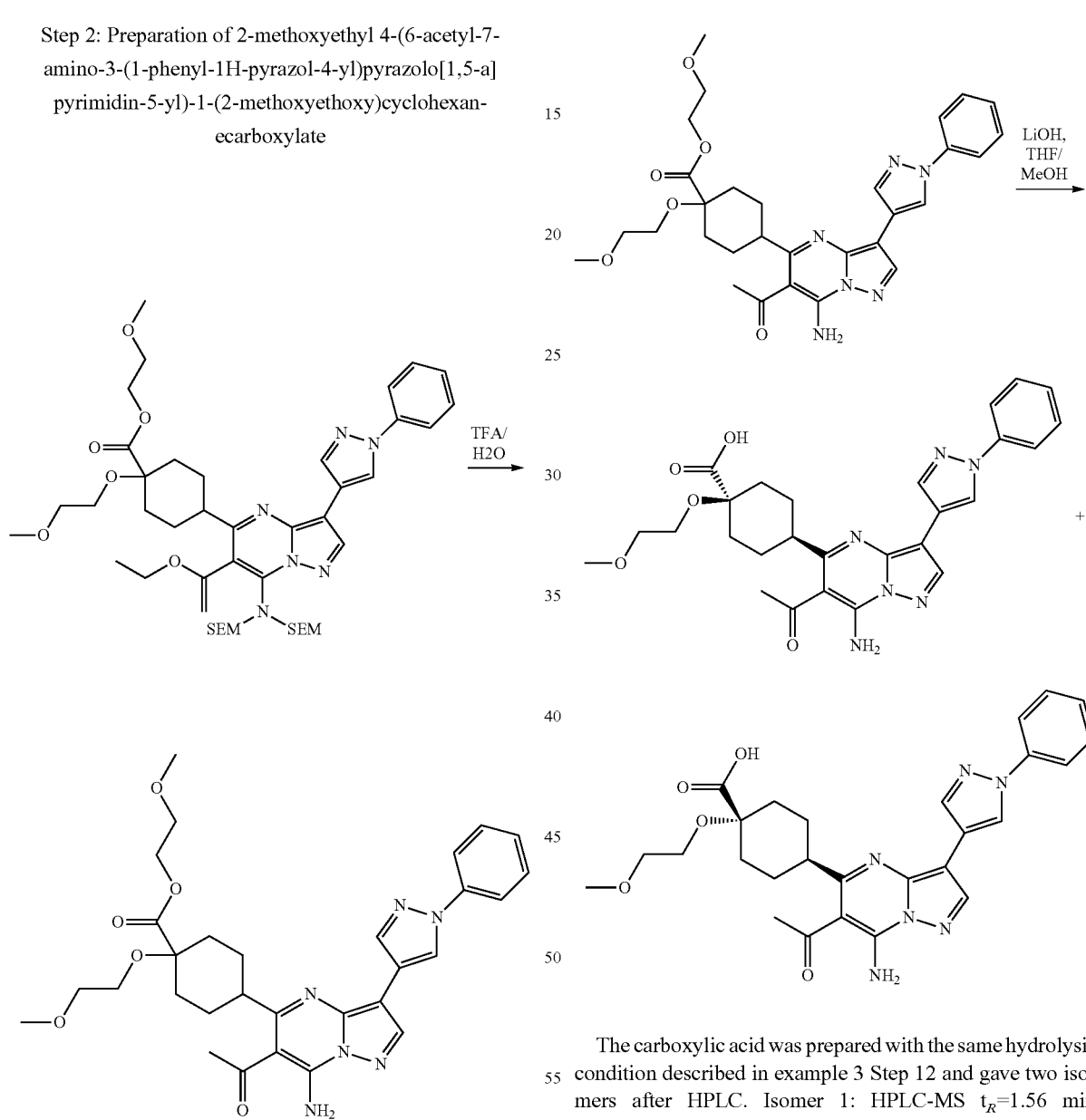

The vinyl-compound was de-protected with the same condition described in example 1 Step 11. HPLC-MS $t_R$=2.13 min (UV$_{254\ nm}$); mass calculated for formula C$_{30}$H$_{36}$N$_6$O$_6$ 576.3, observed LCMS m/z 577.3 (M+H).

The carboxylic acid was prepared with the same hydrolysis condition described in example 3 Step 12 and gave two isomers after HPLC. Isomer 1: HPLC-MS $t_R$=1.56 min (UV$_{254\ nm}$); mass calculated for formula C$_{27}$H$_{30}$N$_6$O$_5$ 518.2, observed LCMS m/z 519.2 (M+H). Isomer 2: HPLC-MS $t_R$=1.86 min (UV$_{254\ nm}$); mass calculated for formula C$_{27}$H$_{30}$N$_6$O$_5$ 518.2, observed LCMS m/z 519.2 (M+H).

Example 15

By essentially the same procedure in Preparative Example 14, compounds in Column 2 of Table 6 can be prepared.

TABLE 6

| Example | Chemical name | Column 2 | Exact mass | MS m/z (M + H) | HPLC MS $t_R$ |
|---------|---------------|----------|------------|----------------|---------------|
| 56 | (1S,4S)-4-(6-acetyl-7-amino-3-(6-phenylpyridin-3-yl)pyrazolo[1,5-a]pyrimidin-5-yl)-1-(2-methoxyethoxy)cyclohexanecarboxylic acid | | 529.2 | 530.2 | 1.20 |
| 57 | (1R,4R)-4-(6-acetyl-7-amino-3-(6-phenylpyridin-3-yl)pyrazolo[1,5-a]pyrimidin-5-yl)-1-(2-methoxyethoxy)cyclohexanecarboxylic acid | | 529.2 | 530.2 | 1.45 |
| 58 | (1R,4R)-4-(6-acetyl-7-amino-3-(6-phenylpyridin-3-yl)pyrazolo[1,5-a]pyrimidin-5-yl)-1-(2-morpholinoethoxy)cyclohexanecarboxylic acid | | 584.3 | 585.3 | 1.17 |
| 59 | (1S,4S)-4-(6-acetyl-7-amino-3-(6-thiazol-2-yl)pyridin-3-yl)pyrazolo[1,5-a]pyrimidin-5-yl)-1-(2-methoxyethoxy)cyclohexanecarboxylic acid | | 536.2 | 537.3 | 1.44 |

TABLE 6-continued

| Example | Chemical name | Column 2 | Exact mass | MS m/z (M + H) | HPLC MS $t_R$ |
|---|---|---|---|---|---|
| 60 | (1R,4R)-4-(6-acetyl-7-amino-3-(6-(thiazol-2-yl)pyridin-3-yl)pyrazolo[1,5-a]pyrimidin-5-yl)-1-(2-methoxyethoxy)cyclohexanecarboxylic acid | | 536.2 | 537.3 | 1.75 |
| 61 | (1S,4S)-4-(6-acetyl-7-amino-3-(6-(thiazol-4-yl)pyridin-3-yl)pyrazolo[1,5-a]pyrimidin-5-yl)-1-(2-methoxyethoxy)cyclohexanecarboxylic acid | | 536.2 | 537.3 | 1.08 |
| 62 | (1R,4R)-4-(6-acetyl-7-amino-3-(6-(thiazol-4-yl)pyridin-3-yl)pyrazolo[1,5-a]pyrimidin-5-yl)-1-(2-methoxyethoxy)cyclohexanecarboxylic acid | | 536.2 | 537.3 | 1.33 |

Example 16

Preparation of (1R,4R)-4-(7-amino-6-(methylthio)-3-(6-phenylpyridin-3-yl)pyrazolo[1,5-a]pyrimidin-5-yl)-1-(2-methoxyethoxy)cyclohexanecarboxylic acid (Compound 63)

Step 1: Preparation of 2-methoxyethyl 4-(7-(bis((2-(trimethylsilyl)ethoxy)methyl)amino)-6-(1-ethoxyvinyl)-3-(1-phenyl-1H-pyrazol-4-yl)pyrazolo[1,5-a]pyrimidin-5-yl)-1-(2-methoxyethoxy)cyclohexanecarboxylate

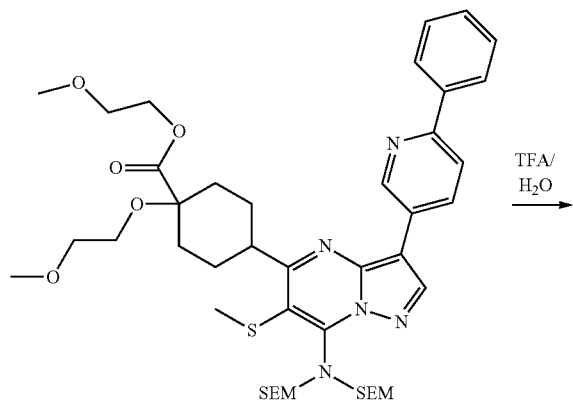

TFA/H₂O →

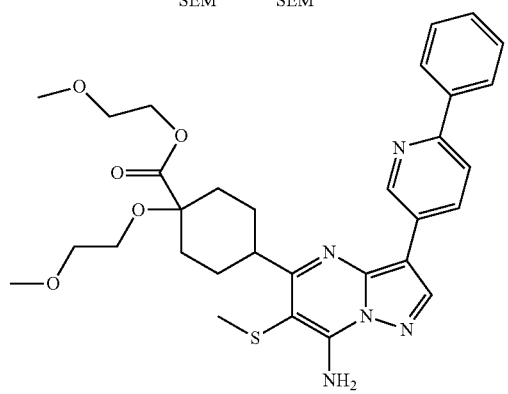

Methylsulfide compound was prepared with the same procedure described in example 11.

The methylsulfide compound was de-protected with the same condition described in example 1 Step 11. HPLC-MS $t_R$=1.75 min (UV$_{254\ nm}$); mass calculated for formula $C_{31}H_{37}N_5O_5S$ 591.3, observed LCMS m/z 592.2 (M+H).

Step 2: Preparation of (1R,4R)-4-(7-amino-6-(methylthio)-3-(6-phenylpyridin-3-yl)pyrazolo[1,5-a]pyrimidin-5-yl)-1-(2-methoxyethoxy)cyclohexanecarboxylic acid (Compound 63)

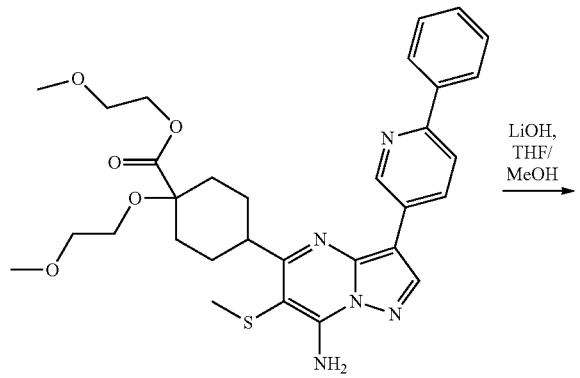

LiOH, THF/MeOH →

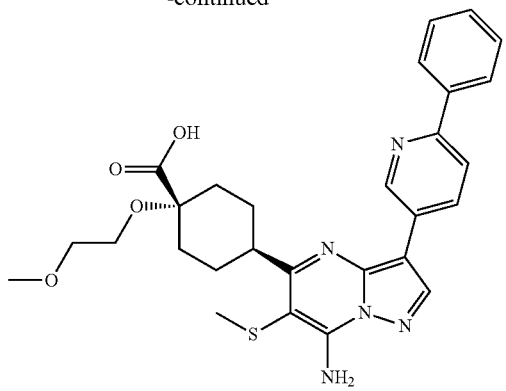

The carboxylic acid was prepared with the same hydrolysis condition described in example 1 Step 12 and the desired enantiomeric pure product was purified by HPLC. HPLC-MS $t_R$=1.65 min (UV$_{254\ nm}$); mass calculated for formula $C_{28}H_{31}N_5O_4S$ 533.2, observed LCMS m/z 534.1 (M+H).

Example 17

Preparation of (1R,4R)-4-(7-amino-6-bromo-3-(6-phenylpyridin-3-yl)pyrazolo[1,5-a]pyrimidin-5-yl)-1-(2-methoxyethoxy)cyclohexanecarboxylic acid (Compound 64)

Step 1: Preparation of 2-methoxyethyl 4-(7-(bis((2-(trimethylsilyl)ethoxy)methyl)amino)-6-(1-ethoxyvinyl)-3-(1-phenyl-1H-pyrazol-4-yl)pyrazolo[1,5-a]pyrimidin-5-yl)-1-(2-methoxyethoxy)cyclohexanecarboxylate

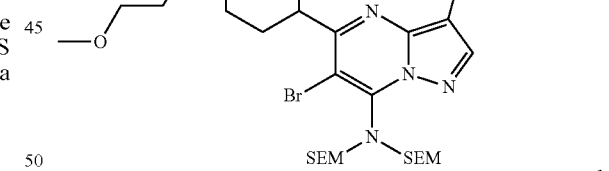

TFA/H₂O →

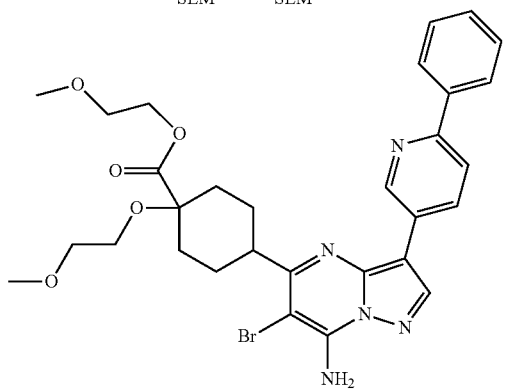

Bromo-compound was prepared with the same procedure described in example 11.

The bromo-compound was de-protected with the same condition described in example 1 Step 11. HPLC-MS $t_R$=2.20 min (UV$_{254\ nm}$); mass calculated for formula $C_{30}H_{34}BrN_5O_5$ 623.2, observed LCMS m/z 624.2 (M+H).

Step 2: Preparation of (1R,4R)-4-(7-amino-6-bromo-3-(6-phenylpyridin-3-yl)pyrazolo[1,5-a]pyrimidin-5-yl)-1-(2-methoxyethoxy)cyclohexanecarboxylic acid (Compound 64)

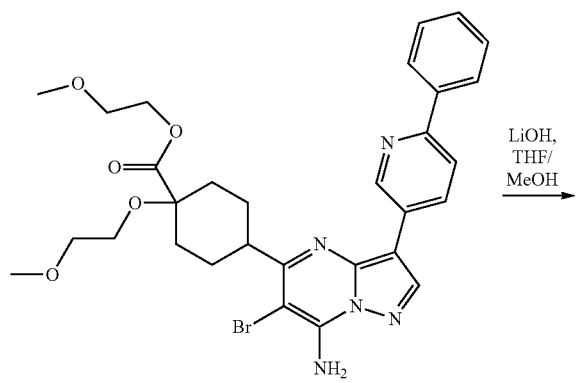

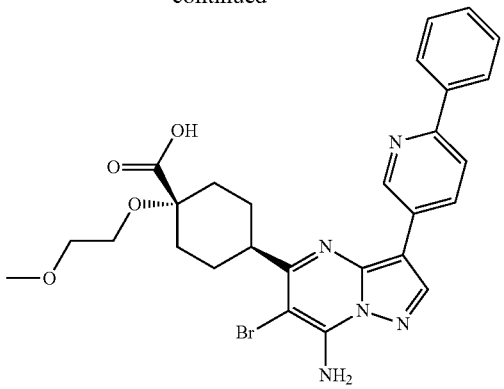

The carboxylic acid was prepared with the same hydrolysis condition described in example 1 Step 12. HPLC-MS $t_R$=2.93 min (10 min.) (UV$_{254\ nm}$); mass calculated for formula $C_{27}H_{28}BrN_5O_4$ 565.1, observed LCMS m/z 566.21 (M+H).

Example 18

By essentially the same procedure in Preparative Example 17, compounds in Column 2 of Table 7 can be prepared.

TABLE 7

| Example | Chemical name | Column 2 | Exact mass | MS m/z (M + H) | HPLC MS $t_R$ |
|---|---|---|---|---|---|
| 65 | (1R,4R)-4-(7-amino-6-bromo-3-(6-phenylpyridin-3-yl)pyrazolo[1,5-a]pyrimidin-5-yl)-1-(2-morpholinoethoxy)cyclohexanecarboxylic acid | | 620.2 | 621.1 | 1.34 |
| 66 | (1S,4S)-4-(7-amino-6-bromo-3-(6-phenylpyridin-3-yl)pyrazolo[1,5-a]pyrimidin-5-yl)-1-(2-morpholinoethoxy)cyclohexanecarboxylic acid | | 620.2 | 621.1 | 1.41 |

TABLE 7-continued

| Example | Chemical name | Column 2 | Exact mass | MS m/z (M + H) | HPLC MS $t_R$ |
|---|---|---|---|---|---|
| 67 | (1R,4R)-4-(7-amino-6-bromo-3-(1-phenyl-1H-pyrazol-4-yl)pyrazolo[1,5-a]pyrimidin-5-yl)-1-(2-morpholinoethoxy)cyclohexanecarboxylic acid | | 609.2 | 610.0 | 1.54 |
| 68 | (1R,4R)-4-(7-amino-6-bromo-3-(6-(3-fluoro-4-methoxyphenyl)-pyridin-3-yl)-pyrazolo[1,5-a]pyrimidin-5-yl)-1-(2-methoxyethoxy)cyclohexanecarboxylic acid | | 613.1 | 614.0 | 1.51 |

Example 19

Preparation of (1R,4R)-4-(7-amino-6-cyano-3-(1-phenyl-1H-pyrazol-4-yl)pyrazolo[1,5-a]pyrimidin-5-yl)-1-(2-methoxyethoxy)cyclohexanecarboxylic acid (Compound 69)

Step 1: Preparation of 2-methoxyethyl 4-(7-(bis((2-(trimethylsilyl)ethoxy)methyl)amino)-6-cyano-3-(1-phenyl-1H-pyrazol-4-yl)pyrazolo[1,5-a]pyrimidin-5-yl)-1-(2-methoxyethoxy)cyclohexanecarboxylate

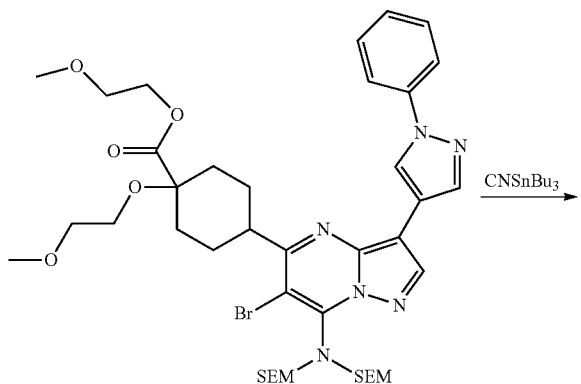

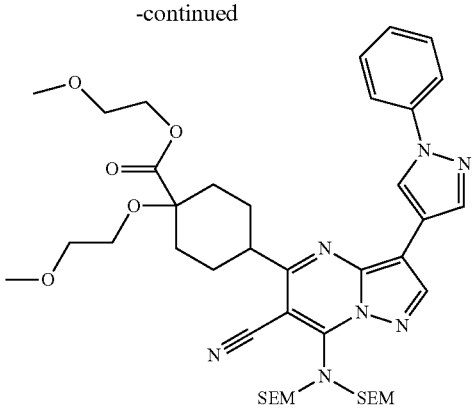

The cyano-compound was prepared with the same condition described in example 5 Step 1. HPLC-MS $t_R$=3.13 min (UV$_{254\ nm}$); mass calculated for formula $C_{41}H_{61}N_7O_7Si_2$ 819.4, observed LCMS m/z 820.2 (M+H).

Step 2: Preparation of 2-methoxyethyl 4-(7-amino-6-cyano-3-(1-phenyl-1H-pyrazol-4-yl)pyrazolo[1,5-a]pyrimidin-5-yl)-1-(2-methoxyethoxy)cyclohexanecarboxylate

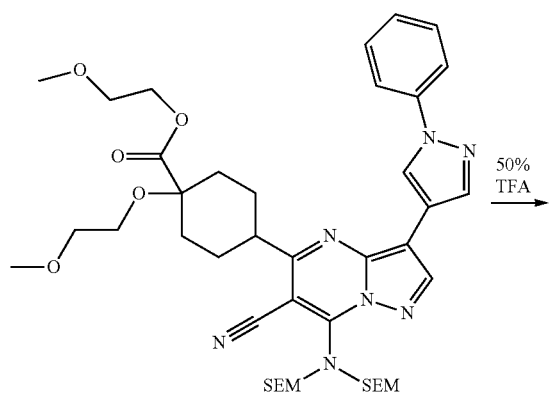

The cyano compound was de-protected with the same condition described in example 1 Step 11. HPLC-MS $t_R$=2.31 min (UV$_{254\ nm}$); mass calculated for formula $C_{29}H_{33}N_7O_5$ 559.3, observed LCMS m/z 560.2 (M+H).

Step 3: Preparation of (1R,4R)-4-(7-amino-6-cyano-3-(1-phenyl-1H-pyrazol-4-yl)pyrazolo[1,5-a]pyrimidin-5-yl)-1-(2-methoxyethoxy)cyclohexanecarboxylic acid (Compound 69)

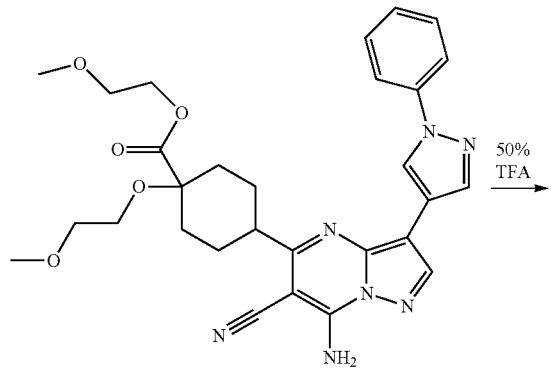

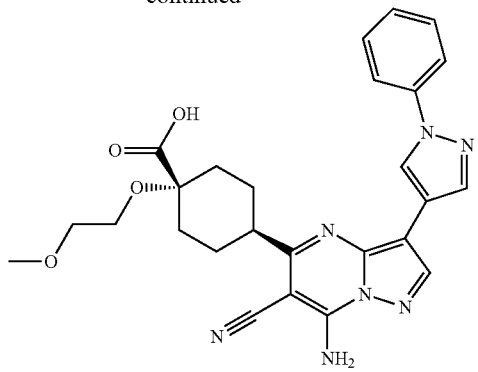

The ester from Part B was hydrolysized with the same condition described in example 1 Step 12. HPLC-MS $t_R$=1.92 min (UV$_{254\ nm}$); mass calculated for formula $C_{26}H_{27}N7O_4$ 501.2, observed LCMS m/z 502.1 (M+H).

Example 20

Preparation of (1R,4R)-4-(6-acetyl-7-amino-3-(1-phenyl-1H-pyrazol-4-yl)pyrazolo[1,5-a]pyrimidin-5-yl)-1-(2-methoxyethoxy)-N-(methylsulfonyl)cyclohexanecarboxamide (Compound 70)

Step 1: Preparation of 4-(7-(bis((2-(trimethylsilyl)ethoxy)methyl)amino)-6-(1-ethoxyvinyl)-3-(1-phenyl-1H-pyrazol-4-yl)pyrazolo[1,5-a]pyrimidin-5-yl)-1-(2-methoxyethoxy)cyclohexanecarboxylic acid

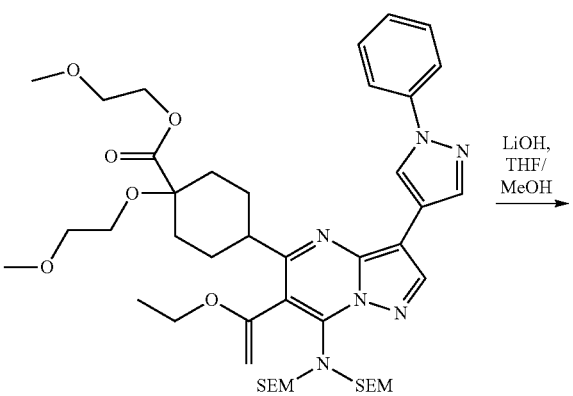

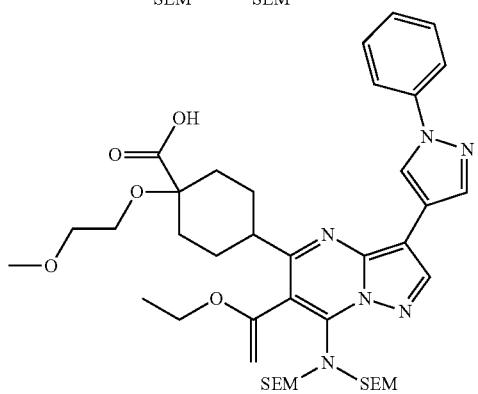

The ester from example 14 was hydrolysized with the same condition described in example 1 Step 12 and used in the next step directly without further purification. HPLC-MS $t_R$=3.18 min (UV$_{254\ nm}$); mass calculated for formula $C_{41}H_{62}N_6O_7Si_2$ 806.4, observed LCMS m/z 807.3 (M+H).

Step 2: Preparation of 4-(7-(bis((2-(trimethylsilyl)ethoxy)methyl)amino)-6-(1-ethoxyvinyl)-3-(1-phenyl-1H-pyrazol-4-yl)pyrazolo[1,5-a]pyrimidin-5-yl)-1-(2-methoxyethoxy)-N-(methylsulfonyl)cyclohexanecarboxamide

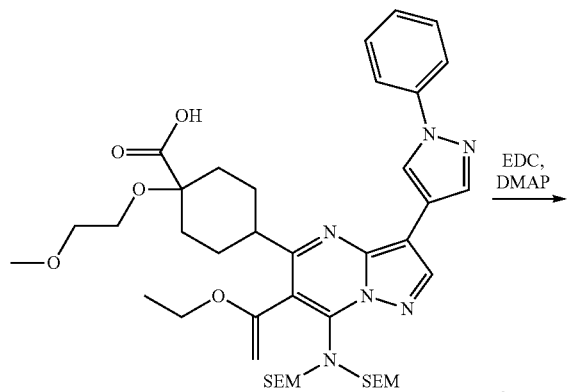

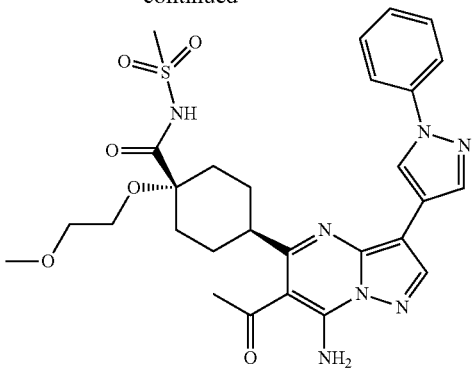

The vinyl ether compound was de-protected with the same condition described in example 1 Step 11. HPLC-MS $t_R$=2.14 min (UV$_{254\,nm}$); mass calculated for formula $C_{28}H_{33}N_7O_6S$ 595.2, observed LCMS m/z 596.0 (M+H).

Example 21

Preparation of 4-(7-amino-6-(methylsulfonyl)-3-(1-phenyl-1H-pyrazol-4-yl)pyrazolo[1,5-a]pyrimidin-5-yl)-1-(2-methoxyethoxy)-N-(methylsulfonyl)cyclohexanecarboxamide (Compound 71)

Step 1: Preparation of 4-(7-(bis((2-(trimethylsilyl)ethoxy)methyl)amino)-6-(methylthio)-3-(1-phenyl-1H-pyrazol-4-yl)pyrazolo[1,5-a]pyrimidin-5-yl)-1-(2-methoxyethoxy)-N-(methylsulfonyl)cyclohexanecarboxamide The crude acid (78 mg, 0.097 mmol), methylsulfamide (19 mg, 0.2 mmol) and DMAP (25 mg, 0.2 mmol) were mixed in DCM (5 mL) and EDC (38 mg, 0.3 mmol) was added. The resulting mixture was stirred at room temperature overnight and EtOAc (50 mL) was added. The organics was washed with water, brine and dried over Na$_2$SO$_4$. After concentration, the crude product was used in the next step without further purification. HPLC-MS $t_R$=3.21 min (UV$_{254\,nm}$); mass calculated for formula $C_{42}H_{65}N_7O_8SSi_2$ 883.4, observed LCMS m/z 884.2 (M+H).

Step 3: Preparation of (1R,4R)-4-(6-acetyl-7-amino-3-(1-phenyl-1H-pyrazol-4-yl)pyrazolo[1,5-a]pyrimidin-5-yl)-1-(2-methoxyethoxy)-N-(methylsulfonyl)cyclohexanecarboxamide (Compound 70)

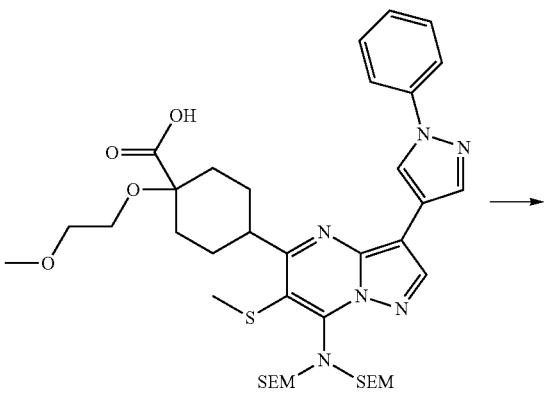

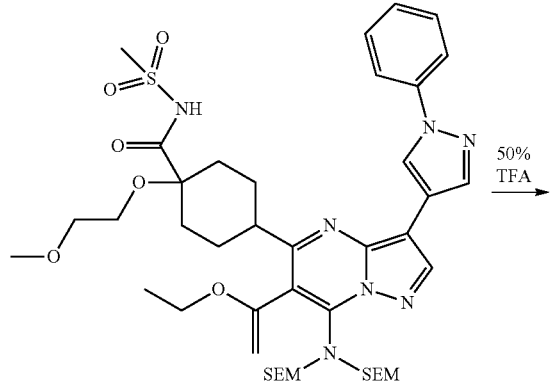

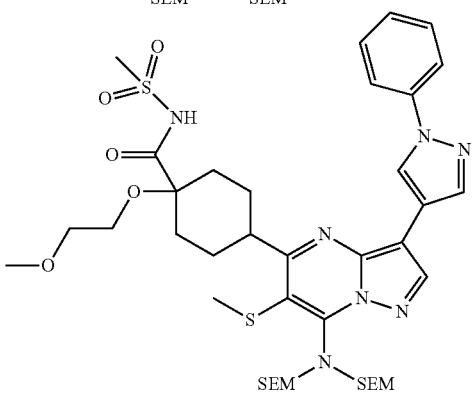

N-(methylsulfonyl)cyclohexanecarboxamide was prepared with the same conditions described in example 20 step 2. HPLC-MS $t_R$=3.14 min (UV$_{254\,nm}$); mass calculated for formula $C_{39}H_{61}N_7O_7S_2Si_2$ 859.4, observed LCMS m/z 860.2 (M+H).

Step 2: Preparation of 4-(7-amino-6-(methylthio)-3-(1-phenyl-1H-pyrazol-4-yl)pyrazolo[1,5-a]pyrimidin-5-yl)-1-(2-methoxyethoxy)-N-(methylsulfonyl)cyclohexanecarboxamide

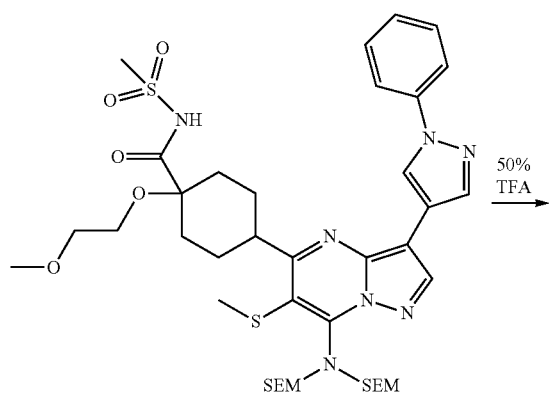

The methylsulfide compound was de-protected with the same condition described in example 1 Step 11. HPLC-MS $t_R$=2.52 min (UV$_{254\ nm}$); mass calculated for formula $C_{27}H_{33}N_7O_5S_2$ 599.2, observed LCMS m/z 600.0 (M+H).

Step 3: Preparation of 4-(7-amino-6-(methylsulfonyl)-3-(1-phenyl-1H-pyrazol-4-yl)pyrazolo[1,5-a]pyrimidin-5-yl)-1-(2-methoxyethoxy)-N-(methylsulfonyl)cyclohexanecarboxamide (Compound 71)

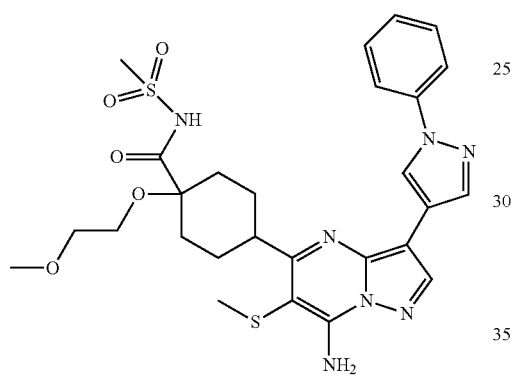

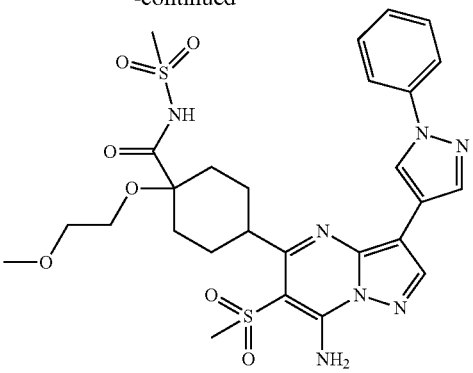

The methylsulfide was oxidized with the same conditions described in example 13 step 5. HPLC-MS $t_R$=1.92 min (UV$_{254\ nm}$); mass calculated for formula $C_{27}H_{33}N_7O_7S_2$ 631.2, observed LCMS m/z 632.2 (M+H).

Example 22

Preparation of 8-(7-amino-6-bromo-3-(6-phenylpyridin-3-yl)pyrazolo[1,5-a]pyrimidin-5-yl)-1,3-diazaspiro[4.5]decane-2,4-dione (Compound 72)

Step 1: Preparation of 8-(7-(bis((2-(trimethylsilyl)ethoxy)methyl)amino)pyrazolo[1,5-a]pyrimidin-5-yl)-1,3-diazaspiro[4.5]decane-2,4-dione

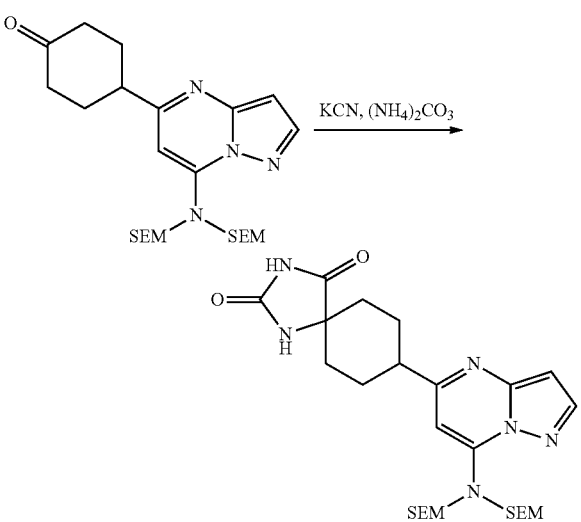

Ketone (855 mg, 1.7 mmol) was mixed with (NH$_4$)$_2$CO$_3$ (752 mg, 7.83 mmol) and KCN (125 mg, 1.9 mmol) in EtOH (5 mL) and water (5 mL) in a sealed tube. The mixture was heated to 80° C. and stirred overnight. After cooling to room temperature, EtOAc (100 mL) was added and washed with water, brine. The crude product was used in the next step directly after concentration without further purification. HPLC-MS $t_R$=2.39 min (UV$_{254\ nm}$); mass calculated for formula $C_{26}H_{44}N_6O_4Si_2$ 560.3, observed LCMS m/z 561.3 (M+H).

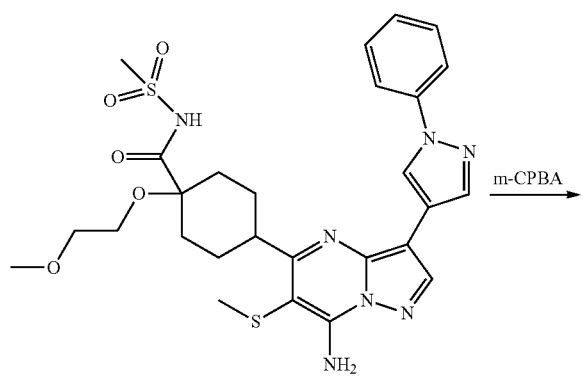

Step 2: Preparation of 8-(7-(bis((2-(trimethylsilyl)ethoxy)methyl)amino)-3-bromopyrazolo[1,5-a]pyrimidin-5-yl)-1,3-diazaspiro[4.5]decane-2,4-dione

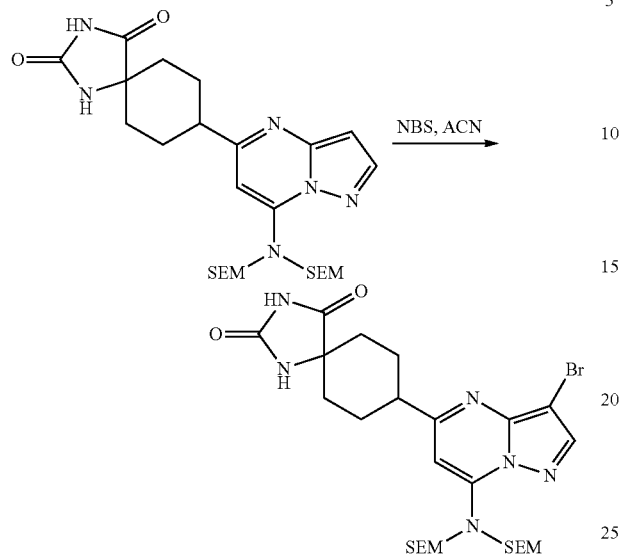

The bromonation was performed with the same condition described in example 1 Step 7 with NBS. HPLC-MS $t_R$=2.77 min (UV$_{254\ nm}$); mass calculated for formula $C_{26}H_{43}BrN_6O_4Si_2$ 638.2, observed LCMS m/z 639.1 (M+H).

Step 3: Preparation of 8-(7-(bis((2-(trimethylsilyl)ethoxy)methyl)amino)-3-(6-phenylpyridin-3-yl)pyrazolo[1,5-a]pyrimidin-5-yl)-1,3-diazaspiro[4.5]decane-2,4-dione

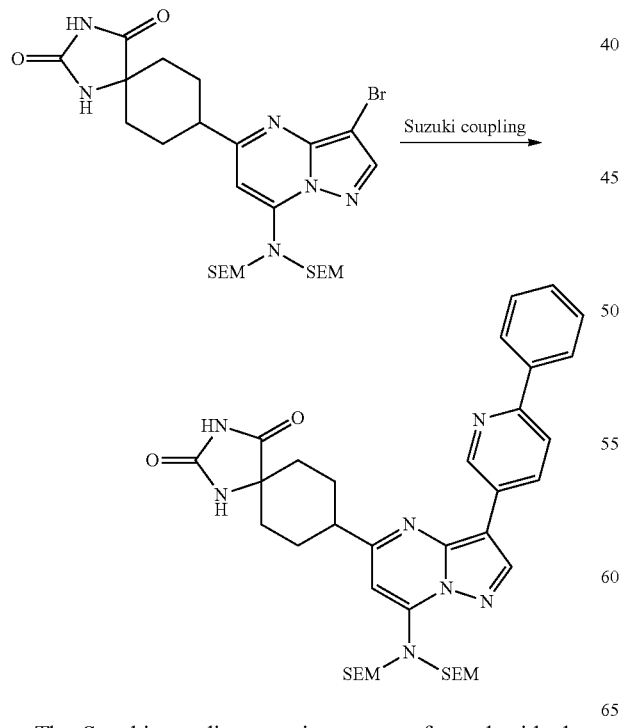

The Suzuki coupling reaction was performed with the same condition described in example 1 Step 8. HPLC-MS $t_R$=2.47 min (UV$_{254\ nm}$); mass calculated for formula $C_{37}H_{51}N_7O_4Si_2$ 713.4, observed LCMS m/z 714.3 (M+H).

Step 4: Preparation of 8-(7-amino-3-(6-phenylpyridin-3-yl)pyrazolo[1,5-a]pyrimidin-5-yl)-1,3-diazaspiro[4.5]decane-2,4-dione

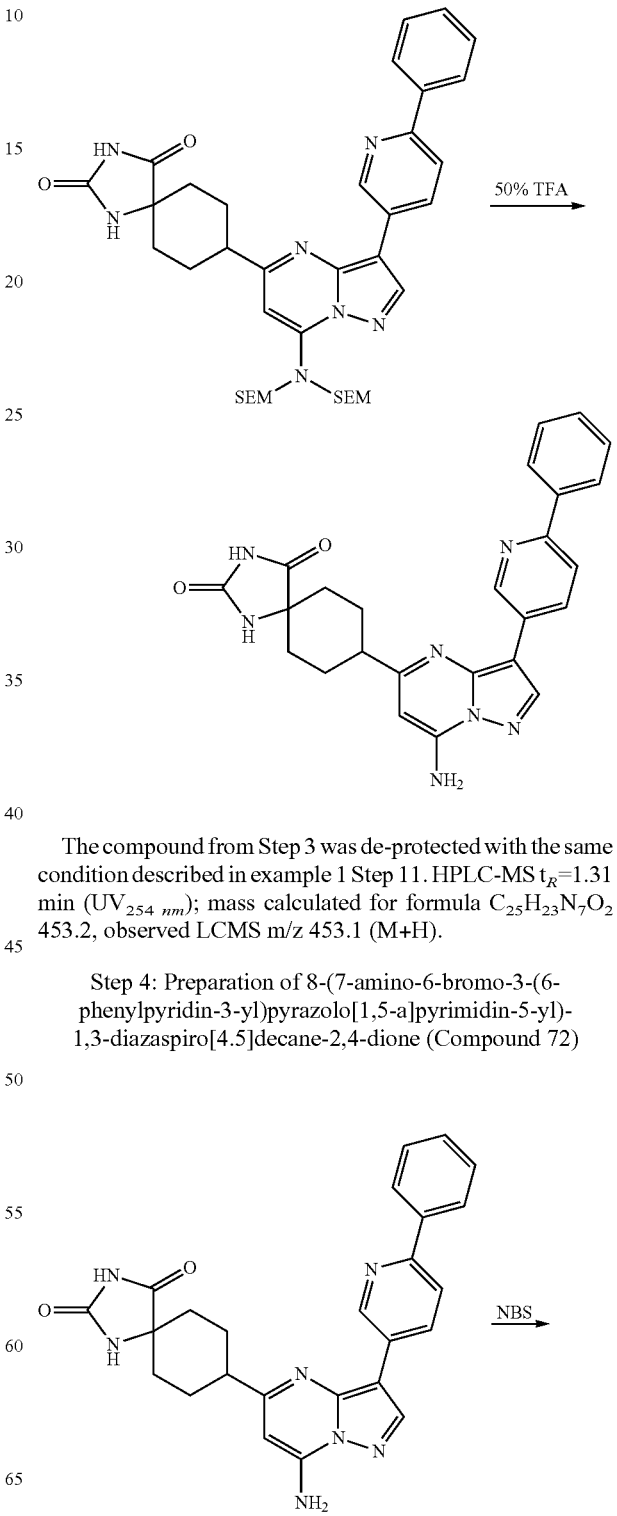

The compound from Step 3 was de-protected with the same condition described in example 1 Step 11. HPLC-MS $t_R$=1.31 min (UV$_{254\ nm}$); mass calculated for formula $C_{25}H_{23}N_7O_2$ 453.2, observed LCMS m/z 453.1 (M+H).

Step 4: Preparation of 8-(7-amino-6-bromo-3-(6-phenylpyridin-3-yl)pyrazolo[1,5-a]pyrimidin-5-yl)-1,3-diazaspiro[4.5]decane-2,4-dione (Compound 72)

-continued

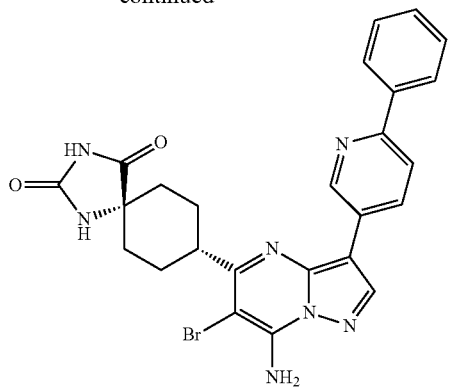

The bromonation was performed with the same condition described in example 1 Step 7 with NBS and purified with HPLC to give the enantiomeric pure product. HPLC-MS $t_R$=1.47 min (UV$_{254\ nm}$); mass calculated for formula C$_{25}$H$_{22}$BrN$_7$O$_2$ 531.1, observed LCMS m/z 532.0 (M+H).

Example 23

Prepare of 1-amino-4-(7-amino-6-bromo-3-(6-phenylpyridin-3-yl)pyrazolo[1,5-a]pyrimidin-5-yl)cyclohexanecarboxylic acid (Compound 73)

Step 1: Preparation of 1-amino-4-(7-amino-3-(6-phenylpyridin-3-yl)pyrazolo[1,5-a]pyrimidin-5-yl)cyclohexanecarboxylic acid

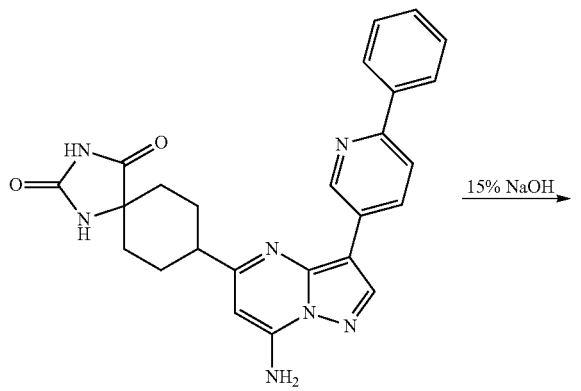

The starting material (400 mg, 0.88 mmol) was treated with NaOH (15%, 15 ml) at 110° C. and stirred for 1 day. After cooling to room temperature, crushed ice was added and the pH value was adjusted to ~7 with concentrated HCl. The solid was collected with filtration and purified with HPLC (131 mg). HPLC-MS $t_R$=1.03 min (UV$_{254\ nm}$); mass calculated for formula C$_{24}$H$_{24}$N$_6$O$_2$ 428.2, observed LCMS m/z 429.2 (M+H).

Step 2: Preparation of 1-amino-4-(7-amino-6-bromo-3-(6-phenylpyridin-3-yl)pyrazolo[1,5-a]pyrimidin-5-yl)cyclohexanecarboxylic acid (Compound 73)

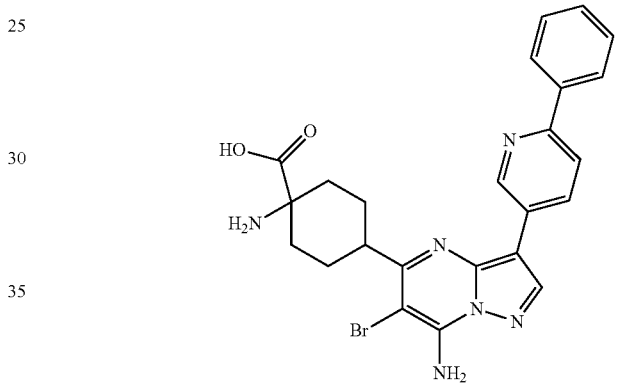

The bromonation was performed with the same condition described in example 1 Step 10 with NBS. HPLC-MS $t_R$=1.24 min (UV$_{254\ nm}$); mass calculated for formula C$_{24}$H$_{23}$BrN$_6$O$_2$ 506.1, observed LCMS m/z 507.0 (M+H).

Example 24

Preparation of 4-(7-amino-6-bromo-3-(6-phenylpyridin-3-yl)pyrazolo[1,5-a]pyrimidin-5-yl)-1-hydroxycyclohexanecarbonitrile (Compound 74)

Step 1: Preparation of 4-(7-(bis((2-(trimethylsilyl)ethoxy)methyl)amino)-3-iodopyrazolo[1,5-a]pyrimidin-5-yl)cyclohexanone

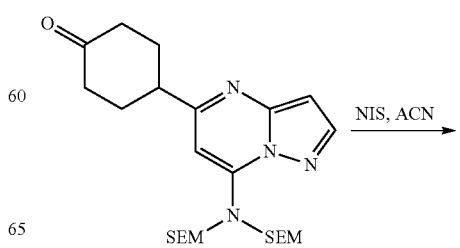

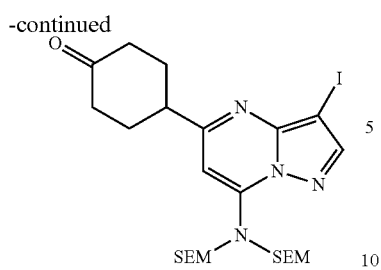

The iodination was performed with the same condition described in example 1 Step 7 with NIS. HPLC-MS $t_R$=2.78 min (UV$_{254\ nm}$); mass calculated for formula $C_{24}H_{41}IN_4O_3Si_2$ 616.2, observed LCMS m/z 617.2 (M+H).

Step 2: Preparation of 4-(7-(bis((2-(trimethylsilyl)ethoxy)methyl)amino)-3-(6-phenylpyridin-3-yl)pyrazolo[1,5-a]pyrimidin-5-yl)cyclohexanone

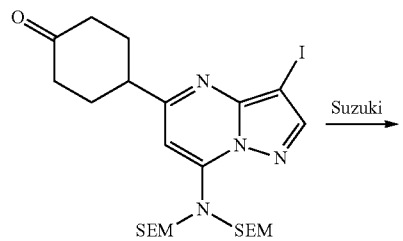

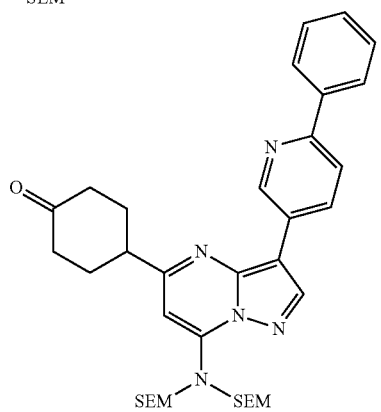

The Suzuki coupling reaction was performed with the same condition described in example 1 Step 8. HPLC-MS $t_R$=2.66 min (UV$_{254\ nm}$); mass calculated for formula $C_{35}H_{49}N_5O_3Si_2$ 643.3, observed LCMS m/z 644.2 (M+H).

Step 3: Preparation of 4-(7-(bis((2-(trimethylsilyl)ethoxy)methyl)amino)-3-(6-phenylpyridin-3-yl)pyrazolo[1,5-a]pyrimidin-5-yl)-1-hydroxycyclohexanecarbonitrile

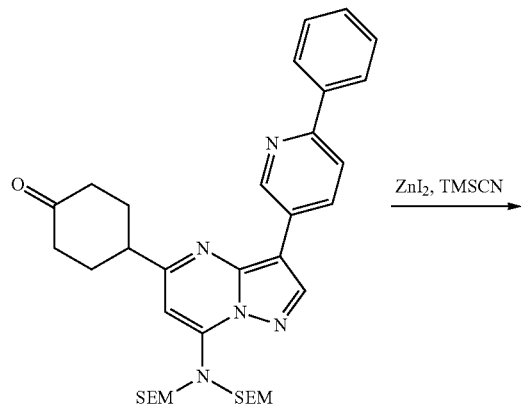

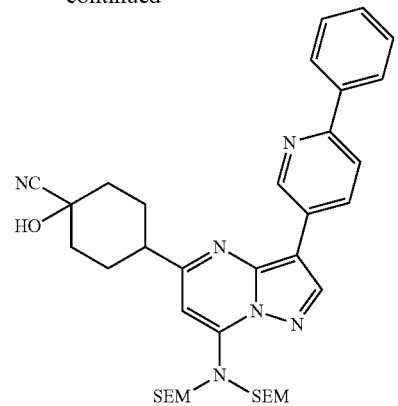

The ketone (64 mg, 0.1 mmol) and TMSCN (25 uL, 0.2 mmol) dissolved in dry DCM (5 mL) and ZnI$_2$ (3 mg, 0.01 mmol) was added. The mixture was stirred at room temperature for 3 hours and HCl (1N, 0.2 mL) was added and stirred for another 10 min. The mixture was diluted with EtOAc (50 mL) and washed with water, brine and dried over Na$_2$SO$_4$. The crude product was purified with a column (silica gel, 0~40% EtOAc/hexane) (39 mg). HPLC-MS $t_R$=2.52 min (UV$_{254\ nm}$); mass calculated for formula $C_{36}H_{50}N_6O_3Si_2$ 670.3, observed LCMS m/z 671.2 (M+H).

Step 4: Preparation of 4-(7-amino-3-(6-phenylpyridin-3-yl)pyrazolo[1,5-a]pyrimidin-5-yl)-1-hydroxycyclohexanecarbonitrile

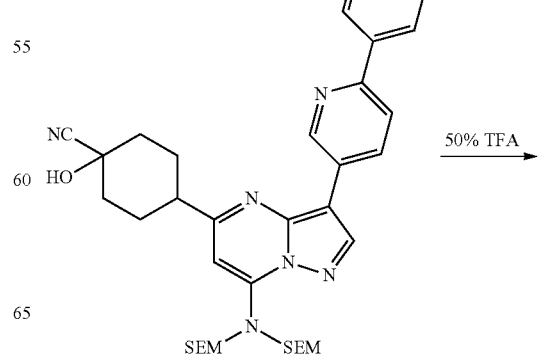

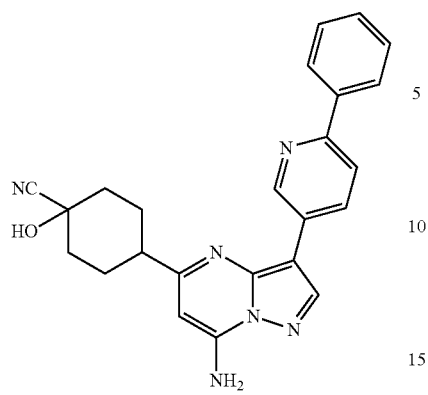

The hydroxyl compound from Step 3 was de-protected with the same condition described in example 1 Step 11. HPLC-MS $t_R$=1.41 min (UV$_{254\ nm}$); mass calculated for formula C$_{24}$H$_{22}$N$_6$O 410.2, observed LCMS m/z 411.1 (M+H).

Step 5: Preparation of 4-(7-amino-6-bromo-3-(6-phenylpyridin-3-yl)pyrazolo[1,5-a]pyrimidin-5-yl)-1-hydroxycyclohexanecarbonitrile (Compound 74)

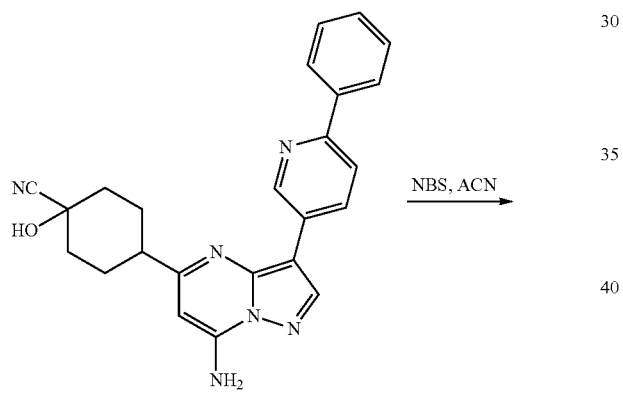

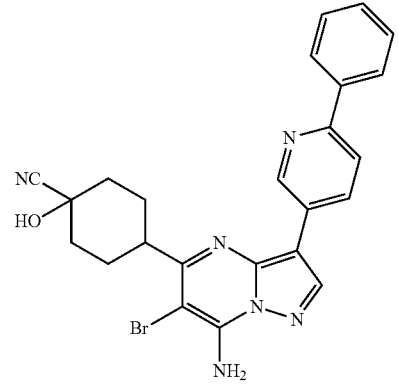

The bromonation was performed with the same condition described in example 1 Step 7 with NBS. HPLC-MS $t_R$=1.43 min (UV$_{254\ nm}$); mass calculated for formula C$_{24}$H$_{21}$BrN$_6$O 488.1, observed LCMS m/z 489.1 (M+H).

Example 25

By essentially the same procedure in Preparative Example 24, the compound in Column 2 of Table 8 can be prepared started from the product of Step 5 of example 7.

TABLE 8

| Example | Chemical name | Column 2 | Exact mass | MS m/z (M + H) | HPLC MS $t_R$ |
| --- | --- | --- | --- | --- | --- |
| 75 | 4-(7-amino-6-bromo-3-(6-phenylpyridin-3-yl)pyrazolo[1,5-a]pyrimidin-5-yl)-1-methoxycyclohexane-carbonitrile | | 502.1 | 503.0 | 1.49 |

Example 26

Preparation of 2-((1R,4R)-4-(7-amino-6-bromo-3-(6-phenylpyridin-3-yl)pyrazolo[1,5-a]pyrimidin-5-yl)-1-hydroxycyclohexyl)acetic acid (Compound 76)

Step 1: Preparation of methyl 2-((1S,4S)-4-(7-(bis((2-(trimethylsilyl)ethoxy)methyl)amino)-3-(6-phenylpyridin-3-yl)pyrazolo[1,5-a]pyrimidin-5-yl)-1-hydroxycyclohexyl)acetate and methyl 2-((1R,4R)-4-(7-(bis((2-(trimethylsilyl)ethoxy)methyl)amino)-3-(6-phenylpyridin-3-yl)pyrazolo[1,5-a]pyrimidin-5-yl)-1-hydroxycyclohexyl)acetate

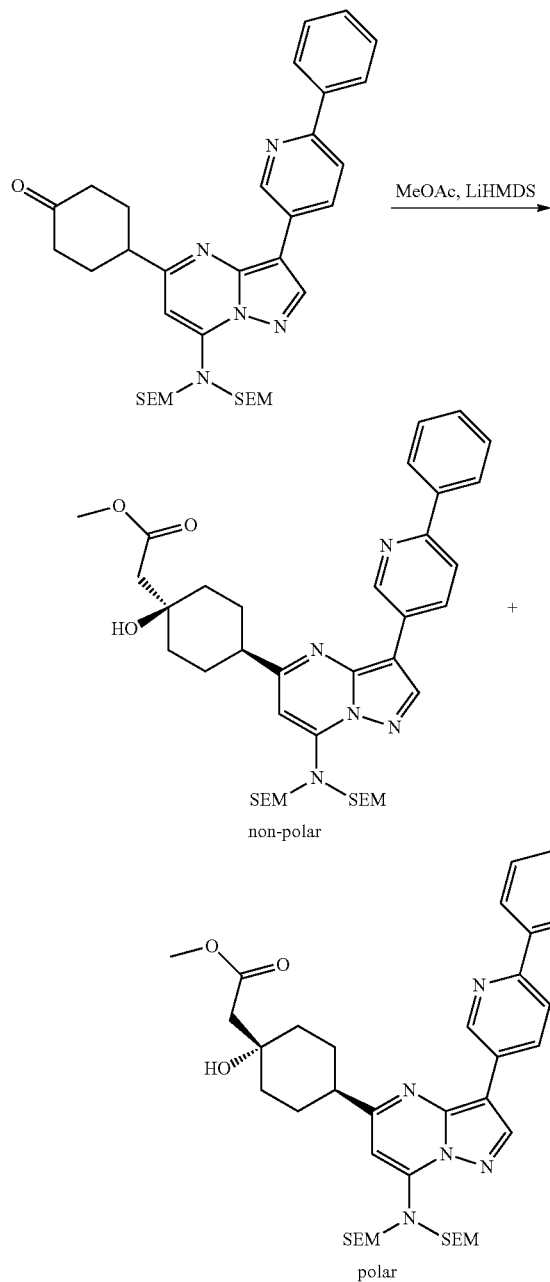

The methyl acetate (150 uL, 1.89 mmol) was dissolved in dry THF (20 mL) and cooled to −78° C. The LiHMDS (1.8 M in THF, 1.05 mL, 1.89 mmol) was added dropwise. The mixture was stirred at −78° C. for 20 min and followed by 0° C. for another 30 min. Then, the reaction was cooled to −78° C. again and ketone (587 mg, 0.911 mmol) was added. The resulting mixture was allowed to warm to 0° C. and stirred for 3 hours. The $NH_4Cl$ (aq.) was added to quench the reaction and extracted with EtOAc. After concentration, the crude was purified with column (silica gel, 0-40% EtOAc/Hexane) and two isomers were obtained. Isomer 1 (185 mg, non-polar): HPLC-MS $t_R$=2.70 min ($UV_{254\ nm}$); mass calculated for formula $C_{38}H_{55}N_5O_5Si_2$ 717.4, observed LCMS m/z 718.3 (M+H). Isomer 2 (400 mg, polar): HPLC-MS $t_R$=2.73 min ($UV_{254\ nm}$); mass calculated for formula $C_{38}H_{55}N_5O_5Si_2$ 717.4, observed LCMS m/z 718.3 (M+H).

Step 2: Preparation of methyl 2-((1R,4R)-4-(7-(bis((2-(trimethylsilyl)ethoxy)methyl)amino)-6-bromo-3-(6-phenylpyridin-3-yl)pyrazolo[1,5-a]pyrimidin-5-yl)-1-hydroxycyclohexyl)

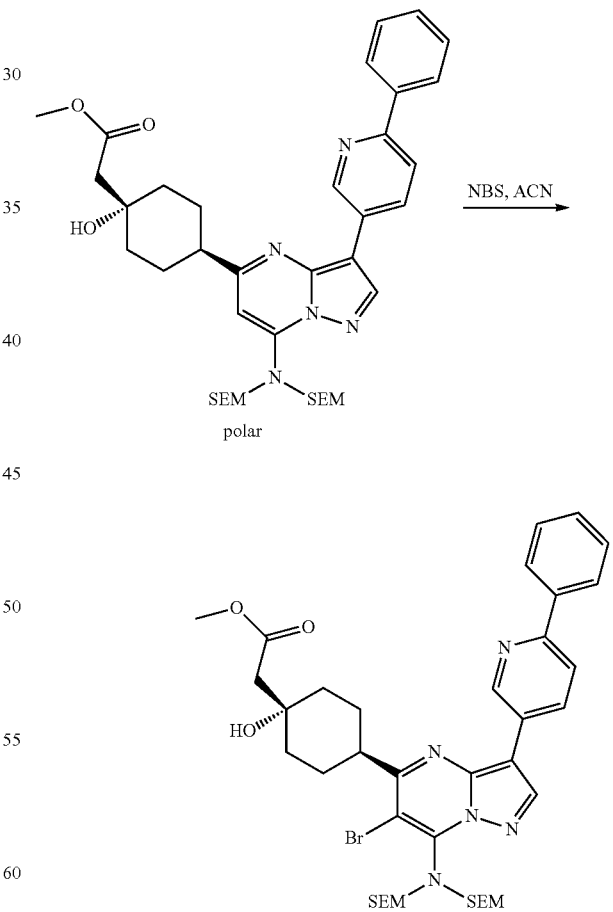

The bromo compound was prepared with the same condition described in example 1 Step 10. HPLC-MS $t_R$=2.98 min ($UV_{254\ nm}$); mass calculated for formula $C_{38}H_{54}BrN_5O_5Si_2$ 795.3, observed LCMS m/z 796.2 (M+H).

Step 3: Preparation of methyl 2-((1R,4R)-4-(7-amino-6-bromo-3-(6-phenylpyridin-3-yl)pyrazolo[1,5-a]pyrimidin-5-yl)-1-hydroxycyclohexyl)acetate Step 4: Preparation of 2-((1R,4R)-4-(7-amino-6-bromo-3-(6-phenylpyridin-3-yl)pyrazolo[1,5-a]pyrimidin-5-yl)-1-hydroxycyclohexyl)acetic acid (Compound 76)

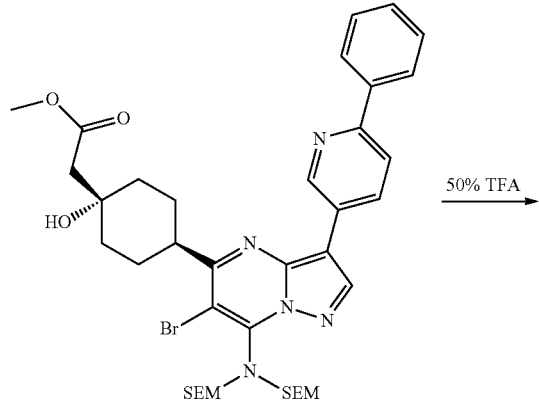

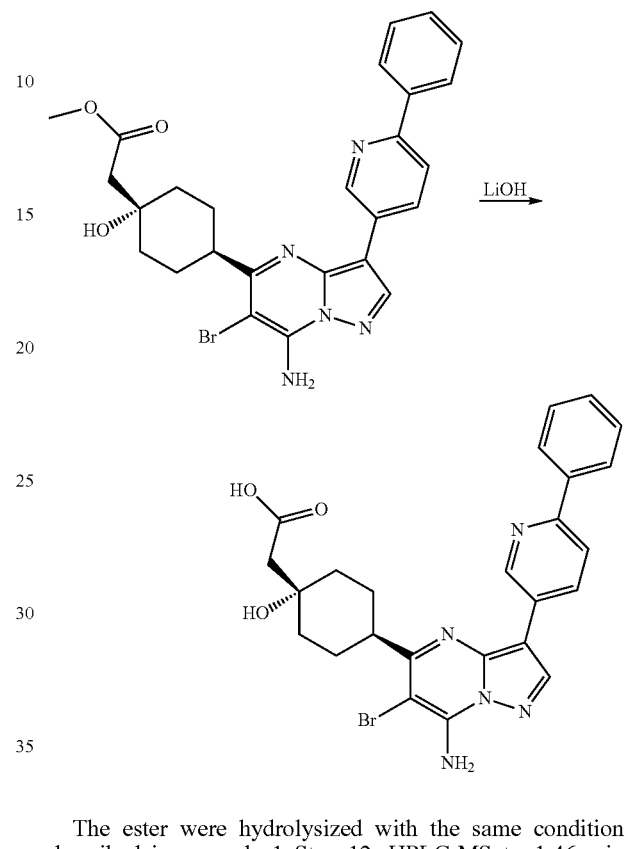

The bromo-compound was de-protected with the same condition described in example 1 Step 11. HPLC-MS $t_R$=1.62 min (UV$_{254\ nm}$); mass calculated for formula $C_{26}H_{26}BrN_5O_3$ 535.1, observed LCMS m/z 536.2 (M+H).

The ester were hydrolysized with the same condition described in example 1 Step 12. HPLC-MS $t_R$=1.46 min (UV$_{254\ nm}$); mass calculated for formula $C_{25}H_{24}BrN_5O_3$ 521.1, observed LCMS m/z 522.0 (M+H).

Example 27

By essentially the same procedure in Preparative Example 26, the compounds in Column 2 of Table 9 can be prepared.

TABLE 9

| Example | Chemical name | Column 2 | Exact mass | MS m/z (M + H) | HPLC MS $t_R$ |
|---|---|---|---|---|---|
| 77 | 2-((1S,4S)-4-(7-amino-6-bromo-3-(6-phenylpyridin-3-yl)pyrazolo[1,5-a]pyrimidin-5-yl)-1-hydroxycyclohexyl)-acetic acid | | 521.1 | 522.0 | 1.48 |

TABLE 9-continued

| Example | Chemical name | Column 2 | Exact mass | MS m/z (M + H) | HPLC MS $t_R$ |
|---|---|---|---|---|---|
| 78 | 2-((1S,4S)-4-(7-amino-6-bromo-3-(1-phenyl-1H-pyrazol-4-yl)pyrazolo[1,5-a]pyrimidin-5-yl)-1-hydroxycyclohexyl)acetic acid | | 510.1 | 511.0 | 1.89 |
| 79 | 2-((1R,4R)-4-(7-amino-6-bromo-3-(1-phenyl-1H-pyrazol-4-yl)pyrazolo[1,5-a]pyrimidin-5-yl)-1-hydroxycyclohexyl)acetic acid | | 510.1 | 511.0 | 1.86 |

Example 28

Preparation of 2-((1S,4S)-4-(7-amino-6-bromo-3-(6-phenylpyridin-3-yl)pyrazolo[1,5-a]pyrimidin-5-yl)-1-methoxycyclohexyl)acetic acid (Compound 80)

Step 1: Preparation of methyl 2-((1S,4S)-4-(7-(bis((2-(trimethylsilyl)ethoxy)methyl)amino)-6-bromo-3-(6-phenylpyridin-3-yl)pyrazolo[1,5-a]pyrimidin-5-yl)-1-methoxycyclohexyl)acetate

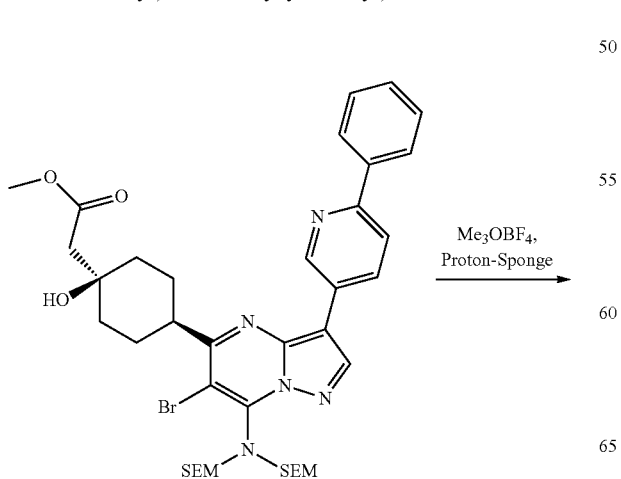

Me₃OBF₄, Proton-Sponge

-continued

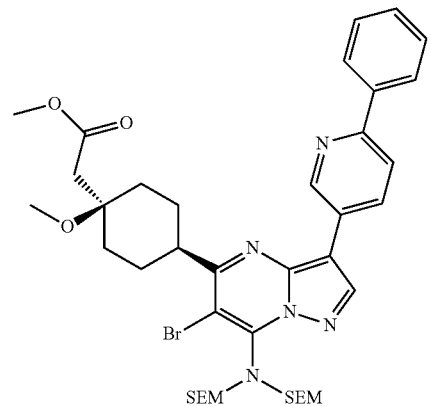

The methylation of the hydroxyl compound was performed with same condition described in example 7 step 2. HPLC-MS $t_R$=2.30 min (UV$_{254\ nm}$); mass calculated for formula $C_{39}H_{56}BrN_5O_5Si_2$ 809.3, observed LCMS m/z 810.3 (M+H).

Step 2: Preparation of methyl 2-((1S,4S)-4-(7-amino-6-bromo-3-(6-phenylpyridin-3-yl)pyrazolo[1,5-a]pyrimidin-5-yl)-1-methoxycyclohexyl)acetate Step 3: Preparation of 2-((1S,4S)-4-(7-amino-6-bromo-3-(6-phenylpyridin-3-yl)pyrazolo[1,5-a]pyrimidin-5-yl)-1-methoxycyclohexyl)acetic acid (Compound 80)

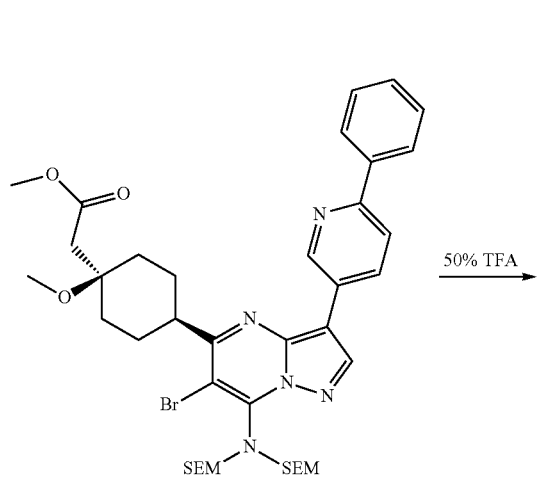

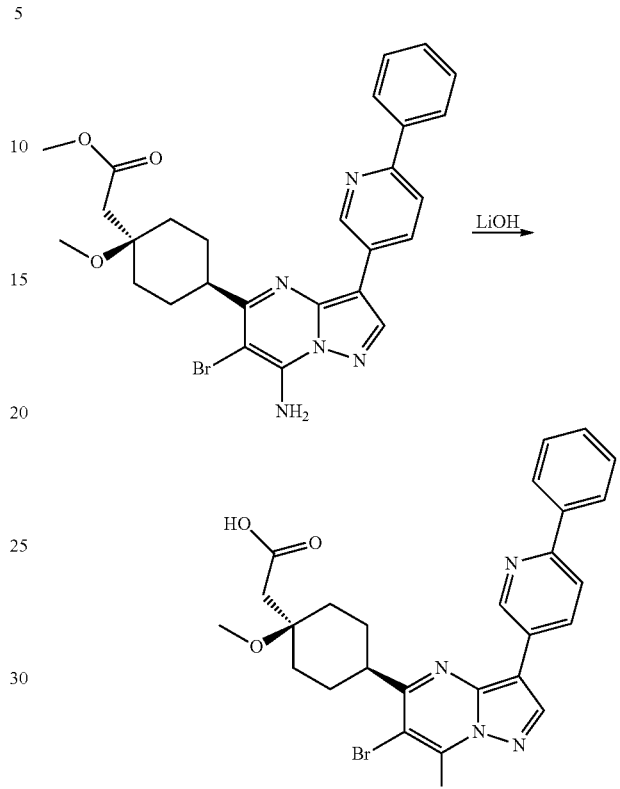

The bromo-compound was de-protected with the same condition described in example 1 step 11. HPLC-MS $t_R$=1.55 min (UV$_{254\ nm}$); mass calculated for formula $C_{27}H_{28}BrN_5O_3$ 549.1, observed LCMS m/z 550.0 (M+H).

The ester were hydrolyzed with the same condition described in example 1 Step 12. HPLC-MS $t_R$=1.39 min (UV$_{254\ nm}$); mass calculated for formula $C_{26}H_{26}BrN_5O_3$ 535.1, observed LCMS m/z 536.0 (M+H).

Example 29

By essentially the same procedure in Preparative Example 28, the isomer compound in Column 2 of Table 19 can be prepared.

TABLE 10

| Example | Chemical name | Column 2 | Exact mass | MS m/z (M + H) | HPLC MS $t_R$ |
|---|---|---|---|---|---|
| 81 | 2-((1R,4R)-4-(7-amino-6-bromo-3-(6-phenylpyridin-3-yl)pyrazolo[1,5-a]pyrimidin-5-yl)-1-methoxycyclohexyl)-acetic acid | | 535.1 | 536.0 | 1.34 |

Example 30

Preparation of (4-(7-amino-6-bromo-3-(6-phenylpyridin-3-yl)pyrazolo[1,5-a]pyrimidin-5-yl)-1-methoxycyclohexyl)methanol (Compound 82)

Step 1: Preparation of (4-(7-(bis((2-(trimethylsilyl)ethoxy)methyl)amino)pyrazolo[1,5-a]pyrimidin-5-yl)-1-methoxycyclohexyl)methanol

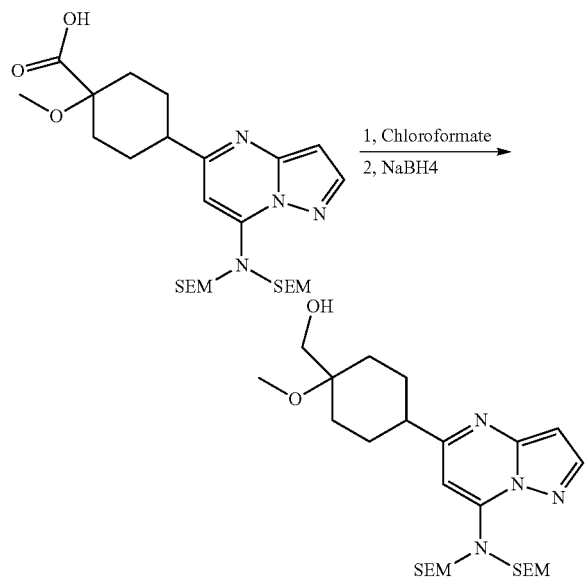

The carboxylic acid (3.35 g, 6.1 mmol) was dissolved in dry THF (50 mL) and cooled to 0° C. The N-methylmorpholine (657 mg, 6.5 mmol) was added followed by the addition of iso-butyl chloroformate (888 mg, 6.5 mmol). The mixture was stirred at 0° C. for 2 hours and NaBH$_4$ (495 mg, 13 mmol) in water (5 mL) was added carefully. The resulting mixture was stirred at 0° C. for 30 min followed by room temperature for another 30 min. The solvent was removed under reduced pressure and extracted with EtOAc. After concentration, the crude was purified with column (silica gel, 0~40% EtOAc/hexane) to give the product (2.32 g). HPLC-MS $t_R$=2.07 min (UV$_{254\ nm}$); mass calculated for formula $C_{26}H_{48}N_4O_4Si_2$ 536.3, observed LCMS m/z 537.4 (M+H).

Step 2: Preparation of (4-(7-(bis((2-(trimethylsilyl)ethoxy)methyl)amino)-3-iodopyrazolo[1,5-a]pyrimidin-5-yl)-1-methoxycyclohexyl)methanol

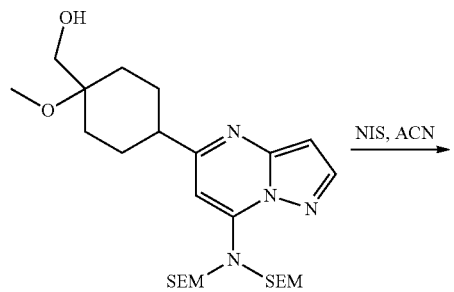

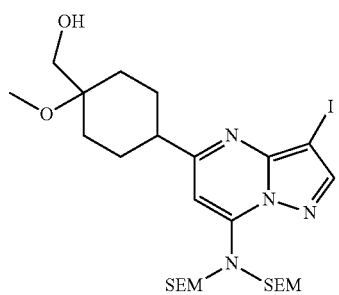

The iodo compound was prepared with the same condition described in example 1 Step 7. HPLC-MS $t_R$=2.62 min (UV$_{254\ nm}$); mass calculated for formula $C_{26}H_{47}IN_4O_4Si_2$ 662.2, observed LCMS m/z 663.3 (M+H).

Step 3: Preparation of (4-(7-(bis((2-(trimethylsilyl)ethoxy)methyl)amino)-3-(6-phenylpyridin-3-yl)pyrazolo[1,5-a]pyrimidin-5-yl)-1-methoxycyclohexyl)methanol

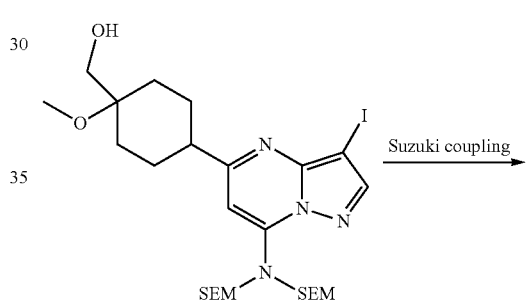

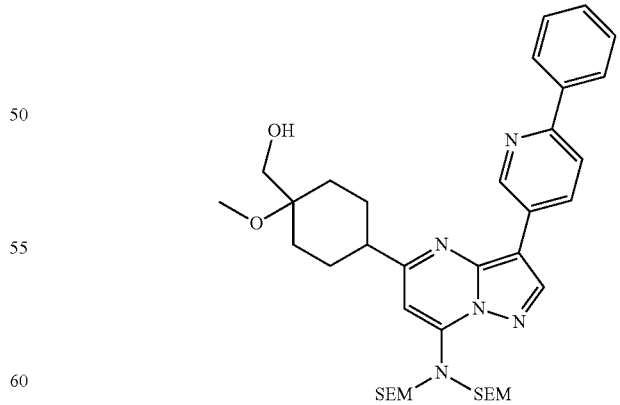

The 3-phenylpyridyl compound was prepared with the same condition described in example 1 Step 8. HPLC-MS $t_R$=2.29 min (UV$_{254\ nm}$); mass calculated for formula $C_{37}H_{55}N_5O_4Si_2$ 689.4, observed LCMS m/z 690.4 (M+H).

149

Step 4: Preparation of (4-(7-(bis((2-(trimethylsilyl)ethoxy)methyl)amino)-6-bromo-3-(6-phenylpyridin-3-yl)pyrazolo[1,5-a]pyrimidin-5-yl)-1-methoxycyclohexyl)methanol

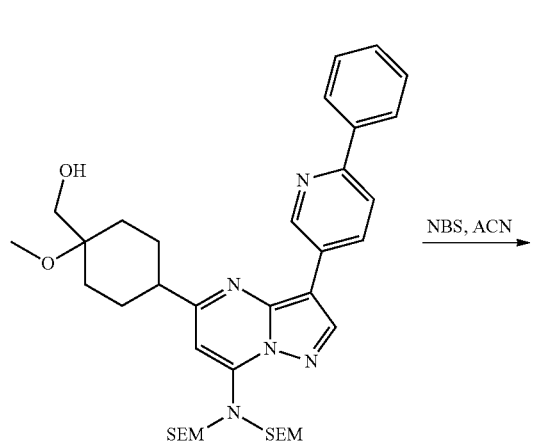

The bromo compound was prepared with the same condition described in example 1 Step 10. HPLC-MS $t_R$=2.69 min (UV$_{254\ nm}$); mass calculated for formula $C_{37}H_{54}BrN_5O_4Si_2$ 767.3, observed LCMS m/z 768.2 (M+H).

150

Step 5: Preparation of (4-(7-amino-6-bromo-3-(6-phenylpyridin-3-yl)pyrazolo[1,5-a]pyrimidin-5-yl)-1-methoxycyclohexyl)methanol (Compound 82)

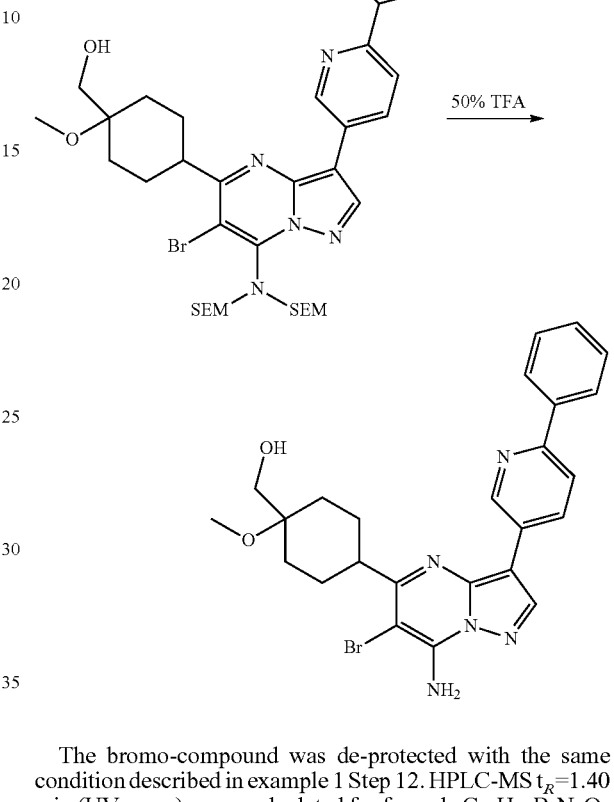

The bromo-compound was de-protected with the same condition described in example 1 Step 12. HPLC-MS $t_R$=1.40 min (UV$_{254\ nm}$); mass calculated for formula $C_{25}H_{26}BrN_5O_2$ 507.1, observed LCMS m/z 508.1 (M+H).

Example 31

By essentially the same procedure given in Preparative Example 30, the compound given in Column 2 of Table 11 can be prepared.

TABLE 11

| Example | Chemical name | Column 2 | Exact mass | MS m/z (M + H) | HPLC MS $t_R$ |
|---|---|---|---|---|---|
| 83 | (4-(7-amino-6-bromo-3-(1-phenyl-1H-pyrazol-4-yl)pyrazolo[1,5-a]pyrimidin-5-yl)-1-(2-methoxyethoxy)-cyclohexyl)methanol | | 540.1 | 541.2 | 1.97 |

TABLE 11-continued

| Example | Chemical name | Column 2 | MS Exact mass | MS m/z (M + H) | HPLC MS $t_R$ |
|---|---|---|---|---|---|
| 167 | (4-(7-amino-6-bromo-3-(1-phenyl-1H-pyrazol-4-yl)pyrazolo[1,5-a]pyrimidin-5-yl)-1-(methoxymethyl)-cyclohexyl)methanol | | 510.1 | 511.2 | 2.01 |
| 168 | ((1S,4S)-4-(7-amino-6-bromo-3-(6-phenylpyridin-3-yl)pyrazolo[1,5-a]pyrimidin-5-yl)-1-((2-methoxyethoxy)-methyl)cyclohexyl)-methanol | | 565.2 | 566.2 | 1.87 |
| 169 | ((1R,4R)-4-(7-amino-6-bromo-3-(6-phenylpyridin-3-yl)pyrazolo[1,5-a]pyrimidin-5-yl)-1-((2-methoxyethoxy)-methyl)cyclohexyl)-methanol | | 565.2 | 566.2 | 1.83 |

Example 32

Preparation of 1-(7-amino-5-((1R,4R)-4-(hydroxymethyl)-4-methoxycyclohexyl)-3-(6-phenylpyridin-3-yl)pyrazolo[1,5-a]pyrimidin-6-yl)ethanone (Compound 84)

Step 1: Preparation of ((1R,4R)-4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-1-methoxycyclohexyl)methanol

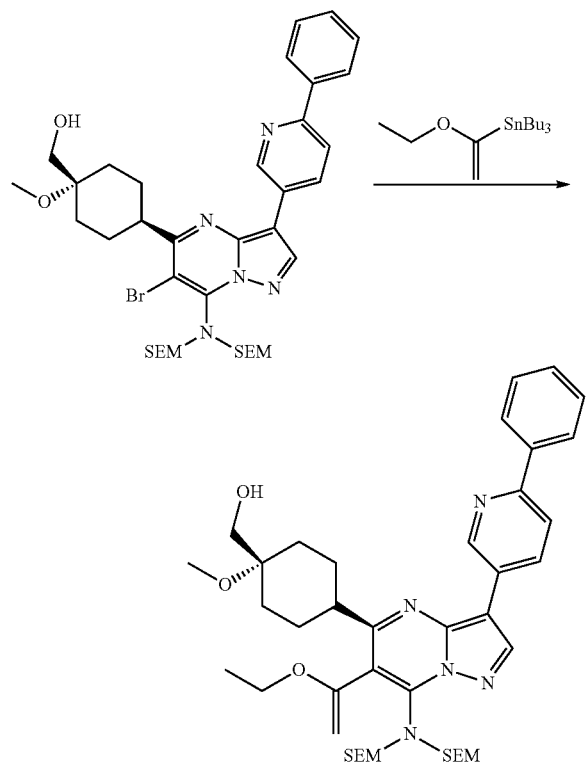

The Stille coupling reaction was performed with the same conditions described in example 3 Step 1. HPLC-MS $t_R$=2.43 min (UV$_{254\,nm}$); mass calculated for formula $C_{41}H_{61}N_5O_5Si_2$ 759.4, observed LCMS m/z 760.5 (M+H).

Step 2: Preparation of 1-(7-amino-5-((1R,4R)-4-(hydroxymethyl)-4-methoxycyclohexyl)-3-(6-phenylpyridin-3-yl)pyrazolo[1,5-a]pyrimidin-6-yl)ethanone (Compound 84)

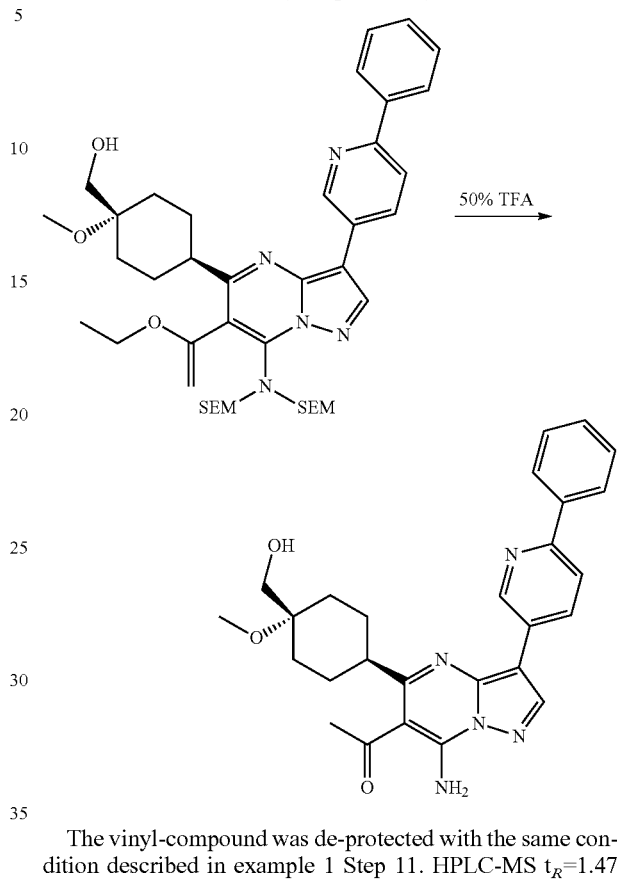

The vinyl-compound was de-protected with the same condition described in example 1 Step 11. HPLC-MS $t_R$=1.47 min (UV$_{254\,nm}$); mass calculated for formula $C_{27}H_{29}N_5O_3$ 471.2, observed LCMS m/z 472.1 (M+H).

Example 33

By essentially the same procedure given in Preparative Example 32, the compounds given in Column 2 of Table 12 can be prepared.

TABLE 12

| Example | Chemical name | Column 2 | Exact mass | MS m/z (M + H) | HPLC MS $t_R$ |
|---|---|---|---|---|---|
| 85 | 1-(7-amino-5-((1S,4S)-4-(hydroxymethyl)-4-methoxycyclohexyl)-3-(6-phenylpyridin-3-yl)pyrazolo[1,5-a]pyrimidin-6-yl)ethanone | | 471.2 | 472.1 | 1.47 |

TABLE 12-continued

| Example | Chemical name | Column 2 | Exact mass | MS m/z (M + H) | HPLC MS $t_R$ |
|---|---|---|---|---|---|
| 86 | 1-(7-amino-5-(4-(hydroxymethyl)-4-(2-methoxyethoxy)-cyclohexyl)-3-(6-phenylpyridin-3-yl)pyrazolo[1,5-a]pyrimidin-6-yl)ethanone | | 515.3 | 516.3 | 1.43 |
| 87 | 1-(7-amino-5-(4-(hydroxymethyl)-4-(2-methoxyethoxy)-cyclohexyl)-3-(1-phenyl-1H-pyrazol-4-yl)pyrazolo[1,5-a]pyrimidin-6-yl)ethanone | | 504.2 | 505.3 | 1.91 |
| 170 | 1-(7-amino-5-(4-(hydroxymethyl)-4-(methoxymethyl)-cyclohexyl)-3-(6-phenylpyridin-3-yl)pyrazolo[1,5-a]pyrimidin-6-yl)ethanone | | 485.2 | 486.3 | 1.57 |
| 171 | 1-(7-amino-5-(4-(hydroxymethyl)-4-methoxycyclohexyl)-3-(6'-methoxy-2,3'-bipyridin-5-yl)pyrazolo[1,5-a]pyrimidin-6-yl)ethanone | | 502.2 | 503.3 | 1.37 |

TABLE 12-continued

| Example | Chemical name | Column 2 | Exact mass | MS m/z (M + H) | HPLC MS $t_R$ |
|---|---|---|---|---|---|
| 172 | 1-(7-amino-5-(4,4-bis(hydroxymethyl)-cyclohexyl)-3-(6-phenylpyridin-3-yl)pyrazolo[1,5-a]pyrimidin-6-yl)ethanone | | 471.2 | 472.3 | 1.35 |

Example 34

Preparation of (1R,4R)-4-(7-amino-6-(methylsulfonyl)-3-(1-phenyl-1H-pyrazol-4-yl)pyrazolo[1,5-a]pyrimidin-5-yl)-N-hydroxy-1-(2-methoxyethoxy)cyclohexanecarboxamide (Compound 88)

Step 1: Preparation of (1R,4R)-4-(7-amino-6-(methylsulfonyl)-3-(1-phenyl-1H-pyrazol-4-yl)pyrazolo[1,5-a]pyrimidin-5-yl)-N-hydroxy-1-(2-methoxyethoxy)cyclohexanecarboxamide (Compound 88)

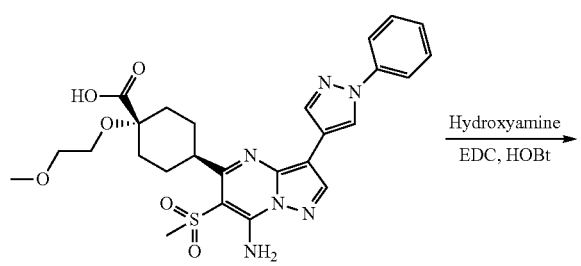

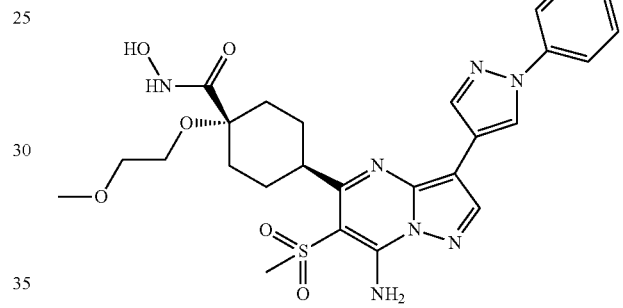

The carboxylic acid (60 mg, ~0.1 mmol) was dissolved in DMF (2 mL). Hydroxyamine hydrochloride (21.5 mg, 0.3 mmol), HOBt (41 mg, 0.3 mmol) and DIEA (52 uL, 0.3 mmol) were added followed by the addition of EDC (57 mg, 0.3 mmol). The resulting mixture was stirred at room temperature overnight and purified with HPLC. HPLC-MS $t_R$=1.11 min ($UV_{254\ nm}$); mass calculated for formula $C_{26}H_{31}N_7O_6S$ 569.2, observed LCMS m/z 570.1 (M+H).

Example 35

By essentially the same procedure in Preparative Example 34, the compounds in Column 2 of Table 13 can be prepared.

TABLE 13

| Example | Chemical name | Column 2 | Exact mass | MS m/z (M + H) | HPLC MS $t_R$ |
|---|---|---|---|---|---|
| 89 | (1R,4R)-4-(7-amino-6-(methylsulfonyl)-3-(1-phenyl-1H-pyrazol-4-yl)pyrazolo[1,5-a]pyrimidin-5-yl)-N-methoxy-1-(2-methoxyethoxy)-cyclohexane-carboxamide | | 583.2 | 584.2 | 1.23 |

TABLE 13-continued

| Example | Chemical name | Column 2 | Exact mass | MS m/z (M + H) | HPLC MS $t_R$ |
|---|---|---|---|---|---|
| 90 | (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-N-methylcyclohexane-carboxamide | | 567.2 | 568.0 | 1.13 |
| 91 | (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-N,N-dimethylcyclohexane-carboxamide | | 581.2 | 582.0 | 1.19 |
| 92 | (1R,4R)-4-(7-amino-6-(methylsulfonyl)-3-(1-phenyl-1H-pyrazol-4-yl)pyrazolo[1,5-a]pyrimidin-5-yl)-N-(2-hydroxyethyl)-1-(2-methoxyethoxy)-cyclohexane-carboxamide | | 597.2 | 598.0 | 1.01 |
| 93 | (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-N-(2-methoxyethyl)-cyclohexane-carboxamide | | 611.3 | 612.0 | 1.16 |

TABLE 13-continued

| Example | Chemical name | Column 2 | Exact mass | MS m/z (M + H) | HPLC MS $t_R$ |
|---|---|---|---|---|---|
| 94 | 1-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-cyclohexanecarbonyl)-1H-pyrazol-3(2H)-one | | 620.2 | 621.0 | 1.08 |
| 95 | 1-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarbonyl)-pyrazolidin-3-one | | 622.2 | 622.9 | 1.04 |
| 96 | (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-N-morpholinocyclohexane-carboxamide | | 638.3 | 639.0 | 1.07 |
| 97 | (1R,4R)-4-(7-amino-6-(methylsulfonyl)-3-(1-phenyl-1H-pyrazol-4-yl)pyrazolo[1,5-a]pyrimidin-5-yl)-N-methoxy-1-(2-methoxyethoxy)-N-methylcyclohexane-carboxamide | | 597.2 | 598.2 | 1.30 |

TABLE 13-continued

| Example | Chemical name | Column 2 | Exact mass | MS m/z (M + H) | HPLC MS $t_R$ |
|---|---|---|---|---|---|
| 98 | (1R,4R)-4-(7-amino-6-(methylsulfonyl)-3-(1-phenyl-1H-pyrazol-4-yl)pyrazolo[1,5-a]pyrimidin-5-yl)-N-ethoxy-1-(2-methoxyethoxy)-cyclohexane-carboxamide | | 597.2 | 598.2 | 1.27 |
| 99 | (1R,4R)-4-(7-amino-6-(methylsulfonyl)-3-(1-phenyl-1H-pyrazol-4-yl)pyrazolo[1,5-a]pyrimidin-5-yl)-N-(cyclopropylmethoxy)-1-(2-methoxyethoxy)-cyclohexane-carboxamide | | 623.3 | 624.0 | 1.23 |
| 100 | (1R,R-4-(7-amino-6-(methylsulfonyl)-3-(1-phenyl-1H-pyrazol-4-yl)pyrazolo[1,5-a]pyrimidin-5-yl)-N-(2-hydroxyethoxy)-1-(2-methoxyethoxy)cyclohexane-carboxamide | | 613.2 | 614.2 | 1.11 |
| 101 | (1R,4R)-4-amino-6-(methylsulfonyl)-3-(1-phenyl-1H-pyrazol-4-yl)pyrazolo[1,5-a]pyrimidin-5-yl)-N,1-bis(2-methoxyethoxy)cyclohexane-carboxamide | | 627.2 | 628.2 | 1.22 |

TABLE 13-continued

| Example | Chemical name | Column 2 | Exact mass | MS m/z (M + H) | HPLC MS $t_R$ |
|---|---|---|---|---|---|
| 102 | (1R,4R)-4-(6-acetyl-7-amino-3-(6-phenylpyridin-3-yl)pyrazolo[1,5-a]pyrimidin-5-yl)-N-hydroxy-1-(2-methoxyethoxy)-cyclohexane-carboxamide | | 544.2 | 545.2 | 0.93 |
| 103 | (1R,4R)-4-(6-acetyl-7-amino-3-(6-phenylpyridin-3-yl)pyrazolo[1,5-a]pyrimidin-5-yl)-N-methoxy-1-(2-methoxyethoxy)-cyclohexane-carboxamide | | 558.3 | 559.3 | 0.99 |
| 104 | (1R,4R)-4-(7-amino-6-(methylsulfonyl)-3-(6-phenylpyridin-3-yl)pyrazolo[1,5-a]pyrimidin-5-yl)-N-hydroxy-1-(2-methoxyethoxy)-cyclohexane-carboxamide | | 580.2 | 581.2 | 0.88 |
| 105 | (1R,4R)-4-(7-amino-6-(methylsulfonyl)-3-(6-phenylpyridin-3-yl)pyrazolo[1,5-a]pyrimidin-5-yl)-N-methoxy-1-(2-methoxyethoxy)-cyclohexane-carboxamide | | 594.2 | 595.2 | 0.99 |

TABLE 13-continued

| Example | Chemical name | Column 2 | Exact mass | MS m/z (M + H) | HPLC MS $t_R$ |
|---|---|---|---|---|---|
| 106 | (1R,4R)-4-(7-amino-6-(methylsulfonyl)-3-(6-phenylpyridin-3-yl)pyrazolo[1,5-a]pyrimidin-5-yl)-N-(cyclopropylmethoxy)-1-(2-methoxyethoxy)-cyclohexane-carboxamide | | 634.3 | 635.2 | 1.09 |
| 107 | (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-cyclohexane-carbohydrazide | | 568.2 | 569.1 | 1.03 |

Example 36

Preparation of 5-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-1,3,4-oxadiazol-2-amine (Compound 108)

Step 1: Preparation of 2-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarbonyl)hydrazinecarboximidamide The peptide coupling was performed with the same condition described in example 34 Step 1 with aminoguanidine hydrochloride and purified with HPLC. HPLC-MS $t_R$=0.92 min (UV$_{254\,nm}$); mass calculated for formula $C_{27}H_{34}N_{10}O_5S$ 610.2, observed LCMS m/z 611.2 (M+H).

Step 2: Preparation of 5-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-1,3,4-oxadiazol-2-amine (Compound 108)

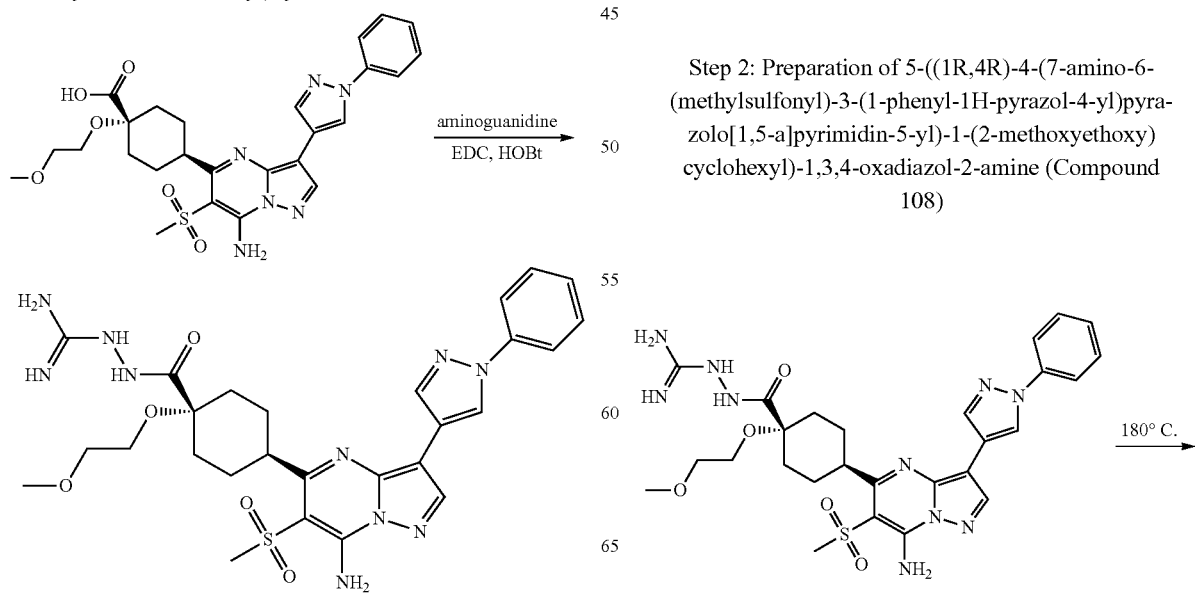

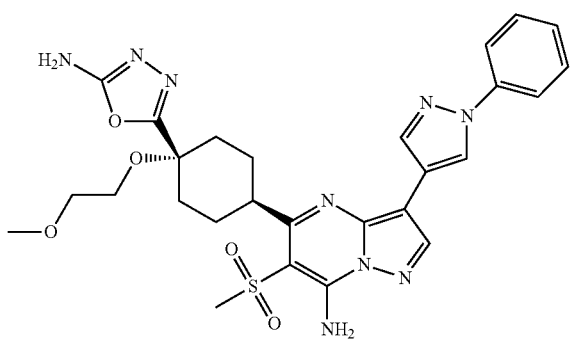

The starting material (68 mg, TFA salt) was mixed with phenyl ether (2 mL) in the sealed tube and heated to 180° C. After stirring at that temperature for 1 hour, the reaction was cooled to room temperature and the solvent was removed under reduced pressure. The crude product was purified with HPLC and the heterocyclic product was obtained (37 mg). HPLC-MS $t_R$=0.94 min ($UV_{254\ nm}$); mass calculated for formula $C_{27}H_{31}N_9O_5S$ 593.2, observed LCMS m/z 594.0 (M+H).

Example 37

By essentially the same procedure in Preparative Example 36, the compounds in Column 2 of Table 14 can be prepared started from acetamidrazone hydrochloride.

TABLE 14

| Example | Chemical name | Column 2 | Exact mass | MS m/z (M + H) | HPLC MS $t_R$ |
|---|---|---|---|---|---|
| 109 | 5-((1R,4R)-4-(2-methoxyethoxy)-4-(5-methyl-1,3,4-oxadiazol-2-yl)cyclohexyl)-6-(methylsulfonyl)-3-(1-phenyl-1H-pyrazol-4-yl)pyrazolo[1,5-a]pyrimidin-7-amine | | 592.2 | 593.0 | 1.14 |

Example 38

Preparation of (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboxamide (Compound 110)

Step 1: Preparation of 4-(7-(bis((2-(trimethylsilyl)ethoxy)methyl)amino)-3-(1-phenyl-1H-pyrazol-4-yl)pyrazolo[1,5-a]pyrimidin-5-yl)-1-(2-methoxyethoxy)cyclohexanecarboxylic acid

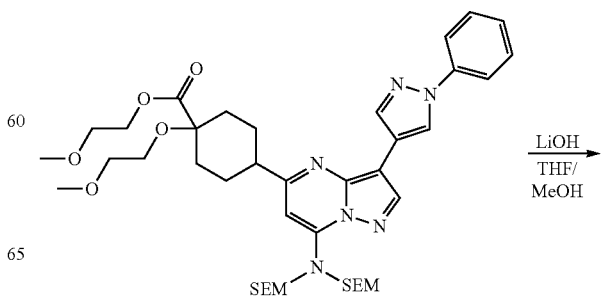

-continued

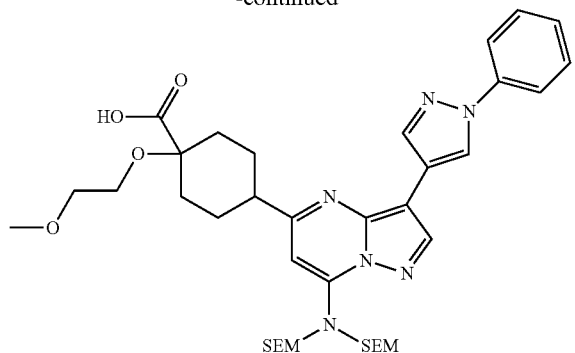

The ester was hydrolyzed with the same condition described in example 1 step 12. HPLC-MS $t_R$=1.88 min (UV$_{254\ nm}$); mass calculated for formula $C_{37}H_{56}N_6O_6Si_2$ 736.4, observed LCMS m/z 737.3 (M+H).

Step 2: Preparation of 4-(7-(bis((2-(trimethylsilyl)ethoxy)methyl)amino)-3-(1-phenyl-1H-pyrazol-4-yl)pyrazolo[1,5-a]pyrimidin-5-yl)-1-(2-methoxyethoxy)cyclohexanecarboxamide

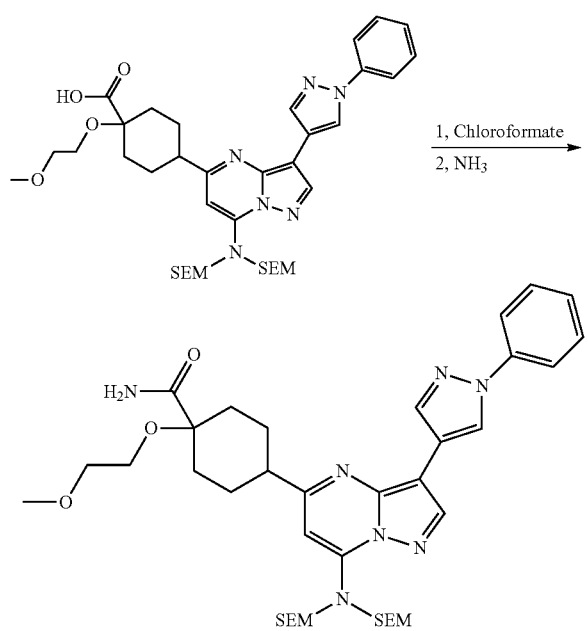

The carboxylic acid (3.9 g, 5.29 mmol) was dissolved in dry THF (50 mL) and cooled to 0° C. The Et$_3$N (2.76 mL, 20 mmol) was added followed by the addition of ethyl chloroformate (1.5 mL, 15.7 mmol). The resulting mixture was stirred at 0° C. for 1 hour and the ammonia (3 ml, 7 N in methanol) was added and the mixture was stirred for another 1 hour. The reaction was taken up with EtOAc (200 mL) and washed with water, brine and dried over Na$_2$SO$_4$. After concentration, the crude was purified with column (silica gel, 0~50% EtOAc/hexane) and the product was obtained (3.66 g). HPLC-MS $t_R$=1.84 min (UV$_{254\ nm}$); mass calculated for formula $C_{37}H_{57}N_7O_5Si_2$ 735.4, observed LCMS m/z 736.3 (M+H).

Step 3: Preparation of 4-(7-(bis((2-(trimethylsilyl)ethoxy)methyl)amino)-6-iodo-3-(1-phenyl-1H-pyrazol-4-yl)pyrazolo[1,5-a]pyrimidin-5-yl)-1-(2-methoxyethoxy)cyclohexanecarboxamide

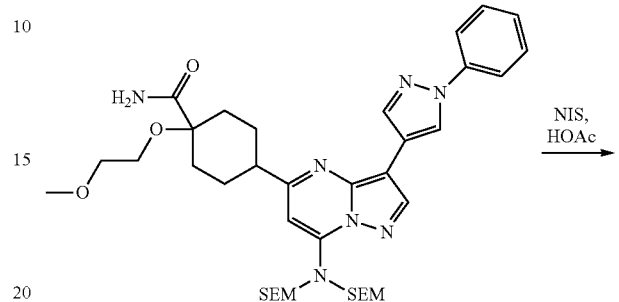

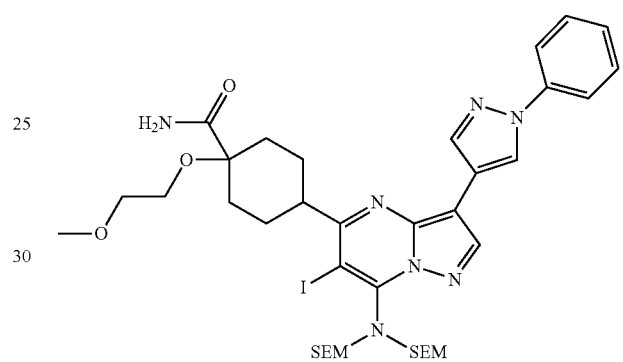

The product in step 2 (737 mg, 1.0 mmol) was dissolved in HOAc (5 mL) and NIS (235 mg, 1.0 mmol) was added. The mixture was stirred at room temperature for 1 hour and concentrated. The crude was purified with column (silica gel, 0~40% EtOAc/hexane) and the desired product (687 mg) and some mono-de-SEM product was obtained. HPLC-MS $t_R$=1.76 min (UV$_{254\ nm}$); mass calculated for formula $C_{37}H_{56}IN_7O_5Si_2$ 861.3, observed LCMS m/z 862.8 (M+H).

Step 4: Preparation of 4-(7-(bis((2-(trimethylsilyl)ethoxy)methyl)amino)-6-(methylsulfonyl)-3-(1-phenyl-1H-pyrazol-4-yl)pyrazolo[1,5-a]pyrimidin-5-yl)-1-(2-methoxyethoxy)cyclohexanecarboxamide

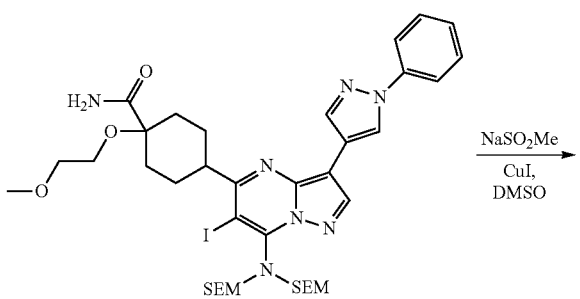

-continued

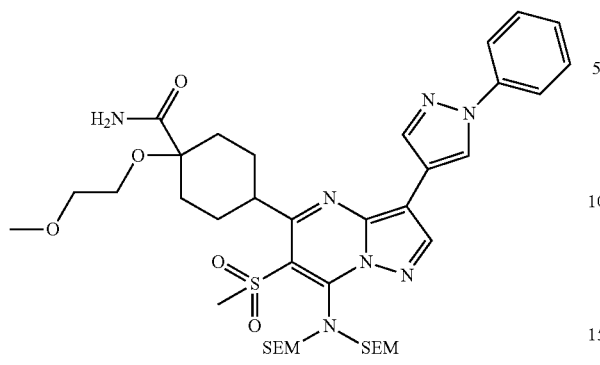

Step 5: Preparation of (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboxamide (Compound 110)

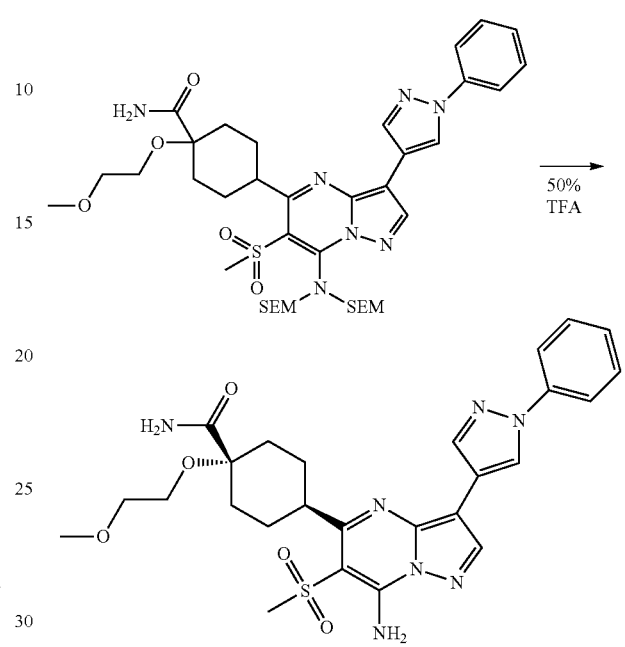

The iodo compound (861 mg, 1.0 mmol), CuI (1.14 g, 6.0 mmol) and NaSO$_2$Me (310 mg, 3.0 mmol) was mixed in DMSO (8 mL) under the Ar and heated to 90° C. and stirred for 2 hour. After cooled to room temperature, the EtOAc (100 mL) was added followed by concentrated ammonia (28%, 5 mL) and washed with water and brine. After concentration, the crude was purified with column (silica gel, 0-40% EtOAc/hexane) and the mixture of desired product and de-iodo product was obtained. The mixture was used in the next step directly. HPLC-MS t$_R$=1.76 min (UV$_{254\,nm}$); mass calculated for formula C$_{38}$H$_{59}$N$_7$O$_7$SSi$_2$ 813.4, observed LCMS m/z 814.3 (M+H).

The methylsulfone-compound was de-protected with the same condition described in example 1 step 12 and purified with HPLC and the enantiomeric pure product was obtained. HPLC-MS t$_R$=1.09 min (UV$_{254\,nm}$); mass calculated for formula C$_{26}$H$_{31}$N$_7$O$_5$S 553.2, observed LCMS m/z 553.9 (M+H).

Example 39

By essentially the same procedure in Preparative Example 38, the compound in Column 2 of Table 15 can be prepared.

TABLE 15

| Example | Chemical name | Column 2 | Exact mass | MS m/z (M + H) | HPLC MS t$_R$ |
|---|---|---|---|---|---|
| 111 | (1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexanecarboxamide | | 564.2 | 565.2 | 0.93 |

Example 40

Preparation of (1R,4R)-4-(3-(6-(1H-imidazol-2-yl)pyridin-3-yl)-6-acetyl-7-aminopyrazolo[1,5-a]pyrimidin-5-yl)-1-(2-methoxyethoxy)cyclohexanecarboxamide (Compound 112)

Step 1: Preparation of 2-methoxyethyl 4-(7-(bis((2-(trimethylsilyl)ethoxy)methyl)amino)-3-(6-(hydroxymethyl)pyridin-3-yl)pyrazolo[1,5-a]pyrimidin-5-yl)-1-(2-methoxyethoxy)cyclohexanecarboxylate

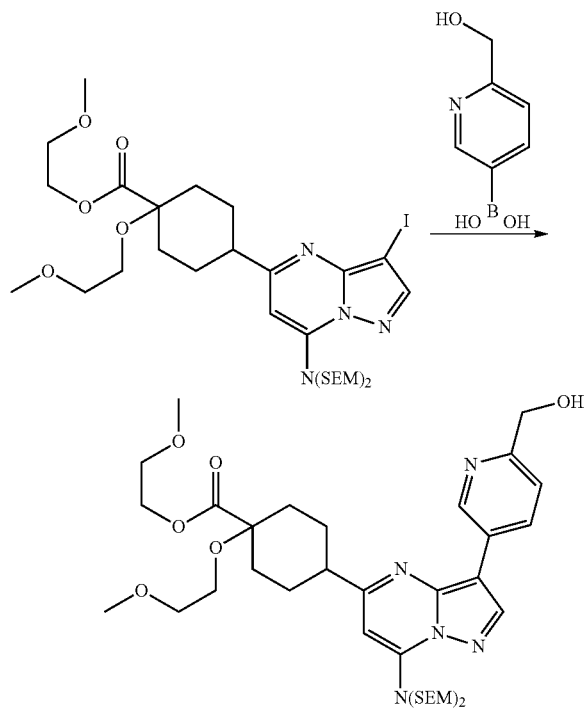

The 2-hydroxymethylpyridine compound was prepared with the same condition described in example 1 Step 8. HPLC-MS $t_R$=1.29 min (UV$_{254\ nm}$); mass calculated for formula $C_{37}H_{61}N_5O_8Si_2$ 759.4, observed LCMS m/z 760.0 (M+H).

Step 2: Preparation of 2-methoxyethyl 4-(7-(bis((2-(trimethylsilyl)ethoxy)methyl)amino)-3-(6-formylpyridin-3-yl)pyrazolo[1,5-a]pyrimidin-5-yl)-1-(2-methoxyethoxy)cyclohexanecarboxylate

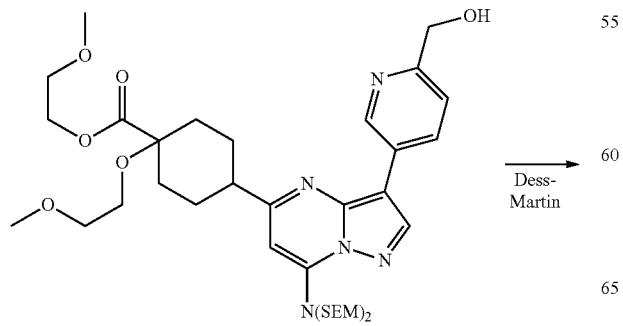

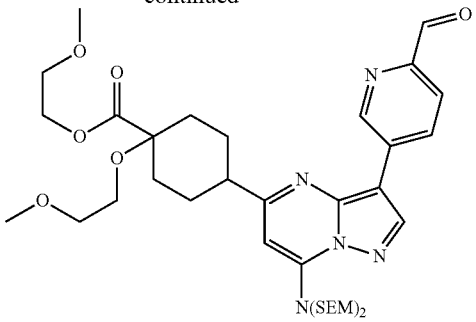

The alcohol (2.307 g, 3.03 mmol) was dissolved in DCM (50 mL) and Dess-Martin reagent (2.57 g, 6.06 mmol) was added. The mixture was stirred at room temperature for 1 hour and diluted with EtOAc (200 mL) and washed with NaHCO$_3$ (aq.) followed by brine and dried over Na$_2$SO$_4$. After concentration, the crude was purified with column (silica gel, 30~60% EtOAc/Hexane) the product was obtained (2.137 g). HPLC-MS $t_R$=1.70 min (UV$_{254\ nm}$); mass calculated for formula $C_{37}H_{59}N_5O_8Si_2$ 757.4, observed LCMS m/z 758.0 (M+H).

Step 3: Preparation of 2-methoxyethyl 4-(7-(bis((2-(trimethylsilyl)ethoxy)methyl)amino)-3-(6-formylpyridin-3-yl)pyrazolo[1,5-a]pyrimidin-5-yl)-1-(2-methoxyethoxy)cyclohexanecarboxylate

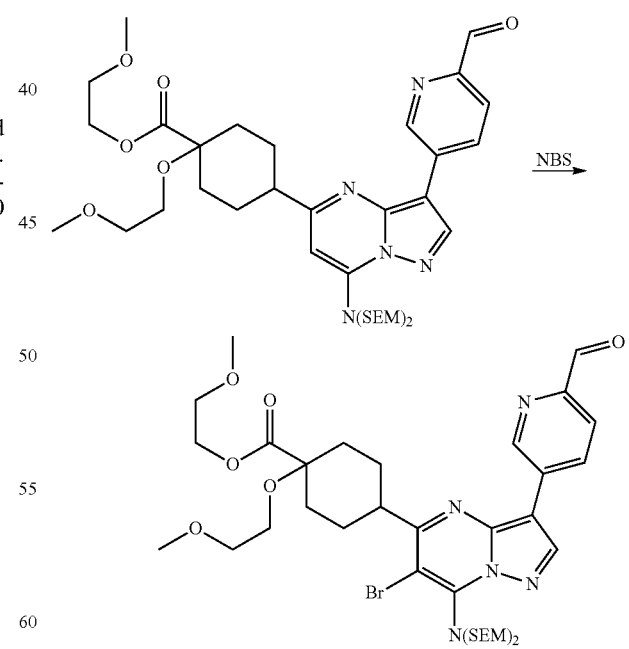

The bromo compound was prepared with the same condition described in example 1 Step 10. HPLC-MS $t_R$=1.76 min (UV$_{254\ nm}$); mass calculated for formula $C_{37}H_{58}BrN_5O_8Si_2$ 835.3, observed LCMS m/z 835.9 (M+H).

Step 4: Preparation of 2-methoxyethyl 4-(7-(bis((2-(trimethylsilyl)ethoxy)methyl)amino)-3-(6-formylpyridin-3-yl)pyrazolo[1,5-a]pyrimidin-5-yl)-1-(2-methoxyethoxy)cyclohexanecarboxylate

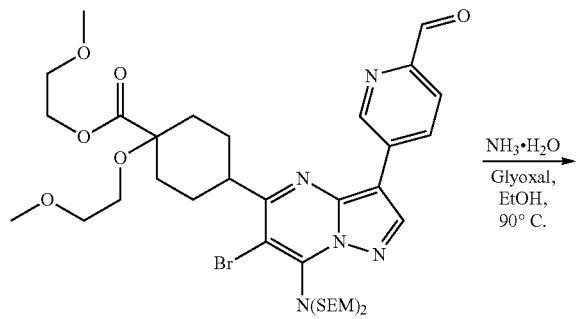

NH₃·H₂O
Glyoxal,
EtOH,
90° C.

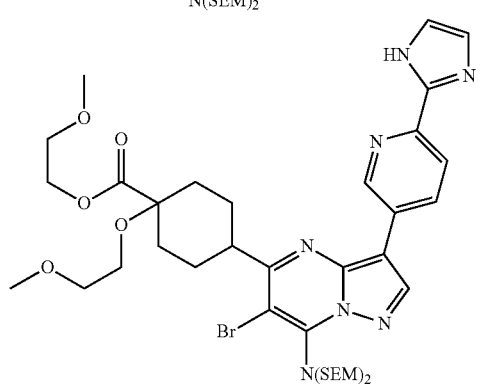

The aldehyde (1.325 g, 1.58 mmol) and ammonia (28%, 1.6 mL) was mixed in ethanol (6 mL) in the tube and glyoxal (272 uL) was added. The tube was sealed and heated to 90° C. and stirred for 1 hour. After cooling to room temperature, the reaction was diluted with EtOAc and washed with water, brine. The crude product was purified with column (silica gel, 50~100% EtOAc/Hexane) and the product was obtained (1.14 g). HPLC-MS $t_R$=1.50 min (UV$_{254\,nm}$); mass calculated for formula $C_{39}H_{60}BrN_7O_7Si_2$ 873.3, observed LCMS m/z 874.2 (M+H).

Step 5: Preparation of 2-methoxyethyl 4-(7-(bis((2-(trimethylsilyl)ethoxy)methyl)amino)-6-bromo-3-(6-(1-((2-(trimethylsilyl)ethoxy)methyl)-1H-imidazol-2-yl)pyridin-3-yl)pyrazolo[1,5-a]pyrimidin-5-yl)-1-(2-methoxyethoxy)cyclohexanecarboxylate

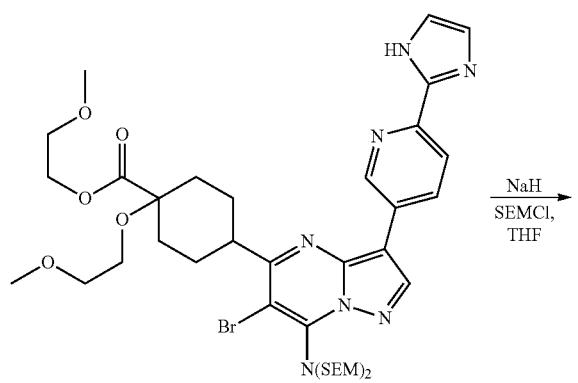

NaH
SEMCl,
THF

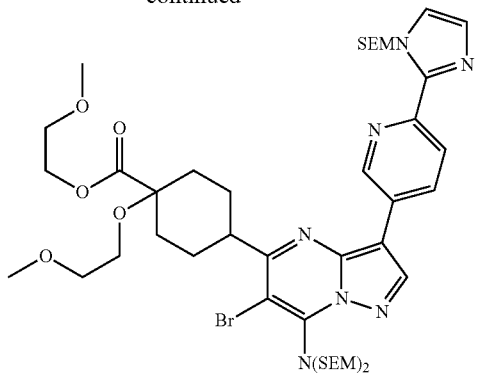

The imidazole (1.14 g, 1.3 mmol) was dissolved in dry THF (30 mL) and NaH (80 mg, 60% in oil, 2.0 mmol) was added carefully. The resulting mixture was stirred at room temperature for 20 min and SEMCl (333 mg, 2.0 mmol) in THF (2 mL) was added and the mixture was stirred for another 1 hour. The mixture was diluted with EtOAc (200 mL) and washed with water, brine and dried over Na₂SO₄. After concentration, the crude was purified with column (silica gel, 30~60% EtOAc/hexane) to give the product (1.13 g). HPLC-MS $t_R$=1.65 min (UV$_{254}$ nm); mass calculated for formula $C_{45}H_{74}BrN_7O_8Si_3$ 1003.4, observed LCMS m/z 904.2 (M+H-TMS-ethyl).

Step 6: Preparation of 2-methoxyethyl 4-(7-(bis((2-(trimethylsilyl)ethoxy)methyl)amino)-6-(1-ethoxyvinyl)-3-(6-(1-((2-(trimethylsilyl)ethoxy)methyl)-1H-imidazol-2-yl)pyridin-3-yl)pyrazolo[1,5-a]pyrimidin-5-yl)-1-(2-methoxyethoxy)cyclohexanecarboxylate

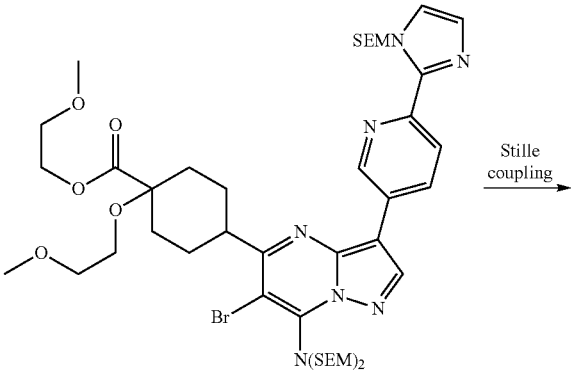

Stille coupling

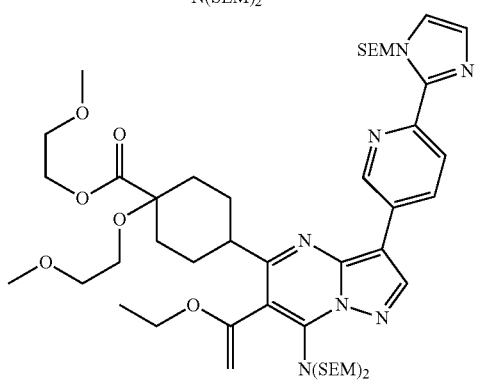

The Stille coupling reaction was performed with the same conditions described in example 3 step 1. HPLC-MS $t_R$=1.83 min (UV$_{254\ nm}$); mass calculated for formula C$_{49}$H$_{81}$N$_7$O$_9$Si$_3$ 995.5, observed LCMS m/z 996.4 (M+H).

Step 7: Preparation of 4-(7-(bis((2-(trimethylsilyl)ethoxy)methyl)amino)-6-(1-ethoxyvinyl)-3-(6-(1-((2-(trimethylsilyl)ethoxy)methyl)-1H-imidazol-2-yl)pyridin-3-yl)pyrazolo[1,5-a]pyrimidin-5-yl)-1-(2-methoxyethoxy)cyclohexanecarboxylic acid

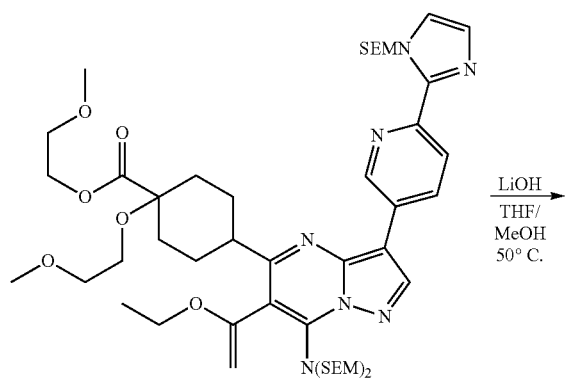

The ester was hydrolyzed with the same condition described in example 1 step 12. HPLC-MS $t_R$=1.51 min (UV$_{254\ nm}$); mass calculated for formula C$_{46}$H$_{75}$N$_7$O$_8$Si$_3$ 937.5, observed LCMS m/z 938.0 (M+H).

Step 8: Preparation of 4-(7-(bis((2-(trimethylsilyl)ethoxy)methyl)amino)-6-(1-ethoxyvinyl)-3-(6-(1-((2-(trimethylsilyl)ethoxy)methyl)-1H-imidazol-2-yl)pyridin-3-yl)pyrazolo[1,5-a]pyrimidin-5-yl)-1-(2-methoxyethoxy)cyclohexanecarboxamide

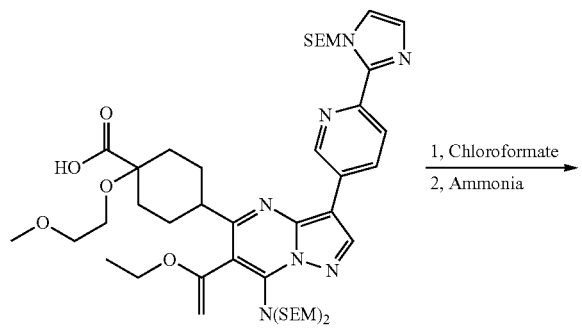

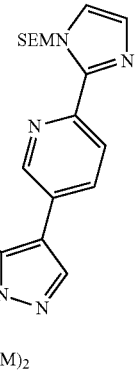

The primary amide was prepared with the same condition described in example 38 Step 2. HPLC-MS $t_R$=1.59 min (UV$_{254\ nm}$); mass calculated for formula C$_{46}$H$_{76}$N$_8$O$_7$Si$_3$ 936.5, observed LCMS m/z 937.5 (M+H).

Step 9: Preparation of (1R,4R)-4-(3-(6-(1H-imidazol-2-yl)pyridin-3-yl)-6-acetyl-7-aminopyrazolo[1,5-a]pyrimidin-5-yl)-1-(2-methoxyethoxy)cyclohexanecarboxamide (Compound 112)

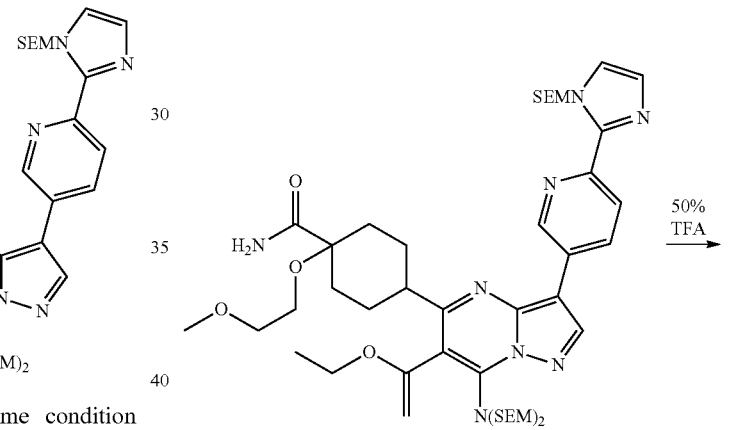

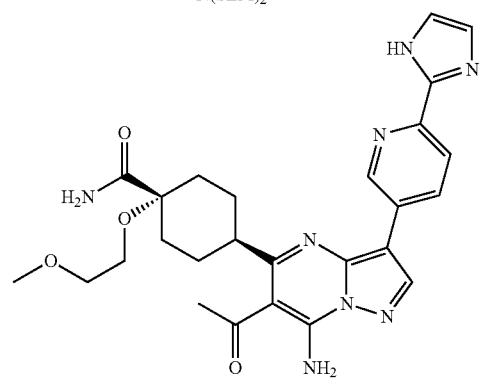

The amide was de-protected with the same condition described in example 1 Step 11 and purified with HPLC and the enantiomeric pure product and another isomer was obtained. HPLC-MS $t_R$=0.71 min (UV$_{254\ nm}$); mass calculated for formula C$_{26}$H$_{30}$N$_8$O$_4$ 518.2, observed LCMS m/z 519.0 (M+H).

Example 41

By essentially the same procedure in Preparative Example 40, the compounds in Column 2 of Table 16 can be prepared.

TABLE 16

| Example | Chemical name | Column 2 | Exact mass | MS m/z (M + H) | HPLC MS $t_R$ |
|---------|---------------|----------|------------|----------------|---------------|
| 113 | (1S,4S)-4-(3-(6-(1H-imidazol-2-yl)pyridin-3-yl)-6-acetyl-7-aminopyrazolo[1,5-a]pyrimidin-5-yl)-1-(2-methoxyethoxy)cyclohexanecarboxamide | | 518.2 | 519.0 | 0.66 |
| 114 | (1S,4S)-4-(3-(6-1H-imidazol-2-yl)pyridin-3-yl)-6-acetyl-7-aminopyrazolo[1,5-a]pyrimidin-5-yl)-N-hydroxy-1-(2-methoxyethoxy)cyclohexanecarboxamide | | 534.2 | 535.0 | 0.63 |
| 115 | (1R,4R)-(3-(6-(1H-imidazol-2-yl)pyridin-3-yl)-6-acetyl-7-aminopyrazolo[1,5-a]pyrimidin-5-yl)-N-hydroxy-1-(2-methoxyethoxy)cyclohexanecarboxamide | | 534.2 | 535.0 | 0.69 |

Example 42

Preparation of (1R,4R)-4-(3-(6-(1H-imidazol-2-yl)pyridin-3-yl)-7-amino-6-(methylsulfonyl)pyrazolo[1,5-a]pyrimidin-5-yl)-N-hydroxy-1-(2-methoxyethoxy)cyclohexanecarboxamide (Compound 116)

Step 1: Preparation of 2-methoxyethyl 4-(7-(bis((2-(trimethylsilyl)ethoxy)methyl)amino)-3-(6-formylpyridin-3-yl)-6-iodopyrazolo[1,5-a]pyrimidin-5-yl)-1-(2-methoxyethoxy)cyclohexanecarboxylate

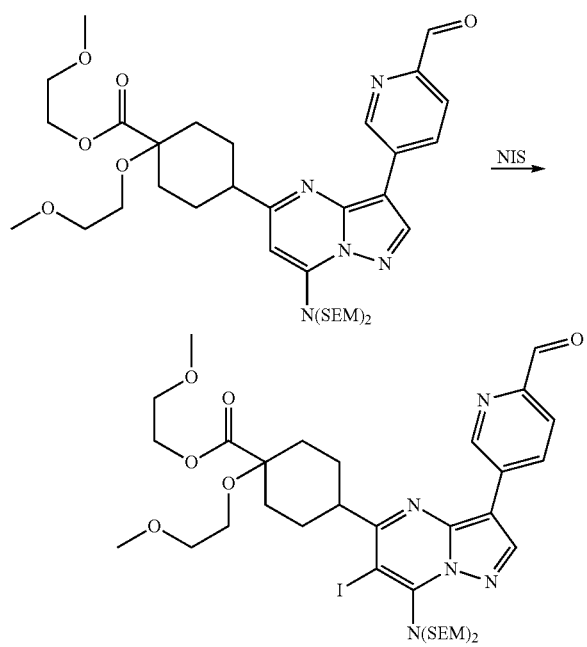

The iodination was prepared with the same condition described in example 38 Step 3. HPLC-MS $t_R$=1.76 min (UV$_{254\ nm}$); mass calculated for formula $C_{37}H_{58}IN_5O_8Si_2$ 883.3, observed LCMS m/z 883.9 (M+H).

Step 2: Preparation of 2-methoxyethyl 4-(3-(6-(1H-imidazol-2-yl)pyridin-3-yl)-7-(bis((2-(trimethylsilyl)ethoxy)methyl)amino)-6-iodopyrazolo[1,5-a]pyrimidin-5-yl)-1-(2-methoxyethoxy)cyclohexanecarboxylate

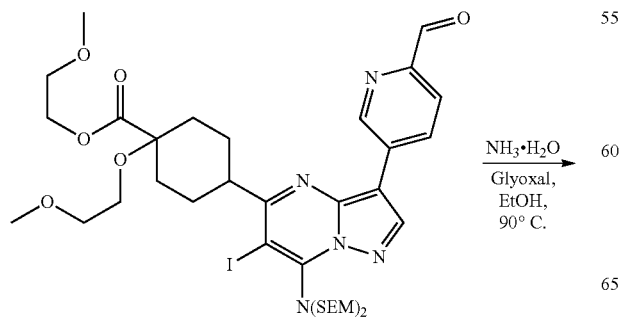

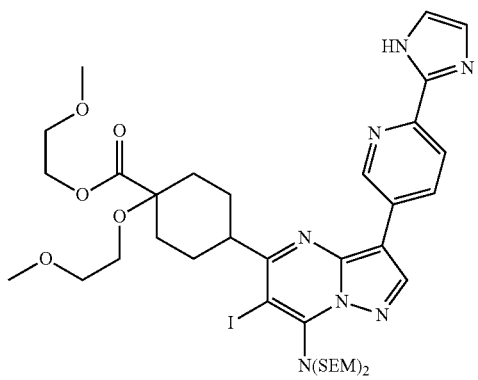

The imidazole was prepared with the same condition described in example 40 Step 4. HPLC-MS $t_R$=1.50 min (UV$_{254\ nm}$); mass calculated for formula $C_{37}H_{58}IN_5O_8Si_2$ 921.3, observed LCMS m/z 922.0 (M+H).

Step 3: Preparation of 4-(3-(6-(1H-imidazol-2-yl)pyridin-3-yl)-7-(bis((2-(trimethylsilyl)ethoxy)methyl)amino)-6-iodopyrazolo[1,5-a]pyrimidin-5-yl)-1-(2-methoxyethoxy)cyclohexanecarboxylic acid

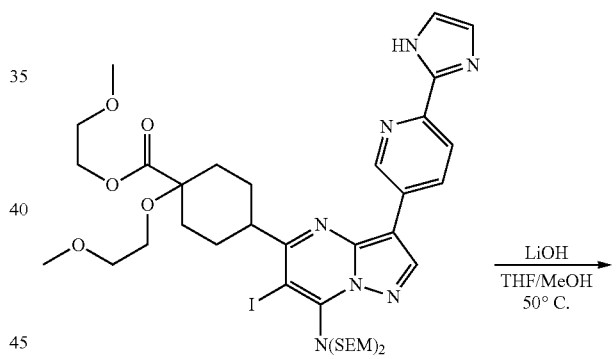

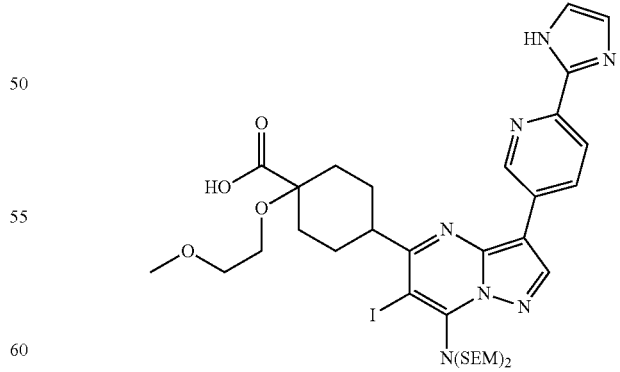

The ester was hydrolyzed with the same condition described in example 1 Step 12. HPLC-MS $t_R$=1.48 min (UV$_{254\ nm}$); mass calculated for formula $C_{36}H_{54}IN_7O_6Si_2$ 863.3, observed LCMS m/z 864.1 (M+H).

Step 4: Preparation of 4-(3-(6-(1H-imidazol-2-yl)
pyridin-3-yl)-7-(bis((2-(trimethylsilyl)ethoxy)me-
thyl)amino)-6-(methylsulfonyl)pyrazolo[1,5-a]pyri-
midin-5-yl)-1-(2-methoxyethoxy)
cyclohexanecarboxylic acid

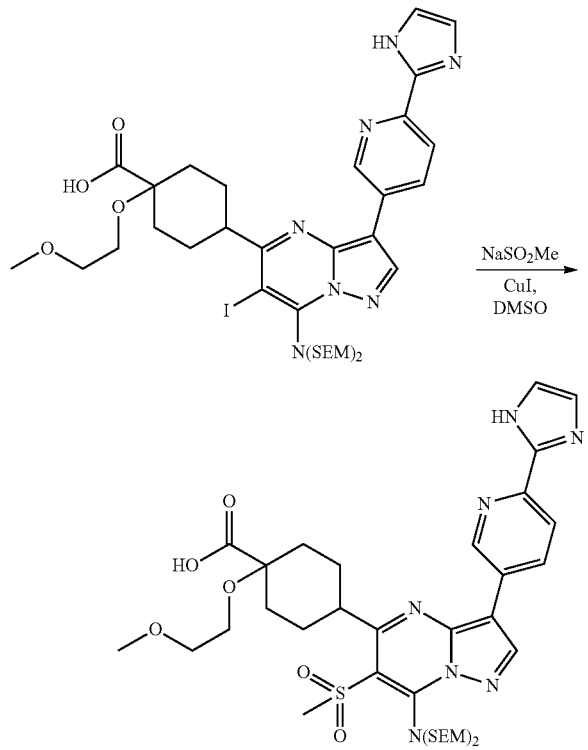

The methylsulfone was prepared with the same condition described in example 38 Step 4. HPLC-MS $t_R$=1.40 min (UV$_{254\ nm}$); mass calculated for formula $C_{37}H_{57}N_7O_8SSi_2$ 815.4, observed LCMS m/z 816.2 (M+H).

Step 5: Preparation of 4-(3-(6-(1H-imidazol-2-yl)
pyridin-3-yl)-7-(bis((2-(trimethylsilyl)ethoxy)me-
thyl)amino)-6-(methylsulfonyl)pyrazolo[1,5-a]pyri-
midin-5-yl)-1-(2-methoxyethoxy)
cyclohexanecarboxamide

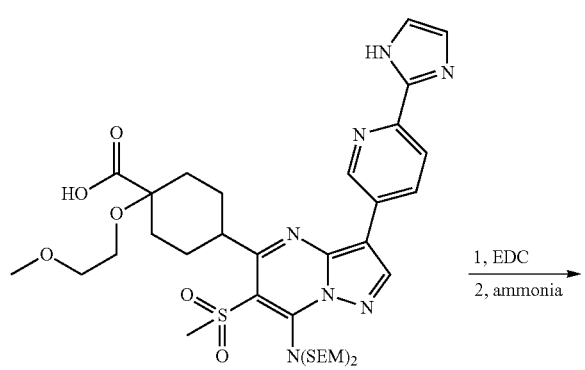

-continued

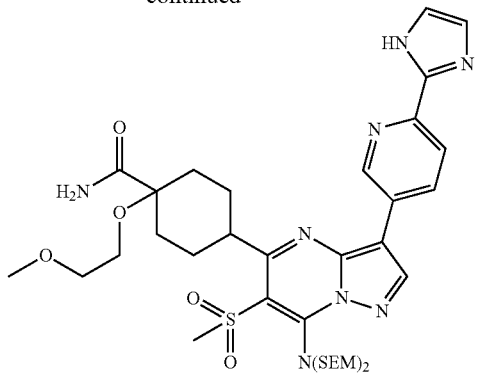

The crude acid (233 mg, 0.27 mmol), HOBt (110 mg, 0.81 mmol), DIEA (156 ul, 0.81 mmol) and EDC (154 mg, 0.81 mmol) were mixed in the dry DMF (5 mL) and stirred at room temperature for 1 hour. The ammonia (28%, 1 mL) was added and the mixture was heated to 50° C. and stirred for 1 hour. The reaction was diluted with EtOAc and washed with water, brine and dried over Na$_2$SO$_4$. After concentration, the crude was used in the next step directly without further purification. HPLC-MS $t_R$=1.37 min (UV$_{254\ nm}$); mass calculated for formula $C_{37}H_{58}N_8O_7SSi_2$ 814.4, observed LCMS m/z 815.2 (M+H).

Step 6: Preparation of (1R,4R)-4-(3-(6-(1H-imida-
zol-2-yl)pyridin-3-yl)-7-amino-6-(methylsulfonyl)
pyrazolo[1,5-a]pyrimidin-5-yl)-N-hydroxy-1-(2-
methoxyethoxy)cyclohexanecarboxamide
(Compound 116)

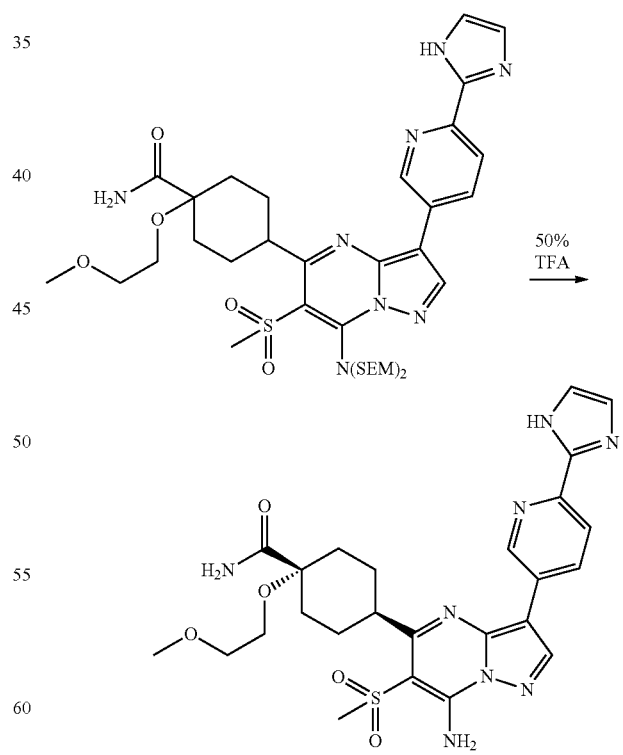

The amide was de-protected with the same condition described in example 1 Step 11 and purified with HPLC and the enantiomeric pure product was obtained. HPLC-MS $t_R$=0.82 min (UV$_{254\ nm}$); mass calculated for formula $C_{25}H_{30}N_8O_5S$ 554.2, observed LCMS m/z 555.1 (M+H).

Example 43

Preparation of (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarbonitrile (Compound 117)

Step 1: Preparation of 4-(7-(bis((2-(trimethylsilyl)ethoxy)methyl)amino)-3-(1-phenyl-1H-pyrazol-4-yl)pyrazolo[1,5-a]pyrimidin-5-yl)-1-(2-methoxyethoxy)cyclohexanecarbonitrile

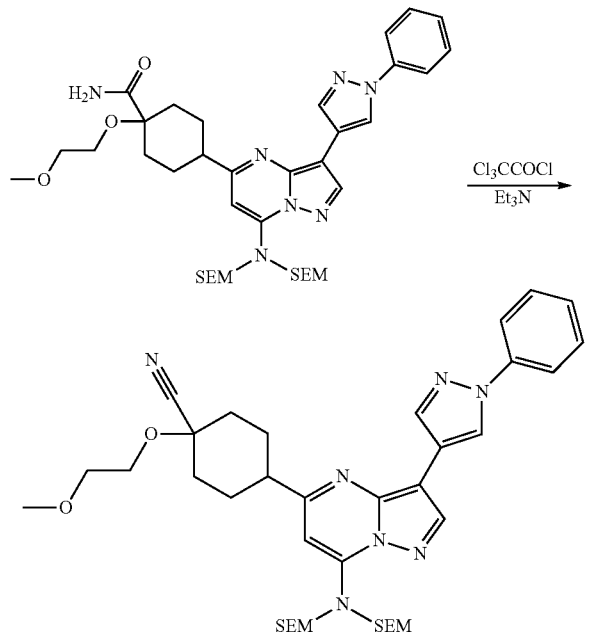

The amide (1.17 g, 1.6 mmol) and Et$_3$N (323 mg, 3.2 mmol) were dissolved in dry DCM (20 mL) and cooled to 0° C. The trichloroacetyl chloride (333 mg, 1.83 mmol) in DCM (1 mL) was added dropwise. The resulting mixture was allowed to warm to room temperature and stirred for 1 hour. EtOAc was added to dilute the reaction and washed with water, brine and dried over Na$_2$SO$_4$. After concentration, the crude was purified with column (silica gel, 0~30% EtOAc/hexane) to give the product (997 mg). HPLC-MS $t_R$=1.92 min (UV$_{254\,nm}$); mass calculated for formula C$_{37}$H$_{55}$N$_7$O$_4$Si$_2$ 717.4, observed LCMS m/z 718.3 (M+H).

Step 2: Preparation of 4-(7-amino-3-(1-phenyl-1H-pyrazol-4-yl)pyrazolo[1,5-a]pyrimidin-5-yl)-1-(2-methoxyethoxy)cyclohexanecarbonitrile

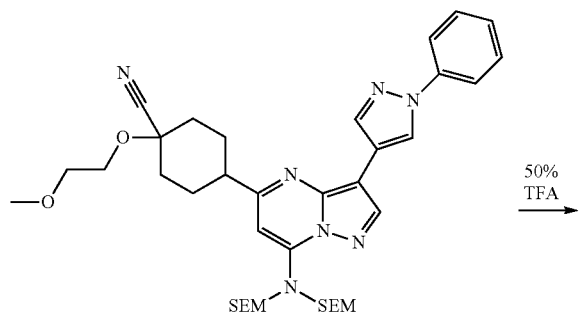

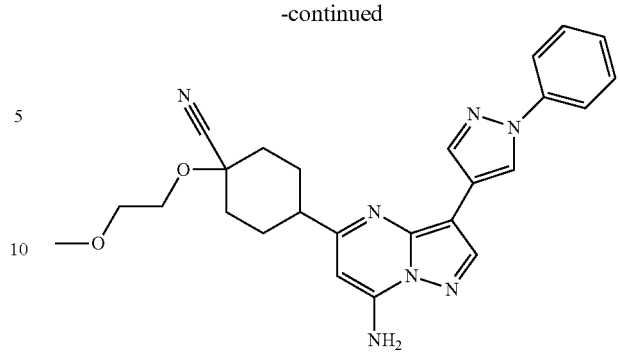

The cyano-compound was de-protected with the same condition described in example 1 step 11. HPLC-MS $t_R$=1.19 min (UV$_{254\,nm}$); mass calculated for formula C$_{25}$H$_{27}$N$_7$O$_2$ 457.2, observed LCMS m/z 458.2 (M+H).

Step 3: Preparation of 4-(7-amino-6-iodo-3-(1-phenyl-1H-pyrazol-4-yl)pyrazolo[1,5-a]pyrimidin-5-yl)-1-(2-methoxyethoxy)cyclohexanecarbonitrile

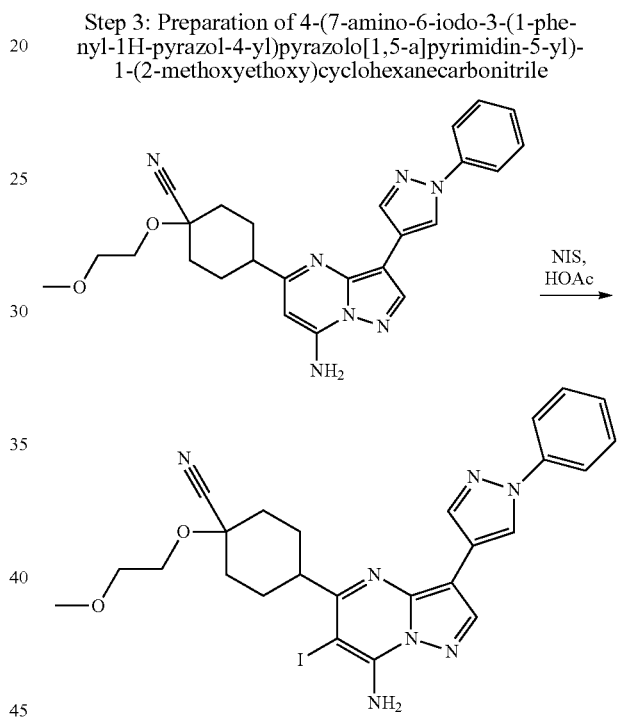

The iodination was prepared with the same condition described in example 38 Step 3. HPLC-MS $t_R$=1.33 min (UV$_{254\,nm}$); mass calculated for formula C$_{25}$H$_{26}$IN$_7$O$_2$ 583.1, observed LCMS m/z 583.9 (M+H).

Step 4: Preparation of (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarbonitrile (Compound 117)

-continued

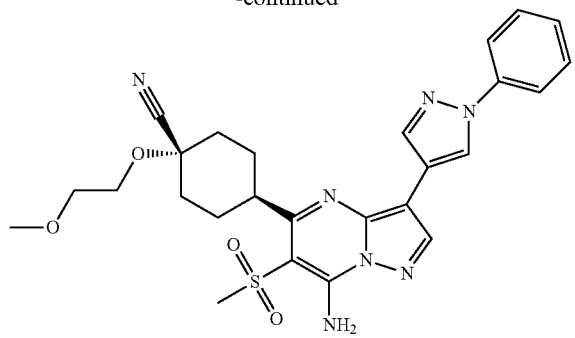

The methylsulfone was prepared with the same condition described in example 38 Step 4 and purified with HPLC and the desired enantiomeric pure product was obtained. HPLC-MS $t_R$=1.34 min (UV$_{254\ nm}$); mass calculated for formula $C_{26}H_{29}N_7O_4S$ 535.2, observed LCMS m/z 536.2 (M+H).

Example 44

Preparation of 5-((1R,4R)-4-(2-methoxyethoxy)-4-(1H-tetrazol-5-yl)cyclohexyl)-6-(methylsulfonyl)-3-(1-phenyl-1H-pyrazol-4-yl)pyrazolo[1,5-a]pyrimidin-7-amine (Compound 118)

Step 1: Preparation of 5-(4-(2-methoxyethoxy)-4-(1H-tetrazol-5-yl)cyclohexyl)-3-(1-phenyl-1H-pyrazol-4-yl)-N,N-bis((2-(trimethylsilyl)ethoxy)methyl)pyrazolo[1,5-a]pyrimidin-7-amine

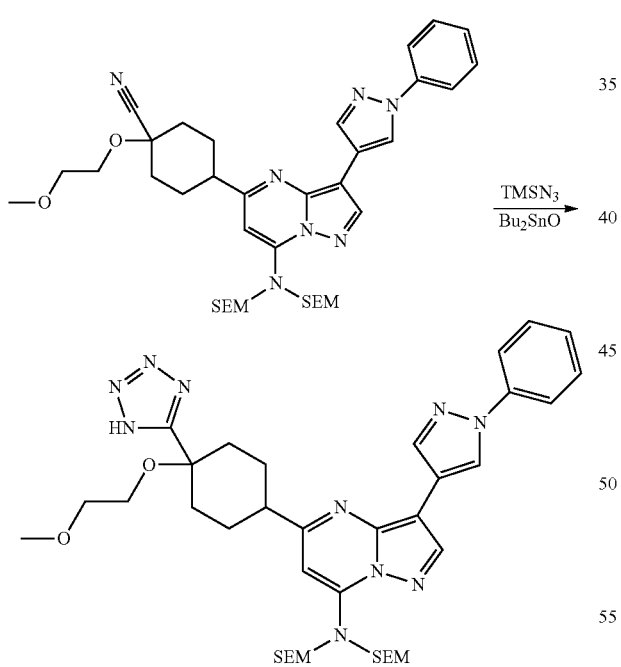

The cyano-compound (114 mg, 0.16 mmol), TMSN$_3$ (50 uL, 0.36 mmol), and Bu$_2$SnO (25 mg, 0.098 mmol) were mixed in the dry toluene (0.6 mL) in a tube under Ar. The tube was sealed and heated to 120° C. and stirred overnight. After cooling to room temperature, the mixture was taken with EtOAc and washed with KF (1% aq.), water and brine and dried over Na$_2$SO$_4$. After concentration, the crude was used in the next step directly without further purification. HPLC-MS $t_R$=1.80 min (UV$_{254\ nm}$); mass calculated for formula $C_{37}H_{56}N_{10}O_4Si_2$ 760.4, observed LCMS m/z 761.3 (M+H).

Step 2: Preparation of 5-(4-(2-methoxyethoxy)-4-(1H-tetrazol-5-yl)cyclohexyl)-3-(1-phenyl-1H-pyrazol-4-yl)pyrazolo[1,5-a]pyrimidin-7-amine

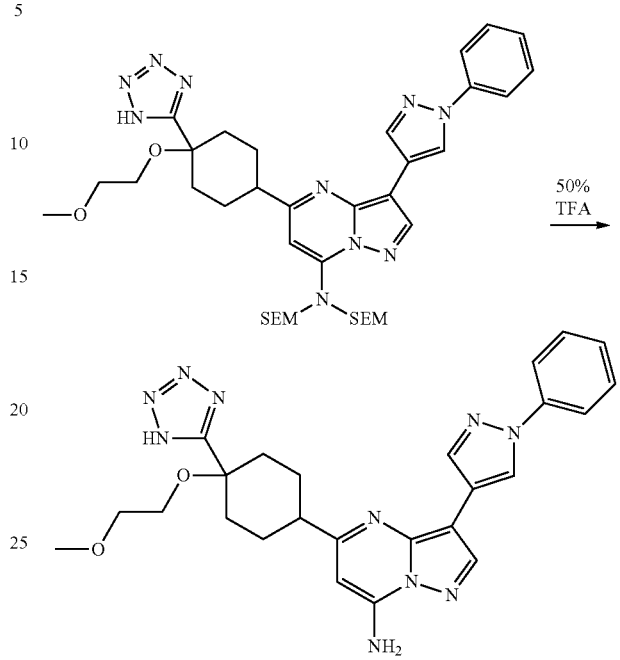

The tetrazole compound was de-protected with the same condition described in example 1 Step 11. HPLC-MS $t_R$=0.91 min (UV$_{254\ nm}$); mass calculated for formula $C_{25}H_{28}N_{10}O_2$ 500.2, observed LCMS m/z 501.1 (M+H).

Step 3: Preparation of 6-iodo-5-(4-(2-methoxyethoxy)-4-(1H-tetrazol-5-yl)cyclohexyl)-3-(1-phenyl-1H-pyrazol-4-yl)pyrazolo[1,5-a]pyrimidin-7-amine

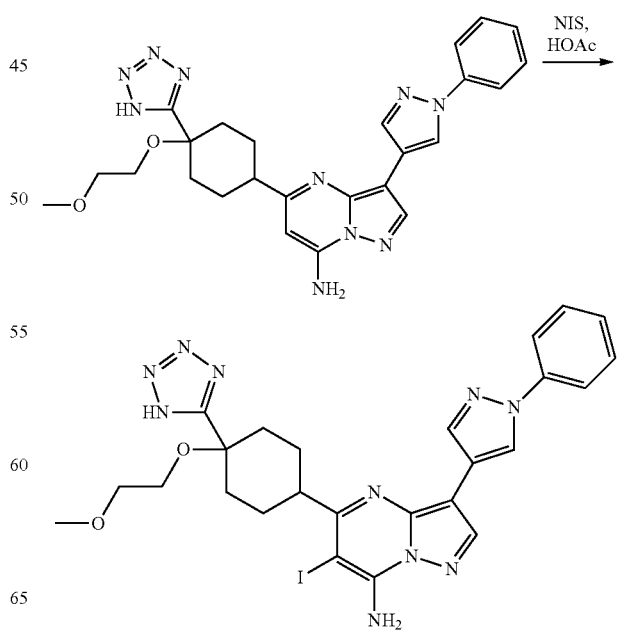

The iodination was prepared with the same condition described in example 38 Step 3. HPLC-MS $t_R$=1.26 min (UV$_{254\ nm}$); mass calculated for formula $C_{25}H_{27}IN_{10}O_2$ 626.1, observed LCMS m/z 627.0 (M+H).

Step 4: Preparation of 5-((1R,4R)-4-(2-methoxy-ethoxy)-4-(1H-tetrazol-5-yl)cyclohexyl)-6-(methyl-sulfonyl)-3-(1-phenyl-1H-pyrazol-4-yl)pyrazolo[1,5-a]pyrimidin-7-amine (Compound 118)

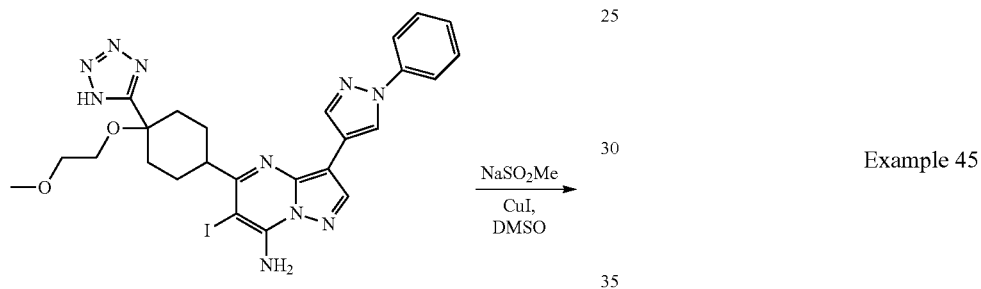

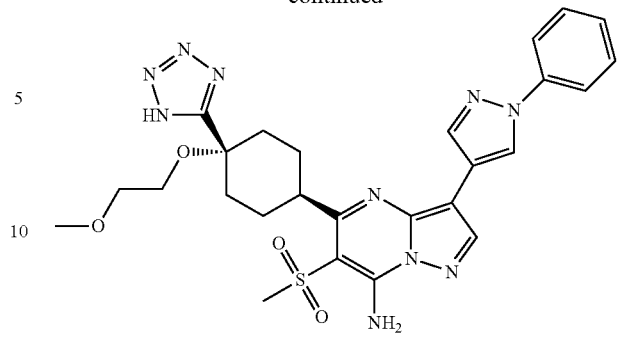

The methylsulfone was prepared with the same condition described in example 38 Step 4 and purified with HPLC to give the desired enantiomeric pure product. HPLC-MS $t_R$=1.16 min (UV$_{254\ nm}$); mass calculated for formula $C_{26}H_{30}N_{10}O_4S$ 578.2, observed LCMS m/z 579.2 (M+H).

Example 45

By essentially the same procedure in Preparative Example 44, the compound in Column 2 of Table 17 can be prepared.

TABLE 17

| Example | Chemical name | Column 2 | Exact mass | MS m/z (M + H) | HPLC MS $t_R$ |
|---|---|---|---|---|---|
| 119 | 5-((1R,4R)-4-(2-methoxyethoxy)-4-(1H-tetrazol-5-yl)cyclohexyl)-6-(methylsulfonyl)-3-(6-phenylpyridin-3-yl)pyrazolo[1,5-a]pyrimidin-7-amine | | 589.2 | 590.2 | 0.93 |

Example 46

Preparation of (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboximidamide (Compound 120) and Preparation of 3-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-1,2,4-oxadiazol-5(4H)-one (Compound 121)

Step 1: Preparation of (Z)-4-(7-(bis((2-(trimethylsilyl)ethoxy)methyl)amino)-3-(1-phenyl-1H-pyrazol-4-yl)pyrazolo[1,5-a]pyrimidin-5-yl)-N'-hydroxy-1-(2-methoxyethoxy)cyclohexanecarboximidamide

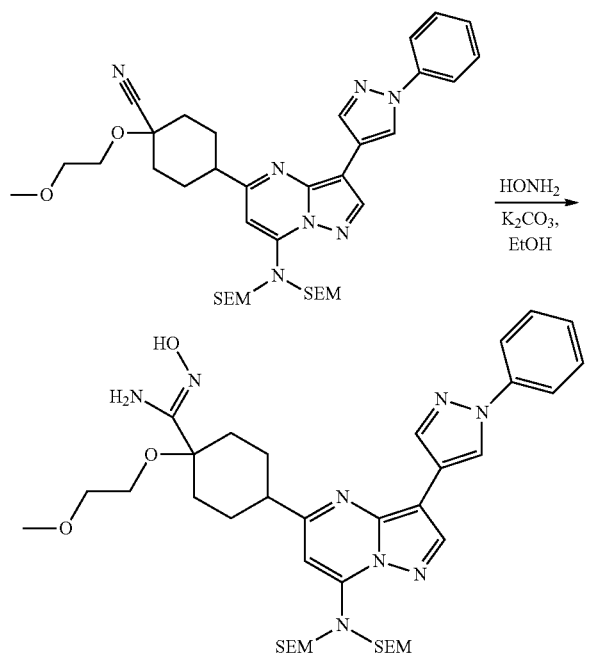

The cyano-compound (360 mg, 0.5 mmol) was dissolved in ethanol (5 ml). The K$_2$CO$_3$ (380 mg, 2.75 mmol) and hydroxylamine hydrochloride (173 mg, 2.5 mmol) were added. The mixture was heated to 80° C. and stirred overnight. After cooling to room temperature, EtOAc was added to dilute the reaction and filtered through celite and washed with EtOAc. After concentration, the crude was used in the next step directly without further purification.

Step 2: Preparation of (Z)-4-(7-amino-3-(1-phenyl-1H-pyrazol-4-yl)pyrazolo[1,5-a]pyrimidin-5-yl)-N'-hydroxy-1-(2-methoxyethoxy)cyclohexanecarboximidamide

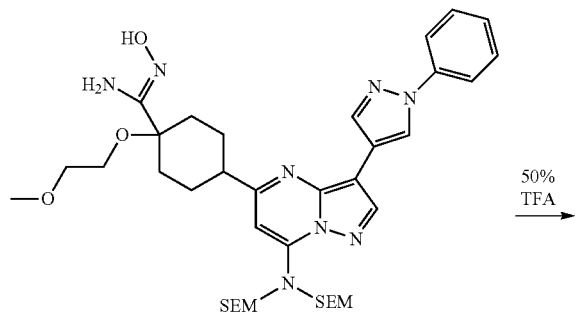

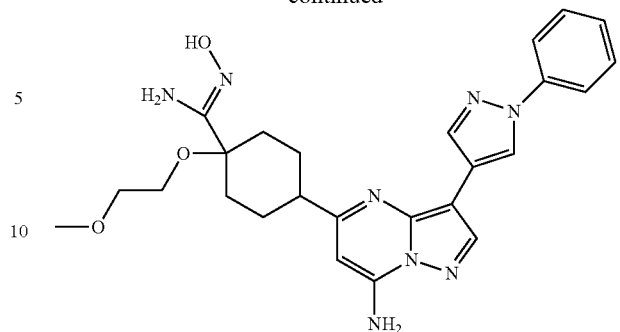

The crude product from Step 1 was de-protected with the same condition described in example 1 Step 11 and purified with HPLC to give the product. HPLC-MS $t_R$=0.86 min (UV$_{254\,nm}$); mass calculated for formula C$_{25}$H$_{30}$N$_8$O$_3$ 490.2, observed LCMS m/z 491.2 (M+H).

Step 3: Preparation of 3-(4-(7-amino-3-(1-phenyl-1H-pyrazol-4-yl)pyrazolo[1,5-a]pyrimidin-5-yl)-1-(2-methoxyethoxy)cyclohexyl)-1,2,4-oxadiazol-5(4H)-one and 4-(7-amino-3-(1-phenyl-1H-pyrazol-4-yl)pyrazolo[1,5-a]pyrimidin-5-yl)-1-(2-methoxyethoxy)cyclohexanecarboximidamide

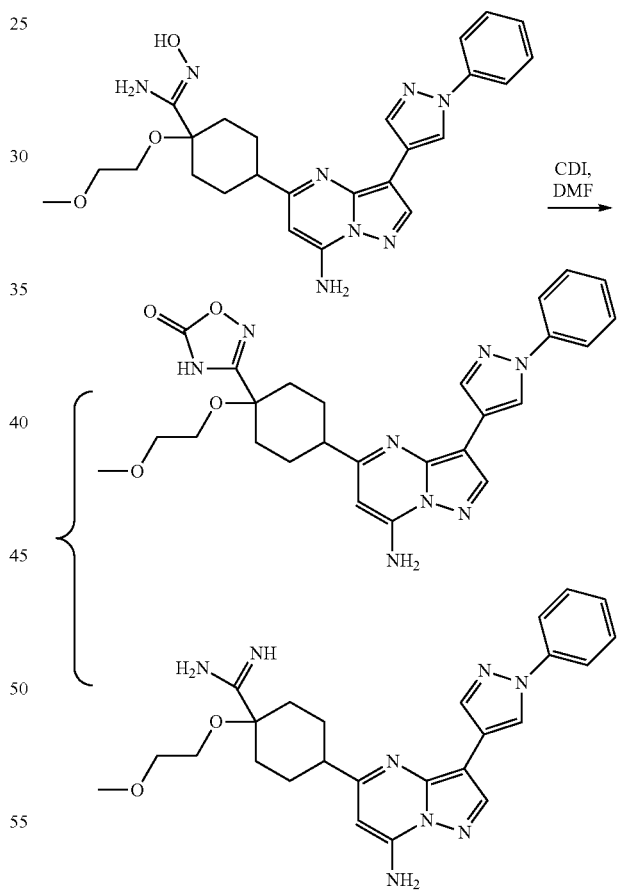

The starting material (253 mg, TFA salt, 0.369 mmol) and CDI (60 mg, 0.37 mmol) were mixed in dry DMF (2 mL) and the mixture was heated up to 75° C. and stirred for 1 hour. After cooling to room temperature, the crude was used in the next step without further purification. Formimidamide: HPLC-MS $t_R$=0.89 min (UV$_{254\,nm}$); mass calculated for formula C$_{25}$H$_{30}$N$_8$O$_2$ 474.2, observed LCMS m/z 475.1 (M+H).
Oxadiazole compound: HPLC-MS $t_R$=0.95 min (UV$_{254\,nm}$); mass calculated for formula C$_{26}$H$_{28}$N$_8$O$_4$ 516.2, observed LCMS m/z 517.1 (M+H).

Step 4: Preparation of 3-(4-(7-amino-6-iodo-3-(1-phenyl-1H-pyrazol-4-yl)pyrazolo[1,5-a]pyrimidin-5-yl)-1-(2-methoxyethoxy)cyclohexyl)-1,2,4-oxadiazol-5(4H)-one and 4-(7-amino-6-iodo-3-(1-phenyl-1H-pyrazol-4-yl)pyrazolo[1,5-a]pyrimidin-5-yl)-1-(2-methoxyethoxy)cyclohexanecarboximidamide

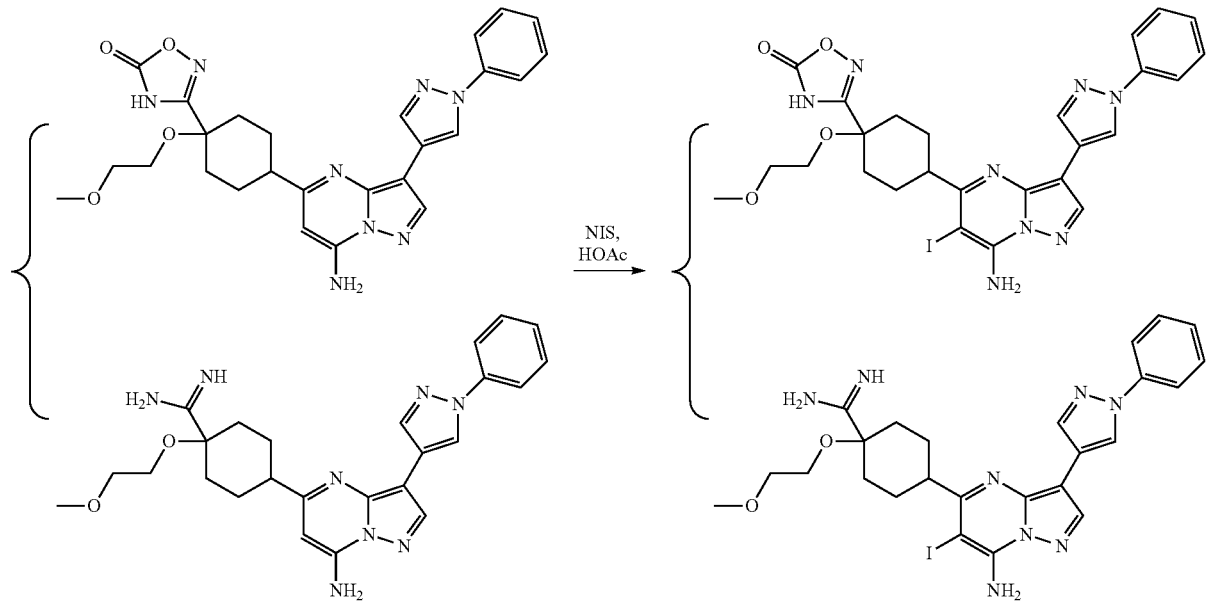 [SMILES: COCCOC1(c2noc(=O)[nH]2)CCC(c2cc(N)n3ncc(-c4cnn(-c5ccccc5)c4)c3n2)CC1 ; COCCOC1(c2noc(=O)[nH]2)CCC(c2nc3c(-c4cnn(-c5ccccc5)c4)cnn3c(N)c2I)CC1 ; COCCOC1(C(=N)N)CCC(c2cc(N)n3ncc(-c4cnn(-c5ccccc5)c4)c3n2)CC1 ; COCCOC1(C(=N)N)CCC(c2nc3c(-c4cnn(-c5ccccc5)c4)cnn3c(N)c2I)CC1]

The iodination was prepared with the same condition described in example 38 Step 3 and purified with HPLC to give two products. Formimidamide: HPLC-MS $t_R$=1.06 min ($UV_{254\,nm}$); mass calculated for formula $C_{25}H_{29}IN_8O_2$ 600.1, observed LCMS m/z 601.0 (M+H). Oxadiazole compound: HPLC-MS $t_R$=1.31 min ($UV_{254\,nm}$); mass calculated for formula $C_{26}H_{27}IN_8O_4$ 642.1, observed LCMS m/z 643.0 (M+H).

Step 5: Preparation of (1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboximidamide (Compound 120) and Preparation of 3-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-1,2,4-oxadiazol-5(4H)-one (Compound 121)

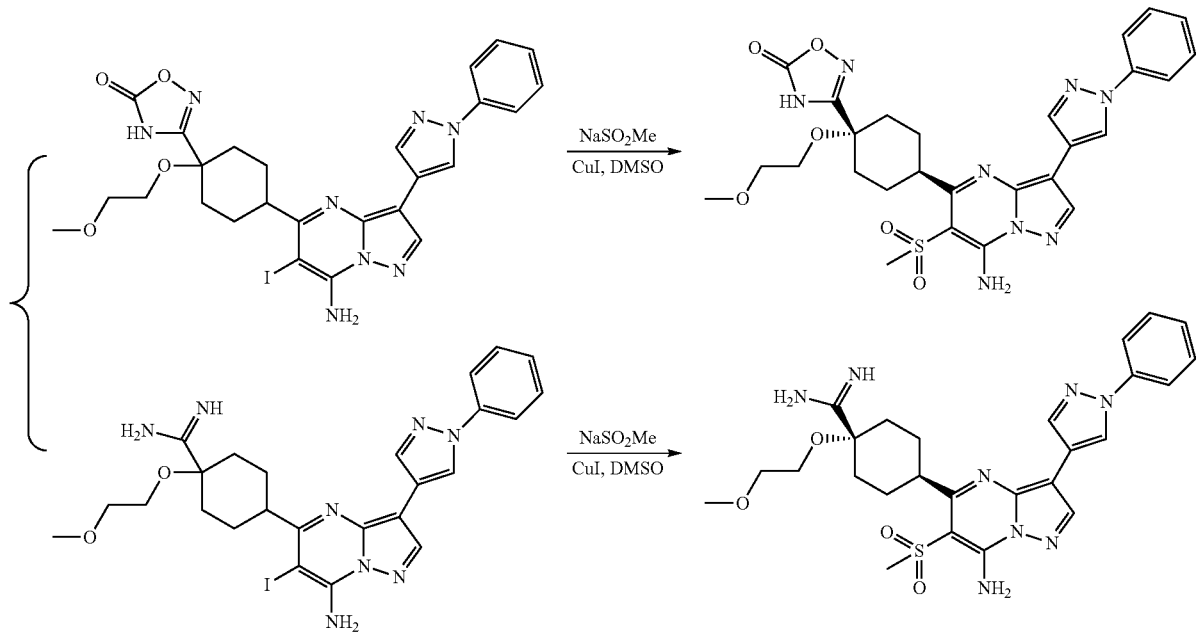

The methylsulfone was prepared with the same condition described in the example 38 Step 4 and purified with HPLC to give the desired enantiomeric pure product. Formimidamide: HPLC-MS $t_R$=0.84 min (UV$_{254\ nm}$); mass calculated for formula $C_{26}H_{32}N_8O_4S$ 552.2, observed LCMS m/z 553.0 (M+H). Oxadiazole compound: HPLC-MS $t_R$=1.08 min (UV$_{254\ nm}$); mass calculated for formula $C_{27}H_{30}N_8O_6S$ 594.2, observed LCMS m/z 594.8 (M+H).

Example 47

Preparation of ((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)(4H-1,2,4-triazol-3-yl)methanone (Compound 122) and ((1S,4S)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)(4H-1,2,4-triazol-3-yl)methanone (Compound 123)

Step 1: Preparation of 2-methoxyethyl 4-(7-(bis((2-(trimethylsilyl)ethoxy)methyl)amino)-3-(1-phenyl-1H-pyrazol-4-yl)pyrazolo[1,5-a]pyrimidin-5-yl)-1-(2-methoxyethoxy)cyclohexanecarboxylate

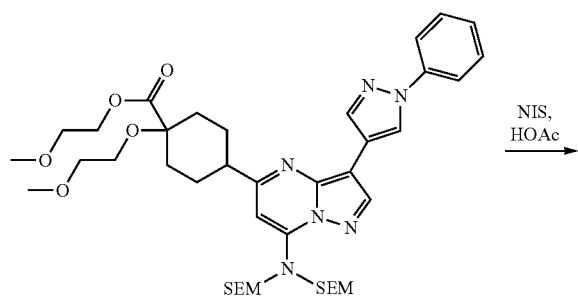

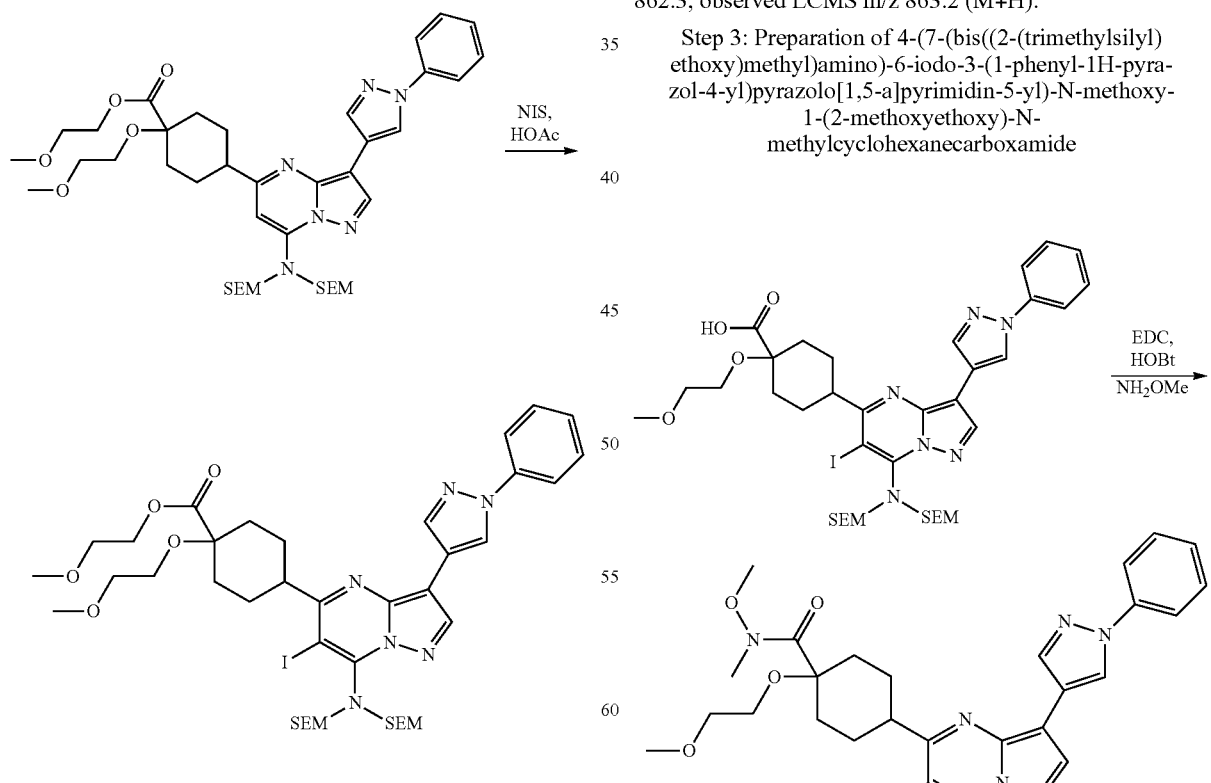

The iodination was prepared with the same condition described in example 38 Step 3. HPLC-MS $t_R$=2.00 min (UV$_{254\ nm}$); mass calculated for formula $C_{40}H_{61}IN_6O_7Si_2$ 920.3, observed LCMS m/z 921.3 (M+H).

Step 2: Preparation of 4-(7-(bis((2-(trimethylsilyl)ethoxy)methyl)amino)-6-iodo-3-(1-phenyl-1H-pyrazol-4-yl)pyrazolo[1,5-a]pyrimidin-5-yl)-1-(2-methoxyethoxy)cyclohexanecarboxylic acid

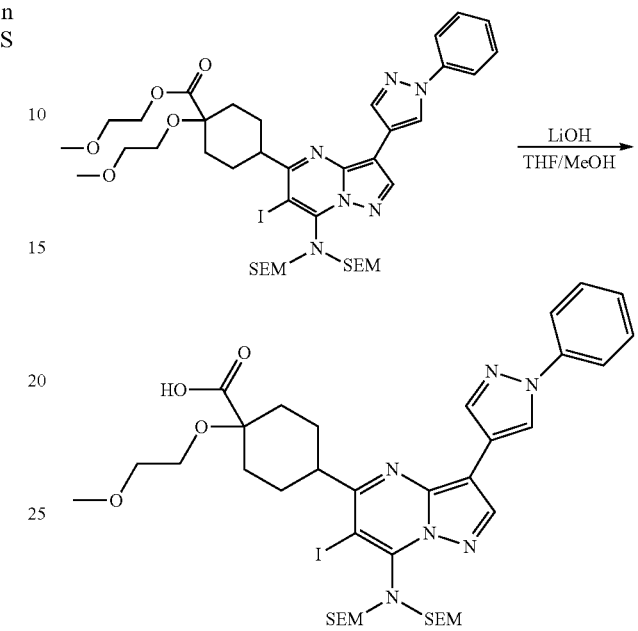

The ester was hydrolyzed with the same condition described in example 1 Step 12. HPLC-MS $t_R$=1.89 min (UV$_{254\ nm}$); mass calculated for formula $C_{37}H_{55}IN_6O_6Si_2$ 862.3, observed LCMS m/z 863.2 (M+H).

Step 3: Preparation of 4-(7-(bis((2-(trimethylsilyl)ethoxy)methyl)amino)-6-iodo-3-(1-phenyl-1H-pyrazol-4-yl)pyrazolo[1,5-a]pyrimidin-5-yl)-N-methoxy-1-(2-methoxyethoxy)-N-methylcyclohexanecarboxamide The peptide coupling was performed with the same condition described in example 34 Step 1. HPLC-MS $t_R$=2.11 min (UV$_{254\ nm}$); mass calculated for formula $C_{39}H_{60}IN_7O_6Si_2$ 905.3, observed LCMS m/z 906.3 (M+H).

Step 4: Preparation of (4-(7-(bis((2-(trimethylsilyl)ethoxy)methyl)amino)-6-iodo-3-(1-phenyl-1H-pyrazol-4-yl)pyrazolo[1,5-a]pyrimidin-5-yl)-1-(2-methoxyethoxy)cyclohexyl)(4-((2-(trimethylsilyl)ethoxy)methyl)-4H-1,2,4-triazol-3-yl)methanone

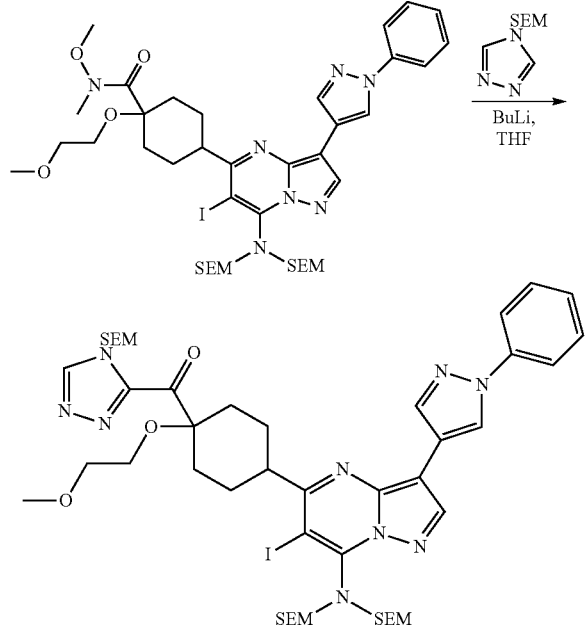

The N-SEM-triazole (100 mg, 0.5 mmol) was dissolved in dry THF (10 mL) and cooled to −78° C. BuLi (2.5 M in hexane, 0.2 mL, 0.5 mmol) was added dropwise. The mixture was stirred 30 min and allowed to warm to 0° C. and stirred for another 5 min. Then, the reaction was cooled to −78° C. again and the amide (317 mg, 0.35 mmol) in THF (1 mL) was added. The resulting mixture was stirred for 30 min and then was allowed to warm to room temperature slowly and stirred for another 1 hour. NH$_4$Cl (aq.) was added to quench the reaction and extracted with EtOAc. The combined organics was dried over Na$_2$SO$_4$ and concentrated. The crude was purified with column (silica gel, 0~30% EtOAc/hexane) to give the product (290 mg). HPLC-MS $t_R$=2.00 min (UV$_{254\ nm}$); mass calculated for formula $C_{45}H_{70}IN_9O_6Si_3$ 1043.4, observed LCMS m/z 944.0 (M+H-SEM).

Step 5: Preparation of (4-(7-(bis((2-(trimethylsilyl)ethoxy)methyl)amino)-6-(methylsulfonyl)-3-(1-phenyl-1H-pyrazol-4-yl)pyrazolo[1,5-a]pyrimidin-5-yl)-1-(2-methoxyethoxy)cyclohexyl)(4-((2-(trimethylsilyl)ethoxy)methyl)-4H-1,2,4-triazol-3-yl)methanone

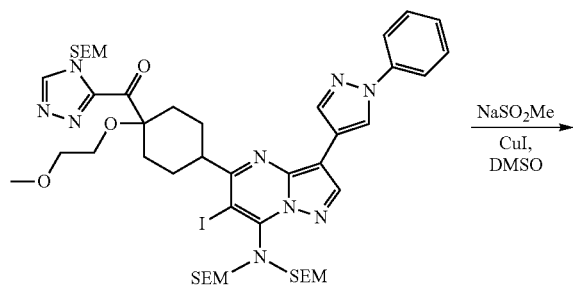

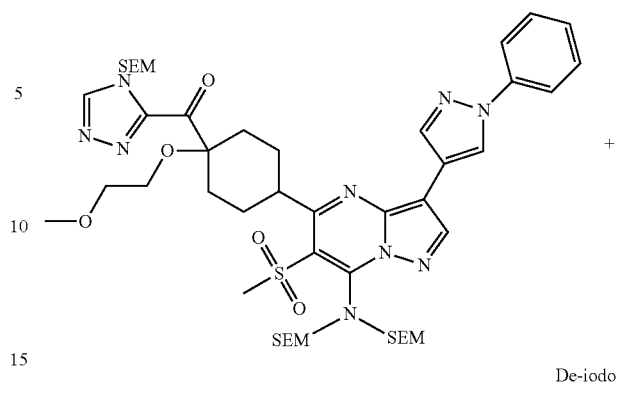

The methylsulfone was prepared with the same condition described in example 38 Step 4 to give the mixture of desired product and de-iodo product. HPLC-MS $t_R$=2.01 min (UV$_{254\ nm}$); mass calculated for formula $C_{46}H_{73}N_9O_8SSi_3$ 995.5, observed LCMS m/z 996.4 (M+H).

Step 6: Preparation of ((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)(4H-1,2,4-triazol-3-yl)methanone (Compound 122) and ((1S,4S)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)(4H-1,2,4-triazol-3-yl)methanone (Compound 123)

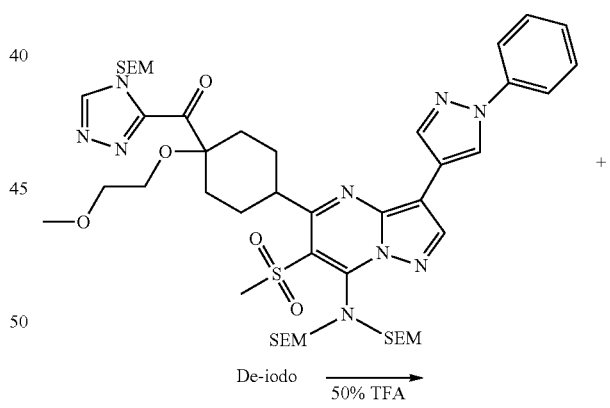

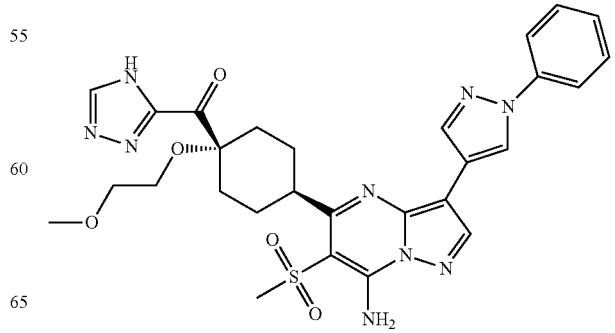

-continued

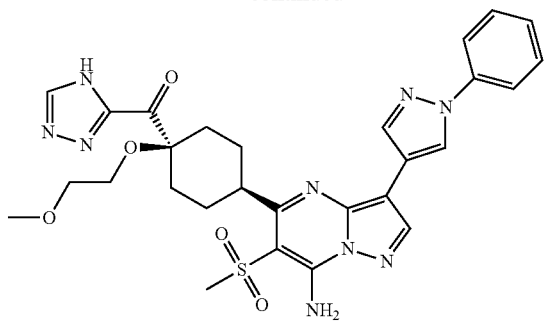

C-6-H Product

The crude product from Step 5 was de-protected with the same condition described in example 1 Step 11 and purified with HPLC to give the two enantiomeric pure products and C-6 de-iodo product. Enantiomer 1: HPLC-MS $t_R$=1.15 min (UV$_{254\ nm}$); mass calculated for formula $C_{28}H_{31}N_9O_5S$ 605.2, observed LCMS m/z 606.2 (M+H). Enantiomer 2: HPLC-MS $t_R$=1.20 min (UV$_{254\ nm}$); mass calculated for formula $C_{28}H_{31}N_9O_5S$ 605.2, observed LCMS m/z 606.2 (M+H).

Example 48

By essentially the same procedure in Preparative Example 47, the compounds in Column 2 of Table 18 can be prepared.

TABLE 18

| Example | Chemical name | Column 2 | Exact mass | MS m/z (M + H) | HPLC MS $t_R$ |
|---|---|---|---|---|---|
| 124 | ((1S,4S)-4-(7-amino-6-(methylsulfonyl)-3-(6-phenylpyridin-3-yl)pyrazolo[1,5-a]pyrimidin-5-yl)-1-(2-methoxyethoxy)cyclohexyl)(4H-1,2,4-triazol-3-yl)methanone | | 616.2 | 617.2 | 0.97 |
| 125 | ((1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexyl)(4H-1,2,4-triazol-3-yl)methanone | | 616.2 | 617.2 | 0.95 |
| 126 | ((1R,4R)-4-(7-amino-3-(6-phenylpyridin-3-yl)pyrazolo[1,5-a]pyrimidin-5-yl)-1-(2-methoxyethoxy)cyclohexyl)(4H-1,2,4-triazol-3-yl)methanone | | 538.2 | 539.1 | 0.88 |

Example 49

Preparation of 5-((1R,4R)-4-(2-methoxyethoxy)-4-(4H-1,2,4-triazol-3-yl)cyclohexyl)-6-(methylsulfonyl)-3-(1-phenyl-1H-pyrazol-4-yl)pyrazolo[1,5-a]pyrimidin-7-amine (Compound 127)

Step 1: Preparation of 4-(7-(bis((2-(trimethylsilyl)ethoxy)methyl)amino)-6-iodo-3-(1-phenyl-1H-pyrazol-4-yl)pyrazolo[1,5-a]pyrimidin-5-yl)-N-formyl-1-(2-methoxyethoxy)cyclohexanecarboxamide

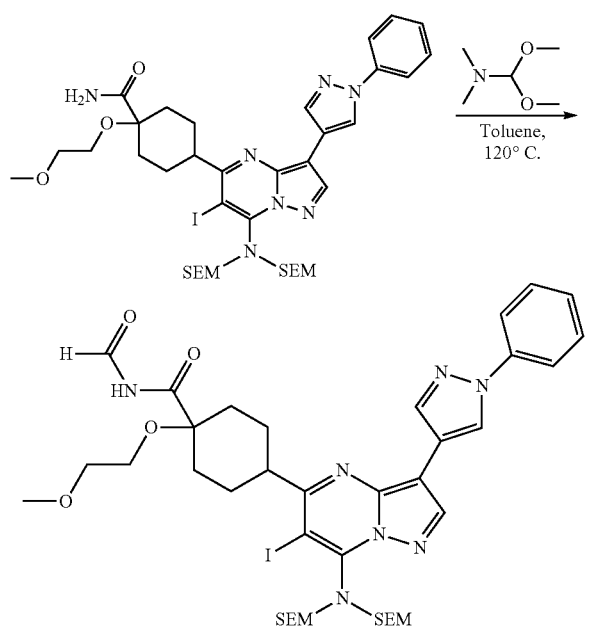

The amide was prepared in Example 38 Step 3.

The primary amide (800 mg, 0.93 mmol) and DMF dimethyl acetal (155 mg, 1.3 mmol) were mixed in toluene (5 mL) and the mixture was heated up to 120° C. under Ar for 3 hours. After cooling to room temperature, the solvent was removed under reduced pressure and the crude was purified with column (silica gel, EtOAc/hexane 0~50%) to give the product (740 mg). HPLC-MS $t_R$=1.96 min (UV$_{254\,nm}$); mass calculated for formula $C_{38}H_{56}IN_7O_6Si_2$ 889.3, observed LCMS m/z 890.2 (M+H).

Step 2: Preparation of 5-(4-(2-methoxyethoxy)-4-(4H-1,2,4-triazol-3-yl)cyclohexyl)-3-(1-phenyl-1H-pyrazol-4-yl)pyrazolo[1,5-a]pyrimidin-7-amine

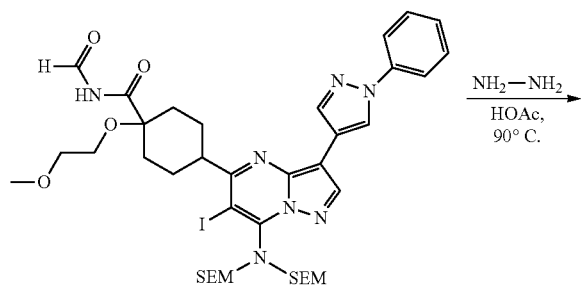

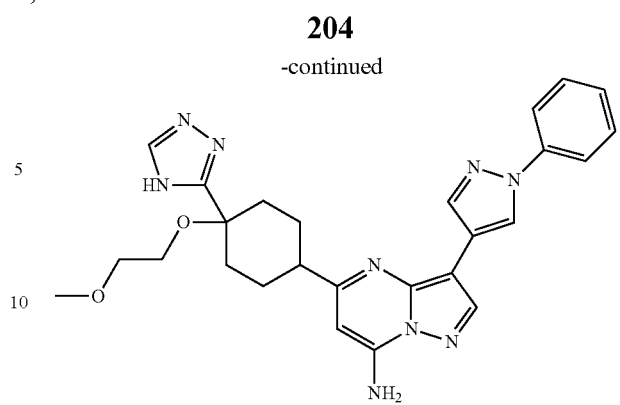

The formamide (740 mg, 0.83 mmol) was dissolved in HOAc (5 mL) and hydrazine hydrate (5 drops) was added and the mixture was heated at 90° C. under Ar and stirred for 2 hours. After concentration, the crude was purified with HPLC to give the product (448 mg). HPLC-MS $t_R$=0.72 min (UV$_{254\,nm}$); mass calculated for formula $C_{26}H_{29}N_9O_2$ 499.2, observed LCMS m/z 500.0 (M+H).

Step 3: Preparation of 6-iodo-5-(4-(2-methoxyethoxy)-4-(4H-1,2,4-triazol-3-yl)cyclohexyl)-3-(1-phenyl-1H-pyrazol-4-yl)pyrazolo[1,5-a]pyrimidin-7-amine

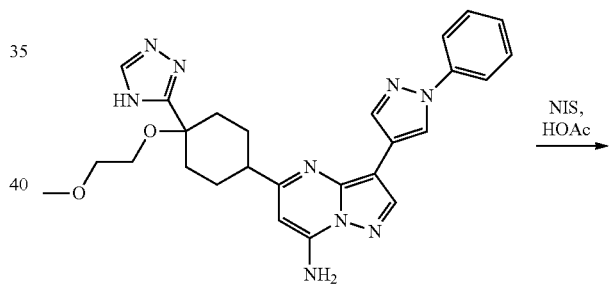

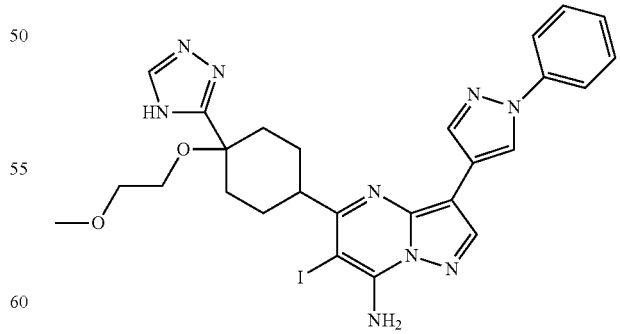

The iodination was prepared with the same condition described in example 38 Step 3. HPLC-MS $t_R$=1.05 min (UV$_{254\,nm}$); mass calculated for formula $C_{26}H_{28}IN_9O_2$ 625.1, observed LCMS m/z 625.9 (M+H).

Step 4: Preparation of 5-((1R,4R)-4-(2-methoxy-ethoxy)-4-(4H-1,2,4-triazol-3-yl)cyclohexyl)-6-(methylsulfonyl)-3-(1-phenyl-1H-pyrazol-4-yl)pyrazolo[1,5-a]pyrimidin-7-amine (Compound 127)

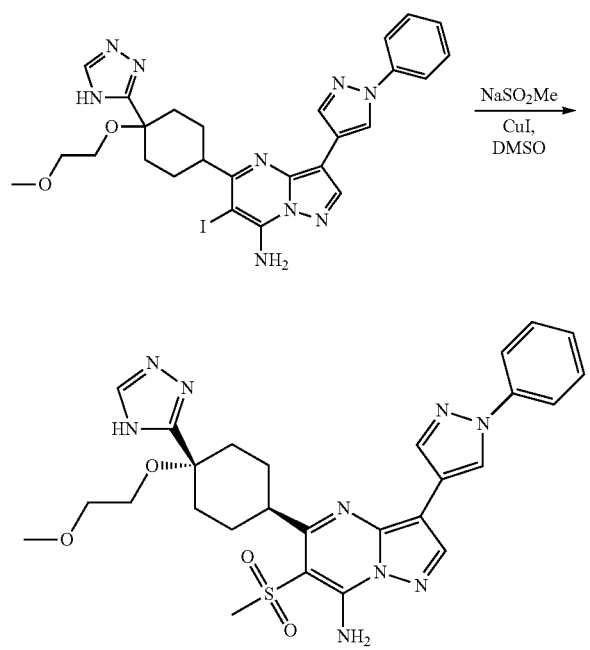

The methylsulfone was prepared with the same condition described in the example 38 Step 4 to give the desired enantiomeric pure product. HPLC-MS $t_R$=1.05 min (UV$_{254\,nm}$); mass calculated for formula $C_{27}H_{31}N_9O_4S$ 577.2, observed LCMS m/z 578.2 (M+H).

Example 50

By essentially the same procedure in Preparative Example 49, the compound in Column 2 of Table 19 can be prepared.

Example 51

Preparation of 1-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-2-hydroxyethanone (Compound 129)

Step 1: Preparation of 2-(benzyloxy)-1-(4-(7-(bis((2-(trimethylsilyl)ethoxy)methyl)amino)-6-iodo-3-(1-phenyl-1H-pyrazol-4-yl)pyrazolo[1,5-a]pyrimidin-5-yl)-1-(2-methoxyethoxy)cyclohexyl)ethanone

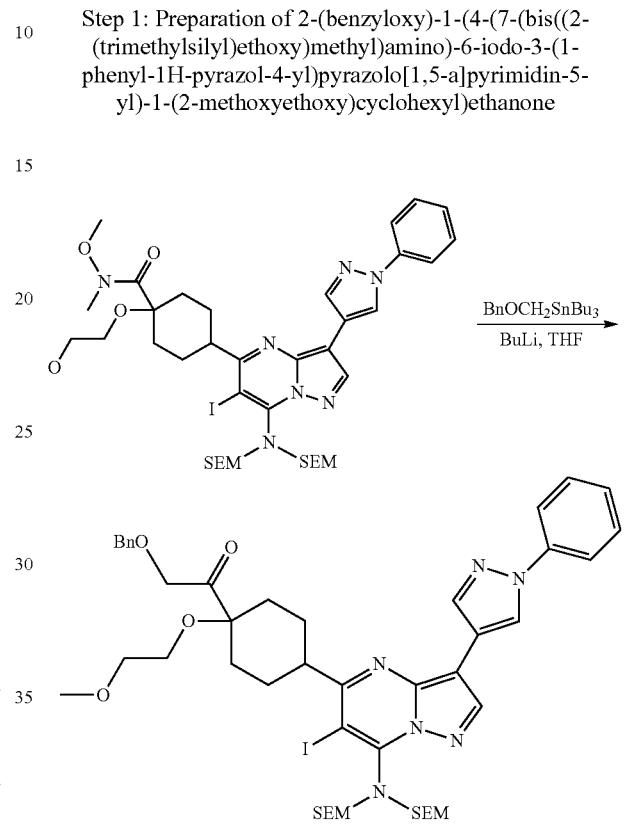

The ketone was prepared with the same conditions described in example 47 Step 4 with BnOCH$_2$SnBu$_3$. HPLC-MS $t_R$=2.09 min (UV$_{254\,nm}$); mass calculated for formula $C_{45}H_{63}IN_6O_6Si_2$ 966.3, observed LCMS m/z 967.2 (M+H).

TABLE 19

| Example | Chemical name | Column 2 | Exact mass | MS m/z (M + H) | HPLC MS $t_R$ |
|---|---|---|---|---|---|
| 128 | 5-((1R,4R)-4-(2-methoxyethoxy)-4-(4H-1,2,4-triazol-3-yl)cyclohexyl)-6-(methylsulfonyl)-3-(6-phenylpyridin-3-yl)pyrazolo[1,5-a]pyrimidin-7-amine | | 588.2 | 589.2 | 0.90 |

Step 2: Preparation of 2-(benzyloxy)-1-(4-(7-(bis((2-(trimethylsilyl)ethoxy)methyl)amino)-6-(methylsulfonyl)-3-(1-phenyl-1H-pyrazol-4-yl)pyrazolo[1,5-a]pyrimidin-5-yl)-1-(2-methoxyethoxy)cyclohexyl)ethanone

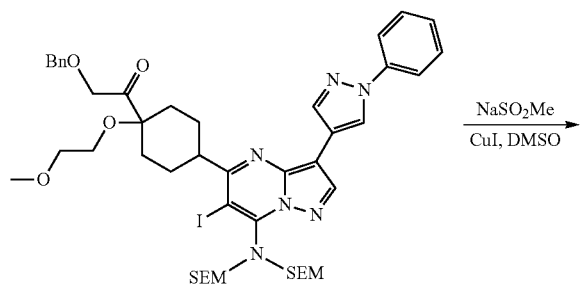

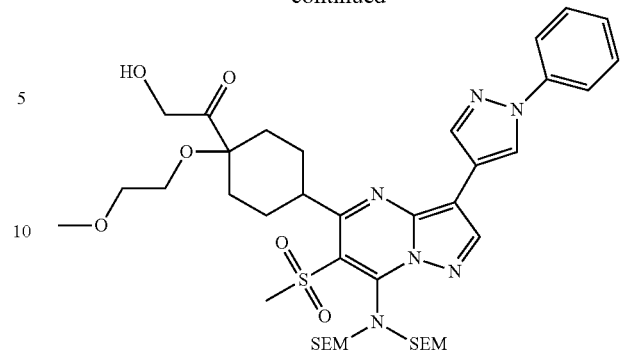

The hydrogenation was performed with the same condition described in example 1 Step 9. HPLC-MS $t_R$=1.78 min (UV$_{254\ nm}$); mass calculated for formula $C_{39}H_{60}N_6O_8SSi_2$ 828.4, observed LCMS m/z 829.3 (M+H).

Step 4: Preparation of 1-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-2-hydroxyethanone (Compound 129)

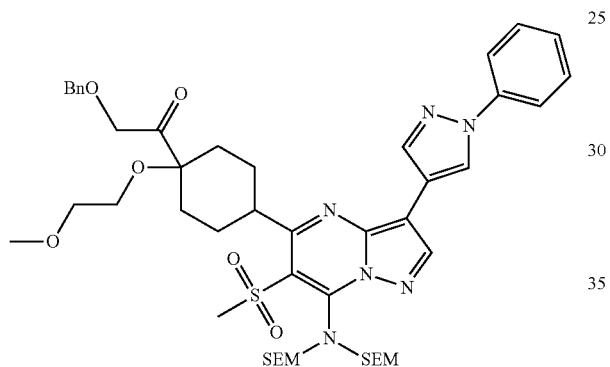

The methylsulfone was prepared with the same condition described in the example 38 Step 4. HPLC-MS $t_R$=1.88 min (UV$_{254\ nm}$); mass calculated for formula $C_{46}H_{66}N_6O_9SSi_2$ 918.4, observed LCMS m/z 919.3 (M+H).

Step 3: Preparation of 1-(4-(7-(bis((2-(trimethylsilyl)ethoxy)methyl)amino)-6-(methylsulfonyl)-3-(1-phenyl-1H-pyrazol-4-yl)pyrazolo[1,5-a]pyrimidin-5-yl)-1-(2-methoxyethoxy)cyclohexyl)-2-hydroxyethanone

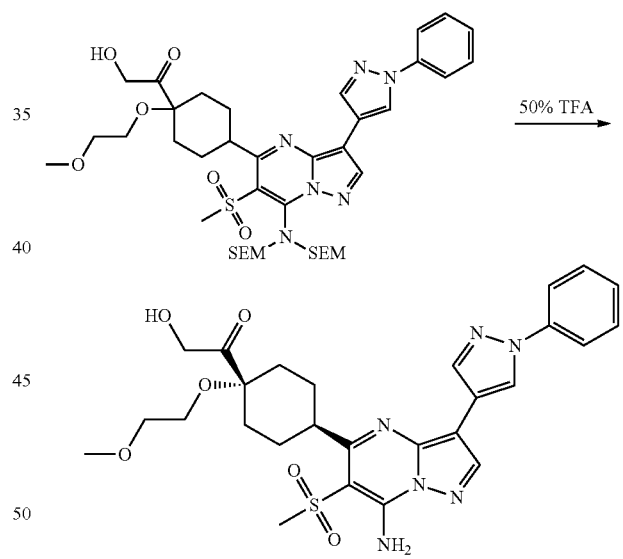

The crude product from Step 3 was de-protected with the same condition described in example 1 Step 11 and purified with HPLC to give the desired enantiomeric pure products. HPLC-MS $t_R$=1.19 min (UV$_{254\ nm}$); mass calculated for formula $C_{27}H_{32}N_6O_6S$ 568.2, observed LCMS m/z 569.2 (M+H).

Example 52

By essentially the same procedure in Preparative Example 51, the compound in Column 2 of Table 20 can be prepared.

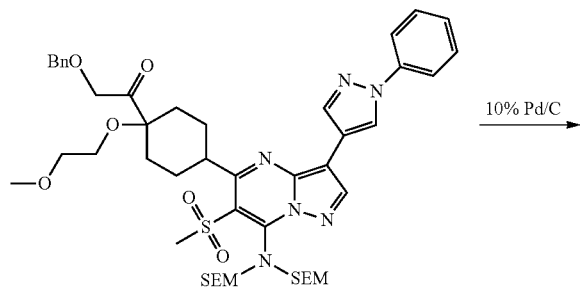

TABLE 20

| Example | Chemical name | Column 2 | Exact mass | MS m/z (M + H) | HPLC MS $t_R$ |
|---|---|---|---|---|---|
| 130 | 1-((1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexyl)-2-hydroxyethanone | | 579.2 | 580.2 | 0.96 |

Example 53

Preparation of 4-(7-amino-6-bromo-3-(6-phenylpyridin-3-yl)pyrazolo[1,5-a]pyrimidin-5-yl)-1-hydroxy-cyclohexanecarboxylic acid (Compound 131)

Step 1: Preparation of 4-(7-(bis((2-(trimethylsilyl)ethoxy)methyl)amino)-3-iodopyrazolo[1,5-a]pyrimidin-5-yl)cyclohexanone

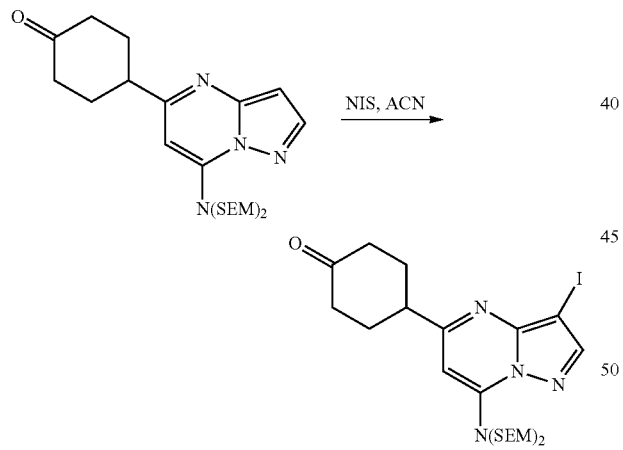

To a solution of 4-(7-(bis((2-(trimethylsilyl)ethoxy)methyl)amino)pyrazolo[1,5-a]pyrimidin-5-yl)cyclohexanone (775 mg, 1.58 mmol) in $CH_3CN$ (10 mL) was added NIS (391 mg, 1.74 mmol). The resulting solution was stirred at rt for 30 min before quenching with $Na_2S_2O_3$ (sat.). $CH_3CN$ was removed under reduced pressure. The residue was diluted with EtOAc, washed with $H_2O$ and brine, dried over $Na_2SO_4$, and concentrated. The crude product was purified by a $SiO_2$ column (0-20% EtOAc/Hexanes, $R_f$=0.3 in 20% EtOAc) to afford 4-(7-(bis((2-(trimethylsilyl)ethoxy)methyl)amino)-3-iodopyrazolo[1,5-a]pyrimidin-5-yl)cyclohexanone as a pale yellow oil (751 mg).

Step 2: Preparation of 4-(7-(bis((2-(trimethylsilyl)ethoxy)methyl)amino)-3-(6-phenylpyridin-3-yl)pyrazolo[1,5-a]pyrimidin-5-yl)cyclohexanone

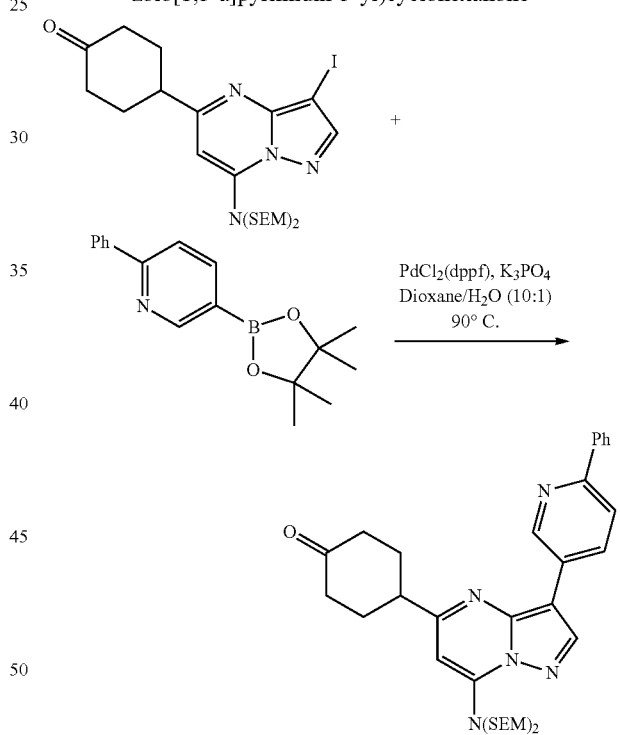

A mixture of 4-(7-(bis((2-(trimethylsilyl)ethoxy)methyl)amino)-3-iodopyrazolo[1,5-a]pyrimidin-5-yl)cyclohexanone (751 mg, 1.22 mmol), 2-phenyl-5-(4,4,5,5-tetramethyl-1,3,2-dioxaborolan-2-yl)pyridine (444 mg, 1.58 mmol), $PdCl_2(dppf)CH_2Cl_2$ (99.6 mg, 0.122 mmol), and $K_3PO_4$ (777 mg, 3.66 mmol) in dioxane/$H_2O$ (7/0.7 mL) was degassed and then heated at 90° C. for 16 h. After cooling, the reaction mixture was diluted with EtOAc and washed with $H_2O$ and brine, dried over $Na_2SO_4$, and concentrated. The crude product was purified by a $SiO_2$ column (0-40% EtOAc/Hexanes, $R_f$=0.2 in 20% EtOAc/Hexanes) to afford 4-(7-(bis((2-(trimethylsilyl)ethoxy)methyl)amino)-3-(6-phenylpyridin-3-yl)pyrazolo[1,5-a]pyrimidin-5-yl)cyclohexanone as a pale yellow solid (643 mg). HPLC-MS $T_R$=3.12 min (UV 254 nm, 5 min method); mass calculated for formula $C_{35}H_{49}N_5O_3Si_2$ 643.3, observed LCMS m/z 644.2 (M+H).

Step 3: Preparation of 4-(7-(bis((2-(trimethylsilyl)ethoxy)methyl)amino)-6-bromo-3-(6-phenylpyridin-3-yl)pyrazolo[1,5-a]pyrimidin-5-yl)cyclohexanone

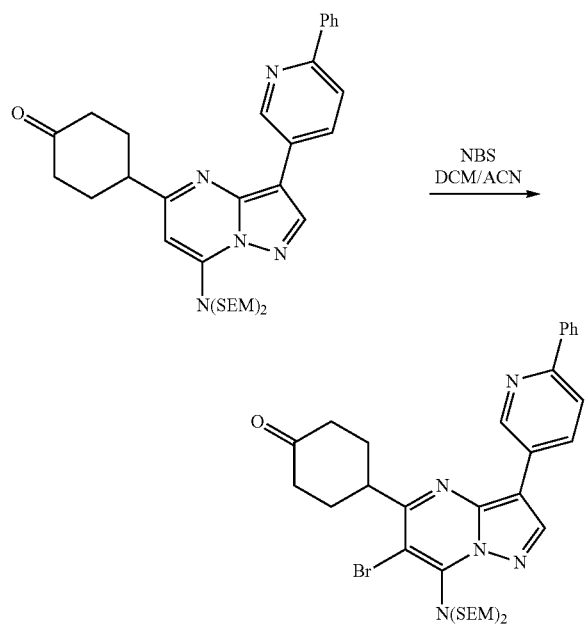

To a solution of 4-(7-(bis((2-(trimethylsilyl)ethoxy)methyl)amino)-3-(6-phenylpyridin-3-yl)pyrazolo[1,5-a]pyrimidin-5-yl)cyclohexanone (128 mg, 0.199 mmol) in CH₃CN/DCM (3/1 mL) was added NBS (42.5 mg, 0.239 mmol) and stirred at rt for 30 min. TLC showed complete conversion. All the volatiles were removed under reduced pressure and the residue was purified by a SiO₂ column (0-15% EtOAc/Hexanes, $R_f$=0.6 in 20% EtOAc) to afford 4-(7-(bis((2-(trimethylsilyl)ethoxy)methyl)amino)-6-bromo-3-(6-phenylpyridin-3-yl)pyrazolo[1,5-a]pyrimidin-5-yl)cyclohexanone as a pale yellow oil (125 mg).

Step 4: Preparation of 4-(7-amino-6-bromo-3-(6-phenylpyridin-3-yl)pyrazolo[1,5-a]pyrimidin-5-yl)-1-hydroxycyclohexanecarboxylic acid (Compound 131)

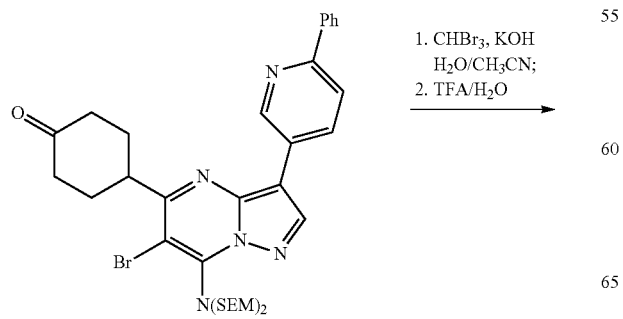

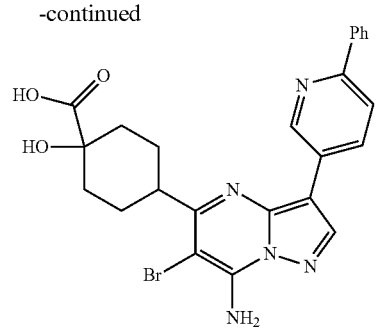

To an ice-cooled mixture of 4-(7-(bis((2-(trimethylsilyl)ethoxy)methyl)amino)-6-bromo-3-(6-phenylpyridin-3-yl)pyrazolo[1,5-a]pyrimidin-5-yl)cyclohexanone (125 mg, 0.173 mmol) and tribromomethane (151 uL, 1.73 mmol) in CH₃CN/H₂O (1/0.5 mL) was added a solution of KOH in H₂O (87.3 mg, 1.56 mmol, 1 g/mL) dropwise during 5 min. The resulting reaction mixture was stirred vigorously at rt overnight. All the volatiles were removed and the residue was treated with TFA/H₂O (1/1 mL) overnight. After removal of TFA/H₂O, the crude product was purified by a reverse phase HPLC to afford 4-(7-amino-6-bromo-3-(6-phenylpyridin-3-yl)pyrazolo[1,5-a]pyrimidin-5-yl)-1-hydroxycyclohexanecarboxylic acid (Compound 131) as a pale yellow solid (5.0 mg). HPLC-MS $T_R$=1.52 min (UV 254 nm, 5 min method); mass calculated for formula $C_{24}H_{22}BrN_5O_3$ 507.1, observed LCMS m/z 508.0 (M+H).

Example 54

Preparation of 4-(6-acetyl-7-amino-3-(1-phenyl-1H-pyrazol-4-yl)pyrazolo[1,5-a]pyrimidin-5-yl)-1-(hydroxymethyl)cyclohexanecarboxylic acid (Compound 132)

Step 1: Preparation of ethyl 1-(benzyloxymethyl)-4-oxocyclohexanecarboxylate

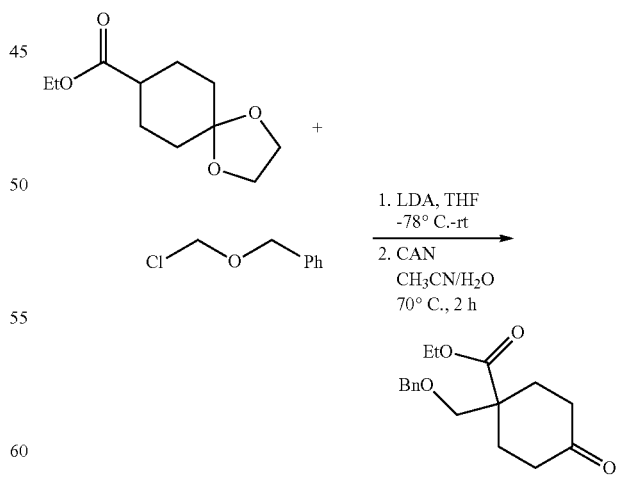

To a solution of ethyl 1,4-dioxaspiro[4.5]decane-8-carboxylate (7.89 g, 36.8 mmol) in THF (120 mL) was added LDA (1.5 eq) at −78° C. and stirred for 30 min. Then, benzyl chloromethyl ether (10.7 mL, 92.1 mmol) was added dropwise. The resulting mixture was slowly warmed to rt and stirred overnight. The reaction was quenched with H₂O and combined with ammonium choloride. All the volatiles were removed. The residue was diluted with EtOAc, washed with H₂O and brine, dried over Na₂SO₄, and concentrated. The resulting brownish oil was dissolved in CH₃CN (150 mL) and a solution of CAN (2.02 g 3.68 mmol) in H₂O (150 mL) was added. The resulting mixture was heated at 70° C. for 6 h. Organic solvent was removed under reduced pressure. The aqueous residue was extracted with EtOAc (*3) and the combined organic layers were washed brine, dried over Na₂SO₄ and concentrated. The crude product was purified by two SiO₂ columns (firstly 0-30% EtOAc/Hexanes, then 50-100% DCM/Hexanes, $R_f$=0.2 in 20% EtOAc) to afford ethyl 1-(benzyloxymethyl)-4-oxocyclohexanecarboxylate as a pale yellow oil (5.72 g). HPLC-MS $T_R$=2.08 min (UV 254 nm, 5 min method); mass calculated for formula $C_{17}H_{22}O_4$ 290.2, observed LCMS m/z 291.1 (M+H).

Step 2: Preparation of ethyl 1-(benzyloxymethyl)-4-(trifluoromethylsulfonyloxy)cyclohex-3-enecarboxylate

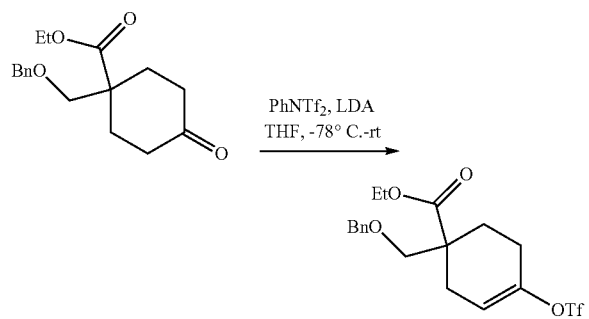

To a solution of ethyl 1-(benzyloxymethyl)-4-oxocyclohexanecarboxylate (1.95 g, 6.72 mmol) in THF (25 mL) was added LDA (1.5 eq) at −78° C. and stirred for 30 min. Then, a solution of PhNTf₂ in THF (10 mL) was added dropwise at −78° C. The resulting mixture was slowly warmed to rt and stirred overnight. The reaction was quenched with NH₄Cl. THF was removed under reduced pressure. The aqueous residue was diluted with EtOAc, washed with H₂O and brine, dried over Na₂SO₄, and concentrated. The crude product was purified by a SiO₂ column (0-15% EtOAc/Hexanes, $R_f$=0.5 in 20% EtOAc) and afforded ethyl 1-(benzyloxymethyl)-4-(trifluoromethylsulfonyloxy)cyclohex-3-enecarboxylate as a pale yellow oil (2.81 g).

Step 3: Preparation of ethyl 1-(benzyloxymethyl)-4-(4,4,5,5-tetramethyl-1,3,2-dioxaborolan-2-yl)cyclohex-3-enecarboxylate

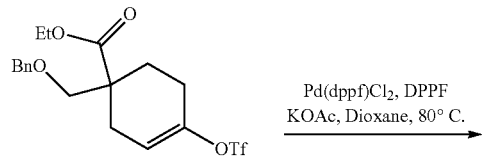

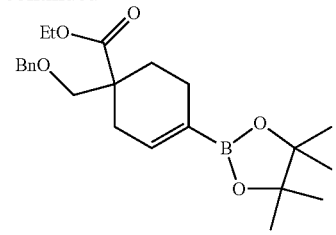

A mixture of ethyl 1-(benzyloxymethyl)-4-(trifluoromethylsulfonyloxy)cyclohex-3-enecarboxylate (3.53 g, 8.36 mmol), bis(pinacolato)diboron (2.54 g, 10.0 mmol), PdCl₂(dppf)CH₂Cl₂ (683 mg, 0.836 mmol), DPPF (463 mg, 0.836 mmol), and KOAc (2.46 g, 25.1 mmol) in dioxane was degassed and then heated at 80° C. for 16 h. The resulting crude product ethyl 1-(benzyloxymethyl)-4-(4,4,5,5-tetramethyl-1,3,2-dioxaborolan-2-yl)cyclohex-3-enecarboxylate was used without further purification.

HPLC-MS $T_R$=2.69 min (UV 254 nm, 5 min method); mass calculated for formula $C_{23}H_{33}BO_5$ 400.2, observed LCMS m/z 401.2 (M+H).

Step 4: Preparation of ethyl 1-(benzyloxymethyl)-4-(7-(bis((2-(trimethylsilyl)ethoxy)methyl)amino)pyrazolo[1,5-a]pyrimidin-5-yl)cyclohex-3-enecarboxylate

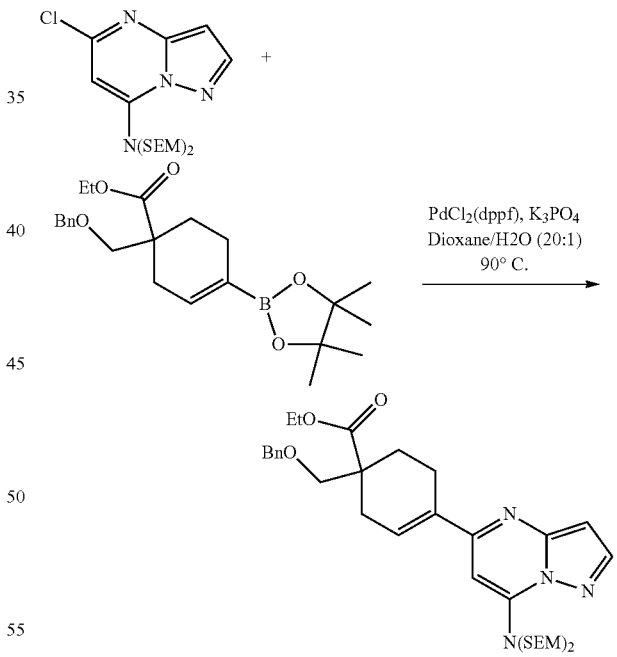

A mixture of 5-chloro-N,N-bis((2-(trimethylsilyl)ethoxy)methyl)pyrazolo[1,5-a]pyrimidin-7-amine (2.99 g, 6.97 mmol), ethyl 1-(benzyloxymethyl)-4-(4,4,5,5-tetramethyl-1,3,2-dioxaborolan-2-yl)cyclohex-3-enecarboxylate (8.36 mmol), PdCl₂(dppf)CH₂Cl₂ (683 mg, 0.836 mmol), and K₃PO₄ (5.32 g, 25.1 mmol) in dioxane/H₂O (40/2 mL) was degassed and then heated at 90° C. for 16 h. After cooling, the reaction mixture was diluted with EtOAc and washed with H₂O and brine, dried over Na₂SO₄, and concentrated. The crude product was purified by a SiO₂ column (0-20% EtOAc/

Hexanes, $R_f$=0.45 in 20% EtOAc) to afford ethyl 1-(benzyloxymethyl)-4-(7-(bis((2-(trimethylsilyl)ethoxy)methyl)amino)pyrazolo[1,5-a]pyrimidin-5-yl)cyclohex-3-enecarboxylate as a pale yellow oil (3.06 g). HPLC-MS $T_R$=3.17 min (UV 254 nm, 5 min method); mass calculated for formula $C_{35}H_{54}N_4O_5Si_2$ 666.4, observed LCMS m/z 667.3 (M+H).

Step 5: Preparation of ethyl 4-(7-(bis((2-(trimethylsilyl)ethoxy)methyl)amino)pyrazolo[1,5-a]pyrimidin-5-yl)-1-(hydroxymethyl)cyclohexanecarboxylate

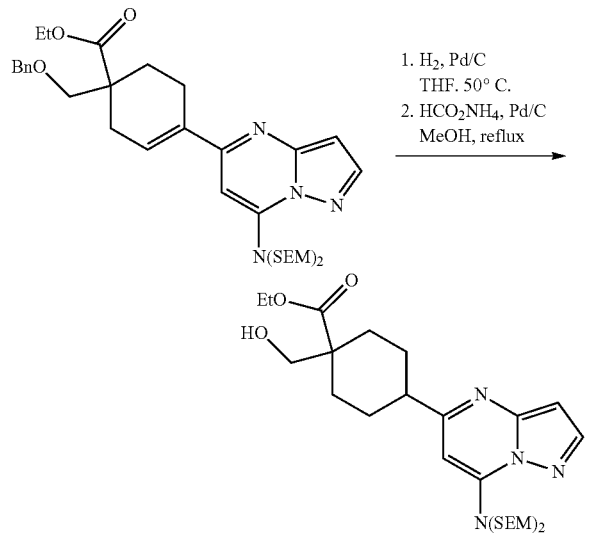

A mixture of ethyl 1-(benzyloxymethyl)-4-(7-(bis((2-(trimethylsilyl)ethoxy)methyl)amino)pyrazolo[1,5-a]pyrimidin-5-yl)cyclohex-3-enecarboxylate (3.06 g, 4.59 mmol) and Pd/C (cat.) in THF (25 mL) was heated at 50° C. under 1.0 atm of $H_2$ for 16 h. LCMS indicated complete reduction of double bond. The reaction mixture was filtered and evaporated. The residue was dissolved in MeOH and $HCO_2NH_4$ and Pd/C (cat.) was added. The resulting mixture was heated under reflux for 24 h. After cooling to rt, the reaction mixture was filtered. The filtrate was concentrated and purified by a $SiO_2$ column (0-40% EtOAc/Hexanes, $R_f$=0.5 in 50% EtOAc) to afford ethyl 4-(7-(bis((2-(trimethylsilyl)ethoxy)methyl)amino)pyrazolo[1,5-a]pyrimidin-5-yl)-1-(hydroxymethyl)cyclohexanecarboxylate as colorless oil (733 mg). HPLC-MS $T_R$=2.78 min (UV 254 nm, 5 min method); mass calculated for formula $C_{28}H_{50}N_4O_5Si_2$ 578.3, observed LCMS m/z 579.2 (M+H).

Step 6: Preparation of ethyl 4-(7-(bis((2-(trimethylsilyl)ethoxy)methyl)amino)-3-iodopyrazolo[1,5-a]pyrimidin-5-yl)-1-(hydroxymethyl)cyclohexanecarboxylate

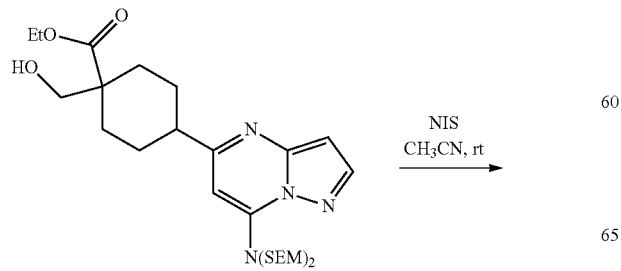

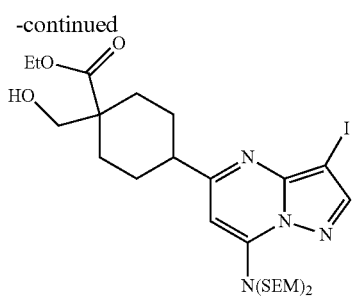

To a solution of ethyl 4-(7-(bis((2-(trimethylsilyl)ethoxy)methyl)amino)pyrazolo[1,5-a]pyrimidin-5-yl)-1-(hydroxymethyl)cyclohexanecarboxylate (733 mg, 1.27 mmol) in $CH_3CN$ (10 mL) was added NIS (313 mg, 1.39 mmol). The resulting solution was stirred at rt for 30 min before quenching with $Na_2S_2O_3$ (sat.). $CH_3CN$ was removed under reduced pressure. The residue was diluted with EtOAc, washed with $H_2O$ and brine, dried over $Na_2SO_4$, and concentrated. The crude product was purified by a $SiO_2$ column (0-40% EtOAc/Hexanes, $R_f$=0.6 in 50% EtOAc) to afford ethyl 4-(7-(bis((2-(trimethylsilyl)ethoxy)methyl)amino)-3-iodopyrazolo[1,5-a]pyrimidin-5-yl)-1-(hydroxymethyl)cyclohexanecarboxylate as a colorless oil (811 mg).

Step 7: Preparation of ethyl 4-(7-(bis((2-(trimethylsilyl)ethoxy)methyl)amino)-3-(1-phenyl-1H-pyrazol-4-yl)pyrazolo[1,5-a]pyrimidin-5-yl)-1-(hydroxymethyl)cyclohexanecarboxylate

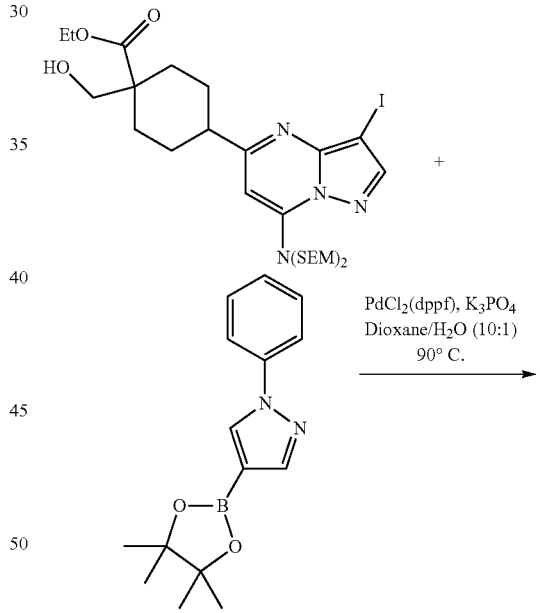

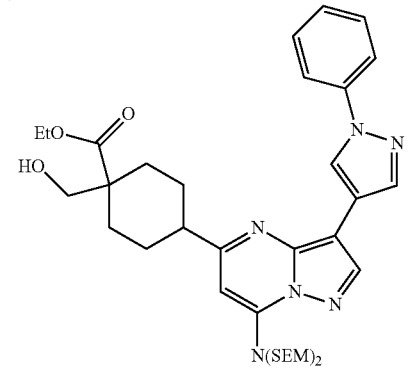

A mixture of ethyl 4-(7-(bis((2-(trimethylsilyl)ethoxy)methyl)amino)-3-iodopyrazolo[1,5-a]pyrimidin-5-yl)-1-(hydroxymethyl)cyclohexanecarboxylate (270 mg, 0.383 mmol), 1-phenyl-4-(4,4,5,5-tetramethyl-1,3,2-dioxaborolan-2-yl)-1H-pyrazole (135 mg, 0.498 mmol), PdCl$_2$(dppf) CH$_2$Cl$_2$ (31.3 mg, 0.038 mmol), and K$_3$PO$_4$ (244 mg, 1.15 mmol) in dioxane/H$_2$O (3/0.3 mL) was degassed and then heated at 90° C. for 16 h. After cooling, the reaction mixture was diluted with EtOAc and washed with H$_2$O and brine, dried over Na$_2$SO$_4$, and concentrated. The crude product was purified by a SiO$_2$ column (0-40% EtOAc/Hexanes, R$_f$=0.55 in 50% EtOAc) to afford ethyl 4-(7-(bis((2-(trimethylsilyl)ethoxy)methyl)amino)-3-(1-phenyl-1H-pyrazol-4-yl)pyrazolo[1,5-a]pyrimidin-5-yl)-1-(hydroxymethyl)cyclohexanecarboxylate as a pale yellow solid (200 mg). HPLC-MS T$_R$=3.06 min (UV 254 nm, 5 min method); mass calculated for formula C$_{37}$H$_{56}$N$_6$O$_5$Si$_2$ 720.4, observed LCMS m/z 721.3 (M+H).

Step 8: Preparation of ethyl 4-(7-(bis((2-(trimethylsilyl)ethoxy)methyl)amino)-6-bromo-3-(1-phenyl-1H-pyrazol-4-yl)pyrazolo[1,5-a]pyrimidin-5-yl)-1-(hydroxymethyl)cyclohexanecarboxylate

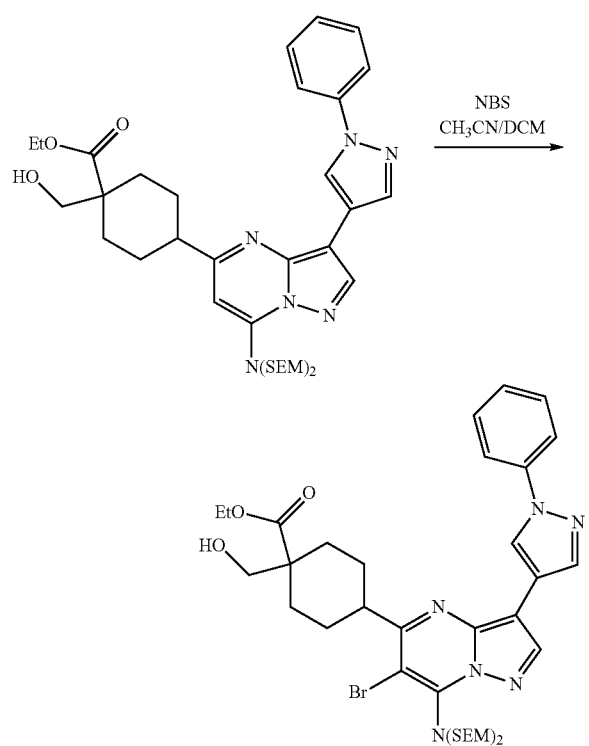

To a solution of ethyl 4-(7-(bis((2-(trimethylsilyl)ethoxy)methyl)amino)-3-(1-phenyl-1H-pyrazol-4-yl)pyrazolo[1,5-a]pyrimidin-5-yl)-1-(hydroxymethyl)cyclohexanecarboxylate (200 mg, 0.277 mmol) in CH$_3$CN/DCM (5/3 mL) was added NBS (54.3 mg, 0.305 mmol) and stirred at rt for 30 min. TLC showed complete conversion. All the volatiles were removed under reduced pressure and the residue was purified by a SiO$_2$ column (0-35% EtOAc/Hexanes, R$_f$=0.7 in 50% EtOAc) to afford ethyl 4-(7-(bis((2-(trimethylsilyl)ethoxy)methyl)amino)-6-bromo-3-(1-phenyl-1H-pyrazol-4-yl)pyrazolo[1,5-a]pyrimidin-5-yl)-1-(hydroxymethyl)cyclohexanecarboxylate as a pale yellow oil (201 mg).

Step 9: Preparation of ethyl 4-(7-(bis((2-(trimethylsilyl)ethoxy)methyl)amino)-6-(1-ethoxyvinyl)-3-(1-phenyl-1H-pyrazol-4-yl)pyrazolo[1,5-a]pyrimidin-5-yl)-1-(hydroxymethyl)cyclohexanecarboxylate

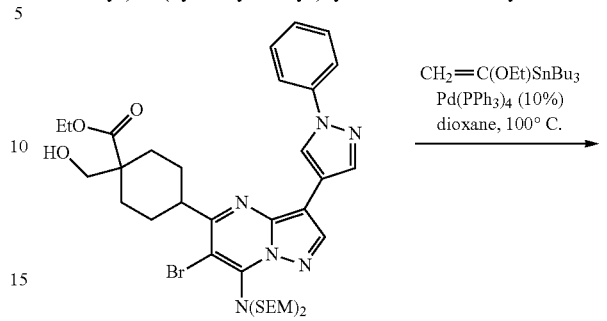

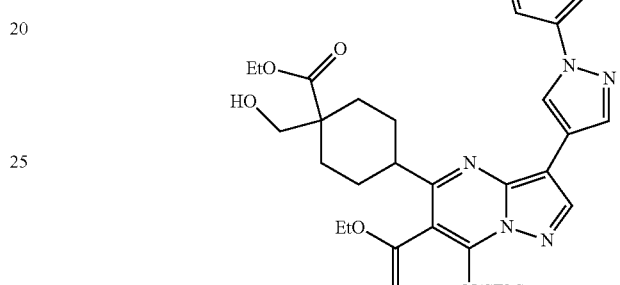

A mixture of ethyl 4-(7-(bis((2-(trimethylsilyl)ethoxy)methyl)amino)-6-bromo-3-(1-phenyl-1H-pyrazol-4-yl)pyrazolo[1,5-a]pyrimidin-5-yl)-1-(hydroxymethyl)cyclohexanecarboxylate (201 mg, 0.251 mmol), tributyl(1-ethoxyvinyl)stannane (0.255 mL, 0.754 mmol), Pd(PPh$_3$)$_4$ (29.0 g, 0.025 mmol) in dioxane was stirred at 100° C. under Ar$_2$ for 16 h. The reaction mixture was passed through a short SiO$_2$/KF (9:1) plug to remove majority of the Sn species, and then purified by a SiO$_2$ column (0-30% EtOAc/Hexanes, R$_f$=0.7 in 50% EtOAc) to afford ethyl 4-(7-(bis((2-(trimethylsilyl)ethoxy)methyl)amino)-6-(1-ethoxyvinyl)-3-(1-phenyl-1H-pyrazol-4-yl)pyrazolo[1,5-a]pyrimidin-5-yl)-1-(hydroxymethyl)cyclohexanecarboxylate as a pale yellow oil (167 mg). HPLC-MS T$_R$=3.18 min (UV 254 nm, 5 min method); mass calculated for formula C$_{41}$H$_{62}$N$_6$O$_6$Si$_2$ 790.4, observed LCMS m/z 791.2 (M+H).

Step 10: Preparation of 4-(6-acetyl-7-amino-3-(1-phenyl-1H-pyrazol-4-yl)pyrazolo[1,5-a]pyrimidin-5-yl)-1-(hydroxymethyl)cyclohexanecarboxylic acid (Compound 132)

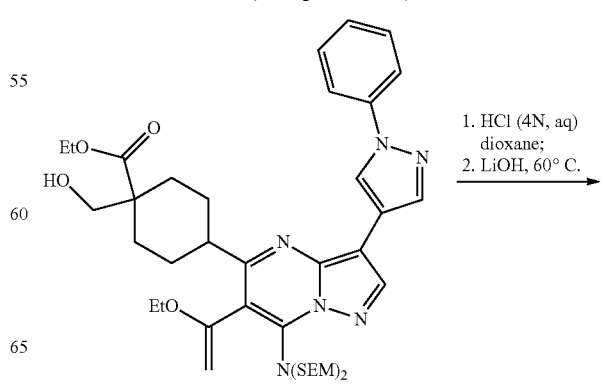

-continued

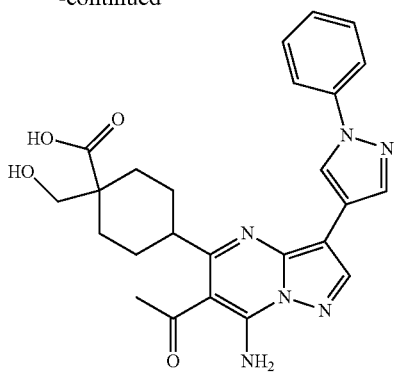

To a solution of ethyl 4-(7-(bis((2-(trimethylsilyl)ethoxy)methyl)amino)-6-(1-ethoxyvinyl)-3-(1-phenyl-1H-pyrazol-4-yl)pyrazolo[1,5-a]pyrimidin-5-yl)-1-(hydroxymethyl)cyclohexanecarboxylate (167 mg, 0.211 mmol) in dioxane (2 mL) was added 2 mL of HCl (4 N, aq) at 0° C. The reaction mixture was stirred at rt for 1 h, then 60° C. for 1 h. The reaction mixture was evaporated to dryness. The residue was treated with LiOH (10 eq) in THF/MeOH/H$_2$O (2/1/1 mL) at 80° C. overnight. The reaction mixture was carefully acidified with HCl (aq) to pH=6-7, and evaporated to dryness. The crude product was purified by a reverse phase HPLC to afford 4-(6-acetyl-7-amino-3-(1-phenyl-1H-pyrazol-4-yl)pyrazolo[1,5-a]pyrimidin-5-yl)-1-(hydroxymethyl)cyclohexanecarboxylic acid as a pale yellow solid (27.7 mg). HPLC-MS T$_R$=4.39 min (UV 254 nm, 10 min method); mass calculated for formula C$_{25}$H$_{26}$N$_6$O$_4$ 474.2, observed LCMS m/z 475 (M+H).

Example 55

Preparation of 4-(6-acetyl-7-amino-3-(6-phenylpyridin-3-yl)pyrazolo[1,5-a]pyrimidin-5-yl)-1-(hydroxymethyl)cyclohexanecarboxylic acid (Compound 133)

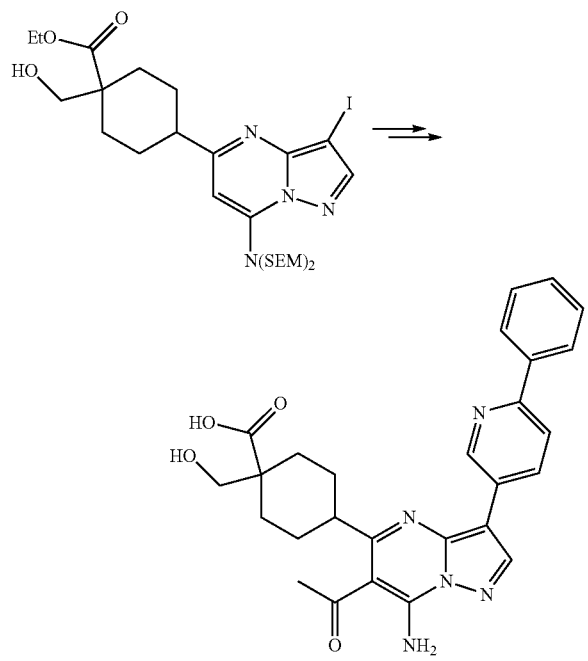

By essentially the same procedures in Preparative Example 54, Step 7-10, 4-(6-acetyl-7-amino-3-(6-phenylpyridin-3-yl)pyrazolo[1,5-a]pyrimidin-5-yl)-1-(hydroxymethyl)cyclohexanecarboxylic acid (Compound 133) can be prepared. HPLC-MS T$_R$=3.75 min (UV 254 nm, 10 min method); mass calculated for formula C$_{27}$H$_{27}$N$_5$O$_4$ 485.2, observed LCMS m/z 486 (M+H).

Example 56

Preparation of 4-(7-amino-6-bromo-3-(6-phenylpyridin-3-yl)pyrazolo[1,5-a]pyrimidin-5-yl)-1-(hydroxymethyl)cyclohexanol (Compound 134)

Step 1: Preparation of 4-(7-(bis((2-(trimethylsilyl)ethoxy)methyl)amino)pyrazolo[1,5-a]pyrimidin-5-yl)-1-(hydroxymethyl)cyclohexanol

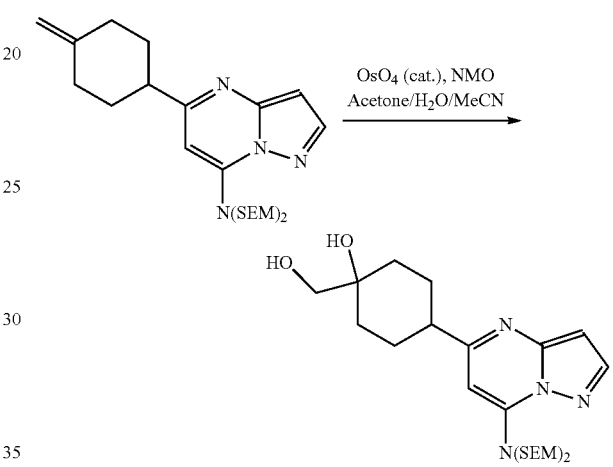

To a slurry of 5-(4-methylenecyclohexyl)-N,N-bis((2-(trimethylsilyl)ethoxy)methyl)pyrazolo[1,5-a]pyrimidin-7-amine (4.89 g, 10.0 mmol) in Acetone/H$_2$O/MeCN (60/20/20) was added NMO (4.15 mL, 20 mmol), followed by OsO$_4$ (2.5 wt. % in $^t$BuOH) (6.27 mL, 0.50 mmol) at rt. The resulting reaction mixture was stirred at rt overnight. Organic solvent were evaporated and the aqueous residue was extracted with EtOAc three times, dried over Na$_2$SO$_4$ and concentrated to afford 4-(7-(bis((2-(trimethylsilyl)ethoxy)methyl)amino)pyrazolo[1,5-a]pyrimidin-5-yl)-1-(hydroxymethyl)cyclohexanol as a pale brownish oil (5.52 g), which was used without further purification. HPLC-MS T$_R$=2.48 min (UV 254 nm, 5 min method); mass calculated for formula C$_{25}$H$_{46}$N$_4$O$_4$Si$_2$ 522.3, observed LCMS m/z 523.3 (M+H).

Step 2: Preparation of 4-(7-(bis((2-(trimethylsilyl)ethoxy)methyl)amino)-3-(6-phenylpyridin-3-yl)pyrazolo[1,5-a]pyrimidin-5-yl)-1-(hydroxymethyl)cyclohexanol

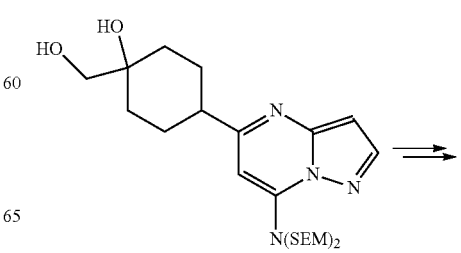

-continued

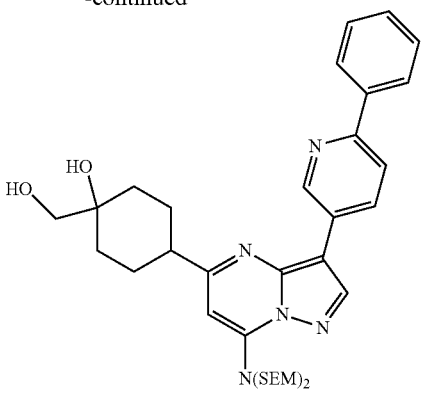

By essentially the same procedures in Preparative Example 54, Step 6-7, 4-(7-(bis((2-(trimethylsilyl)ethoxy)methyl) amino)-3-(6-phenylpyridin-3-yl)pyrazolo[1,5-a]pyrimidin-5-yl)-1-(hydroxymethyl)cyclohexanol can be prepared from the diol compound. HPLC-MS $T_R$=2.14 min (UV 254 nm, 5 min method); mass calculated for formula $C_{36}H_{53}N_5O_4Si_2$ 675.4, observed LCMS m/z 676.3 (M+H).

Step 3: Preparation of 4-(7-(bis((2-(trimethylsilyl) ethoxy)methyl)amino)-6-bromo-3-(6-phenylpyridin-3-yl)pyrazolo[1,5-a]pyrimidin-5-yl)-1-(hydroxymethyl)cyclohexanol

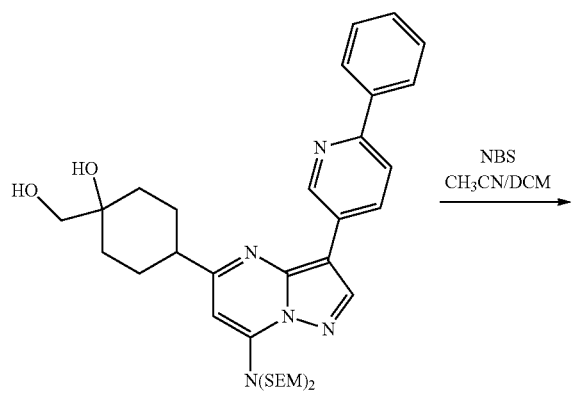

By essentially the same procedures in Preparative Example 54, Step 8, 4-(7-(bis((2-(trimethylsilyl)ethoxy)methyl) amino)-6-bromo-3-(6-phenylpyridin-3-yl)pyrazolo[1,5-a] pyrimidin-5-yl)-1-(hydroxymethyl)cyclohexanol can be prepared. HPLC-MS $T_R$=3.06 min (UV 254 nm, 5 min method); mass calculated for formula $C_{36}H_{52}BrN_5O_4Si_2$ 753.3, observed LCMS m/z 754.2 (M+H).

Step 4: Preparation of 4-(7-amino-6-bromo-3-(6-phenylpyridin-3-yl)pyrazolo[1,5-a]pyrimidin-5-yl)-1-(hydroxymethyl)cyclohexanol (Compound 134)

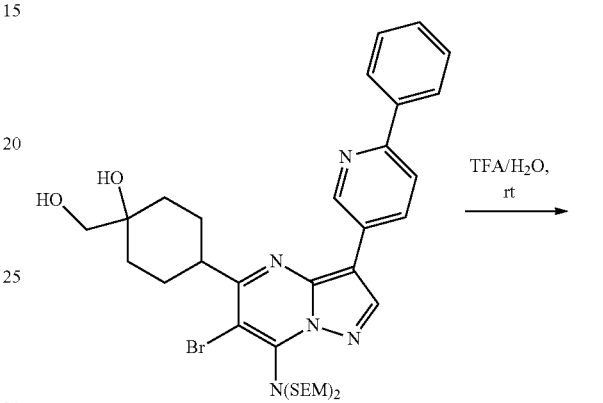

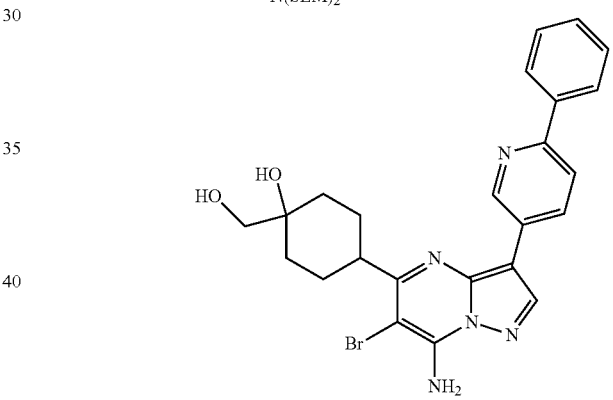

4-(7-(bis((2-(trimethylsilyl)ethoxy)methyl)amino)-6-bromo-3-(6-phenylpyridin-3-yl)pyrazolo[1,5-a]pyrimidin-5-yl)-1-(hydroxymethyl)cyclohexanol (385 mg, 0.510 mmol) was treated with a mixture of TFA/H$_2$O (2/2 mL) at rt overnight. The reaction mixture was evaporated to dryness and purified by a reverse phase HPLC to afford 4-(7-amino-6-bromo-3-(6-phenylpyridin-3-yl)pyrazolo[1,5-a]pyrimidin-5-yl)-1-(hydroxymethyl)cyclohexanol as a pale yellow solid (99 mg). HPLC-MS $T_R$=3.27 min (isomer 1) and 3.32 min (isomer 2) (UV 254 nm, 10 min method); mass calculated for formula $C_{24}H_{24}BrN_5O_2$ 493.1, observed LCMS m/z 494 (M+H).

Example 57

By essentially the same procedure in Preparative Example 56, the compounds in Column 2 of Table 21 can be prepared.

TABLE 21

| Compound | Chemical name | Structure | Exact mass | MS m/z (M + H) | HPLC-MS T$_R$ (Method) |
|---|---|---|---|---|---|
| 135 | 4-(7-amino-6-bromo-3-(1-phenyl-1H-pyrazol-4-yl)pyrazolo[1,5-a]pyrimidin-5-yl)-1-(hydroxymethyl)-cyclohexanol | 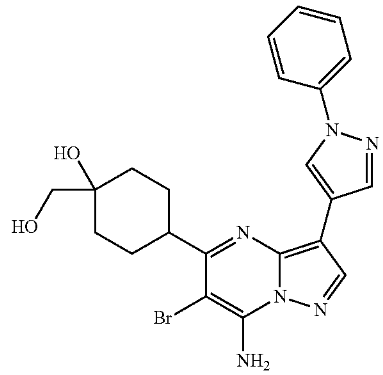 [SMILES: Nc1c(Br)c(C2CCC(O)(CO)CC2)nc2c(-c3cnn(-c4ccccc4)c3)cnn12] | 482.1 | 483 | 4.07 (10 min) |
| 136 | 4-(7-amino-6-bromo-3-(6-fluoroquinolin-3-yl)pyrazolo[1,5-a]pyrimidin-5-yl)-1-(hydroxymethyl) cyclohexanol | 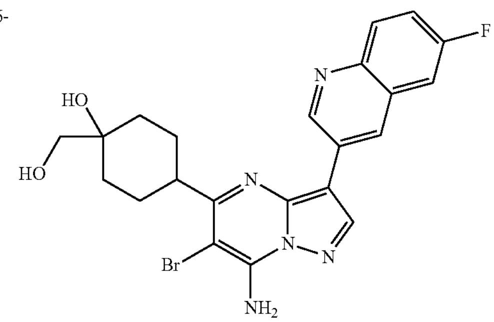 | 485.1 | 486 | 3.27 (10 min) |

Example 58

Preparation of (1S,4S)-4-(7-amino-6-bromo-3-(6-phenylpyridin-3-yl)pyrazolo[1,5-a]pyrimidin-5-yl)-1-(2-hydroxyethyl)cyclohexanol (Compound 137)

Step 1: Preparation of methyl 2-((1S,4S)-4-(7-(bis((2-(trimethylsilyl)ethoxy)methyl)amino)-3-(6-phenylpyridin-3-yl)pyrazolo[1,5-a]pyrimidin-5-yl)-1-hydroxycyclohexyl)acetate

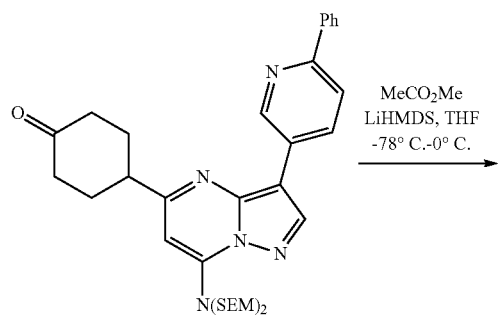

To a LiHMDS solution in THF (5 mL) at −78° C. was added slowly a solution of MeOAc in THF (3 mL). The resulting reaction mixture was stirred at −78° C. for 1 h, then a solution of 4-(7-(bis((2-(trimethylsilyl)ethoxy)methyl)amino)-3-(6-phenylpyridin-3-yl)pyrazolo[1,5-a]pyrimidin-5-yl)cyclohexanone (443 mg, 0.688 mmol) in THF (5 mL) was added dropwise. The reaction mixture was kept at −78° C. for 1 h, and then warmed to rt before being quenched with NH$_4$Cl. THF was removed. After an aqueous workup, the crude product was purified by a SiO$_2$ column (0-30% EtOAc/Hexanes) to afford the major isomer methyl 2-((1S,4S)-4-(7-(bis((2-(trimethylsilyl)ethoxy)methyl)amino)-3-(6-phenylpyridin-3-yl)pyrazolo[1,5-a]pyrimidin-5-yl)-1-hydroxycyclohexyl) acetate as a pale yellow oil (293 mg, R$_f$=0.6 in 50% EtOAc), and the minor isomer methyl 2-((1R,4R)-4-(7-(bis((2-(trimethylsilyl)ethoxy)methyl)amino)-3-(6-phenylpyridin-3-yl) pyrazolo[1,5-a]pyrimidin-5-yl)-1-hydroxycyclohexyl)acetate as a pale yellow oil (103 mg, R$_f$=0.7 in 50% EtOAc).

Step 2: Preparation of (1S,4S)-4-(7-(bis((2-(trimethylsilyl)ethoxy)methyl)amino)-3-(6-phenylpyridin-3-yl)pyrazolo[1,5-a]pyrimidin-5-yl)-1-(2-hydroxyethyl)cyclohexanol

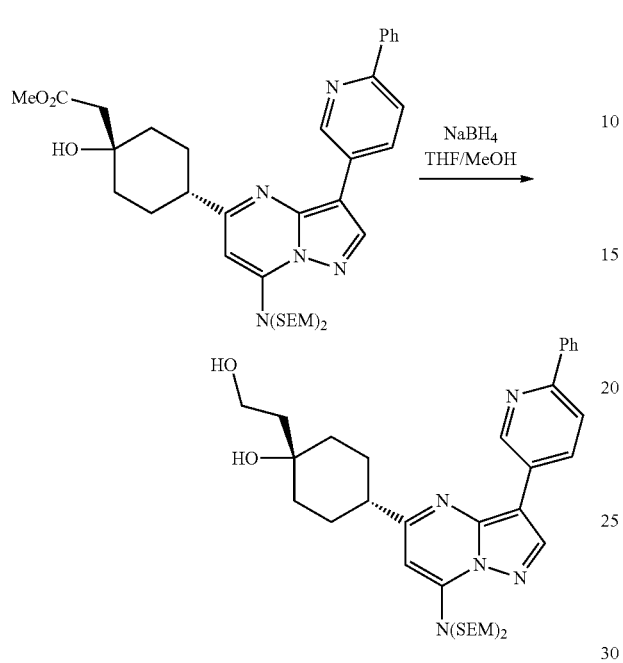

To a solution of methyl 2-((1S,4S)-4-(7-(bis((2-(trimethylsilyl)ethoxy)methyl)amino)-3-(6-phenylpyridin-3-yl)pyrazolo[1,5-a]pyrimidin-5-yl)-1-hydroxycyclohexyl)acetate (213 mg, 0.297 mmol) in THF/MeOH (6/0.3 mL) was added NaBH$_4$ (1.5 eq) at 0° C. The reaction mixture was stirred at rt overnight. All the volatiles were removed and the residue was diluted with H$_2$O and extracted with EtOAc. The combined organic layers were dried over Na$_2$SO$_4$ and concentrated. The crude product was purified by a SiO$_2$ column (0-70% EtOAc/Hexanes, R$_f$=0.40 in 50% EtOAc) to afford (1S,4S)-4-(7-(bis((2-(trimethylsilyl)ethoxy)methyl)amino)-3-(6-phenylpyridin-3-yl)pyrazolo[1,5-a]pyrimidin-5-yl)-1-(2-hydroxyethyl)cyclohexanol as a colorless oil (118 mg). HPLC-MS T$_R$=2.79 min (UV 254 nm, 5 min method); mass calculated for formula C$_{37}$H$_{55}$N$_5$O$_4$Si$_2$ 689.4, observed LCMS m/z 690.3 (M+H).

Step 3: Preparation of (1S,4S)-4-(7-amino-6-bromo-3-(6-phenylpyridin-3-yl)pyrazolo[1,5-a]pyrimidin-5-yl)-1-(2-hydroxyethyl)cyclohexanol (Compound 137)

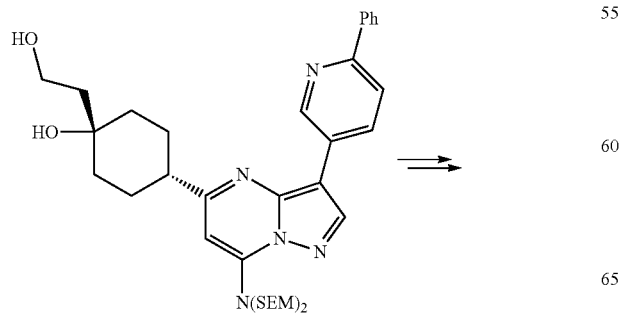

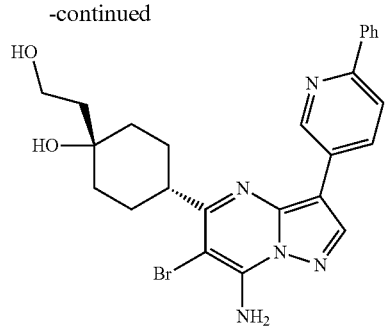

By essentially the same procedures in Preparative Example 54, Step 8, and Example 56, Step 3, (1S,4S)-4-(7-amino-6-bromo-3-(6-phenylpyridin-3-yl)pyrazolo[1,5-a]pyrimidin-5-yl)-1-(2-hydroxyethyl)cyclohexanol (Compound 138) can be prepared. HPLC-MS T$_R$=3.50 min (UV 254 nm, 10 min method); mass calculated for formula C$_{25}$H$_{26}$BrN$_5$O$_2$ 507.1, observed LCMS m/z 508 (M+H).

Example 59

Preparation of 1-(7-amino-5-(4-hydroxy-4-(hydroxymethyl)cyclohexyl)-3-(6-phenylpyridin-3-yl)pyrazolo[1,5-a]pyrimidin-6-yl)ethanone (Compound 138)

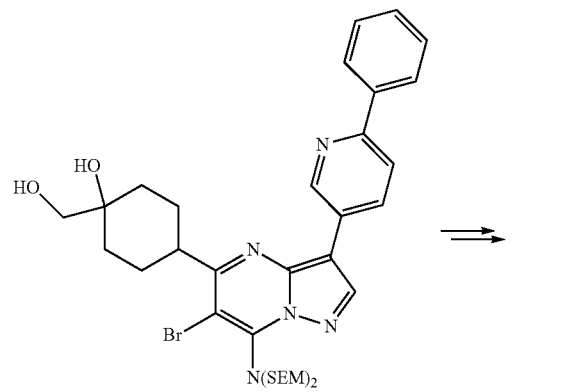

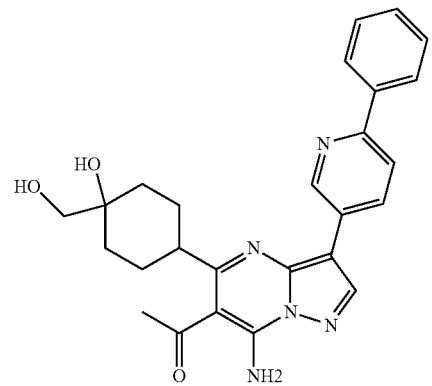

By essentially the same procedures in Preparative Example 54, Step 9, and Example 56, Step 4, 1-(7-amino-5-(4-hydroxy-4-(hydroxymethyl)cyclohexyl)-3-(6-phenylpyridin-3-yl)pyrazolo[1,5-a]pyrimidin-6-yl)ethanone (Compound 138) can be prepared. HPLC-MS T$_R$=3.19 min (isomer 1) and 3.28 min (isomer 2) (UV 254 nm, 10 min method); mass calculated for formula C$_{26}$H$_{27}$N$_5$O$_3$ 457.2, observed LCMS m/z 458 (M+H).

Example 60

Preparation of 1-(7-amino-5-((1R,4R)-4-hydroxy-4-(hydroxymethyl)cyclohexyl)-3-(6-phenylpyridin-3-yl)pyrazolo[1,5-a]pyrimidin-6-yl)ethanone (Compound 139) and 1-(7-amino-5-((1S,4S)-4-hydroxy-4-(hydroxymethyl)cyclohexyl)-3-(6-phenylpyridin-3-yl)pyrazolo[1,5-a]pyrimidin-6-yl)ethanone (Compound 140)

Step 1: Preparation of (1R,4R)-4-(7-(bis((2-(trimethylsilyl)ethoxy)methyl)amino)-3-(6-phenylpyridin-3-yl)pyrazolo[1,5-a]pyrimidin-5-yl)-1-(hydroxymethyl)cyclohexanol and (1S,4S)-4-(7-(bis((2-(trimethylsilyl)ethoxy)methyl)amino)-3-(6-phenylpyridin-3-yl)pyrazolo[1,5-a]pyrimidin-5-yl)-1-(hydroxymethyl)cyclohexanol

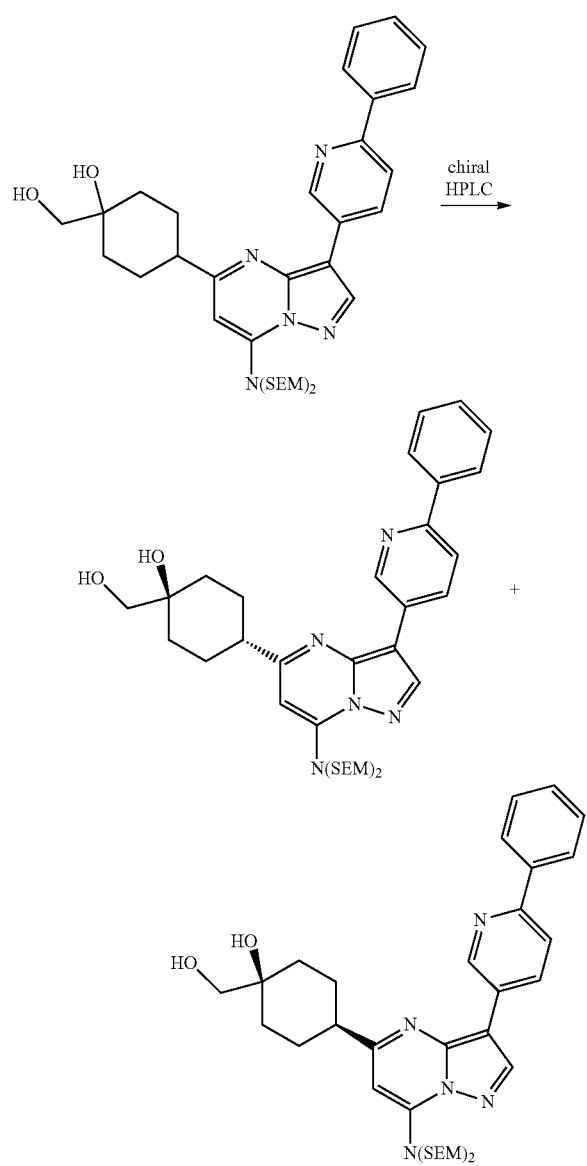

4-(7-(bis((2-(trimethylsilyl)ethoxy)methyl)amino)-3-(6-phenylpyridin-3-yl)pyrazolo[1,5-a]pyrimidin-5-yl)-1-(hydroxymethyl)cyclohexanol (2.40 g) was subjected to HPLC using a chiral column to afford (1R,4R)-4-(7-(bis((2-(trimethylsilyl)ethoxy)methyl)amino)-3-(6-phenylpyridin-3-yl)pyrazolo[1,5-a]pyrimidin-5-yl)-1-(hydroxymethyl)cyclohexanol as a pale yellow solid (1.70 g) and (1S,4S)-4-(7-(bis((2-(trimethylsilyl)ethoxy)methyl)amino)-3-(6-phenylpyridin-3-yl)pyrazolo[1,5-a]pyrimidin-5-yl)-1-(hydroxymethyl)cyclohexanol as a pale yellow solid (0.50 g).

Step 2: Preparation of 1-(7-amino-5-((1R,4R)-4-hydroxy-4-(hydroxymethyl)cyclohexyl)-3-(6-phenylpyridin-3-yl)pyrazolo[1,5-a]pyrimidin-6-yl)ethanone (Compound 139) and 1-(7-amino-5-((1S,4S)-4-hydroxy-4-(hydroxymethyl)cyclohexyl)-3-(6-phenylpyridin-3-yl)pyrazolo[1,5-a]pyrimidin-6-yl)ethanone (Compound 140)

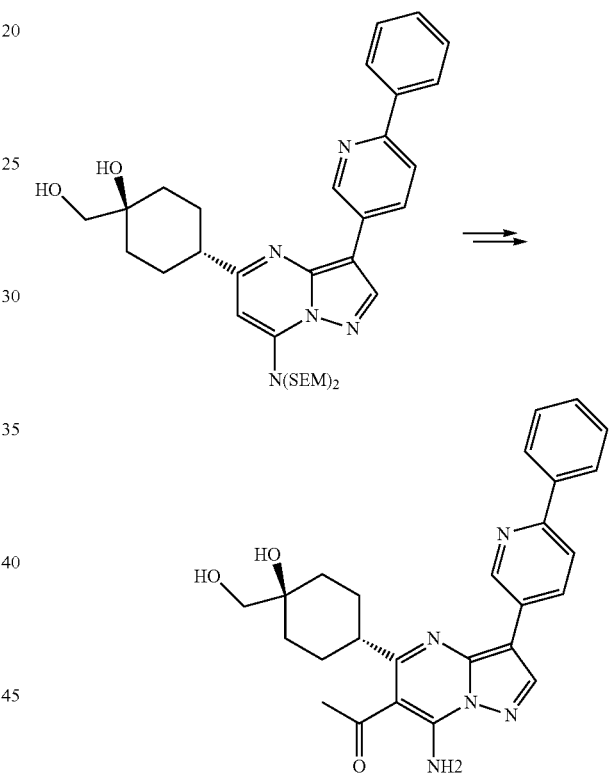

By essentially the same procedures in Preparative Example 56, Step 3, and Example 60, 1-(7-amino-5-((1R,4R)-4-hydroxy-4-(hydroxymethyl)cyclohexyl)-3-(6-phenylpyridin-3-yl)pyrazolo[1,5-a]pyrimidin-6-yl)ethanone can be prepared. HPLC-MS $T_R$=3.28 min (UV 254 nm, 10 min method); mass calculated for formula $C_{26}H_{27}N_5O_3$ 457.2, observed LCMS m/z 458 (M+H).

In a similar manner, 1-(7-amino-5-((1S,4S)-4-hydroxy-4-(hydroxymethyl)cyclohexyl)-3-(6-phenylpyridin-3-yl)pyrazolo[1,5-a]pyrimidin-6-yl)ethanone (Compound 140) can be prepared. HPLC-MS $T_R$=3.19 min (UV 254 nm, 10 min method); mass calculated for formula $C_{26}H_{27}N_5O_3$ 457.2, observed LCMS m/z 458 (M+H).

Example 61

By essentially the same procedure in Preparative Example 60, the compound in Column 2 of Table 22 can be prepared.

TABLE 22

| Compound | Chemical name | Structure | Exact mass | MS m/z (M + H) | HPLC-MS T$_R$ (Method) |
|---|---|---|---|---|---|
| 141 | 1-(7-amino-5-(4-hydroxy-4-(hydroxymethyl)cyclohexyl)-3-(1-phenyl-1H-pyrazol-4-yl)pyrazolo[1,5-a]pyrimidin-6-yl)ethanone | 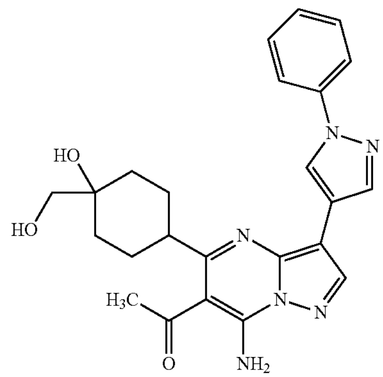 [SMILES: CC(=O)c1c(C2CCC(O)(CO)CC2)nc2c(-c3cnn(-c4ccccc4)c3)cnn2c1N] | 482.1 | 483 | 4.07 (10 min) |
| 142 | 1-(7-amino-3-(6-fluoroquinolin-3-yl)-5-(4-hydroxy-4-(hydroxymethyl)-cyclohexyl)-pyrazolo-[1,5-a]pyrimidin-6-yl)ethanone | 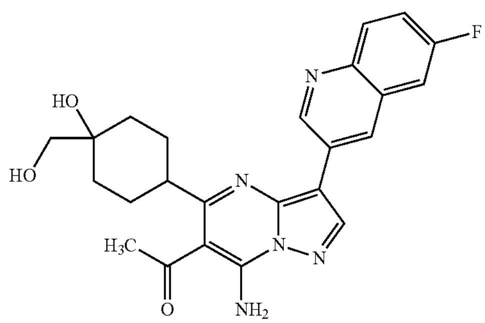 [SMILES: CC(=O)c1c(C2CCC(O)(CO)CC2)nc2c(-c3cnc4ccc(F)cc4c3)cnn2c1N] | 485.1 | 486 | 3.27 (10 min) |
| 143 | 1-(3-(2,3'-bipyridin-5-yl)-7-amino-5-(4-hydroxy-4-(hydroxymethyl)-cyclohexyl)-pyrazolo-[1,5-a]pyrimidin-6-yl)ethanone | 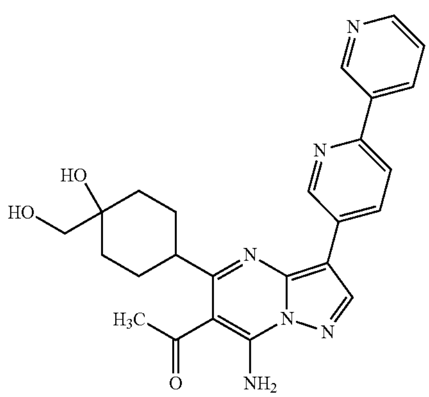 [SMILES: CC(=O)c1c(C2CCC(O)(CO)CC2)nc2c(-c3ccc(-c4cccnc4)nc3)cnn2c1N] | 458.2 | 459 | 2.63 (10 min) |
| 144 | 1-(7-amino-5-(4-hydroxy-4-(hydroxymethyl)-cyclohexyl)-3-(6-(thiazol-4-yl)pyridin-3-yl)pyrazolo[1,5-a]pyrimidin-6-yl)ethanone | 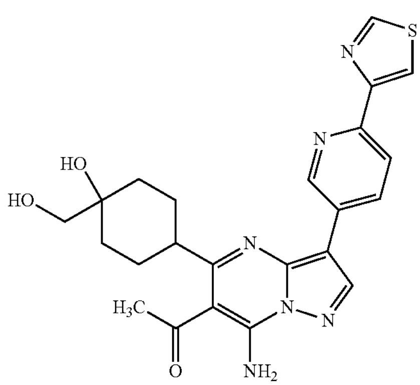 [SMILES: CC(=O)c1c(C2CCC(O)(CO)CC2)nc2c(-c3ccc(-c4cscn4)nc3)cnn2c1N] | 464.2 | 465 | 3.05 isomer1 3.14 isomer2 (10 min) |

TABLE 22-continued

| Compound | Chemical name | Structure | Exact mass | MS m/z (M + H) | HPLC-MS T$_R$ (Method) |
|---|---|---|---|---|---|
| 145 | 1-(7-amino-5-(4-hydroxy-4-(hydroxymethyl)-cyclohexyl)-3-(6-(1-methyl-1H-pyrazol-4-yl)pyridin-3-yl)pyrazolo[1,5-a]pyrimidin-6-yl)ethanone | 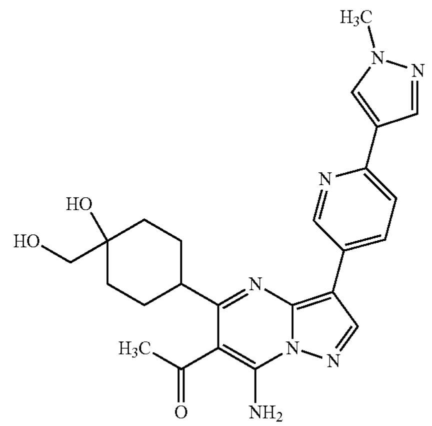 [SMILES: CC(=O)c1c(C2CCC(O)(CO)CC2)nc2c(-c3ccc(-c4cnn(C)c4)nc3)cnn2c1N] | 461.2 | 462 | 2.46 (10 min) |
| 146 | 1-(7-amino-5-(4-hydroxy-4-(hydroxymethyl)-cyclohexyl)-3-(6'-methoxy-2,3'-bipyridin-5-yl)pyrazolo[1,5-a]pyrimidin-6-yl)ethanone | 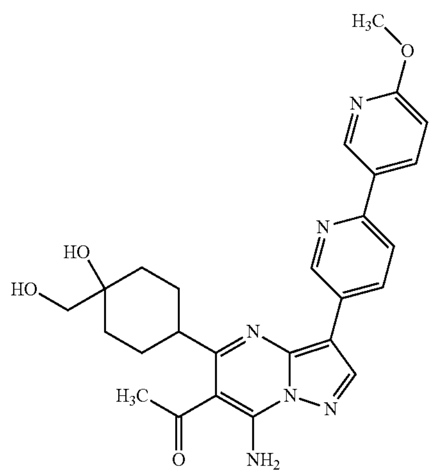 [SMILES: COc1ccc(-c2ccc(-c3cnn4c(N)c(C(C)=O)c(C5CCC(O)(CO)CC5)nc34)cn2)cn1] | 488.2 | 489 | 3.69 isomer1 3.77 isomer2 (10 min) |
| 147 | 1-(7-amino-3-(6'-hydroxy-2,3'-bipyridin-5-yl)-5-(4-hydroxy-4-(hydroxymethyl)-cyclohexyl)-pyrazolo-[1,5-a]pyrimidin-6-yl)ethanone | 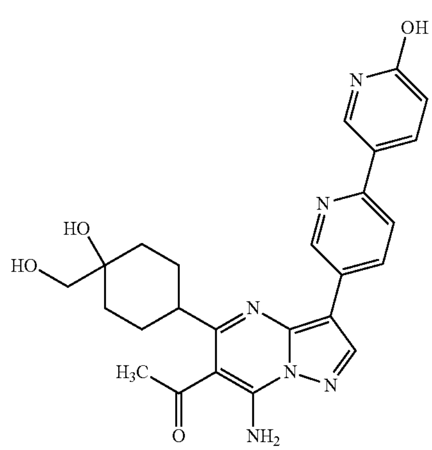 [SMILES: CC(=O)c1c(C2CCC(O)(CO)CC2)nc2c(-c3ccc(-c4ccc(O)nc4)nc3)cnn2c1N] | 474.2 | 475 | 2.83 (10 min) |

TABLE 22-continued

| Compound | Chemical name | Structure | Exact mass | MS m/z (M + H) | HPLC-MS T$_R$ (Method) |
|---|---|---|---|---|---|
| 148 | 1-(7-amino-5-((1R,4R)-4-hydroxy-4-(hydroxymethyl)cyclohexyl)-3-(1'-methyl-1'H-1,4'-bipyrazol-4-yl)pyrazolo[1,5-a]pyrimidin-6-yl)ethanone | 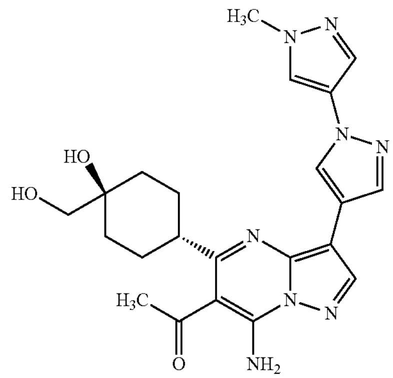 [SMILES: CC(=O)c1c(N)n2ncc(-c3cnn(-c4cnn(C)c4)c3)c2nc1[C@H]1CC[C@@](O)(CO)CC1] | 450.2 | 451 | 3.37 (10 min) |
| 149 | 1-(7-amino-5-((1S,4S)-4-hydroxy-4-(hydroxymethyl)cyclohexyl)-3-(1'-methyl-1'H-1,4'-bipyrazol-4-yl)pyrazolo[1,5-a]pyrimidin-6-yl)ethanone | 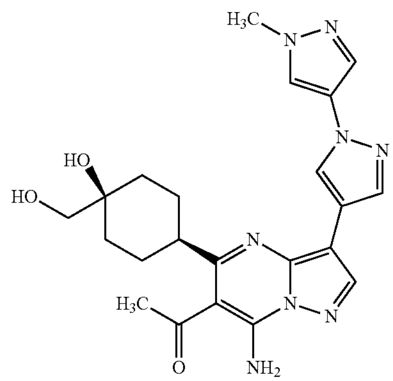 [SMILES: CC(=O)c1c(N)n2ncc(-c3cnn(-c4cnn(C)c4)c3)c2nc1[C@H]1CC[C@](O)(CO)CC1] | 450.2 | 451 | 2.19 (10 min) |
| 150 | methyl 3-(5-(6-acetyl-7-amino-5-(4-hydroxy-4-(hydroxymethyl)cyclohexyl)-pyrazolo-[1,5-a]pyrimidin-3-yl)pyridin-2-yl)benzoate | 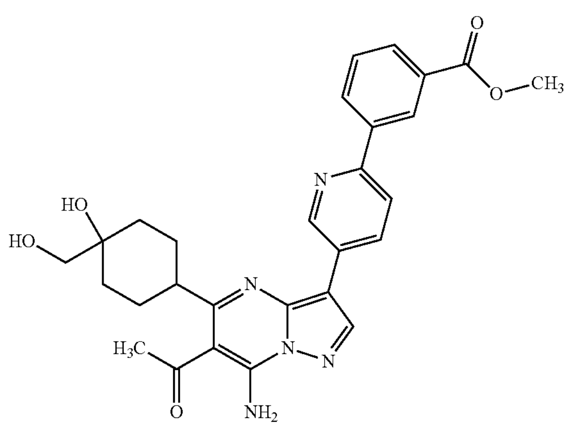 [SMILES: COC(=O)c1cccc(-c2ccc(-c3cnn4c(N)c(C(C)=O)c(C5CCC(O)(CO)CC5)nc34)cn2)c1] | 515.2 | 516 | 3.68 (10 min) |

TABLE 22-continued

| Compound | Chemical name | Structure | Exact mass | MS m/z (M + H) | HPLC-MS T$_R$ (Method) |
|---|---|---|---|---|---|
| 151 | 3-(5-(6-acetyl-7-amino-5-(4-hydroxy-4-(hydroxymethyl)-cyclohexyl)-pyrazolo-[1,5-a]pyrimidin-3-yl)pyridin-2-yl)benzoic acid | 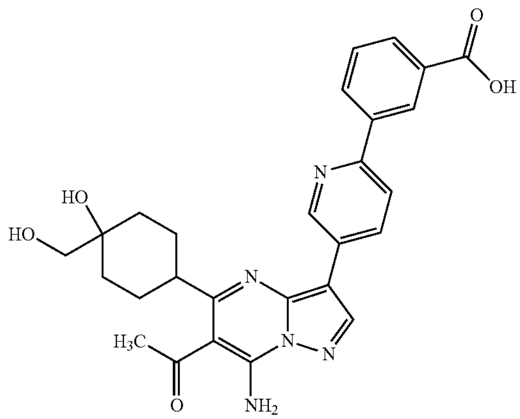 [SMILES: CC(=O)c1c(C2CCC(O)(CO)CC2)nc2c(-c3ccc(-c4cccc(C(=O)O)c4)nc3)cnn2c1N] | 501.2 | 502 | 3.07 (10 min) |
| 152 | 1-(7-amino-5-(4-hydroxy-4-(hydroxymethyl)-cyclohexyl)-3-(1-(thiazol-4-yl)-1H-pyrazol-4-yl)pyrazolo[1,5-a]pyrimidin-6-yl)ethanone | 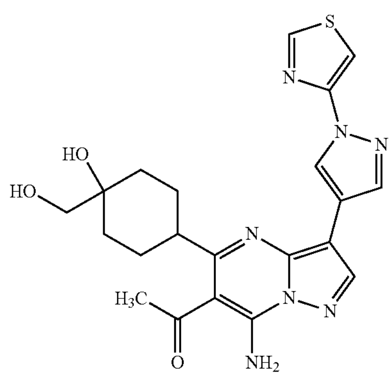 [SMILES: CC(=O)c1c(C2CCC(O)(CO)CC2)nc2c(-c3cnn(-c4cscn4)c3)cnn2c1N] | 453.2 | 454 | 3.71 isomer1 3.76 isomer2 (10 min) |
| 153 | methyl 5-(5-(6-acetyl-7-amino-5-((1R,4R)-4-hydroxy-4-(hydroxymethyl)-cyclohexyl)-pyrazolo-[1,5-a]pyrimidin-3-yl)pyridin-2-yl)-2-methoxybenzoate | 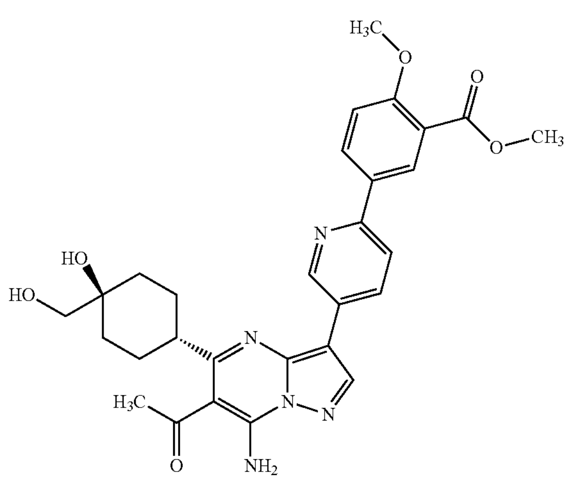 [SMILES: COC(=O)c1cc(-c2ccc(-c3cnn4c(N)c(C(C)=O)c([C@H]5CC[C@@](O)(CO)CC5)nc34)cn2)ccc1OC] | 545.2 | 546 | 3.36 (10 min) |

TABLE 22-continued

| Compound | Chemical name | Structure | Exact mass | MS m/z (M + H) | HPLC-MS $T_R$ (Method) |
| --- | --- | --- | --- | --- | --- |
| 154 | methyl 5-(5-(6-acetyl-7-amino-5-((1S,4S)-4-hydroxy-4-(hydroxymethyl)-cyclohexyl)-pyrazolo-[1,5-a]pyrimidin-3-yl)pyridin-2-yl)-2-methoxybenzoate | 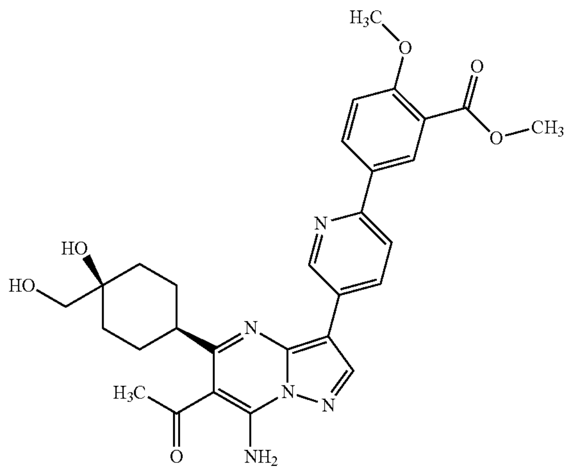 [SMILES: COC(=O)c1cc(-c2ccc(-c3cnn4c(N)c(C(C)=O)c([C@H]5CC[C@](O)(CO)CC5)nc34)cn2)ccc1OC] | 545.2 | 546 | 3.38 (10 min) |
| 155 | 5-(5-(6-acetyl-7-amino-5-(4-hydroxy-4-(hydroxymethyl)-cyclohexyl)-pyrazolo-[1,5-a]pyrimidin-3-yl)pyridin-2-yl)-2-methoxybenzoic acid | 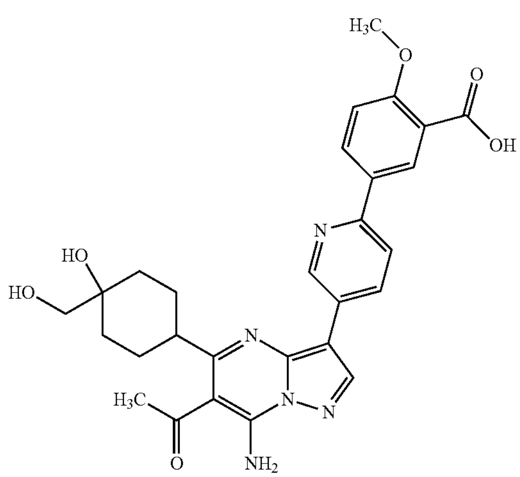 [SMILES: COc1ccc(-c2ccc(-c3cnn4c(N)c(C(C)=O)c(C5CCC(O)(CO)CC5)nc34)cn2)cc1C(=O)O] | 531.2 | 532 | 2.95 (10 min) |
| 156 | 1-(7-amino-5-(4-hydroxy-4-(hydroxymethyl)-cyclohexyl)-3-(6-(thiazol-2-yl)pyridin-3-yl)pyrazolo[1,5-a]pyrimidin-6-yl)ethanone | 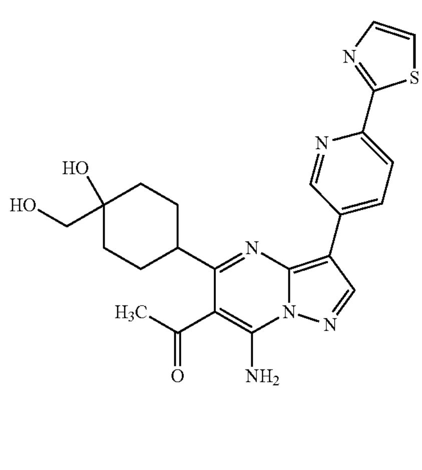 [SMILES: CC(=O)c1c(C2CCC(O)(CO)CC2)nc2c(-c3ccc(-c4nccs4)nc3)cnn2c1N] | 464.2 | 465 | 3.94 (10 min) |

TABLE 22-continued

| Compound | Chemical name | Structure | Exact mass | MS m/z (M + H) | HPLC-MS $T_R$ (Method) |
|---|---|---|---|---|---|
| 157 | 1-(7-amino-5-(4-hydroxy-4-(hydroxymethyl)-cyclohexyl)-3-(6-(thiazol-5-yl)pyridin-3-yl)pyrazolo[1,5-a]pyrimidin-6-yl)ethanone | 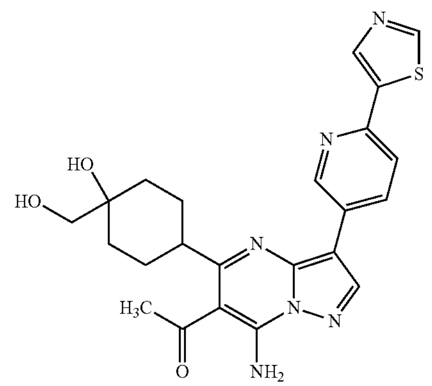 [SMILES: CC(=O)c1c(C2CCC(O)(CO)CC2)nc2c(-c3ccc(-c4cncs4)nc3)cnn2c1N] | 464.2 | 465 | 3.54 (10 min) |
| 158 | 1-(7-amino-5-(4-hydroxy-4-(hydroxymethyl)-cyclohexyl)-3-(2-phenylpyrimidin-5-yl)pyrazolo[1,5-a]pyrimidin-6-yl)ethanone | 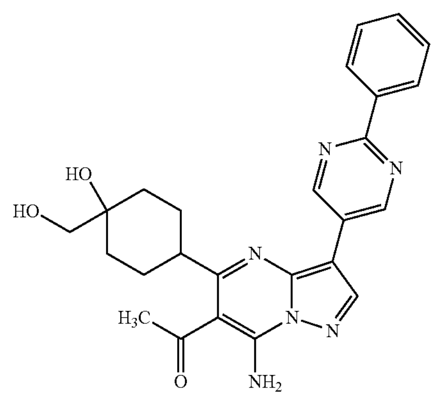 | 458.2 | 459 | 4.49 (10 min) |
| 159 | 1-(7-amino-5-((1S,4S)-4-hydroxy-4-(2-hydroxyethyl)-cyclohexyl)-3-(6-phenylpyridin-3-yl)pyrazolo[1,5-a]pyrimidin-6-yl)ethanone | 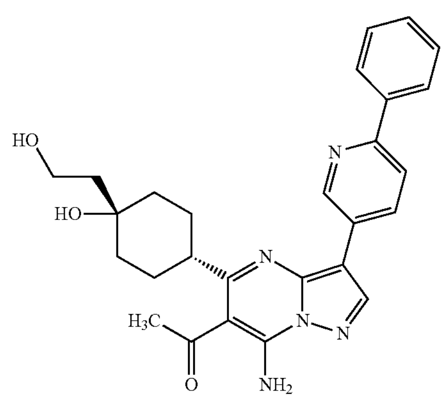 [SMILES: CC(=O)c1c(N)n2ncc(-c3ccc(-c4ccccc4)nc3)c2nc1[C@H]1CC[C@](O)(CCO)CC1] | 471.2 | 472 | 3.41 (10 min) |

Example 62

Preparation of N-((4-(6-acetyl-7-amino-3-(6-phenylpyridin-3-yl)pyrazolo[1,5-a]pyrimidin-5-yl)-1-hydroxycyclohexyl)methyl)methanesulfonamide (Compound 160)

Step 1: Preparation of N-((4-(7-(bis((2-(trimethylsilyl)ethoxy)methyl)amino)-3-(6-phenylpyridin-3-yl)pyrazolo[1,5-a]pyrimidin-5-yl)-1-hydroxycyclohexyl)methyl)methanesulfonamide

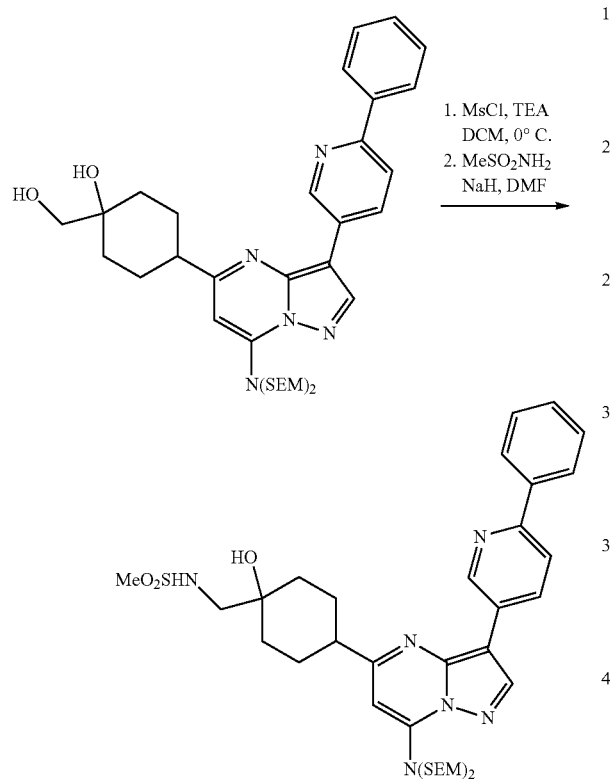

Step 2: Preparation of N-((4-(6-acetyl-7-amino-3-(6-phenylpyridin-3-yl)pyrazolo[1,5-a]pyrimidin-5-yl)-1-hydroxycyclohexyl)methyl)methanesulfonamide (Compound 160)

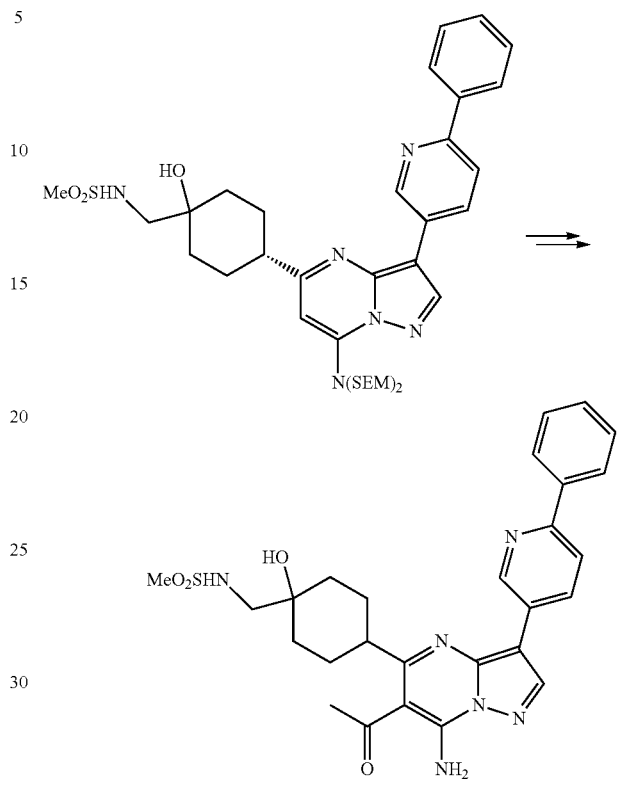

By essentially the same procedures in Preparative Example 56, Step 3, and Example 59, N-((4-(6-acetyl-7-amino-3-(6-phenylpyridin-3-yl)pyrazolo[1,5-a]pyrimidin-5-yl)-1-hydroxycyclohexyl)methyl)methanesulfonamide (Compound 160) can be prepared.

Example 63

Preparation of 1-(7-amino-5-((1R,4R)-4-hydroxy-4-(methylsulfonylmethyl)cyclohexyl)-3-(6-phenylpyridin-3-yl)pyrazolo[1,5-a]pyrimidin-6-yl)ethanone (Compound 161)

Step 1: Preparation of (1R,4R)-4-(7-(bis((2-(trimethylsilyl)ethoxy)methyl)amino)-3-(6-phenylpyridin-3-yl)pyrazolo[1,5-a]pyrimidin-5-yl)-1-(methylthiomethyl)cyclohexanol

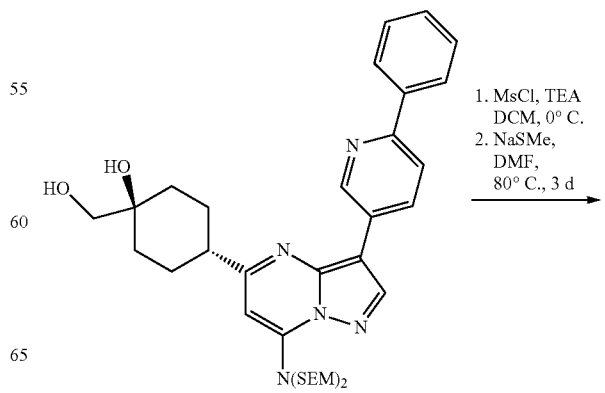

To a solution of 4-(7-(bis((2-(trimethylsilyl)ethoxy)methyl)amino)-3-(6-phenylpyridin-3-yl)pyrazolo[1,5-a]pyrimidin-5-yl)-1-(hydroxymethyl)cyclohexanol (820 mg, 1.21 mmol) in DCM (10 mL) was added TEA (0.337 mL, 2.42 mmol), followed by MsCl (0.104 mL, 1.33 mmol) at 0° C. and stirred for 1 h. The reaction mixture was concentrated, and then dissolved in EtOAc, washed with $H_2O$ and brine, dried over $Na_2SO_4$, and concentrated to afford a pale yellow oil. This oil was dissolved in DMF (10 mL). $MeSO_2NH_2$ (1.5 eq) was added, followed by NaH (4.0 eq). The resulting reaction mixture was heated at 90° C. for 2 d. The reaction mixture was diluted with EtOAc, neutralized with $NH_4Cl$, washed with $H_2O$ and brine, dried over $Na_2SO_4$, and concentrated. The crude product was purified by a $SiO_2$ column (0-10% MeOH/DCM, $R_f$=0.65 in 10% MeOH/DCM) to afford N-((4-(7-(bis((2-(trimethylsilyl)ethoxy)methyl)amino)-3-(6-phenylpyridin-3-yl)pyrazolo[1,5-a]pyrimidin-5-yl)-1-hydroxycyclohexyl)methyl)methanesulfonamide as a brownish oil (594 mg). HPLC-MS $T_R$=2.86 min (UV 254 nm, 10 min method); mass calculated for formula $C_{37}H_{56}N_6O_5SSi_2$ 752.4, observed LCMS m/z 753.1 (M+H).

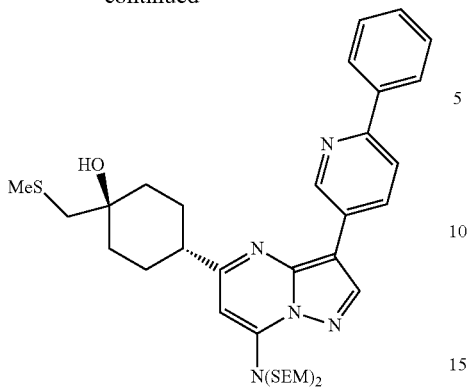

To a solution of 4-(7-(bis((2-(trimethylsilyl)ethoxy)methyl)amino)-3-(6-phenylpyridin-3-yl)pyrazolo[1,5-a]pyrimidin-5-yl)-1-(hydroxymethyl)cyclohexanol (820 mg, 1.21 mmol) in DCM (10 mL) was added TEA (0.337 mL, 2.42 mmol), followed by MsCl (0.104 mL, 1.33 mmol) at 0° C. and stirred for 1 h. The reaction mixture was concentrated, and then dissolved in EtOAc, washed with H₂O and brine, dried over Na₂SO₄, and concentrated to afford a pale yellow oil. This oil was dissolved in DMF (10 mL). NaSMe (2.0 eq) was added. The resulting reaction mixture was heated at 80° C. for 3 d. The reaction mixture was diluted with EtOAc, neutralized with NH₄Cl, washed with H₂O and brine, dried over Na₂SO₄, and concentrated. The crude product was purified by a SiO₂ column (0-30% EtOAc/Hexanes, $R_f$=0.80 in 50% EtOAc) to afford (1R,4R)-4-(7-(bis((2-(trimethylsilyl)ethoxy)methyl)amino)-3-(6-phenylpyridin-3-yl)pyrazolo[1,5-a]pyrimidin-5-yl)-1-(methylthiomethyl)cyclohexanol as a pale yellow oil (674 mg). HPLC-MS $T_R$=3.22 min (UV 254 nm, 10 min method); mass calculated for formula $C_{37}H_{55}N_5O_3SSi_2$ 705.4, observed LCMS m/z 706.2 (M+H).

Step 2: Preparation of (1R,4R)-4-(7-(bis((2-(trimethylsilyl)ethoxy)methyl)amino)-3-(6-phenylpyridin-3-yl)pyrazolo[1,5-a]pyrimidin-5-yl)-1-(methylsulfonylmethyl)cyclohexanol

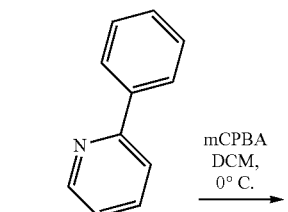

mCPBA
DCM,
0° C.
⟶

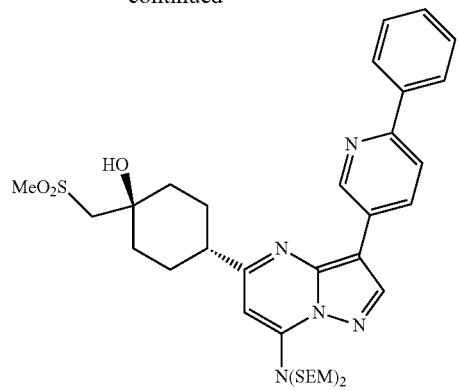

To a solution of (1R,4R)-4-(7-(bis((2-(trimethylsilyl)ethoxy)methyl)amino)-3-(6-phenylpyridin-3-yl)pyrazolo[1,5-a]pyrimidin-5-yl)-1-(methylthiomethyl)cyclohexanol (73.0 mg, 0.103 mmol) in DCM (3 mL) was added mCPBA (51.0 mg, 0.207 mmol) at 0° C. and stirred for 1 h. The reaction mixture was diluted with DCM, washed with Na₂CO₃ (2*) and brine, dried over Na₂SO₄, and concentrated. The crude product was purified by a SiO₂ column (0-50% EtOAc/Hexanes, then 70% EtOAc, $R_f$=0.35 in 50% EtOAc) to afford (1R,4R)-4-(7-(bis((2-(trimethylsilyl)ethoxy)methyl)amino)-3-(6-phenylpyridin-3-yl)pyrazolo[1,5-a]pyrimidin-5-yl)-1-(methylsulfonylmethyl)cyclohexanol as a pale yellow oil (50.0 mg). HPLC-MS $T_R$=2.90 min (UV 254 nm, 10 min method); mass calculated for formula $C_{37}H_{55}N_5O_5SSi_2$ 737.3, observed LCMS m/z 738.3 (M+H).

Step 3: Preparation of 1-(7-amino-5-((1R,4R)-4-hydroxy-4-(methylsulfonylmethyl)cyclohexyl)-3-(6-phenylpyridin-3-yl)pyrazolo[1,5-a]pyrimidin-6-yl)ethanone (Compound 161)

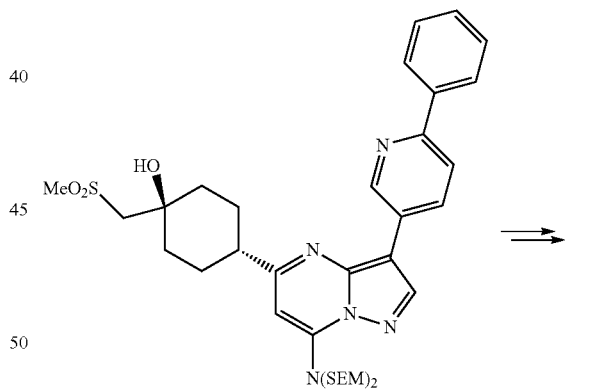

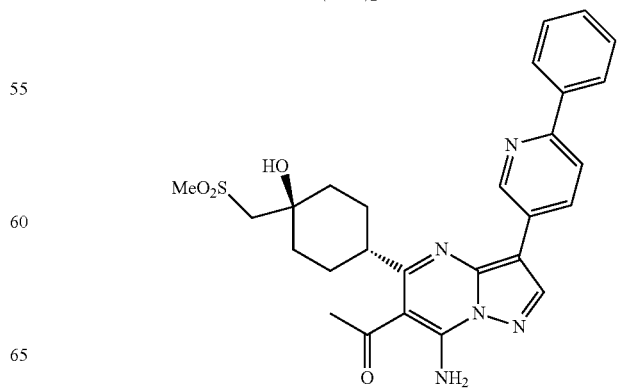

245

By essentially the same procedures in Preparative Example 57, Step 3, and Example 60, 1-(7-amino-5-((1R,4R)-4-hydroxy-4-(methylsulfonylmethyl)cyclohexyl)-3-(6-phenylpyridin-3-yl)pyrazolo[1,5-a]pyrimidin-6-yl)ethanone (Compound 161) can be prepared. HPLC-MS $T_R$=3.65 min (UV 254 nm, 10 min method); mass calculated for formula $C_{27}H_{29}N_5O_4S$ 519.2, observed LCMS m/z 520 (M+H).

Example 64

Preparation of 1-(7-amino-5-((1S,4S)-4-hydroxy-4-(methylsulfonylmethyl)cyclohexyl)-3-(6-phenylpyridin-3-yl)pyrazolo[1,5-a]pyrimidin-6-yl)ethanone (Compound 162)

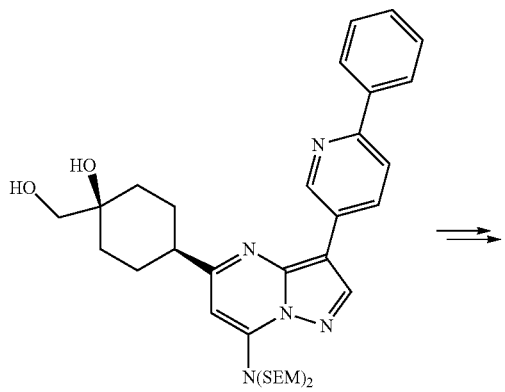

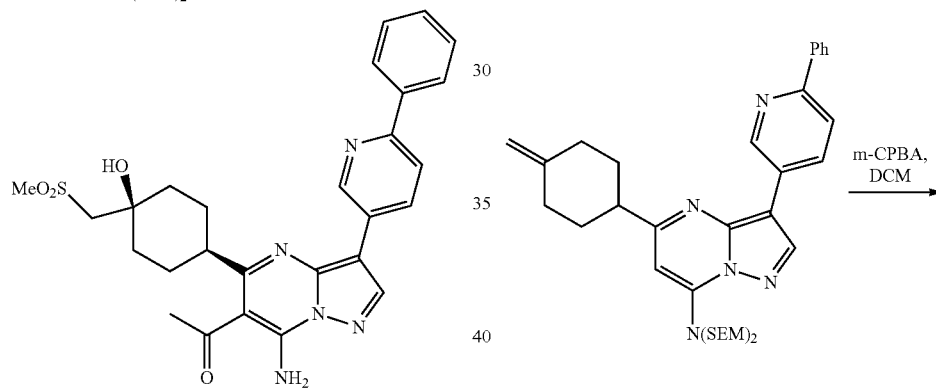

By essentially the same procedures in Preparative Example 63, 1-(7-amino-5-((1S,4S)-4-hydroxy-4-(methylsulfonylmethyl)cyclohexyl)-3-(6-phenylpyridin-3-yl)pyrazolo[1,5-a]pyrimidin-6-yl)ethanone (Compound 162) can be prepared from the diol compound. HPLC-MS $T_R$=3.59 min (UV 254 nm, 10 min method); mass calculated for formula $C_{27}H_{29}N_5O_4S$ 519.2, observed LCMS m/z 520.2 (M+H).

Example 65

Preparation of (1R,4R)-4-(7-amino-6-bromo-3-(6-phenylpyridin-3-yl)pyrazolo[1,5-a]pyrimidin-5-yl)-1-(methoxymethyl)cyclohexanol (Compound 163)

Step 1: Preparation of 5-(4-methylenecyclohexyl)-3-(6-phenylpyridin-3-yl)-N,N-bis((2-(trimethylsilyl)ethoxy)methyl)pyrazolo[1,5-a]pyrimidin-7-amine

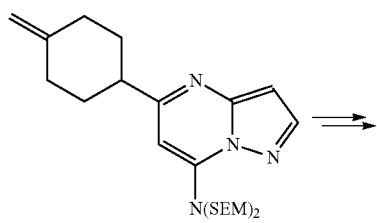

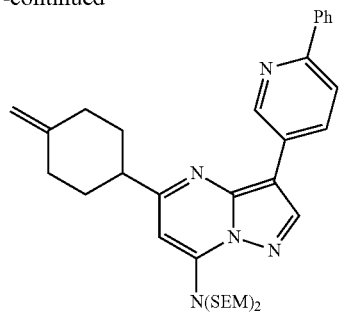

By essentially the same procedures in Preparative Example 53, Step 1-2, 5-(4-methylenecyclohexyl)-3-(6-phenylpyridin-3-yl)-N,N-bis((2-(trimethylsilyl)ethoxy)methyl)pyrazolo[1,5-a]pyrimidin-7-amine can be prepared. HPLC-MS $T_R$=3.39 min (UV 254 nm, 5 min method); mass calculated for formula $C_{36}H_{51}N_5O_2Si_2$ 641.4, observed LCMS m/z 642.3 (M+H).

Step 2: Preparation of 3-(6-phenylpyridin-3-yl)-5-(1-oxaspiro[2.5]octan-6-yl)-N,N-bis((2-(trimethylsilyl)ethoxy)methyl)pyrazolo[1,5-a]pyrimidin-7-amine

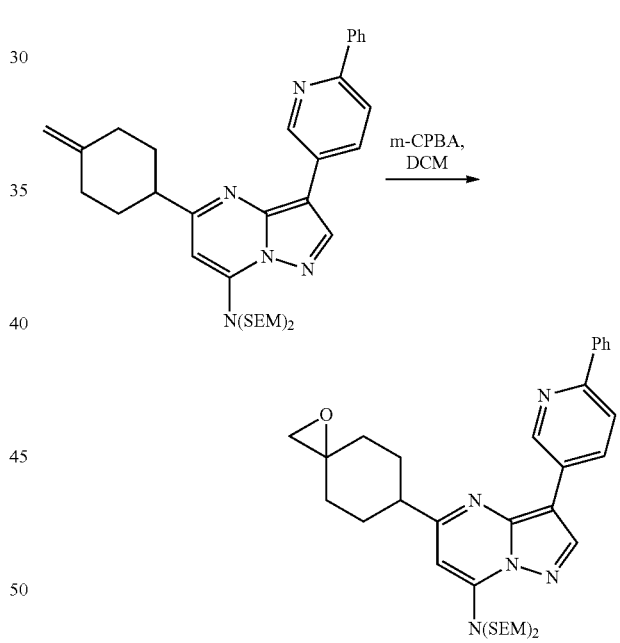

To a solution of 5-(4-methylenecyclohexyl)-3-(6-phenylpyridin-3-yl)-N,N-bis((2-(trimethylsilyl)ethoxy)methyl)pyrazolo[1,5-a]pyrimidin-7-amine (455 mg, 0.709 mmol) in DCM (4 mL) at 0° C. was added a solution of m-CPBA (191 mg, 0.850 mmol) in DCM (3 mL). The resulting mixture was warmed to rt and stirred for 4 h. All the volatiles were removed under reduced pressure and the residue was purified by a $SiO_2$ column (0-20% EtOAc/Hexanes, $R_f$=0.25 in 20% EtOAc) to afford 3-(6-phenylpyridin-3-yl)-5-(1-oxaspiro[2.5]octan-6-yl)-N,N-bis((2-(trimethylsilyl)ethoxy)methyl)pyrazolo[1,5-a]pyrimidin-7-amine as a pale yellow oil (163 mg). HPLC-MS $T_R$=3.32 min (UV 254 nm, 5 min method); mass calculated for formula $C_{36}H_{51}N_5O_3Si_2$ 657.4, observed LCMS m/z 658.3 (M+H).

Step 3: Preparation of (1r,4r)-4-(7-(bis((2-(trimethylsilyl)ethoxy)methyl)amino)-3-(6-phenylpyridin-3-yl)pyrazolo[1,5-a]pyrimidin-5-yl)-1-(methoxymethyl)cyclohexanol and (1s,4s)-4-(7-(bis((2-(trimethylsilyl)ethoxy)methyl)amino)-3-(6-phenylpyridin-3-yl)pyrazolo[1,5-a]pyrimidin-5-yl)-1-(methoxymethyl)cyclohexanol

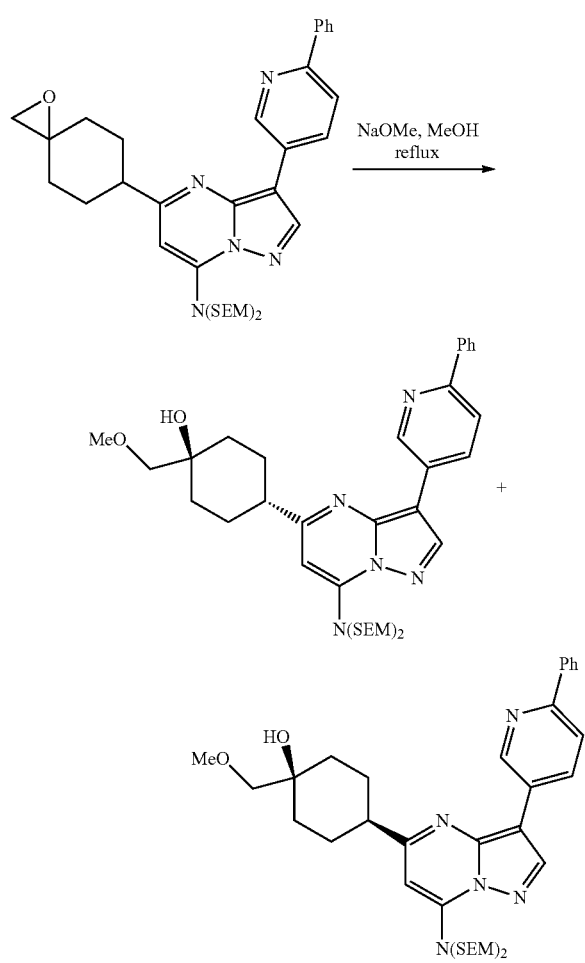

To a solution of 3-(6-phenylpyridin-3-yl)-5-(1-oxaspiro[2.5]octan-6-yl)-N,N-bis((2-(trimethylsilyl)ethoxy)methyl)pyrazolo[1,5-a]pyrimidin-7-amine (160 mg, 0.243 mmol) in MeOH (4 mL) was added NaOMe (0.5 M in MeOH, 0.972 mL, 0.486 mmol) and the resulting solution was heated under reflux for 6 h. MeOH was removed. The residue was dissolved in $H_2O$ and carefully adjusted pH to 6-7 with 1N HCl. The aqueous mixture was extracted with EtOAc, washed with brine, dried over $Na_2SO_4$, and concentrated. The crude product was purified by a $SiO_2$ column (0-30% EtOAc/Hexanes) to afford the major isomer (1R,4R)-4-(7-(bis((2-(trimethylsilyl)ethoxy)methyl)amino)-3-(6-phenylpyridin-3-yl)pyrazolo[1,5-a]pyrimidin-5-yl)-1-(methoxymethyl)cyclohexanol ($R_f$=0.15 in 20% EtOAc) as a pale yellow oil (68.2 mg), and the minor isomer (1S,4S)-4-(7-(bis((2-(trimethylsilyl)ethoxy)methyl)amino)-3-(6-phenylpyridin-3-yl)pyrazolo[1,5-a]pyrimidin-5-yl)-1-(methoxymethyl)cyclohexanol ($R_f$=0.1 in 20% EtOAc) as a pale yellow oil (20.3 mg).

Step 4: Preparation of (1R,4R)-4-(7-amino-6-bromo-3-(6-phenylpyridin-3-yl)pyrazolo[1,5-a]pyrimidin-5-yl)-1-(methoxymethyl)cyclohexanol (Compound 163)

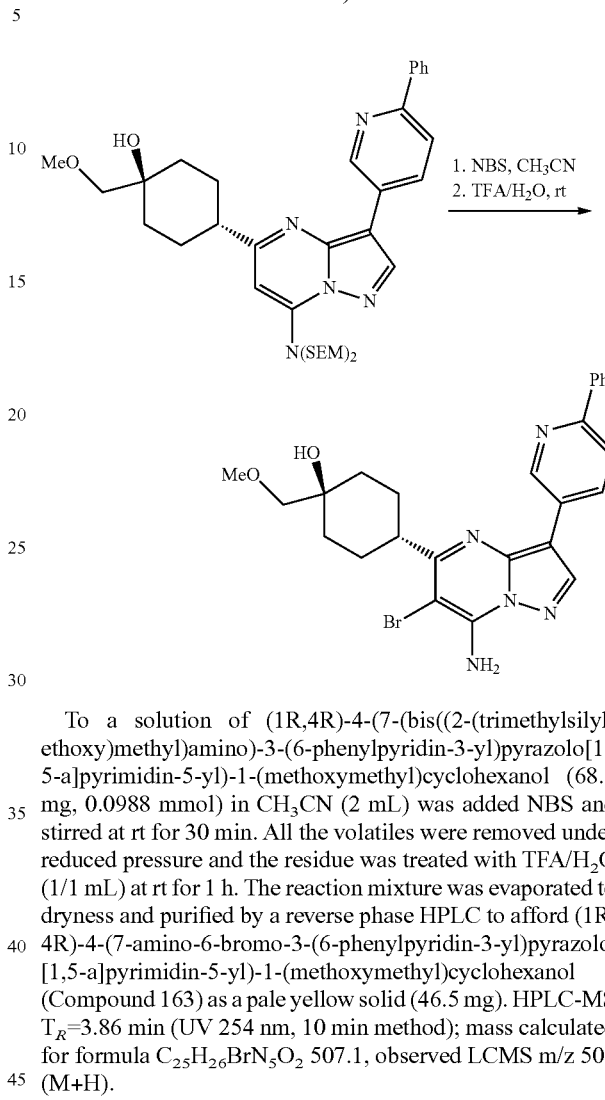

To a solution of (1R,4R)-4-(7-(bis((2-(trimethylsilyl)ethoxy)methyl)amino)-3-(6-phenylpyridin-3-yl)pyrazolo[1,5-a]pyrimidin-5-yl)-1-(methoxymethyl)cyclohexanol (68.2 mg, 0.0988 mmol) in $CH_3CN$ (2 mL) was added NBS and stirred at rt for 30 min. All the volatiles were removed under reduced pressure and the residue was treated with $TFA/H_2O$ (1/1 mL) at rt for 1 h. The reaction mixture was evaporated to dryness and purified by a reverse phase HPLC to afford (1R,4R)-4-(7-amino-6-bromo-3-(6-phenylpyridin-3-yl)pyrazolo[1,5-a]pyrimidin-5-yl)-1-(methoxymethyl)cyclohexanol (Compound 163) as a pale yellow solid (46.5 mg). HPLC-MS $T_R$=3.86 min (UV 254 nm, 10 min method); mass calculated for formula $C_{25}H_{26}BrN_5O_2$ 507.1, observed LCMS m/z 508 (M+H).

Example 66

Preparation of (1S,4S)-4-(7-amino-6-bromo-3-(6-phenylpyridin-3-yl)pyrazolo[1,5-a]pyrimidin-5-yl)-1-(methoxymethyl)cyclohexanol (Compound 164)

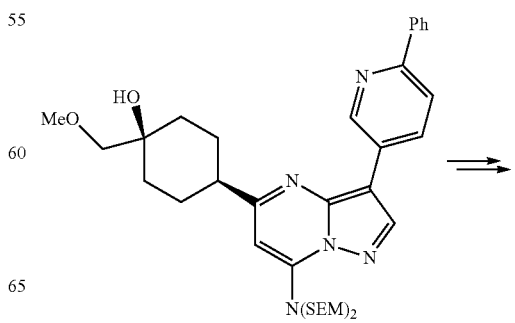

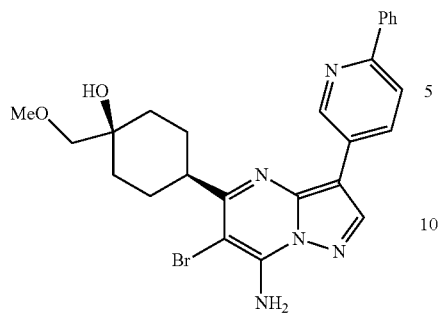

By essentially the same procedures in Preparative Example 65, Step 4, (1S,4S)-4-(7-amino-6-bromo-3-(6-phenylpyridin-3-yl)pyrazolo[1,5-a]pyrimidin-5-yl)-1-(methoxymethyl)cyclohexanol (Compound 164) can be prepared. HPLC-MS $T_R$=3.66 min (UV 254 nm, 10 min method); mass calculated for formula $C_{25}H_{26}BrN_5O_2$ 507.1, observed LCMS m/z 508 (M+H).

Example 67

Preparation of 4-(7-amino-6-bromo-3-(6-fluoroquinolin-3-yl)pyrazolo[1,5-a]pyrimidin-5-yl)-1-(methoxymethyl)cyclohexanol (Compound 165)

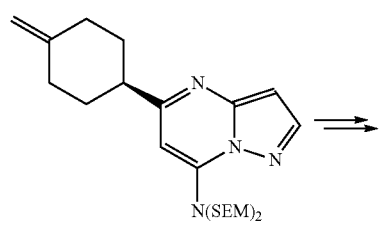

By essentially the same procedures in Preparative Example 65, Step 1-4, 4-(7-amino-6-bromo-3-(6-fluoroquinolin-3-yl)pyrazolo[1,5-a]pyrimidin-5-yl)-1-(methoxymethyl)cyclohexanol (Compound 165) can be prepared with 6-fluoro-3-(4,4,5,5-tetramethyl-1,3,2-dioxaborolan-2-yl)quinoline. HPLC-MS $T_R$=4.36 min (UV 254 nm, 10 min method); mass calculated for formula $C_{23}H_{23}BrFN_5O_2$ 499.1, observed LCMS m/z 500 (M+H).

Example 68

Preparation of 4-(7-amino-6-(methylsulfonyl)-3-(1-phenyl-1H-pyrazol-4-yl)pyrazolo[1,5-a]pyrimidin-5-yl)-1-(hydroxymethyl)cyclohexanol (Compound 166)

Step 1: Preparation of 4-(7-(bis((2-(trimethylsilyl)ethoxy)methyl)amino)-6-bromo-3-(1-phenyl-1H-pyrazol-4-yl)pyrazolo[1,5-a]pyrimidin-5-yl)-1-(hydroxymethyl)cyclohexanol

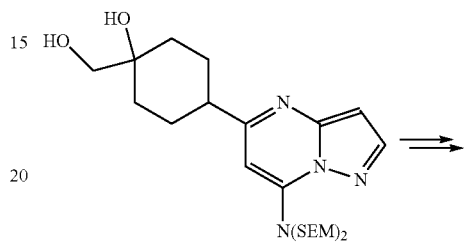

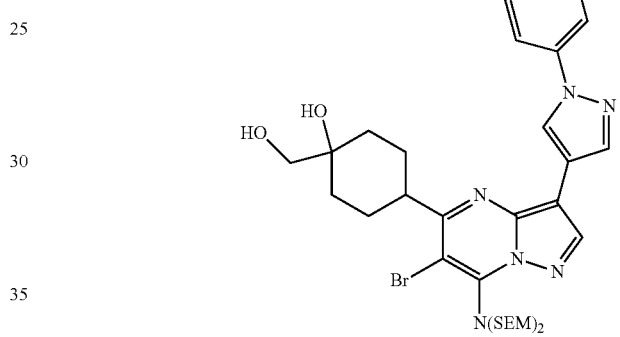

By essentially the same procedures in Preparative Example 54, Steps 6-8, 4-(7-(bis((2-(trimethylsilyl)ethoxy)methyl)amino)-6-bromo-3-(1-phenyl-1H-pyrazol-4-yl)pyrazolo[1,5-a]pyrimidin-5-yl)-1-(hydroxymethyl)cyclohexanol can be prepared from diol compound and 1-phenyl-4-(4,4,5,5-tetramethyl-1,3,2-dioxaborolan-2-yl)-1H-pyrazole.

Step 2: Preparation of 4-(7-amino-6-bromo-3-(1-phenyl-1H-pyrazol-4-yl)pyrazolo[1,5-a]pyrimidin-5-yl)-1-(hydroxymethyl)cyclohexanol

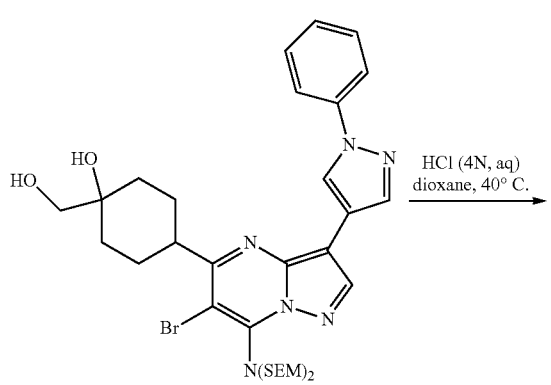

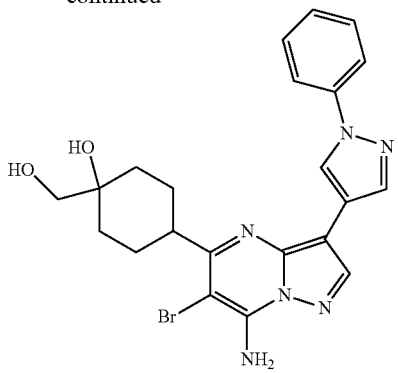

To a solution of 4-(7-(bis((2-(trimethylsilyl)ethoxy)methyl)amino)-6-bromo-3-(1-phenyl-1H-pyrazol-4-yl)pyrazolo[1,5-a]pyrimidin-5-yl)-1-(hydroxymethyl)cyclohexanol (542 mg, 0.729 mmol) in dioxane (4 mL) was added HCl (4 N, aq, 4 mL) at rt. The resulting mixture was stirred at 40° C. for 1 h. The reaction mixture was evaporated to dryness to afford 4-(7-amino-6-bromo-3-(1-phenyl-1H-pyrazol-4-yl)pyrazolo[1,5-a]pyrimidin-5-yl)-1-(hydroxymethyl)cyclohexanol as a gray solid (296 mg), which was used without further purification. HPLC-MS $T_R$=1.08 min (UV 254 nm, 3 min method); mass calculated for formula $C_{22}H_{23}BrN_6O_2$ 482.1, observed LCMS m/z 483.1 (M+H).

Step 3: Preparation of 4-(7-amino-6-(methylthio)-3-(1-phenyl-1H-pyrazol-4-yl)pyrazolo[1,5-a]pyrimidin-5-yl)-1-(hydroxymethyl)cyclohexanol

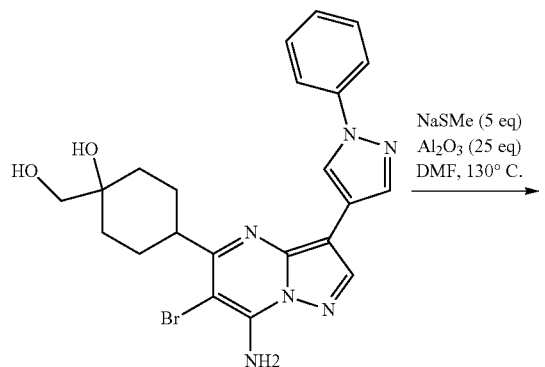

A mixture of 4-(7-amino-6-bromo-3-(1-phenyl-1H-pyrazol-4-yl)pyrazolo[1,5-a]pyrimidin-5-yl)-1-(hydroxymethyl)cyclohexanol (107 mg, 0.221 mmol), NaSMe (77.4 mg, 1.11 mmol), Al$_2$O$_3$ (563 mg, 5.53 mmol) in DMF (2 mL) was heated at 130° C. for 40 min. After cooling to rt, the reaction mixture was filtered and washed with DMF. The filtrate was evaporated and the residue was acidified with 1N HCl (aq) and evaporated again. The solid residue was dissolved in DMSO, filtered and purified by HPLC to afford 4-(7-amino-6-(methylthio)-3-(1-phenyl-1H-pyrazol-4-yl)pyrazolo[1,5-a]pyrimidin-5-yl)-1-(hydroxymethyl)cyclohexanol as a pale yellow solid (61 mg). HPLC-MS $T_R$=1.09 min (UV 254 nm, 3 min method); mass calculated for formula $C_{23}H_{26}N_6O_2S$ 450.2, observed LCMS m/z 451.1 (M+H).

Step 4: Preparation of 4-(7-amino-6-(methylsulfonyl)-3-(1-phenyl-1H-pyrazol-4-yl)pyrazolo[1,5-a]pyrimidin-5-yl)-1-(hydroxymethyl)cyclohexanol (Compound 166)

To a solution of 4-(7-amino-6-(methylthio)-3-(1-phenyl-1H-pyrazol-4-yl)pyrazolo[1,5-a]pyrimidin-5-yl)-1-(hydroxymethyl)cyclohexanol (32.0 mg, 0.0710 mmol) in a mixed solvent of MeOH/H$_2$O (2/0.5 mL) was added NaHCO$_3$ (23.8 mg, 0.284 mmol), followed by Oxone (87.3 mg, 0.142 mmol) at rt. The resulting mixture was stirred at 40° C. for 2.5 h. The reaction mixture was filtered and washed with DMF and MeOH. The combined filtrate was concentrated and purified by a reverse phase HPLC to afford 4-(7-amino-6-(methylsulfonyl)-3-(1-phenyl-1H-pyrazol-4-yl)pyrazolo[1,5-a]pyrimidin-5-yl)-1-(hydroxymethyl)cyclohexanol as a white solid (6.4 mg). HPLC-MS $T_R$=4.08 min (UV 254 nm, 10 min method); mass calculated for formula $C_{23}H_{26}N_6O_4S$ 482.2, observed LCMS m/z 483 (M+H).

Example 69 mTOR Kinase Assay

Methods: An HTRF mTOR enzyme assay was developed to assess the compounds' inhibitory activity. The mTOR assay buffer contained 10 mM Hepes (pH 7.4), 50 mM NaCl, 100 g/ml BSA, 50 mM μ-glycerophosphate, 10 mM $MnCl_2$ and 0.5 mM DTT. An active truncated mTOR enzyme was prepared similarly to that reported by Toral-Barza et al., Biochemical and Biophysical Research Communications 332, pp 304-310 (2005). 20 ng of human mTOR enzyme (<5% pure was preincubated with the compound for 10 minutes followed by the addition of 5 μM ATP and 0.2 μM GST-S6K (Zhang et al., Protein Expression and Purification 46, pp 414-420 (2006)). The reaction was incubated for one hour at 30° C. Anti phospho p70-S6K(Thr389) (~1.7 ng/well, anti-phospho-p70S6K-cryptate (Pho-p70S6-Kin-K cat#64CUSKAY, from Cisbio)) and anti GST-XL665 (1:1 Ratio with the substrate GST-S6K, anti GST-XL665, cat#61GSTXLB) Cisbio) were added after the reaction was stopped. The plates were read (PHERAstar, BMG) at least 2 hours after adding the anti phospho p70-S6K and the anti GST-XL665.

$IC_{50}$ DETERMINATIONS: Dose-response curves were plotted from the inhibition data generated, each in duplicate, from 8 point serial dilutions of inhibitory compounds. Concentration of compound was plotted against the HTRF em665/em590 ratio signal. To generate $IC_{50}$ values, the dose-response curves were fitted to a standard sigmoidal curve and $IC_{50}$ values were derived by nonlinear regression analysis.

Example 70 mTOR Target Engagement Assay

The target engagement of mTOR kinase inhibitors was evaluated using an immunofluorescent cell-based assay. In this assay, inhibition of mTORC1 activity was measured by the reduction in the level of phosphorylated 4E-BP1Thr37/46 (p4E-BP1 Thr37/46), and inhibition of mTORC2 activity was measured by the reduction of phosphorylated AKTSer473 (pAKT S473).

PC3 cells (prostate tumor cell-line that contains a mutation in the tumor suppressor PTEN, that promotes the phosphorylation and activation of AKT and 4E-BP1) were used in the immunofluorescence assay. PC3 cells were seeded on 384 well plates (black clear bottom, Matrix #4332) overnight. PC3 cells were then treated with 40 μl of the serially diluted test compounds (in 5% fetal bovine serum, F12 medium containing 0.25% DMSO) for ninety minutes at 37° C. The test compound solution was removed, and the plates were washed gently two times with 25 μl phosphate buffered saline (PBS). The cells were fixed by adding 25 μl of Prefer reagent (from Anatech LTD, Cat#414, a glyoxal fixative for fixing proteins within a cell) for sixty minutes followed by three washes with PBS. 5% Goat serum in PBS/0.3% Triton was used to block non-specific binding (60 minutes).

The primary antibodies targeting pAKT S473 and p4E-BP1 Thr37/46 were diluted into PBS/0.3% Triton and incubated with the cells overnight at 4° C. The antibodies targeting pAKTS473 (Cat#4085, Cell signaling) and p4E-BP1 Thr37/46 (Cat#2855, Cell signaling) were used at a 1:100 dilution. Plates were washed three times with PBS/0.1% Tween 20 before adding the secondary antibody at a 1:200 dilution. (goat anti-rabbit containing a fluorescent label, Alexa Fluor 488, Cat#A11008, Invitrogen) in PBS/0.3% Triton for 60 minutes.

Finally, the plates were washed three times with PBS/0.1% Tween 20 and the fluorescent intensity was read using an Analyst HT from Molecular Devices. The fluorescent intensity values from the serially diluted compound treatment group were analyzed using the Xlfit 4 program (Microsoft) (Formula 205: Y=Bottom+(Top-Bottom)/(1+($IC_{50}$/X)^Hillslope) to generate the $IC_{50}$ value. Where Top is the maximum signal without Compound (+DMSO only) and Bottom represents maximum inhibition. Y is the fluorescence at some compound concentration. The control used to determine the fluorescent intensities for 100% pAKT S473 or 100% phosphorylated p4E-BP1 Thr37/46 were measured from untreated wells that contained only DMSO, instead of test compound.

Table 23 below lists representative compounds of the invention with activity data whereby the $IC_{50}$ values are rated "A", "B", "C," or "D." The $IC_{50}$ values are rated "A" for $IC_{50}$ values in the range of 1 nM to 100 nM, "B" for $IC_{50}$ values in the range from 100 nM to 1000 nM, "C" for $IC_{50}$ values in the range from 1000 nM to 2000 nM, "D" for $IC_{50}$ values in the range from 2000 nM to 5000 nM and "E" for $IC_{50}$ values of 5000 nM to 15 μM.

TABLE 23

| Compound | hMTOR IC50 | pAKT IC50 nM | P4EBP1 IC50 nM |
|---|---|---|---|
| 1 | 1.33 | 274.92 | 849.83 |
| 2 | A | D | |
| 3 | A | C | |
| 4 | A | B | |
| 5 | A | B | |
| 6 | A | C | |
| 7 | A | C | |
| 8 | A | E | |
| 9 | A | B | |
| 10 | A | D | |
| 11 | 4.61 | 2028.28 | |
| 12 | A | D | |
| 13 | A | E | |
| 14 | A | E | |
| 15 | A | B | B |
| 16 | A | C | |
| 17 | A | B | |
| 18 | A | A | B |
| 19 | A | B | |
| 20 | B | | |
| 21 | A | B | |
| 22 | A | B | |
| 23 | A | D | |
| 24 | A | B | |
| 25 | A | B | B |
| 26 | A | A | B |
| 27 | A | D | |
| 28 | A | A | B |
| 29 | A | B | B |
| 30 | A | B | B |
| 31 | A | A | B |
| 32 | A | B | |
| 33 | A | C | |
| 34 | A | B | B |
| 35 | A | A | B |
| 36 | A | A | B |
| 37 | A | A | B |
| 38 | A | B | |
| 39 | A | B | |
| 40 | A | A | B |
| 41 | A | E | E |
| 42 | A | D | E |
| 43 | A | B | B |
| 44 | A | B | B |
| 45 | A | | |
| 46 | A | E | E |
| 47 | A | D | D |
| 48 | A | E | E |
| 49 | A | | |
| 50 | A | B | B |
| 51 | A | B | C |
| 52 | A | B | B |
| 53 | B | | |
| 54 | A | E | |
| 55 | A | B | |
| 56 | A | E | |
| 57 | A | B | |
| 58 | A | B | |

TABLE 23-continued

| Compound | hMTOR IC50 | pAKT IC50 nM | P4EBP1 IC50 nM |
|---|---|---|---|
| 59 | A | | |
| 60 | A | B | |
| 61 | A | | |
| 62 | A | B | |
| 63 | A | C | |
| 64 | A | B | B |
| 65 | A | C | |
| 66 | A | C | |
| 67 | A | B | B |
| 68 | A | D | D |
| 69 | A | A | A |
| 70 | A | B | B |
| 71 | A | C | C |
| 72 | 11.73 | 869.95 | |
| 73 | A | E | |
| 74 | A | D | |
| 75 | A | D | |
| 76 | A | B | B |
| 77 | A | C | |
| 78 | A | B | B |
| 79 | A | B | |
| 80 | B | | |
| 81 | B | | |
| 82 | A | B | |
| 83 | A | C | |
| 84 | A | B | |
| 85 | A | B | |
| 86 | A | B | |
| 87 | A | B | |
| 88 | A | A | A |
| 89 | A | A | A |
| 90 | A | B | C |
| 91 | A | B | C |
| 92 | A | A | B |
| 93 | A | B | C |
| 94 | A | A | B |
| 95 | A | B | B |
| 96 | A | B | C |
| 97 | A | | |
| 98 | A | | |
| 99 | A | | |
| 100 | A | A | A |
| 101 | A | | |
| 102 | A | B | B |
| 103 | A | B | B |
| 104 | A | A | A |
| 105 | A | A | B |
| 106 | A | | |
| 107 | A | B | |
| 108 | A | A | B |
| 109 | A | B | D |
| 110 | A | A | A |
| 111 | 1 | 47.97 | 140.56 |
| 112 | A | A | A |
| 113 | A | B | B |
| 114 | A | B | B |
| 115 | A | A | A |
| 116 | A | B | A |
| 117 | A | B | C |
| 118 | A | B | B |
| 119 | A | C | D |
| 120 | A | B | B |
| 121 | A | B | B |
| 122 | A | A | A |
| 123 | A | | |
| 124 | A | | |
| 125 | A | A | A |
| 126 | A | B | C |
| 127 | A | B | B |
| 128 | A | B | B |
| 129 | A | A | B |
| 130 | A | | |
| 131 | A | C | D |
| 132 | A | B | |
| 133 | A | B | B |
| 134 | 7.365 | 208.90 | |
| 135 | A | B | |
| 136 | A | B | |
| 137 | A | B | |
| 138 | A | B | |
| 139 | A | B | B |
| 140 | A | A | B |
| 141 | A | A | |
| 142 | A | A | |
| 143 | A | C | |
| 144 | A | B | B |
| 145 | A | C | |
| 146 | A | D | |
| 147 | A | | |
| 148 | A | D | |
| 149 | B | | |
| 150 | A | | |
| 151 | A | | |
| 152 | A | C | |
| 153 | A | E | |
| 154 | A | | |
| 155 | A | E | |
| 156 | A | B | B |
| 157 | A | D | |
| 158 | A | B | B |
| 159 | A | A | |
| 160 | A | B | B |
| 161 | A | B | B |
| 162 | A | A | B |
| 163 | A | | |
| 164 | A | C | |
| 165 | A | C | |
| 166 | A | A | B |
| 167 | A | | |
| 168 | A | C | |
| 169 | A | D | |
| 170 | A | C | |
| 171 | A | D | |
| 172 | A | A | |

CHK1 In Vitro Kinase Assay

This in vitro assay utilizes recombinant His-CHK1 expressed in the baculovirus expression system as an enzyme source and a biotinylated peptide based on CDC25C as substrate (biotin-RSGLYRSPSMPENLNRPR).

Materials and Reagents:

1) CDC25C Ser 216 C-term Biotinylated peptide substrate (25 mg), stored at −20° C., Custom Synthesis by Research Genetics: biotin-RSGLYRSPSMPENLNRPR 2595.4 MW 2) His-CHK1 In House lot P976, 235 g/mL, stored at −80° C.

3) D-PBS (without CaCl and MgCl): GIBCO, Cat.#14190-144

4) SPA beads: Amersham, Cat.#SPQ0032: 500 mg/vial
   Add 10 mL of D-PBS to 500 mg of SPA beads to make a working concentration of 50 mg/mL. Store at 4° C. Use within 2 week after hydration.

5) 96-Well White Microplate with Bonded GF/B filter: Packard, Cat.#6005177

6) Top seal-A 96 well Adhesive Film: Perkin Elmer, Cat.#6005185

7) 96-well Non-Binding White Polystyrene Plate: Corning, Cat. #6005177

8) $MgCl_2$: Sigma, Cat.#M-8266

9) DTT: Promega, Cat.#V3155

10) ATP, stored at 4° C.: Sigma, Cat.#A-5394

11) $\gamma^{33}$P-ATP, 1000-3000 Ci/mMol: Amersham, Cat.#AH9968

12) NaCl: Fisher Scientific, Cat.#BP358-212

13) $H_3PO_4$ 85% Fisher, Cat.#A242-500

14) Tris-HCL pH 8.0: Bio-Whittaker, Cat. #16-015V
15) Staurosporine, 100 µg: CALBIOCHEM, Cat. #569397
16) Hypure Cell Culture Grade Water, 500 mL: HyClone, Cat.#SH30529.02 Reaction Mixtures:
1) Kinase Buffer: 50 mM Tris pH 8.0; 10 mM $MgCl_2$; 1 mM DTT
2) His-CHK1, In House Lot P976, MW ~30 KDa, stored at −80° C.

6 nM is required to yield positive controls of ~5,000 CPM. For 1 plate (100 reaction): dilute 8 µL of 235 µg/mL (7.83 µM) stock in 2 mL Kinase Buffer. This makes a 31 nM mixture. Add 20 µL/well. This makes a final reaction concentration of 6 nM.

3) CDC25C Biotinylated peptide.

Dilute CDC25C to 1 mg/mL (385 µM) stock and store at −20° C. For 1 plate (100 reactions): dilute 10 µL of 1 mg/mL peptide stock in 2 mL Kinase Buffer. This gives a 1.925 µM mix. Add 20 L/reaction. This makes a final reaction concentration of 385 nM.

4) ATP Mix.

For 1 plate (100 reactions): dilute 10 µL of 1 mM ATP (cold) stock and 2 µL fresh P33-ATP (20 Ci) in 5 mL Kinase Buffer. This gives a 2 µM ATP (cold) solution; add 50 µL/well to start the reaction. Final volume is 100 µL/reaction so the final reaction concentrations will be 1 µM ATP (cold) and 0.2 µCi/reaction.

5) Stop Solution:

For 1 plate add: To 10 mL Wash Buffer 2 (2M NaCl 1% $H_3PO_4$): 1 mL SPA bead slurry (50 mg); Add 100 µL/well
6) Wash buffer 1: 2 M NaCl
7) Wash buffer 2: 2 M NaCl, 1% $H_3PO_4$
Assay Procedure:

| Assay Component | Final Concentration | Volume |
| --- | --- | --- |
| CHK1 | 6 nM | 20 µl/rxn |
| Compound (10% DMSO) | — | 10 µl/rxn |
| CDC25C | 0.385 µM | 20 µl/rxn |
| $^{33}$P-ATP | 0.2 µCi/rxn | 50 µl/rxn |
| Cold ATP | 1 µM | |
| Stop solution SPA beads | 0.5 mg/rxn | 100 µl/rxn* |
| | | 200 µl/rxn** |

*Total reaction volume for assay.
**Final reaction volume at termination of reaction (after addition of stop solution).

1) Dilute test compounds to desired concentrations in water/10% DMSO—this will give a final DMSO concentration of 1% in the reaction. Dispense 10 µL/reaction to appropriate wells. Add 10 µL 10% DMSO to positive (CHK1+CDC25C+ATP) and negative (CHK1+ATP only) control wells.
2) Thaw enzyme on ice—dilute enzyme to proper concentration in kinase buffer (see Reaction Mixtures) and dispense 20 µL to each well.
3) Thaw the Biotinylated substrate on ice and dilute in kinase buffer (see Reaction Mixtures). Add 20 µL/well except to negative control wells. Instead, add 20 µL Kinase Buffer to these wells.
4) Dilute ATP (cold) and $P^{33}$-ATP in kinase buffer (see Reaction Mixtures). Add 50 µL/well to start the reaction.
5) Allow the reaction to run for 2 hours at room temperature.
6) Stop reaction by adding 100 µL of the SPA beads/stop solution (see Reaction Mixtures) and leave to incubate for 15 minutes before harvest 7) Place a blank Packard GF/B filter plate into the vacuum filter device (Packard plate harvester) and aspirate 200 mL water through to wet the system.
8) Take out the blank and put in the Packard GF/B filter plate.
9) Aspirate the reaction through the filter plate.
10) Wash: 200 mL each wash; 1× with 2M NaCl; 1× with 2M NaCl/1% $H_3PO_4$
11) Allow filter plate to dry 15 minutes.
12) Put TopSeal-A adhesive on top of filter plate.
13) Run filter plate in Top Count
   Settings:
      Data mode: CPM
      Radio nuclide: Manual SPA:$P^{33}$
      Scintillator: Liq/plast
      Energy Range Low $IC_{50}$ DETERMINATIONS: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.

CDK2 Kinase Assay

BACULOVIRUS CONSTRUCTIONS: Cyclin E was cloned into pVL1393 (Pharmingen, La Jolla, Calif.) by PCR, with the addition of 5 histidine residues at the amino-terminal end to allow purification on nickel resin. The expressed protein was approximately 45 kDa. CDK2 was cloned into pVL1393 by PCR, with the addition of a haemaglutinin epitope tag at the carboxy-terminal end (YDVPDYAS). The expressed protein was approximately 34 kDa in size.

ENZYME PRODUCTION: Recombinant baculoviruses expressing cyclin E and CDK2 were co-infected into SF9 cells at an equal multiplicity of infection (MOI=5), for 48 hrs. Cells were harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates were spun down at 15000 RPM for 10 minutes and the supernatant retained. 5 mL of nickel beads (for one liter of SF9 cells) were washed three times in lysis buffer (Qiagen GmbH, Germany). Imidazole was added to the baculovirus supernatant to a final concentration of 20 mM, then incubated with the nickel beads for 45 minutes at 4° C. Proteins were eluted with lysis buffer containing 250 mM imidazole. Eluate was dialyzed about 15 hours in 2 liters of kinase buffer containing 50 mM Tris pH 8.0, 1 mM DTT, 10 mM $MgCl_2$, 100M sodium orthovanadate and 20% glycerol. Enzyme was stored in aliquots at −70° C.

In Vitro Cyclin E/CDK2 Kinase Assays

Cyclin E/CDK2 kinase assays can be performed as described below in low protein binding 96-well plates (Corning Inc, Corning, N.Y.).

Enzyme is diluted to a final concentration of 50 µg/mL in kinase buffer containing 50 mM Tris pH 8.0, 10 mM $MgCl_2$, 1 mM DTT, and 0.1 mM sodium orthovanadate. The substrate used in these reactions is a biotinylated peptide derived from Histone H1 (from Amersham, UK). The substrate is thawed on ice and diluted to 2 µM in kinase buffer. Test compounds are diluted in 10% DMSO to desirable concentrations. For each kinase reaction, 20 µL of the 50 µg/mL enzyme solution (1 µg of enzyme) and 20 µl of the 2 µM substrate solution are mixed, then combined with 10 µL of diluted compound in each well for testing. The kinase reaction is initiated by addition of 50 µL of 2 µM ATP and 0.1 µCi of $^{33}$P-ATP (from Amersham, UK). The reaction is allowed to run for 1 hour at room temperature, then is stopped by adding 200 µL of stop buffer containing 0.1% Triton X-100, 1 mM ATP, 5 mM EDTA, and 5 mg/mL streptavidine coated SPA beads (from Amersham, UK) for 15 minutes. The SPA beads are then captured onto a 96-well GF/B filter plate (Packard/Perkin Elmer Life Sciences) using a Filtermate universal harvester (Packard/Perkin Elmer Life Sciences.). Non-specific signals are eliminated by washing the beads twice with 2M NaCl then twice with 2 M NaCl with 1% phosphoric acid. The radioactive signal can then be measured using, for example, a Top-Count 96 well liquid scintillation counter (from Packard/Perkin Elmer Life Sciences).

$IC_{50}$ DETERMINATIONS: Dose-response curves are plotted from inhibition data generated, each in duplicate, from 8 point serial dilutions of inhibitory compounds. Concentration of compound is plotted against % kinase activity, calculated by CPM of treated samples divided by CPM of untreated samples. To generate $IC_{50}$ values, the dose-response curves are then fitted to a standard sigmoidal curve and $IC_{50}$ values can be derived using nonlinear regression analysis.

While this invention has been particularly shown and described with references to embodiments thereof, it will be understood by those skilled in the art that various changes in form and details may be made therein without departing from the meaning of the invention described. Rather, the scope of the invention is defined by the claims that follow.

What is claimed is:
1. A compound of Formula I

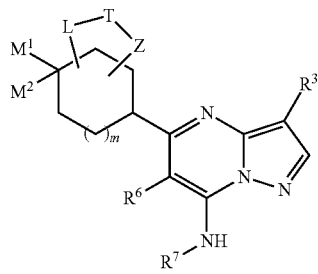

I $M^1$ is —$(CR^aR^b)_nO(CR^cR^d)_qOC_1$-$C_3$alkyl, —$(CR^aR^b)_nO(CR^cR^d)_qOH$, COOH, CN, —OH, —$CH_2OH$, —$CH_2CH_2OH$ or —$(CR^aR^b)_nC(O)OC_1$-$C_3$alkyl;

$M^2$ is selected from the group consisting of CN, —$(CR^aR^b)_nOR^1$, —$(CR^aR^b)_nNR^1R^2$, —$(CR^aR^b)_nSR^1$, —$(CR^aR^b)_nS(O)_2R^1$, —$(CR^aR^b)_nS(O)R^1$, —$(CR^aR^b)_nS(O)_2NR^1R^2$, —$(CR^aR^b)_nNR^1S(O)_2R^4$, —$(CR^aR^b)_nC(O)NR^1S(O)_2R^2$, —$(CR^aR^b)_nC(O)R^1$, —$(CR^aR^b)_nC(O)OR^1$, —$(CR^aR^b)_nC(O)NR^1R^2$, —$(CR^aR^b)_nC(=NR^4)NR^1R^2$, —$(CR^aR^b)_nNR^1C(O)R^4$, —$(CR^aR^b)_nNR^1C(O)OR^4$, —$(CR^aR^b)_nNR^4C(O)NR^1R^2$, —$(CR^aR^b)_nO(CR^cR^d)_qOR^4$, halo, $C_1$-$C_6$alkyl, $C_3$-$C_8$cycloalkyl, $C_3$-$C_8$cycloalkyl$C_1$-$C_6$alkyl, $C_6$-$C_{10}$aryl$C_1$-$C_6$alkyl, $C_6$-$C_{10}$aryl, 5- to 10-membered heteroaryl$C_1$-$C_6$alkyl, 5- to 10-membered heteroaryl, 5- to 10-membered heterocyclyl$C_1$-$C_6$alkyl, 5- to 10-membered heterocyclenyl$C_1$-$C_6$alkyl, 5- to 10-membered heterocyclyl or 5- to 10-membered heterocyclenyl, wherein the alkyl, cycloalkyl, cycloalkylalkyl, arylalkyl, aryl, heteroarylalkyl, heteroaryl, heterocyclylalkyl, heterocyclenylalkyl, heterocyclyl or heterocyclenyl is unsubstituted or substituted with one to three moieties which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —$OR^9$, —$C(O)R^9$, —$NR^8R^9$, —$C(O)O$—$C_1$-$C_6$alkyl, —$C(O)NR^8R^9$, —$NR^8C(O)R^9$, —$S(O)_2NR^8R^9$, —$NR^8S(O)_2R^9$, —$SR^9$, —$S(O)_2R^9$, $C_6$-$C_{10}$aryl, 5- to 10-membered heteroaryl, 5- to 10-membered heterocyclenyl and 5- to 10-membered heterocyclyl;

L and Z are not present, or

L and Z are bonded to any two carbons of the ring which are not attached to $M^1$ and $M^2$ and are independently selected from the group consisting of $CH_2$, $C(H)(R^{10})$, $C(R^{10})(R^{11})$, $N(R^{10})$, C(O), O, S, S(O) and $S(O)_2$;

T is not present such that L is bonded directly to Z, or T is selected from the group consisting of $CH_2$, $C(H)(R^{10})$, $C(R^{10})(R^{11})$, $N(R^{10})$, C(O), O, S, S(O) and $S(O)_2$ and $C_1$-$C_4$ alkylene, wherein said alkylene of T is unsubstituted or substituted with one or two substituents selected from the group consisting of $C_1$-$C_3$ alkyl, halo, hydroxy, $C_1$-$C_3$ alkoxy, amino, $C_1$-$C_3$ alkylamino and $C_1$-$C_3$ dialkylamino;

$R^a$, $R^b$, $R^c$ and $R^d$ are independently selected from H, halogen and $C_1$-$C_6$ alkyl;

$R^1$, $R^2$ and $R^4$ are independently selected from H, OH, $NH_2$, halogen, —$(CR^aR^b)_nO(CR^cR^d)_qR^8$, $C_1$-$C_6$alkyl, $C_3$-$C_8$cycloalkyl, $C_3$-$C_8$cycloalkyl$C_1$-$C_6$alkyl, $C_6$-$C_{10}$aryl$C_1$-$C_6$alkyl, $C_6$-$C_{10}$aryl, 5- to 10-membered heteroaryl$C_1$-$C_6$alkyl, 5- to 10-membered heteroaryl, 5- to 10-membered heterocyclyl$C_1$-$C_6$alkyl, 5- to 10-membered heterocyclenyl$C_1$-$C_6$alkyl, 5- to 10-membered heterocyclyl and 5- to 10-membered heterocyclenyl, wherein the alkyl, cycloalkyl, cycloalkylalkyl, arylalkyl, aryl, heteroarylalkyl, heteroaryl, heterocyclylalkyl, heterocyclenylalkyl, heterocyclyl or heterocyclenyl is unsubstituted or substituted with one to three moieties which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —$OR^9$, —$C(O)R^9$, —$NR^8R^9$, —$C(O)O$—$C_1$-$C_6$alkyl, —$C(O)NR^8R^9$, —$NR^8C(O)R^9$, —$S(O)_2NR^8R^9$, —$NR^8S(O)_2R^9$, —$SR^9$, —$S(O)_2R^9$, $C_6$-$C_{10}$aryl, 5- to 10-membered heteroaryl, 5- to 10-membered heterocyclenyl and 5- to 10-membered heterocyclyl;

Or $R^1$ and $R^2$ form a 3- to 8-membered cycloalkyl, 5- to 6-membered heterocyclyl or 5- to 6-membered heterocyclenyl;

$R^3$ is selected from the group consisting of H, halogen, $C_1$-$C_6$ alkyl, $C_2$-$C_6$ alkenyl, $C_2$-$C_6$ alkynyl, halo-$C_1$-$C_6$alkyl, —$CF_3$, —$C(O)R^9$, $C_6$-$C_{10}$aryl, $C_3$-$C_8$cycloalkyl, 5- to 10-membered heteroaryl, 5- to 10-membered heterocyclyl, 5- to 10-membered heterocyclenyl, $C_6$-$C_{10}$aryl$C_1$-$C_6$alkyl, $C_3$-$C_8$cycloalkyl$C_1$-$C_6$alkyl, 5- to 10-membered heteroaryl$C_1$-$C_6$alkyl, 5- to 10-membered heterocyclyl$C_1$-$C_6$alkyl and 5- to 10-membered heterocyclenyl$C_1$-$C_6$alkyl, wherein each of said aryl, cycloalkyl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to three moieties which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —$(CR^aR^b)_nOR^9$, —$(CR^aR^b)_nC(O)R^9$, —$(CR^aR^b)_nNR^8R^9$, —$(CR^aR^b)_nNR^8$, —$NR^8R^9$, —$(CR^aR^b)_nC(O)O$—$C_1$-$C_6$alkyl, —O-halo$C_1$-$C_6$alkyl, —$(CR^aR^b)_nC(O)NR^8R^9$, —$(CR^aR^b)_nC(O)NR^8SS(O)_2R^9$, —$(CR^aR^b)_nNR^8C(O)R^9$, —$(CR^aR^b)_nNR^8C(O)OR^9$, —$(CR^aR^b)_nNR^8C(O)NR^8R^9$, —$(CR^aR^b)_nS(O)_2NR^8R^9$, —$(CR^aR^b)_nS(O)_2NR^8C(O)R^9$, —$(CR^aR^b)_nNR^8S(O)_2R^9$, —$(CR^aR^b)_nSR^9$, —$(CR^aR^b)_nS(O)_2R^9$, $C_6$-$C_{10}$aryl, 5- to 10-membered heteroaryl, 5- to 10-membered heterocyclenyl, 5- to 10-membered heterocyclyl, $C_6$-$C_{10}$arylalkyl, 5- to 10-membered heteroarylalkyl, 5- to 10-membered heterocyclenylalkyl and 5- to 10-membered heterocyclylalkyl wherein each of said alkyl, cycloalkyl, aryl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to five moieties, which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —O-halo$C_1$-$C_6$alkyl, —$OR^9$, —$C(O)R^9$, —$NR^8R^9$, —$C(O)O$—$C_1$-$C_6$alkyl, —$C(O)NR^8R^9$, —$NR^8C(O)R^9$, —$S(O)_2NR^8R^9$, —$NR^8S(O)_2R^9$, —$SR^9$, and —$S(O)_2R^9$;

$R^6$ is selected from the group consisting of H, —$CHR^8R^9$, —$OR^8$, —$NR^8R^9$, —$SR^8$, —$S(O)R^8$, —$S(O)_2R^8$, —$C(O)C_1$-$C_6$alkyl, —$C(O)NR^8R^9$, —$C(O)OR^8$, —$S(O)_2NR^8R^9$, —$NR^8C(O)R^9$, —$NR^8S(O)_2R^9$, $C_1$-$C_6$alkyl, halo-$C_1$-$C_6$alkyl, $C_1$-$C_6$alkoxy, halogen, hydroxyl, amino, —CN, 5- to 10-membered heteroaryl, 5- to 10 membered heterocyclyl, $C_3$-$C_8$cycloalkyl and $C_6$-$C_{10}$aryl, wherein each of said heteroaryl, heterocyclyl, cycloalkyl and aryl can be unsubstituted or substituted with one to three moieties selected from the group consisting of $C_1$-$C_3$alkyl, $C_1$-$C_3$alkoxy, $C_1$-$C_3$alkylamino, $C_1$-$C_3$dialkylamino, amino, halo;

$R^7$ is selected from the group consisting of H, OH, $OR^8$, $C_1$-$C_6$alkyl, $C_6$-$C_{10}$aryl, $C_6$-$C_{10}$aryl$C_1$-$C_6$alkyl, 5- to 10-membered heteroaryl, 5- to 10-membered heteroaryl$C_1$-$C_6$alkyl, $C_3$-$C_8$cycloalkyl, $C_3$-$C_8$cycloalkyl$C_1$-$C_6$alkyl, 5- to 10-membered heterocyclyl, 5- to 10-membered heterocyclenyl, 5- to 10-membered heterocyclyl$C_1$-$C_6$alkyl, 5- to 10-membered heterocyclenyl$C_1$-$C_6$alkyl, $C_2$-$C_6$alkenyl, $C_2$-$C_6$alkynyl, $C_6$-$C_{10}$aryl-S(O)$C_1$-$C_6$alkyl, —$S(O)_2C_1$-$C_6$alkyl, —$C(O)C_1$-$C_6$alkyl, —$C(O)NR^8R^9$, —$C(O)OR^8$ and —$S(O)_2NR^8R^9$, wherein each of said alkyl, aryl, arylalkyl, heteroaryl, heteroarylalkyl, cycloalkyl, cycloalkylalkyl, heterocyclyl, heterocyclylalkyl, heterocyclenyl, heterocyclenylalkyl, alkenyl and alkynyl can be unsubstituted or substituted with one to three moieties, which can be the same or different, each moiety being selected from the group consisting of halogen, $C_1$-$C_6$alkyl, $C_3$-$C_8$cycloalkyl, —$CF_3$, —CN, —$(CR^aR^b)_nC(O)OH$, —$OCF_3$, —$OR^9$, —$C(O)R^9$, —$NR^8R^9$, —$C(O)O$—$C_1$-$C_6$alkyl, —$C(O)NR^8R^9$, —$SR^9$, and —$S(O)_2R^9$;

$R^8$ and $R^9$ are independently selected from the group consisting of H, OH, $C_1$-$C_6$alkyl, $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl, and said alkyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, $C_1$-$C_6$alkyl, $C_3$-$C_8$cycloalkyl, —$CF_3$, —CN, —$(CR^aR^b)_nC(O)OH$, —$OCF_3$, —$OR^a$, —C(O), amino, —$C(O)O$—$C_1$-$C_6$alkyl, —$C(O)NR^aR^b$, —$SR^a$, and —$S(O)_2R^a$; or $R^8$ and $R^9$ together with the nitrogen atom to which they are attached form a 3- to 6-membered heterocyclyl ring;

$R^{10}$ and $R^{11}$ are independently selected from the group consisting of H, $C_1$-$C_3$alkyl, halo, hydroxy, $C_1$-$C_3$alkoxy, amino, $C_1$-$C_3$alkylamino and $C_1$-$C_3$dialkylamino;

n is independently 0, 1, 2, 3 or 4;

m is 1;

q is independently 0, 1, 2, 3 or 4;

or a pharmaceutically acceptable salt thereof.

2. The compound of claim 1, wherein

L, T and Z are not present, or

L and Z are bonded to any two carbons of the ring which are not attached to $M^1$ and $M^2$ and are both $CH_2$, and T is not present;

$R^a$, $R^b$, $R^c$ and $R^d$ are independently selected from H and $C_1$-$C_6$ alkyl;

$R^1$, $R^2$ and $R^4$ are independently selected from H, OH, $NH_2$, halogen, —$(CR^aR^b)_nO(CR^cR^d)_qR^8$, $C_1$-$C_6$alkyl, $C_3$-$C_8$cycloalkyl, $C_3$-$C_8$cycloalkyl$C_1$-$C_6$alkyl, $C_6$-$C_{10}$aryl$C_1$-$C_6$alkyl, $C_6$-$C_{10}$aryl, 5- to 10-membered heteroaryl$C_1$-$C_6$alkyl, 5- to 10-membered heteroaryl, 5- to 10-membered heterocyclyl$C_1$-$C_6$alkyl, 5- to 10-membered heterocyclyl, 5- to 10-membered heterocyclenyl$C_1$-$C_6$alkyl and 5- to 10-membered heterocyclenyl, wherein the alkyl, cycloalkyl, cycloalkylalkyl, arylalkyl, aryl, heteroarylalkyl, heteroaryl, heterocyclylalkyl, heterocyclyl, heterocyclenylalkyl or heterocyclenyl is unsubstituted or substituted with one to three moieties which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —$OR^a$, —$C(O)R^a$, —$NR^aR^b$, —$C(O)O$—$C_1$-$C_6$alkyl, —$C(O)NR^aR^b$, —$NR^aC(O)R^b$, —$S(O)_2NR^aR^b$, —$NR^aS(O)_2R^b$, —$SR^a$, —$S(O)_2R^a$, $C_6$-$C_{10}$aryl, 5- to 10-membered heteroaryl, 5- to 10-membered heterocyclenyl and 5- to 10-membered heterocyclyl;

$R^3$ is selected from the group consisting of $C_6$-$C_{10}$aryl, 5- to 10-membered heteroaryl, wherein each of said aryl or heteroaryl is unsubstituted or substituted with one to three moieties which can be the same or different, each moiety being selected from the group consisting of halogen, $C_1$-$C_6$alkyl, $C_6$-$C_{10}$aryl, 5- to 10-membered heteroaryl, —$CF_3$, —CN, —C(O)OH, —$(CR^aR^b)_nC(O)OH$, —$OCF_3$, —O-halo$C_1$-$C_6$alkyl, —$OR^8$, —$C(O)R^8$, —$NR^8R^9$, —$C(O)O$—$C_1$-$C_6$alkyl, —$C(O)NR^8R^9$, —$NR^8C(O)R^9$, —$S(O)_2NR^8R^9$, —$NR^8S(O)_2R^9$, —$SR^8$, and —$S(O)_2R^8$, wherein each of said heteroaryl or aryl is unsubstituted or substituted with one to three moieties, which can be the same or different, each moiety being selected from the group consisting of halogen, $C_1$-$C_6$alkyl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —$C(O)O$—$C_1$-$C_6$alkyl, —$C(O)NR^aR^b$, —$NR^aC(O)R^b$, —$S(O)_2NR^aR^b$, —$NR^aS(O)_2R^b$, —$SR^a$, and —$S(O)_2R^a$;

$R^6$ is selected from the group consisting of H, —$CHR^aR^b$, —$OR^a$, —$NR^aR^b$, —$SR^a$, —$S(O)R^a$, —$S(O)_2R^a$, —$C(O)C_1$-$C_6$alkyl, —$C(O)NR^aR^b$, —$C(O)OR^a$, —S(O)$_2$NR$^a$R$^b$, —NR$^a$C(O)R$^b$, —NR$^a$S(O)$_2$R$^b$, C$_1$-C$_6$alkyl, C$_1$-C$_6$alkoxy, halogen, hydroxy, amino and —CN;

R$^7$ is selected from the group consisting of H, OH, OR$^a$, C$_1$-C$_6$alkyl, C$_2$-C$_6$alkenyl, C$_2$-C$_6$alkynyl, —S(O)$_2$C$_1$-C$_6$alkyl, —C(O)C$_1$-C$_6$alkyl, —C(O)NR$^a$R$^b$, —C(O)OR$^a$ and —S(O)$_2$NR$^a$R$^b$, wherein each of said alkyl, alkenyl, alkynyl can be unsubstituted or substituted with one to three moieties, which can be the same or different, each moiety being selected from the group consisting of halogen, —CF$_3$, —CN, —(CR$^a$R$^b$)$_n$C(O)OH, —OCF$_3$, —OH, amino, —C(O)R$^a$, —NR$^a$R$^b$, —C(O)O—C$_1$-C$_6$alkyl, —C(O)NR$^a$R$^b$, —SR$^a$, and —S(O)$_2$R$^a$;

R$^8$ and R$^9$ are independently selected from the group consisting of H, OH, C$_1$-C$_6$alkyl, C$_3$-C$_8$cycloalkyl, C$_6$-C$_{10}$aryl, 5- to 10-membered heteroaryl, 5- to 10-membered heterocyclenyl, 5- to 10-membered heterocyclyl, C$_3$-C$_8$cycloalkylC$_1$-C$_6$alkyl, C$_6$-C$_{10}$arylC$_1$-C$_6$alkyl, 5- to 10-membered heteroarylC$_1$-C$_6$alkyl, 5- to 10-membered heterocyclylC$_1$-C$_6$alkyl, 5- to 10-membered heterocyclenylC$_1$-C$_6$alkyl, and said alkyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, C$_1$-C$_6$alkyl, C$_3$-C$_8$cycloalkyl, —CF$_3$, —CN, —(CR$^a$R$^b$)$_n$C(O)OH, —OCF$_3$, —OR$^a$, —C(O), amino, —C(O)O—C$_1$-C$_6$alkyl, —C(O)NR$^a$R$^b$, —SR$^a$, and —S(O)$_2$R$^a$;

n is independently 0, 1 or 2;
m is 1;
q is independently 0, 1, or 2;
or a pharmaceutically acceptable salt thereof.

3. The compound of claim 1, under the following formula

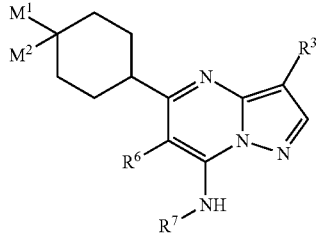

M$^1$ is —(CR$^a$R$^b$)$_n$O(CR$^c$R$^d$)$_q$OC$_1$-C$_3$alkyl, —(CR$^a$R$^b$)$_n$O(CR$^c$R$^d$)$_q$OH, COOH, CN, —OH, —CH$_2$OH, —CH$_2$CH$_2$OH or —(CR$^a$R$^b$)$_n$C(O)OC$_1$-C$_3$alkyl;

M2 is selected from the group consisting of CN, —(CR$^a$R$^b$)$_n$OR$^1$, —(CR$^a$R$^b$)$_n$NR$^1$R$^2$, —(CR$^a$R$^b$)$_n$SR$^1$, —(CR$^a$R$^b$)$_n$S(O)$_2$R$^1$, —(CR$^a$R$^b$)$_n$S(O)R$^1$, —(CR$^a$R$^b$)$_n$S(O)$_2$NR$^1$R$^2$, —(CR$^a$R$^b$)$_n$NR$^1$S(O)$_2$R$^4$, —(CR$^a$R$^b$)$_n$C(O)NR$^1$S(O)$_2$R$^2$, —(CR$^a$R$^b$)$_n$C(O)R$^1$, —(CR$^a$R$^b$)$_n$C(O)OR$^1$, —(CR$^a$R$^b$)$_n$C(O)NR$^1$R$^2$, —(CR$^a$R$^b$)$_n$C(=NR$^4$)NR$^1$R$^2$, —(CR$^a$R$^b$)$_n$NR$^1$C(O)R$^4$, —(CR$^a$R$^b$)$_n$NR$^1$C(O)OR$^4$, —(CR$^a$R$^b$)$_n$NR$^4$C(O)NR$^1$R$^2$, —(CR$^a$R$^b$)$_n$O(CR$^c$R$^d$)$_q$OR$^4$, halo, C$_1$-C$_6$alkyl, C$_3$-C$_8$cycloalkyl, C$_3$-C$_8$cycloalkylC$_1$-C$_6$alkyl, C$_6$-C$_{10}$arylC$_1$-C$_6$alkyl, C$_6$-C$_{10}$aryl, 5- to 10-membered heteroarylC$_1$-C$_6$alkyl, 5- to 10-membered heteroaryl, 5- to 10-membered heterocyclylC$_1$-C$_6$alkyl, 5- to 10-membered heterocyclenylC$_1$-C$_6$alkyl, 5- to 10-membered heterocyclyl or 5- to 10-membered heterocyclenyl, wherein the alkyl, cycloalkyl, cycloalkylalkyl, arylalkyl, aryl, heteroarylalkyl, heteroaryl, heterocyclylalkyl, heterocyclenylalkyl, heterocyclyl or heterocyclenyl is unsubstituted or substituted with one to three moieties which can be the same or different, each moiety being selected from the group consisting of halogen, C$_1$-C$_6$alkyl, C$_3$-C$_8$cycloalkyl, —CF$_3$, —CN, —C(O)OH, —(CR$^a$R$^b$)$_n$C(O)OH, —OCF$_3$, —OR$^9$, —C(O)R$^9$, —NR$^8$R$^9$, —C(O)O—C$_1$-C$_6$alkyl, —C(O)NR$^8$R$^9$, —NR$^8$C(O)R$^9$, —S(O)$_2$NR$^8$R$^9$, —NR$^8$S(O)$_2$R$^9$, —SR$^9$, —S(O)$_2$R$^9$, C$_6$-C$_{10}$aryl, 5- to 10-membered heteroaryl, 5- to 10-membered heterocyclenyl and 5- to 10-membered heterocyclyl;

R$^a$, R$^b$, R$^c$ and R$^d$ are independently selected from H and C$_1$-C$_3$ alkyl;

R$^1$, R$^2$ and R$^4$ are independently selected from H, OH, NH$_2$, —(CR$^a$R$^b$)$_n$O(CR$^c$R$^d$)$_q$R$^8$, C$_1$-C$_3$alkyl, 5- to 10-membered heteroarylC$_1$-C$_6$alkyl, 5- to 10-membered heteroaryl, 5- to 10-membered heterocyclylC$_1$-C$_6$alkyl, 5- to 10-membered heterocyclyl, 5- to 10-membered heterocyclenylC$_1$-C$_6$alkyl and 5- to 10-membered heterocyclenyl, wherein the alkyl, heteroarylalkyl, heteroaryl, heterocyclylalkyl, heterocyclyl, heterocyclenylalkyl or heterocyclenyl is unsubstituted or substituted with one to three moieties which can be the same or different, each moiety being selected from the group consisting of halogen, C$_1$-C$_6$alkyl, —CF$_3$, —CN, —C(O)OH, —(CR$^a$R$^b$)$_n$C(O)OH, —OCF$_3$, —OR$^a$, —C(O)R$^a$, —NR$^a$R$^b$, —C(O)O—C$_1$-C$_6$alkyl, —C(O)NR$^a$R$^b$, —NR$^a$C(O)R$^b$, —S(O)$_2$NR$^a$R$^b$, —NR$^a$S(O)$_2$R$^b$, —SR$^a$ and —S(O)$_2$R$^a$.

4. The compound of claim 1, wherein
M$^1$ is —OCH$_2$CH$_2$OCH$_3$, —OCH$_2$CH$_2$OH, —OH, —CH$_2$OH or —CH$_2$CH$_2$OH, and M$^2$ is selected from the group consisting of halo, CN, —OCH$_3$, —CH$_2$OCH$_3$, —SCH$_3$, —OCH$_2$CH$_2$OCH$_3$, —OH, —CH$_2$OH, —CH$_2$CH$_2$OH, —C(O)OH, —C(O)CH$_2$OH, —C(O)N(CH$_3$)$_2$, —CONH$_2$, C(=NH)NH$_2$, C(O)NH—NH$_2$, —CONHCH$_3$, —C(O)NHOCH$_3$, —C(O)N(CH$_3$)OCH$_3$, —C(O)NHOH, —C(O)NHCH$_2$CH$_2$OH, —CH$_3$, —CH$_2$SO$_2$CH$_3$, CH$_2$NHSO$_2$CH$_3$, —C(O)NHS(O)$_2$CH$_3$, triazolyl, tetrazolyl, oxadiazolyl, wherein said triazolyl, tetrazolyl or oxadiazolyl are optionally substituted with methyl or halo.

5. The compound of claim 1, wherein
R$^3$ is a 5- to 6-membered heteroaryl or phenyl unsubstituted or substituted with one to three moieties, which can be the same or different, each moiety being selected from the group consisting of halogen, C$_1$-C$_6$alkyl, phenyl, 5- to 6-membered heteroaryl, —CF$_3$, —CN, —C(O)OH, —(CR$^a$R$^b$)$_n$C(O)OH, —OCF$_3$, —O-haloC$_1$-C$_6$alkyl, —OR$^a$, —C(O)R$^a$, —NR$^a$R$^b$, —C(O)O—C$_1$-C$_6$alkyl, —C(O)NR$^a$R$^b$, —NR$^a$C(O)R$^b$, —S(O)$_2$NR$^a$R$^b$, —NR$^a$S(O)$_2$R$^b$, —SR$^a$, and —S(O)$_2$R$^a$, wherein the alkyl, phenyl or heteroaryl is optionally substituted with one to three moieties, which can be the same or different, each moiety being selected from the group consisting of halogen, C$_1$-C$_6$alkyl, —CF$_3$, —CN, —C(O)OH, —(CR$^a$R$^b$)$_n$C(O)OH, —OCF$_3$, —O-haloC$_1$-C$_6$alkyl, —OR$^a$, —C(O)R$^a$, —NR$^a$R$^b$, —C(O)O—C$_1$-C$_6$alkyl, —C(O)NR$^a$R$^b$, —NR$^a$C(O)R$^b$, —S(O)$_2$NR$^a$R$^b$, —NR$^a$S(O)$_2$R$^b$, —SR$^a$, and —S(O)$_2$R$^a$.

6. The compound of claim 1, wherein R$^3$ is pyrazolyl, isoquinolinyl, pyrimidinyl, phenyl or pyridyl, unsubstituted or substituted with one to three moieties, which can be the same or different, each moiety being selected from the group consisting of halogen, C$_1$-C$_6$alkyl, phenyl, 5- to 6-membered heteroaryl, —CF$_3$, —CN, —C(O)OH, —(CR$^a$R$^b$)$_n$C(O)OH, —OCF₃, —O-haloC₁-C₆alkyl, —OR$^a$, —C(O)R$^a$, —NR$^a$R$^b$, —C(O)O—C₁-C₆alkyl, —C(O)NR$^a$R$^b$, —NR$^a$C(O)R$^b$, —S(O)₂NR$^a$R$^b$, —NR$^a$S(O)₂R$^b$, —SR$^a$, and —S(O)₂R$^a$, wherein the alkyl, phenyl or heteroaryl is optionally substituted with one to three moieties, which can be the same or different, each moiety being selected from the group consisting of halogen, C₁-C₆alkyl, —CF₃, —CN, —C(O)OH, —(CR$^a$R$^b$)$_n$C(O)OH, —OCF₃, —O-haloC₁-C₆alkyl, —OR$^a$, —C(O)R$^a$, —NR$^a$R$^b$, —C(O)O—C₁-C₆alkyl, —C(O)NR$^a$R$^b$, —NR$^a$C(O)R$^b$, —S(O)₂NR$^a$R$^b$, —NR$^a$S(O)₂R$^b$, —SR$^a$, and —S(O)₂R$^a$.

7. The compound of claim 1, wherein R³ is

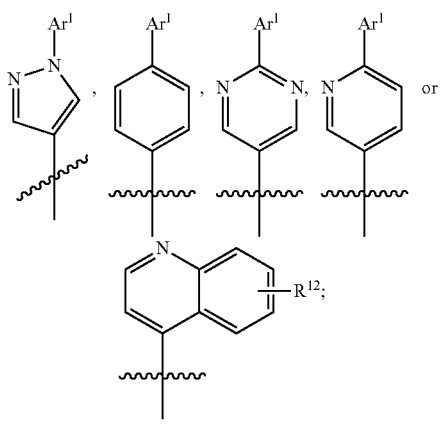

Ar¹ is phenyl or a 5- to 6-membered heteroaryl optionally substituted with one to three of R¹², which can be the same or different, each R¹² being selected from the group consisting of halogen, C₁-C₆alkyl, —CF₃, —CN, —C(O)OH, —(CR$^a$R$^b$)$_n$C(O)OH, —OCF₃, —O-haloC₁-C₆alkyl, —OR$^a$, —C(O)R$^a$, —NR$^a$R$^b$, —C(O)O—C₁-C₆alkyl, —C(O)NR$^a$R$^b$, —NR$^a$C(O)R$^b$, —S(O)₂NR$^a$R$^b$, —NR$^a$S(O)₂R$^b$, —SR$^a$, and —S(O)₂R$^a$.

8. The compound of claim 7 wherein Ar¹ is phenyl, pyridyl, pyrimidinyl, imidazolyl, pyrazinyl, pyrazolyl, or thiazolyl, optionally substituted with one to three of R¹², which can be the same or different, each R¹² being selected from the group consisting of halogen, C₁-C₆alkyl, —CF₃, —CN, —C(O)OH, —(CR$^a$R$^b$)$_n$C(O)OH, —OCF₃, —O-haloC₁-C₆alkyl, —OR$^a$, —C(O)R$^a$, —NR$^a$R$^b$, —C(O)O—C₁-C₆alkyl, —C(O)NR$^a$R$^b$, —NR$^a$C(O)R$^b$, —S(O)₂NR$^a$R$^b$, NR$^a$S(O)₂R$^b$, —SR$^a$, and —S(O)₂R$^a$.

9. The compound of claim 7, wherein R¹² is selected from the group consisting of halogen, C₁-C₆alkyl, —CF₃, and —OCF₃.

10. The compound of claim 1, wherein
R⁶ is selected from the group consisting of halo, —C(O)C₁-C₆alkyl, —S(O)₂C₁-C₆alkyl and CN; and
R⁷ is H.

11. A compound selected from the group consisting of:
(1R,4R)-4-(7-amino-6-bromo-3-(6-phenylpyridin-3-yl)pyrazolo[1,5-a]pyrimidin-5-yl)-1-methylcyclohexanecarboxylic acid;
(1S,4S)-4-(7-amino-6-bromo-3-(6-phenylpyridin-3-yl)pyrazolo[1,5-a]pyrimidin-5-yl)-1-methylcyclohexanecarboxylic acid;
(1S,4S)-4-(7-amino-6-bromo-3-(6-phenylpyridin-3-yl)pyrazolo[1,5-a]pyrimidin-5-yl)-1-fluorocyclohexanecarboxylic acid;
(1R,4R)-4-(7-amino-6-bromo-3-(6-phenylpyridin-3-yl)pyrazolo[1,5-a]pyrimidin-5-yl)-1-fluorocyclohexanecarboxylic acid;
4-(7-amino-6-bromo-3-(6-phenylpyridin-3-yl)pyrazolo[1,5-a]pyrimidin-5-yl)-1-(methoxymethyl)cyclohexanecarboxylic acid;
4-(7-amino-6-bromo-3-(1-phenyl-1H-pyrazol-4-yl)pyrazolo[1,5-a]pyrimidin-5-yl)-1-(methoxymethyl)cyclohexanecarboxylic acid;
(1R,4R)-4-(7-amino-6-bromo-3-(6-fluoroquinolin-3-yl)pyrazolo[1,5-a]pyrimidin-5-yl)-1-(methoxymethyl)cyclohexanecarboxylic acid;
(1S,4S)-4-(7-amino-6-bromo-3-(6-fluoroquinolin-3-yl)pyrazolo[1,5-a]pyrimidin-5-yl)-1-(methoxymethyl)cyclohexanecarboxylic acid;
(1S,4S)-4-(7-amino-6-bromo-3-(1-phenyl-1H-pyrazol-4-yl)pyrazolo[1,5-a]pyrimidin-5-yl)-1-(methylthio)cyclohexanecarboxylic acid;
(1R,4R)-4-(7-amino-6-bromo-3-(1-phenyl-1H-pyrazol-4-yl)pyrazolo[1,5-a]pyrimidin-5-yl)-1-(methylthio)cyclohexanecarboxylic acid;
(1R,4R)-4-(7-amino-6-bromo-3-(6-phenylpyridin-3-yl)pyrazolo[1,5-a]pyrimidin-5-yl)-1-((2-methoxyethoxy)methyl)cyclohexanecarboxylic acid;
(1S,4S)-4-(7-amino-6-bromo-3-(6-phenylpyridin-3-yl)pyrazolo[1,5-a]pyrimidin-5-yl)-1-((2-methoxyethoxy)methyl)cyclohexanecarboxylic acid;
(1R,4R)-4-(7-amino-6-bromo-3-(1-phenyl-1H-pyrazol-4-yl)pyrazolo[1,5-a]pyrimidin-5-yl)-1-((2-methoxyethoxy)methyl)cyclohexanecarboxylic acid;
(1S,4S)-4-(7-amino-6-bromo-3-(1-phenyl-1H-pyrazol-4-yl)pyrazolo[1,5-a]pyrimidin-5-yl)-1-((2-methoxyethoxy)methyl)cyclohexanecarboxylic acid;
(1R,4R)-4-(6-acetyl-7-amino-3-(6-phenylpyridin-3-yl)pyrazolo[1,5-a]pyrimidin-5-yl)-1-methylcyclohexanecarboxylic acid;
(1S,4S)-4-(6-acetyl-7-amino-3-(6-phenylpyridin-3-yl)pyrazolo[1,5-a]pyrimidin-5-yl)-1-fluorocyclohexanecarboxylic acid;
(1R,4R)-4-(6-acetyl-7-amino-3-(6-phenylpyridin-3-yl)pyrazolo[1,5-a]pyrimidin-5-yl)-1-fluorocyclohexanecarboxylic acid;
(1R,4R)-4-(6-acetyl-7-amino-3-(6-phenylpyridin-3-yl)pyrazolo[1,5-a]pyrimidin-5-yl)-1-(methoxymethyl)cyclohexanecarboxylic acid;
(1S,4S)-4-(6-acetyl-7-amino-3-(6-phenylpyridin-3-yl)pyrazolo[1,5-a]pyrimidin-5-yl)-1-(methoxymethyl)cyclohexanecarboxylic acid;
(1R,4R)-4-(6-acetyl-7-amino-3-(1-phenyl-1H-pyrazol-4-yl)pyrazolo[1,5-a]pyrimidin-5-yl)-1-(methoxymethyl)cyclohexanecarboxylic acid;
(1S,4S)-4-(6-acetyl-7-amino-3-(1-phenyl-1H-pyrazol-4-yl)pyrazolo[1,5-a]pyrimidin-5-yl)-1-(methoxymethyl)cyclohexanecarboxylic acid;
(1R,4R)-4-(6-acetyl-7-amino-3-(6-fluoroquinolin-3-yl)pyrazolo[1,5-a]pyrimidin-5-yl)-1-(methoxymethyl)cyclohexanecarboxylic acid;
(1S,4S)-4-(6-acetyl-7-amino-3-(6-fluoroquinolin-3-yl)pyrazolo[1,5-a]pyrimidin-5-yl)-1-(methoxymethyl)cyclohexanecarboxylic acid;
4-(6-acetyl-7-amino-3-(6-phenylpyridin-3-yl)pyrazolo[1,5-a]pyrimidin-5-yl)-1-((2-methoxyethoxy)methyl)cyclohexanecarboxylic acid;
(1R,4R)-4-(7-amino-6-cyano-3-(6-phenylpyridin-3-yl)pyrazolo[1,5-a]pyrimidin-5-yl)-1-methylcyclohexanecarboxylic acid;

(1S,4S)-4-(7-amino-6-cyano-3-(6-phenylpyridin-3-yl)pyrazolo[1,5-a]pyrimidin-5-yl)-1-methylcyclohexanecarboxylic acid;

4-(7-amino-6-bromo-3-(1-phenyl-1H-pyrazol-4-yl)pyrazolo[1,5-a]pyrimidin-5-yl)-1-(methylsulfonyl)cyclohexanecarboxylic acid;

(1S,4S)-4-(7-amino-6-bromo-3-(6-phenylpyridin-3-yl)pyrazolo[1,5-a]pyrimidin-5-yl)-1-methoxycyclohexanecarboxylic acid;

(1R,4R)-4-(7-amino-6-bromo-3-(6-phenylpyridin-3-yl)pyrazolo[1,5-a]pyrimidin-5-yl)-1-methoxycyclohexanecarboxylic acid;

(1R,4R)-4-(7-amino-6-bromo-3-(1-phenyl-1H-pyrazol-4-yl)pyrazolo[1,5-a]pyrimidin-5-yl)-1-methoxycyclohexanecarboxylic acid;

(1S,4S)-4-(7-amino-6-bromo-3-(1-phenyl-1H-pyrazol-4-yl)pyrazolo[1,5-a]pyrimidin-5-yl)-1-methoxycyclohexanecarboxylic acid;

(1S,4S)-4-(7-amino-6-bromo-3-(6-fluoroquinolin-3-yl)pyrazolo[1,5-a]pyrimidin-5-yl)-1-methoxycyclohexanecarboxylic acid;

(1R,4R)-4-(7-amino-6-bromo-3-(6-fluoroquinolin-3-yl)pyrazolo[1,5-a]pyrimidin-5-yl)-1-methoxycyclohexanecarboxylic acid;

(1S,4S)-4-(6-acetyl-7-amino-3-(6-phenylpyridin-3-yl)pyrazolo[1,5-a]pyrimidin-5-yl)-1-methoxycyclohexanecarboxylic acid;

(1R,4R)-4-(6-acetyl-7-amino-3-(6-phenylpyridin-3-yl)pyrazolo[1,5-a]pyrimidin-5-yl)-1-methoxycyclohexanecarboxylic acid;

(1R,4R)-4-(6-acetyl-7-amino-3-(1-phenyl-1H-pyrazol-4-yl)pyrazolo[1,5-a]pyrimidin-5-yl)-1-methoxycyclohexanecarboxylic acid;

(1S,4S)-4-(6-acetyl-7-amino-3-(1-phenyl-1H-pyrazol-4-yl)pyrazolo[1,5-a]pyrimidin-5-yl)-1-methoxycyclohexanecarboxylic acid;

(1S,4S)-4-(6-acetyl-7-amino-3-(6-fluoroquinolin-3-yl)pyrazolo[1,5-a]pyrimidin-5-yl)-1-methoxycyclohexanecarboxylic acid;

(1R,4R)-4-(6-acetyl-7-amino-3-(6-fluoroquinolin-3-yl)pyrazolo[1,5-a]pyrimidin-5-yl)-1-methoxycyclohexanecarboxylic acid;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboxylic acid;

(1S,4S)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboxylic acid;

(1R,4R)-4-(7-amino-3-(6-(1-methyl-1H-pyrazol-3-yl)pyridin-3-yl)-6-(methylsulfonyl)pyrazolo[1,5-a]pyrimidin-5-yl)-1-(2-methoxyethoxy)cyclohexanecarboxylic acid;

(1R,4R)-4-(7-amino-3-(1-(4-fluorophenyl)-1H-pyrazol-4-yl)-6-(methylsulfonyl)pyrazolo[1,5-a]pyrimidin-5-yl)-1-(2-methoxyethoxy)cyclohexanecarboxylic acid;

(1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexanecarboxylic acid;

5-(7-amino-5-((1R,4R)-4-carboxy-4-(2-methoxyethoxy)cyclohexyl)-6-(methylsulfonyl)pyrazolo[1,5-a]pyrimidin-3-yl)-2-(1-methyl-1H-pyrazol-3-yl)pyridine 1-oxide;

(1R,4R)-4-(7-amino-6-(methylsulfonyl)-3-(2-phenylpyrimidin-5-yl)pyrazolo[1,5-a]pyrimidin-5-yl)-1-(2-methoxyethoxy)cyclohexanecarboxylic acid;

(1R,4R)-4-(7-amino-6-(methylsulfonyl)-3-(6-(thiazol-2-yl)pyridin-3-yl)pyrazolo[1,5-a]pyrimidin-5-yl)-1-(2-methoxyethoxy)cyclohexanecarboxylic acid;

(1R,4R)-4-(7-amino-3-(6-(3-fluoro-4-hydroxyphenyl)pyridin-3-yl)-6-(methylsulfonyl)pyrazolo[1,5-a]pyrimidin-5-yl)-1-(2-methoxyethoxy)cyclohexanecarboxylic acid;

(1R,4R)-4-(7-amino-3-(2-(1-methyl-1H-pyrazol-3-yl)pyrimidin-5-yl)-6-(methylsulfonyl)pyrazolo[1,5-a]pyrimidin-5-yl)-1-(2-methoxyethoxy)cyclohexanecarboxylic acid;

(1R,4R)-4-(3-(2,2'-bipyridin-5-yl)-7-amino-6-(methylsulfonyl)pyrazolo[1,5-a]pyrimidin-5-yl)-1-(2-methoxyethoxy)cyclohexanecarboxylic acid;

(1R,4R)-4-(7-amino-6-(methylsulfonyl)-3-(2-(5-methylthiazol-2-yl)pyrimidin-5-yl)pyrazolo[1,5-a]pyrimidin-5-yl)-1-(2-methoxyethoxy)cyclohexanecarboxylic acid;

(1R,4R)-4-(7-amino-3-(6-fluoroquinolin-3-yl)-6-(methylsulfonyl)pyrazolo[1,5-a]pyrimidin-5-yl)-1-(2-methoxyethoxy)cyclohexanecarboxylic acid;

(1R,4R)-4-(7-amino-6-(methylsulfonyl)-3-(1-(4-(methylsulfonyl)phenyl)-1H-pyrazol-4-yl)pyrazolo[1,5-a]pyrimidin-5-yl)-1-(2-methoxyethoxy)cyclohexanecarboxylic acid;

(1S,4S)-4-(6-acetyl-7-amino-3-(1-phenyl-1H-pyrazol-4-yl)pyrazolo[1,5-a]pyrimidin-5-yl)-1-(2-methoxyethoxy)cyclohexanecarboxylic acid;

(1R,4R)-4-(6-acetyl-7-amino-3-(1-phenyl-1H-pyrazol-4-yl)pyrazolo[1,5-a]pyrimidin-5-yl)-1-(2-methoxyethoxy)cyclohexanecarboxylic acid;

(1S,4S)-4-(6-acetyl-7-amino-3-(6-phenylpyridin-3-yl)pyrazolo[1,5-a]pyrimidin-5-yl)-1-(2-methoxyethoxy)cyclohexanecarboxylic acid;

(1R,4R)-4-(6-acetyl-7-amino-3-(6-phenylpyridin-3-yl)pyrazolo[1,5-a]pyrimidin-5-yl)-1-(2-methoxyethoxy)cyclohexanecarboxylic acid;

(1R,4R)-4-(6-acetyl-7-amino-3-(6-phenylpyridin-3-yl)pyrazolo[1,5-a]pyrimidin-5-yl)-1-(2-morpholinoethoxy)cyclohexanecarboxylic acid;

(1S,4S)-4-(6-acetyl-7-amino-3-(6-(thiazol-2-yl)pyridin-3-yl)pyrazolo[1,5-a]pyrimidin-5-yl)-1-(2-methoxyethoxy)cyclohexanecarboxylic acid;

(1R,4R)-4-(6-acetyl-7-amino-3-(6-(thiazol-2-yl)pyridin-3-yl)pyrazolo[1,5-a]pyrimidin-5-yl)-1-(2-methoxyethoxy)cyclohexanecarboxylic acid;

(1S,4S)-4-(6-acetyl-7-amino-3-(6-(thiazol-4-yl)pyridin-3-yl)pyrazolo[1,5-a]pyrimidin-5-yl)-1-(2-methoxyethoxy)cyclohexanecarboxylic acid;

(1R,4R)-4-(6-acetyl-7-amino-3-(6-(thiazol-4-yl)pyridin-3-yl)pyrazolo[1,5-a]pyrimidin-5-yl)-1-(2-methoxyethoxy)cyclohexanecarboxylic acid;

(1R,4R)-4-(7-amino-6-(methylthio)-3-(6-phenylpyridin-3-yl)pyrazolo[1,5-a]pyrimidin-5-yl)-1-(2-methoxyethoxy)cyclohexanecarboxylic acid;

(1R,4R)-4-(7-amino-6-bromo-3-(6-phenylpyridin-3-yl)pyrazolo[1,5-a]pyrimidin-5-yl)-1-(2-methoxyethoxy)cyclohexanecarboxylic acid;

(1R,4R)-4-(7-amino-6-bromo-3-(6-phenylpyridin-3-yl)pyrazolo[1,5-a]pyrimidin-5-yl)-1-(2-morpholinoethoxy)cyclohexanecarboxylic acid;

(1S,4S)-4-(7-amino-6-bromo-3-(6-phenylpyridin-3-yl)pyrazolo[1,5-a]pyrimidin-5-yl)-1-(2-morpholinoethoxy)cyclohexanecarboxylic acid;

(1R,4R)-4-(7-amino-6-bromo-3-(1-phenyl-1H-pyrazol-4-yl)pyrazolo[1,5-a]pyrimidin-5-yl)-1-(2-morpholinoethoxy)cyclohexanecarboxylic acid;

(1R,4R)-4-(7-amino-6-bromo-3-(6-(3-fluoro-4-methoxyphenyl)pyridin-3-yl)pyrazolo[1,5-a]pyrimidin-5-yl)-1-(2-methoxyethoxy)cyclohexanecarboxylic acid;

(1R,4R)-4-(7-amino-6-cyano-3-(1-phenyl-1H-pyrazol-4-yl)pyrazolo[1,5-a]pyrimidin-5-yl)-1-(2-methoxyethoxy)cyclohexanecarboxylic acid;

(1R,4R)-4-(6-acetyl-7-amino-3-(1-phenyl-1H-pyrazol-4-yl)pyrazolo[1,5-a]pyrimidin-5-yl)-1-(2-methoxyethoxy)-N-(methylsulfonyl)cyclohexanecarboxamide;

4-(7-amino-6-(methylsulfonyl)-3-(1-phenyl-1H-pyrazol-4-yl)pyrazolo[1,5-a]pyrimidin-5-yl)-1-(2-methoxyethoxy)-N-(methylsulfonyl)cyclohexanecarboxamide;

1-amino-4-(7-amino-6-bromo-3-(6-phenylpyridin-3-yl)pyrazolo[1,5-a]pyrimidin-5-yl)cyclohexanecarboxylic acid;

4-(7-amino-6-bromo-3-(6-phenylpyridin-3-yl)pyrazolo[1,5-a]pyrimidin-5-yl)-1-hydroxycyclohexanecarbonitrile;

4-(7-amino-6-bromo-3-(6-phenylpyridin-3-yl)pyrazolo[1,5-a]pyrimidin-5-yl)-1-methoxycyclohexanecarbonitrile;

2-((1R,4R)-4-(7-amino-6-bromo-3-(6-phenylpyridin-3-yl)pyrazolo[1,5-a]pyrimidin-5-yl)-1-hydroxycyclohexyl)acetic acid;

2-((1S,4S)-4-(7-amino-6-bromo-3-(6-phenylpyridin-3-yl)pyrazolo[1,5-a]pyrimidin-5-yl)-1-hydroxycyclohexyl)acetic acid;

2-((1S,4S)-4-(7-amino-6-bromo-3-(1-phenyl-1H-pyrazol-4-yl)pyrazolo[1,5-a]pyrimidin-5-yl)-1-hydroxycyclohexyl)acetic acid;

2-((1R,4R)-4-(7-amino-6-bromo-3-(1-phenyl-1H-pyrazol-4-yl)pyrazolo[1,5-a]pyrimidin-5-yl)-1-hydroxycyclohexyl)acetic acid;

2-((1S,4S)-4-(7-amino-6-bromo-3-(6-phenylpyridin-3-yl)pyrazolo[1,5-a]pyrimidin-5-yl)-1-methoxycyclohexyl)acetic acid;

2-((1R,4R)-4-(7-amino-6-bromo-3-(6-phenylpyridin-3-yl)pyrazolo[1,5-a]pyrimidin-5-yl)-1-methoxycyclohexyl)acetic acid;

(4-(7-amino-6-bromo-3-(6-phenylpyridin-3-yl)pyrazolo[1,5-a]pyrimidin-5-yl)-1-methoxycyclohexyl)methanol;

(4-(7-amino-6-bromo-3-(1-phenyl-1H-pyrazol-4-yl)pyrazolo[1,5-a]pyrimidin-5-yl)-1-(2-methoxyethoxy)cyclohexyl)methanol;

(4-(7-amino-6-bromo-3-(1-phenyl-1H-pyrazol-4-yl)pyrazolo[1,5-a]pyrimidin-5-yl)-1-(methoxymethyl)cyclohexyl)methanol;

((1S,4S)-4-(7-amino-6-bromo-3-(6-phenylpyridin-3-yl)pyrazolo[1,5-a]pyrimidin-5-yl)-1-((2-methoxyethoxy)methyl)cyclohexyl)methanol;

((1R,4R)-4-(7-amino-6-bromo-3-(6-phenylpyridin-3-yl)pyrazolo[1,5-a]pyrimidin-5-yl)-1-((2-methoxyethoxy)methyl)cyclohexyl)methanol;

1-(7-amino-5-((1R,4R)-4-(hydroxymethyl)-4-methoxycyclohexyl)-3-(6-phenylpyridin-3-yl)pyrazolo[1,5-a]pyrimidin-6-yl)ethanone;

1-(7-amino-5-((1S,4S)-4-(hydroxymethyl)-4-methoxycyclohexyl)-3-(6-phenylpyridin-3-yl)pyrazolo[1,5-a]pyrimidin-6-yl)ethanone;

1-(7-amino-5-(4-(hydroxymethyl)-4-(2-methoxyethoxy)cyclohexyl)-3-(6-phenylpyridin-3-yl)pyrazolo[1,5-a]pyrimidin-6-yl)ethanone;

1-(7-amino-5-(4-(hydroxymethyl)-4-(2-methoxyethoxy)cyclohexyl)-3-(1-phenyl-1H-pyrazol-4-yl)pyrazolo[1,5-a]pyrimidin-6-yl)ethanone;

1-(7-amino-5-(4-(hydroxymethyl)-4-(methoxymethyl)cyclohexyl)-3-(6-phenylpyridin-3-yl)pyrazolo[1,5-a]pyrimidin-6-yl)ethanone;

1-(7-amino-5-(4-(hydroxymethyl)-4-methoxycyclohexyl)-3-(6'-methoxy-2,3'-bipyridin-5-yl)pyrazolo[1,5-a]pyrimidin-6-yl)ethanone;

1-(7-amino-5-(4,4-bis(hydroxymethyl)cyclohexyl)-3-(6-phenylpyridin-3-yl)pyrazolo[1,5-a]pyrimidin-6-yl)ethanone;

(1R,4R)-4-(7-amino-6-(methylsulfonyl)-3-(1-phenyl-1H-pyrazol-4-yl)pyrazolo[1,5-a]pyrimidin-5-yl)-N-hydroxy-1-(2-methoxyethoxy)cyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-N-methoxy-1-(2-methoxyethoxy)cyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-N-methylcyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-N,N-dimethylcyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-N-(2-hydroxyethyl)-1-(2-methoxyethoxy)cyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-N-(2-methoxyethyl)cyclohexanecarboxamide;

1-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarbonyl)-1H-pyrazol-3(2H)-one;

1-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarbonyl)pyrazolidin-3-one;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)-N-morpholinocyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-N-methoxy-1-(2-methoxyethoxy)-N-methylcyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-N-ethoxy-1-(2-methoxyethoxy)cyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-N-(cyclopropylmethoxy)-1-(2-methoxyethoxy)cyclohexanecarboxamide;

(1R,R-4-(7-amino-6-(methylsulfonyl)-3-(1-phenyl-1H-pyrazol-4-yl)pyrazolo[1,5-a]pyrimidin-5-yl)-N-(2-hydroxyethoxy)-1-(2-methoxyethoxy)cyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-N,1-bis(2-methoxyethoxy)cyclohexanecarboxamide;

(1R,4R)-4-(6-acetyl-7-amino-3-(6-phenylpyridin-3-yl)pyrazolo[1,5-a]pyrimidin-5-yl)-N-hydroxy-1-(2-methoxyethoxy)cyclohexanecarboxamide;

(1R,4R)-4-(6-acetyl-7-amino-3-(6-phenylpyridin-3-yl)pyrazolo[1,5-a]pyrimidin-5-yl)-N-methoxy-1-(2-methoxyethoxy)cyclohexanecarboxamide;

(1R,4R)-4-(7-amino-6-(methylsulfonyl)-3-(6-phenylpyridin-3-yl)pyrazolo[1,5-a]pyrimidin-5-yl)-N-hydroxy-1-(2-methoxyethoxy)cyclohexanecarboxamide;

(1R,4R)-4-(7-amino-6-(methylsulfonyl)-3-(6-phenylpyridin-3-yl)pyrazolo[1,5-a]pyrimidin-5-yl)-N-methoxy-1-(2-methoxyethoxy)cyclohexanecarboxamide;

(1R,4R)-4-(7-amino-6-(methylsulfonyl)-3-(6-phenylpyridin-3-yl)pyrazolo[1,5-a]pyrimidin-5-yl)-N-(cyclopropylmethoxy)-1-(2-methoxyethoxy)cyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarbohydrazide;

5-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-1,3,4-oxadiazol-2-amine;

5-((1R,4R)-4-(2-methoxyethoxy)-4-(5-methyl-1,3,4-oxadiazol-2-yl)cyclohexyl)-6-(methylsulfonyl)-3-(1-phenyl-1H-pyrazol-4-yl)pyrazolo[1,5-a]pyrimidin-7-amine;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboxamide;

(1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexanecarboxamide;

(1R,4R)-4-(3-(6-(1H-imidazol-2-yl)pyridin-3-yl)-6-acetyl-7-aminopyrazolo[1,5-a]pyrimidin-5-yl)-1-(2-methoxyethoxy)cyclohexanecarboxamide;

(1S,4S)-4-(3-(6-(1H-imidazol-2-yl)pyridin-3-yl)-6-acetyl-7-aminopyrazolo[1,5-a]pyrimidin-5-yl)-1-(2-methoxyethoxy)cyclohexanecarboxamide;

(1S,4S)-4-(3-(6-(1H-imidazol-2-yl)pyridin-3-yl)-6-acetyl-7-aminopyrazolo[1,5-a]pyrimidin-5-yl)-N-hydroxy-1-(2-methoxyethoxy)cyclohexanecarboxamide;

(1R,4R)-4-(3-(6-(1H-imidazol-2-yl)pyridin-3-yl)-6-acetyl-7-aminopyrazolo[1,5-a]pyrimidin-5-yl)-N-hydroxy-1-(2-methoxyethoxy)cyclohexanecarboxamide;

(1R,4R)-4-(3-(6-(1H-imidazol-2-yl)pyridin-3-yl)-7-amino-6-(methylsulfonyl)pyrazolo[1,5-a]pyrimidin-5-yl)-N-hydroxy-1-(2-methoxyethoxy)cyclohexanecarboxamide;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarbonitrile;

5-((1R,4R)-4-(2-methoxyethoxy)-4-(1H-tetrazol-5-yl)cyclohexyl)-6-(methylsulfonyl)-3-(1-phenyl-1H-pyrazol-4-yl)pyrazolo[1,5-a]pyrimidin-7-amine;

5-((1R,4R)-4-(2-methoxyethoxy)-4-(1H-tetrazol-5-yl)cyclohexyl)-6-(methylsulfonyl)-3-(6-phenylpyridin-3-yl)pyrazolo[1,5-a]pyrimidin-7-amine;

(1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexanecarboximidamide;

3-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-1,2,4-oxadiazol-5(4H)-one;

((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)(4H-1,2,4-triazol-3-yl)methanone;

((1S,4S)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)(4H-1,2,4-triazol-3-yl)methanone;

((1S,4S)-4-(7-amino-6-(methylsulfonyl)-3-(6-phenylpyridin-3-yl)pyrazolo[1,5-a]pyrimidin-5-yl)-1-(2-methoxyethoxy)cyclohexyl)(4H-1,2,4-triazol-3-yl)methanone;

((1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexyl)(4H-1,2,4-triazol-3-yl)methanone;

((1R,4R)-4-(7-amino-3-(6-phenylpyridin-3-yl)pyrazolo[1,5-a]pyrimidin-5-yl)-1-(2-methoxyethoxy)cyclohexyl)(4H-1,2,4-triazol-3-yl)methanone;

5-((1R,4R)-4-(2-methoxyethoxy)-4-(4H-1,2,4-triazol-3-yl)cyclohexyl)-6-(methylsulfonyl)-3-(1-phenyl-1H-pyrazol-4-yl)pyrazolo[1,5-a]pyrimidin-7-amine;

5-((1R,4R)-4-(2-methoxyethoxy)-4-(4H-1,2,4-triazol-3-yl)cyclohexyl)-6-(methylsulfonyl)-3-(6-phenylpyridin-3-yl)pyrazolo[1,5-a]pyrimidin-7-amine;

1-((1R,4R)-4-(7-amino-6-(methylsulfonyl)-3-(1-phenyl-1H-pyrazol-4-yl)pyrazolo[1,5-a]pyrimidin-5-yl)-1-(2-methoxyethoxy)cyclohexyl)-2-hydroxyethanone;

1-((1R,4R)-4-(7-amino-6-(methylsulfonyl)-3-(6-phenylpyridin-3-yl)pyrazolo[1,5-a]pyrimidin-5-yl)-1-(2-methoxyethoxy)cyclohexyl)-2-hydroxyethanone;

4-(7-amino-6-bromo-3-(6-phenylpyridin-3-yl)pyrazolo[1,5-a]pyrimidin-5-yl)-1-hydroxycyclohexanecarboxylic acid;

4-(6-acetyl-7-amino-3-(1-phenyl-1H-pyrazol-4-yl)pyrazolo[1,5-a]pyrimidin-5-yl)-1-(hydroxymethyl)cyclohexanecarboxylic acid;

4-(6-acetyl-7-amino-3-(6-phenylpyridin-3-yl)pyrazolo[1,5-a]pyrimidin-5-yl)-1-(hydroxymethyl)cyclohexanecarboxylic acid;

4-(7-amino-6-bromo-3-(6-phenylpyridin-3-yl)pyrazolo[1,5-a]pyrimidin-5-yl)-1-(hydroxymethyl)cyclohexanol;

4-(7-amino-6-bromo-3-(1-phenyl-1H-pyrazol-4-yl)pyrazolo[1,5-a]pyrimidin-5-yl)-1-(hydroxymethyl)cyclohexanol;

4-(7-amino-6-bromo-3-(6-fluoroquinolin-3-yl)pyrazolo[1,5-a]pyrimidin-5-yl)-1-(hydroxymethyl)cyclohexanol;

(1S,4S)-4-(7-amino-6-bromo-3-(6-phenylpyridin-3-yl)pyrazolo[1,5-a]pyrimidin-5-yl)-1-(2-hydroxyethyl)cyclohexanol;

1-(7-amino-5-(4-hydroxy-4-(hydroxymethyl)cyclohexyl)-3-(6-phenylpyridin-3-yl)pyrazolo[1,5-a]pyrimidin-6-yl)ethanone;

1-(7-amino-5-((1R,4R)-4-hydroxy-4-(hydroxymethyl)cyclohexyl)-3-(6-phenylpyridin-3-yl)pyrazolo[1,5-a]pyrimidin-6-yl)ethanone;

1-(7-amino-5-((1S,4S)-4-hydroxy-4-(hydroxymethyl)cyclohexyl)-3-(6-phenylpyridin-3-yl)pyrazolo[1,5-a]pyrimidin-6-yl)ethanone;

1-(7-amino-5-(4-hydroxy-4-(hydroxymethyl)cyclohexyl)-3-(1-phenyl-1H-pyrazol-4-yl)pyrazolo[1,5-a]pyrimidin-6-yl)ethanone;

1-(7-amino-3-(6-fluoroquinolin-3-yl)-5-(4-hydroxy-4-(hydroxymethyl)cyclohexyl)pyrazolo[1,5-a]pyrimidin-6-yl)ethanone;

1-(3-(2,3'-bipyridin-5-yl)-7-amino-5-(4-hydroxy-4-(hydroxymethyl)cyclohexyl)pyrazolo[1,5-a]pyrimidin-6-yl)ethanone;

1-(7-amino-5-(4-hydroxy-4-(hydroxymethyl)cyclohexyl)-3-(6-(thiazol-4-yl)pyridin-3-yl)pyrazolo[1,5-a]pyrimidin-6-yl)ethanone;

1-(7-amino-5-(4-hydroxy-4-(hydroxymethyl)cyclohexyl)-3-(6-(1-methyl-1H-pyrazol-4-yl)pyridin-3-yl)pyrazolo[1,5-a]pyrimidin-6-yl)ethanone;

1-(7-amino-5-(4-hydroxy-4-(hydroxymethyl)cyclohexyl)-3-(6'-methoxy-2,3'-bipyridin-5-yl)pyrazolo[1,5-a]pyrimidin-6-yl)ethanone;

1-(7-amino-3-(6'-hydroxy-2,3'-bipyridin-5-yl)-5-(4-hydroxy-4-(hydroxymethyl)cyclohexyl)pyrazolo[1,5-a]pyrimidin-6-yl)ethanone;

1-(7-amino-5-((1R,4R)-4-hydroxy-4-(hydroxymethyl)cyclohexyl)-3-(1'-methyl-1'H-1,4'-bipyrazol-4-yl)pyrazolo[1,5-a]pyrimidin-6-yl)ethanone;

1-(7-amino-5-((1S,4S)-4-hydroxy-4-(hydroxymethyl)cyclohexyl)-3-(1'-methyl-1'H-1,4'-bipyrazol-4-yl)pyrazolo[1,5-a]pyrimidin-6-yl)ethanone;

methyl 3-(5-(6-acetyl-7-amino-5-(4-hydroxy-4-(hydroxymethyl)cyclohexyl)pyrazolo[1,5-a]pyrimidin-3-yl)pyridin-2-yl)benzoate;

3-(5-(6-acetyl-7-amino-5-(4-hydroxy-4-(hydroxymethyl)cyclohexyl)pyrazolo[1,5-a]pyrimidin-3-yl)pyridin-2-yl)benzoic acid;

1-(7-amino-5-(4-hydroxy-4-(hydroxymethyl)cyclohexyl)-3-(1-(thiazol-4-yl)-1H-pyrazol-4-yl)pyrazolo[1,5-a]pyrimidin-6-yl)ethanone;

methyl 5-(5-(6-acetyl-7-amino-5-((1R,4R)-4-hydroxy-4-(hydroxymethyl)cyclohexyl)pyrazolo[1,5-a]pyrimidin-3-yl)pyridin-2-yl)-2-methoxybenzoate;

methyl 5-(5-(6-acetyl-7-amino-5-((1S,4S)-4-hydroxy-4-(hydroxymethyl)cyclohexyl)pyrazolo[1,5-a]pyrimidin-3-yl)pyridin-2-yl)-2-methoxybenzoate;

5-(5-(6-acetyl-7-amino-5-(4-hydroxy-4-(hydroxymethyl)cyclohexyl)pyrazolo[1,5-a]pyrimidin-3-yl)pyridin-2-yl)-2-methoxybenzoic acid;

1-(7-amino-5-(4-hydroxy-4-(hydroxymethyl)cyclohexyl)-3-(6-(thiazol-2-yl)pyridin-3-yl)pyrazolo[1,5-a]pyrimidin-6-yl)ethanone;

1-(7-amino-5-(4-hydroxy-4-(hydroxymethyl)cyclohexyl)-3-(6-(thiazol-5-yl)pyridin-3-yl)pyrazolo[1,5-a]pyrimidin-6-yl)ethanone;

1-(7-amino-5-(4-hydroxy-4-(hydroxymethyl)cyclohexyl)-3-(2-phenylpyrimidin-5-yl)pyrazolo[1,5-a]pyrimidin-6-yl)ethanone;

1-(7-amino-5-((1S,4S)-4-hydroxy-4-(2-hydroxyethyl)cyclohexyl)-3-(6-phenylpyridin-3-yl)pyrazolo[1,5-a]pyrimidin-6-yl)ethanone;

N-((4-(6-acetyl-7-amino-3-(6-phenylpyridin-3-yl)pyrazolo[1,5-a]pyrimidin-5-yl)-1-hydroxycyclohexyl)methyl)methanesulfonamide;

1-(7-amino-5-((1R,4R)-4-hydroxy-4-(methylsulfonylmethyl)cyclohexyl)-3-(6-phenylpyridin-3-yl)pyrazolo[1,5-a]pyrimidin-6-yl)ethanone;

1-(7-amino-5-((1S,4S)-4-hydroxy-4-(methylsulfonylmethyl)cyclohexyl)-3-(6-phenylpyridin-3-yl)pyrazolo[1,5-a]pyrimidin-6-yl)ethanone;

(1R,4R)-4-(7-amino-6-bromo-3-(6-phenylpyridin-3-yl)pyrazolo[1,5-a]pyrimidin-5-yl)-1-(methoxymethyl)cyclohexanol;

(1S,4S)-4-(7-amino-6-bromo-3-(6-phenylpyridin-3-yl)pyrazolo[1,5-a]pyrimidin-5-yl)-1-(methoxymethyl)cyclohexanol;

4-(7-amino-6-bromo-3-(6-fluoroquinolin-3-yl)pyrazolo[1,5-a]pyrimidin-5-yl)-1-(methoxymethyl)cyclohexanol; and 4-(7-amino-6-(methylsulfonyl)-3-(1-phenyl-1H-pyrazol-4-yl)pyrazolo[1,5-a]pyrimidin-5-yl)-1-(hydroxymethyl)cyclohexanol;

or a stereoisomer thereof;
or a pharmaceutically acceptable salt thereof;
or a pharmaceutically acceptable salt of the stereoisomer thereof.

12. A pharmaceutical composition comprising a therapeutically effective amount of the compound of claim 1 and a pharmaceutically acceptable carrier.

13. A method of modulating mammalian target of rapamycin kinase activity in a patient comprising the step of administering a therapeutically effective amount of the compound according to claim 1 to the patient.

\* \* \* \* \*